United States Patent
Nam et al.

(10) Patent No.: US 12,162,858 B2
(45) Date of Patent: Dec. 10, 2024

(54) QUINOLINE DERIVATIVES AS INHIBITORS OF AXL/MER RTK AND CSF1R

(71) Applicant: QURIENT CO., LTD., Gyeonggi-Do (KR)

(72) Inventors: Kiyean Nam, Gyeonggi-Do (KR); Jaeseung Kim, Seoul (KR); Dongsik Park, Gyeonggi-Do (KR); Yeejin Jeon, Gyeonggi-Do (KR); Yeong-In Yang, Gyeonggi-Do (KR); Hwan Kyu Kang, Gyeonggi-Do (KR)

(73) Assignee: QURIENT CO., LTD., Gyeonggi-Do (KR)

( * ) Notice: Subject to any disclaimer, the term of this patent is extended or adjusted under 35 U.S.C. 154(b) by 595 days.

(21) Appl. No.: 17/047,961

(22) PCT Filed: May 31, 2019

(86) PCT No.: PCT/EP2019/064214
§ 371 (c)(1),
(2) Date: Oct. 15, 2020

(87) PCT Pub. No.: WO2019/229251
PCT Pub. Date: Dec. 5, 2019

(65) Prior Publication Data
US 2021/0163448 A1    Jun. 3, 2021

Related U.S. Application Data

(60) Provisional application No. 62/677,902, filed on May 30, 2018.

(51) Int. Cl.
| | |
|---|---|
| *C07D 401/14* | (2006.01) |
| *C07D 401/12* | (2006.01) |
| *C07D 405/14* | (2006.01) |
| *C07D 409/14* | (2006.01) |

(52) U.S. Cl.
CPC ......... *C07D 401/14* (2013.01); *C07D 401/12* (2013.01); *C07D 405/14* (2013.01); *C07D 409/14* (2013.01)

(58) Field of Classification Search
CPC .... C07D 401/14; A61K 31/4709; A61P 25/28
See application file for complete search history.

(56) References Cited

U.S. PATENT DOCUMENTS 8,999,982 B2* 4/2015 Schultz-Fademrecht ................... A61P 35/00
514/312
2018/0093968 A1* 4/2018 Nam .................... C07D 409/14

FOREIGN PATENT DOCUMENTS

| JP | 2013-536813 A | 9/2013 |
|---|---|---|
| JP | 2018-511624 A | 4/2018 |
| WO | 2012/028332 A1 | 3/2012 |
| WO | 2016/166250 A1 | 10/2016 |
| WO | 2019/231942 A1 | 12/2019 |

OTHER PUBLICATIONS

English Translation of Office Action issued by the Japanese Patent Office dated Oct. 18, 2022 in parallel Japanese Patent Application No. 2020-565928.
RN: 2028271-26-1, Database Registry [Online], Retrieved from STN, Nov. 9, 2016.
Myers, Samuel H., et al., "AXL Inhibitors in Cancer: A Medicinal Chemistry Perspective", Journal of Medicinal Chemistry, vol. 59, No. 8, Nov. 10, 2015, pp. 3593-3608.
Office Action issued by the European Patent Office with respect to the European priority application No. 19 728 645.3.

* cited by examiner

*Primary Examiner* — Jeffrey S Lundgren
*Assistant Examiner* — Eric Tran
(74) *Attorney, Agent, or Firm* — SALIWANCHIK, LLOYD & EISENSCHENK

(57) ABSTRACT

The present invention relates to quinoline derivatives which are inhibitors for Axl/Mer RTK (receptor tyrosine kinase) and CSF1R (colony stimulating factor 1 receptor). These compounds are suitable for the treatment of disorders associated with, accompanied by, caused by or induced by Axl/Mer RTK and CSF1R, in particular a hyperfunction thereof. The compounds are suitable for the treatment of hyperproliferative disorders, such as cancer, particularly immune-suppressive cancer (such as those cancers with an immunosuppression of innate immunity in a tumor microenvironment (TME), refractory cancer and cancer metastases. They are also useful in the treatment of inflammatory diseases and/or neurodegenerative diseases.

23 Claims, 2 Drawing Sheets

QUINOLINE DERIVATIVES AS INHIBITORS OF AXL/MER RTK AND CSF1R

CROSS REFERENCE TO RELATED APPLICATIONS

Figure 1:
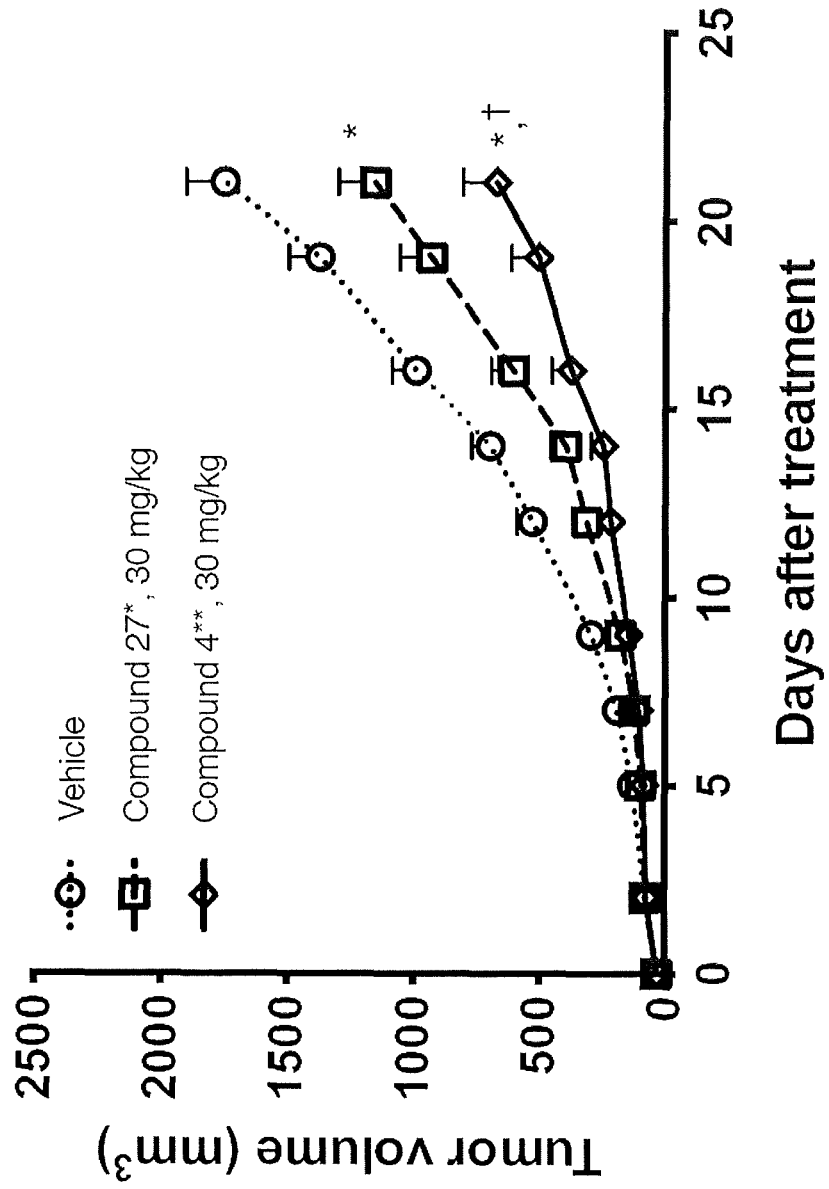

This application is a National Stage Application of International Application Number PCT/EP2019/064214, filed May 31, 2019; which claims the benefit of U.S. Provisional Application Ser. No. 62/677,902, filed May 30, 2018.

The present invention relates to quinoline derivatives which are inhibitors for Axl/Mer RTK (receptor tyrosine kinase) and CSF1R (colony stimulating factor 1 receptor). These compounds are suitable for the treatment of disorders associated with, accompanied by, caused by or induced by Axl/Mer RTK and CSF1R, in particular a hyperfunction thereof. The compounds are suitable for the treatment of hyperproliferative disorders, such as cancer, particularly immune-suppressive cancer (such as those cancers with an immunosuppression of innate immunity in a tumor microenvironment (TME), refractory cancer and cancer metastases. They are also useful in the treatment of inflammatory diseases and/or neurodegenerative diseases.

BACKGROUND OF THE INVENTION

Axl/Mer receptor tyrosine kinase (Axl/Mer RTK) are member of the TAM (Tyrosine, Axl, Mer) receptor tyrosine kinases. They are characterised by extracellular domain, consisting two immunoglobulin-like domains followed by two fibronectin type-3-like domain. The activation of the Axl/Mer occurs by its cognate protein ligand, growth arrest specific 6 (Gas6) and protein S (Pros1), respectively.

Axl/Mer RTK is already known to regulate cell growth, differentiation and survival, but in recent years Axl/Mer RTK has become a promising target for cancer immunotherapy and is known to be a regulator of immune homeostasis. Guided by their cognate ligands Gas6 and Pros1, these receptors ensure the resolution of inflammation by dampening the activation of innate cells as well as by restoring tissue function through promotion of tissue repair and clearance of apoptotic cells in normal condition (Paolino M et al., Cancers (Basel). 2016 Oct. 21; 8(10) pii: E97).

However, in the tumor microenvironment (TME), activation of Axl/Mer receptors can lead to immune evasion via Axl/Mer RTK driven phagocytosis of apoptotic cells, negative regulation of the immune response and subsequent inhibition of T-cell priming (Zagórska A et al., Nat Immunol. 2014 October; 15(10):920-8). In addition, Axl/Mer RTK play a role in modulating the cytokine milieu of the tumor to limit effective CD8+ T cell recruitment and to polarize macrophages toward and M2 anti-inflammatory state which plays important role in enhancing tumor progression. (Akalu Y T et al., Immunol Rev. 2017 March; 276(1):165-177). Moreover, inhibition of TLR pathway by Axl/Mer RTK in DCs triggers suppression of CD8+ cytotoxic T cell population, which can increase anti-tumor immunity. In addition Activation of TAM family is reported to downregulate TLR signaling-mediated inflammatory response through increase in SOCS1 and 3 expressions.

Axl/Mer receptors are also reported to negatively regulate activation of NK cells through regulating Cbl/b as well as suppresses the IFN gamma cytokine production of activated NK cells. Accordingly, inhibiting Axl/Mer receptors are possible with new immunotherapy approaches for various cancers patients by priming host immune response against tumour cell invasion (Davra V et al., Cancers (Basel). 2016 Nov. 29; 8(12). pii: E107).

Colony stimulating factor 1 receptor (CSF1R) is also cell surface homodimeric type III receptor tyrosine kinase by macrophage and other cells of the myeloid lineage that is encoded by the c-fms proto-oncogene. The activation of the CSF1R occurs by bound by its ligand. CSF1 and IL-34 (Hume D A et al., Blood. 2012 Feb. 23; 119(8):1810-20).

CSF1R is known to regulate the differentiation of myeloid progenitors into heterogeneous populations of monocytes, macrophages, dendritic cells (DC) and bone-resorbing osteoclasts. In addition, activated CSF1R promotes the survival, proliferation, differentiation and chemotaxis of differentiated macrophages (Geissmann F et al., Science. 2010 Feb. 5; 327(5966):656-61).

Based on role of CSF1R in immune cells, various approaches targeting either the CSF1R or its ligands is developing against immunotherapy and cancers and currently it in clinical stage.

SUMMARY OF THE INVENTION

It is an object of the present invention to provide compounds and/or pharmaceutically acceptable salts thereof which can be used as pharmaceutically active agents, especially for treatment of cell proliferative diseases like cancer, but also inflammatory diseases and/or neurodegenerative diseases, as well as compositions comprising at least one of those compounds and/or pharmaceutically acceptable salts thereof as pharmaceutically active ingredients.

In a first aspect, the present invention relates to a compound having the general formula I:

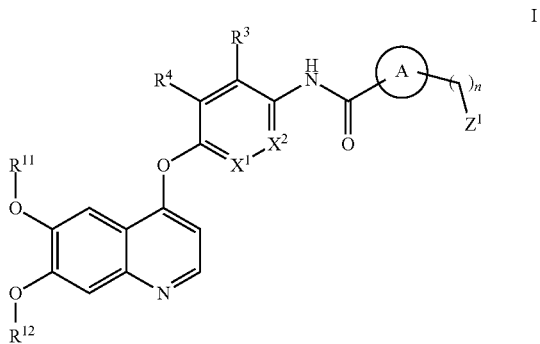

wherein
$X^1$ is, independently at each occurrence, selected from $CR^3$ and N;
$X^2$ is, independently at each occurrence, selected from $CR^4$ and N;
n is, independently at each occurrence, selected from 0, 1 and 2;
A is, at each occurrence, independently selected from any structure as depicted in the following group W;

Group W

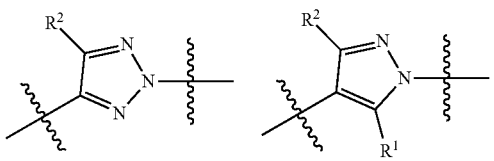

-continued

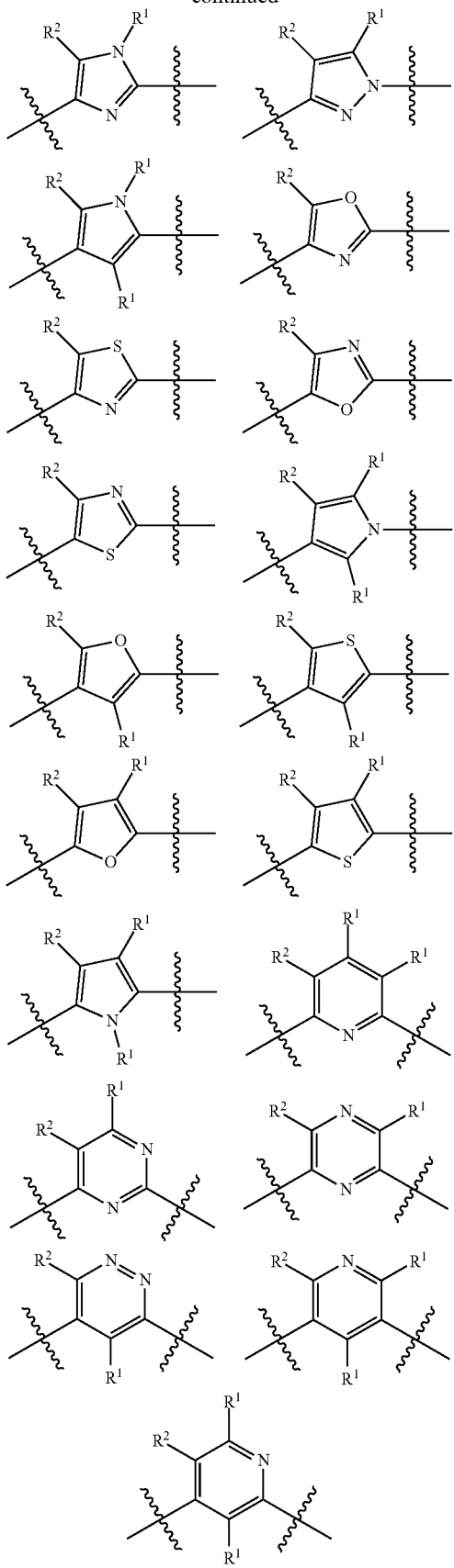

$R^1$ is, at each occurrence, independently selected from the group consisting of hydrogen; C1-C6 alkyl; C1-C6 alkyl substituted with one or two of $OR^5$ and $NR^5R^6$; C3-C10 cycloalkyl; C1-C4 haloalkyl; —(C=O)$R^5$; any of which is optionally substituted;

$R^2$ is, at each occurrence, independently selected from the group consisting of C1-C6 alkyl; C3-C10 cycloalkyl; C1-C4 haloalkyl; —$NR^7R^8$; —$OR^8$; any of which is optionally substituted;

$R^3$ and $R^4$ are, at each occurrence, independently selected from the group consisting of hydrogen; halogen, e.g Cl or F; C1-C3 alkyl; $OR^5$; C1-C4 haloalkyl; any of which is optionally substituted;

$R^5$ and $R^6$ are, at each occurrence, independently selected from the group consisting of hydrogen; C1-C6 alkyl; C3-C10 cycloalkyl; C1-C4 haloalkyl; any of which is optionally substituted;

$R^7$ is, at each occurrence, independently selected from the group consisting of hydrogen; C1-C6 alkyl; C1-C6 alkyl substituted with one or two of $OR^5$ and $NR^5R^6$; C3-C10 cycloalkyl; C1-C4 haloalkyl; any of which is optionally substituted;

$R^8$ is, at each occurrence, independently selected from the group consisting of hydrogen; —CH(CH$_3$)$_2$; —C(CH$_3$)$_3$; C3-C10 cycloalkyl; C3-C10 heterocycloalkyl; C1-C4 haloalkyl; C1-C6 alkyl substituted with one or two of $OR^5$ and $NR^5R^6$; and C1-C6 alkyl substituted with one or two of C3-C10 cycloalkyl, C3-C10 heterocycloalkyl and C1-C4 haloalkyl; any of which is optionally substituted;

$Z^1$ is, at each occurrence, independently selected from the group consisting of hydrogen; C1-C6 alkyl; C1-C6 alkyl substituted with one or two of (=O), CN, $OR^5$ and $NR^5R^6$; C3-C10 cycloalkyl; C3-C10 cycloalkyl substituted with one or several of halogen, $OR^7$ and $NR^9R^{10}$; C3-C10 heterocycloalkyl; C3-C10 heterocycloalkyl substituted with one or several of halogen, C1-C6 alkyl, C3-C10 cycloalkyl and C1-C4 haloalkyl; C1-C4 haloalkyl;

$R^9$ and $R^{10}$ are, at each occurrence, independently selected from the group consisting of hydrogen; C1-C6 alkyl; C3-C10 cycloalkyl; C1-C4 haloalkyl; any of which is optionally substituted;

$R^{11}$ and $R^{12}$ are, at each occurrence, independently selected from the group consisting of C1-C6 alkyl; C3-C10 cycloalkyl; C3-C10 heterocycloalkyl; C1-C4 haloalkyl; any of which is optionally substituted;

and pharmaceutically acceptable salts thereof.

In one embodiment, the compound according to the present invention has the general formula II:

II

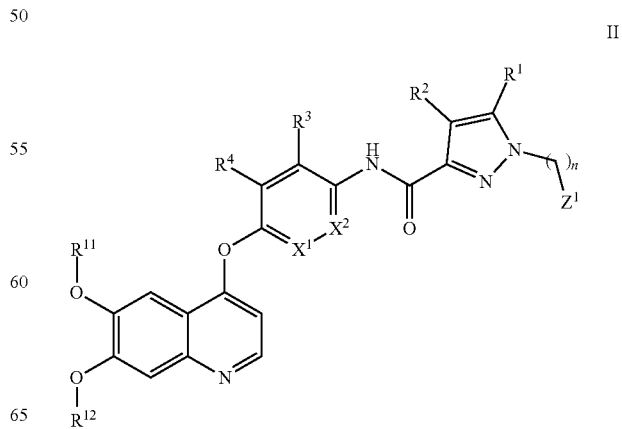

wherein
R¹, R², R³, R⁴, R¹¹, R¹², Z¹, X¹, X² and n are as defined above; and
pharmaceutically acceptable salts thereof.

In one embodiment, the compound according to the present invention has the general formula III:

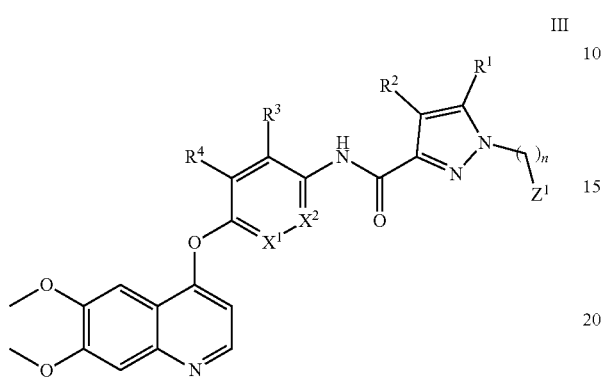

III wherein
R¹, R², R³, R⁴, Z¹, X¹, X² and n are as defined above; and
pharmaceutically acceptable salts thereof,
wherein, preferably,
R³ and R⁴ are, at each occurrence, independently selected from the group consisting of hydrogen; halogen, e.g Cl or F; C1-C3 alkyl, which is optionally substituted;
R⁸ is, at each occurrence, independently selected from the group consisting of hydrogen; —CH(CH₃)₂; —C(CH₃)₃; C3-C10 cycloalkyl; C1-C4 haloalkyl; C1-C6 alkyl substituted with one or two of OR⁵ and NR⁵R⁶; or C1-C6 alkyl substituted with one or two of C3-C10 cycloalkyl and C1-C4 haloalkyl; any of which is optionally substituted; and
Z¹ is, at each occurrence, independently selected from the group consisting of hydrogen; C1-C6 alkyl; C1-C6 alkyl substituted with one or two of OR⁵ and NR⁵R⁶; C3-C10 cycloalkyl; C3-C10 cycloalkyl substituted with one or several of halogen, OR⁷ and NR⁹R¹⁰; C3-C10 heterocycloalkyl; C3-C10 heterocycloalkyl substituted with one or several of halogen, C1-C6 alkyl, C3-C10 cycloalkyl and C1-C4 haloalkyl; C1-C4 haloalkyl; and pharmaceutically acceptable salts thereof.

In one embodiment, the compound according to the present invention has the general formula IV:

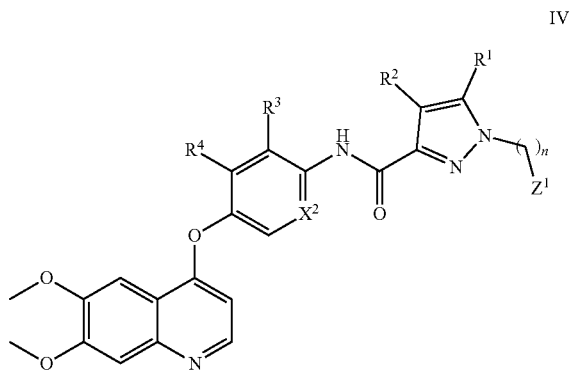

IV wherein
R¹, R², R³, R⁴, Z¹, X² and n are as defined above; and
pharmaceutically acceptable salts thereof.

In one embodiment, the compound according to the present invention has the general formula V:

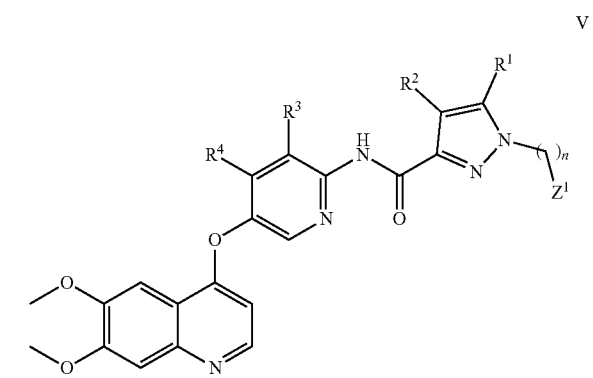

V wherein
R¹, R², R³, R⁴, Z¹ and n are as defined above; and
pharmaceutically acceptable salts thereof;
wherein, preferably,
R³ and R⁴ are hydrogen;
and pharmaceutically acceptable salts thereof.

In one embodiment n=0 or 1, and Z¹ is selected from C1-C6 alkyl, in particular methyl, ethyl, propyl or isopropyl; C3-C10 cycloalkyl, in particular C3 cycloalkyl; C3-C10 heterocycloalkyl; C1-C6 alkyl substituted with one or two of OR⁵ and NR⁵R⁶; and pharmaceutically acceptable salts thereof.

In one embodiment R² is OR⁸, and R⁸ is selected from —CH(CH₃)₂; —C(CH₃)₃; C1-C4 haloalkyl; C1-C6 alkyl substituted with one or two of C3-C10 cycloalkyl, C3-C10 heterocycloalkyl and C1-C4 haloalkyl; or C1-C6 alkyl substituted with C1-C4 haloalkyl, in particular one of trifluoromethyl, difluoromethyl, fluoromethyl, trifluoroethyl, difluoroethyl, fluoroethyl, trifluoropropyl, difluoropropyl, fluoropropyl, trifluoroisopropyl, difluoroisopropyl, and fluoroisopropyl and pharmaceutically acceptable salts thereof.

In one embodiment, n=0 or 1, and Z¹ is selected from C1-C6 alkyl, in particular methyl, ethyl, propyl or isopropyl; C3-C10 cycloalkyl, in particular C3 cycloalkyl; C3-C10 heterocycloalkyl; C1-C6 alkyl substituted with one or two of OR⁵ and NR⁵R⁶; wherein R⁵ and R⁶ are, at each occurrence, independently selected from the group consisting of hydrogen; C1-C6 alkyl; C3-C10 cycloalkyl; C1-C4 haloalkyl; any of which is optionally substituted;
and
R² is OR⁸, and R⁸ is selected from —CH(CH₃)₂; —C(CH₃)₃; C1-C4 haloalkyl; C1-C6 alkyl substituted with one or two of C3-C10 cycloalkyl, C3-C10 heterocycloalkyl and C1-C4 haloalkyl; or C1-C6 alkyl substituted with C1-C4 haloalkyl, in particular one of trifluoromethyl, difluoromethyl, fluoromethyl, trifluoroethyl, difluoroethyl, fluoroethyl, trifluoropropyl, difluoropropyl, fluoropropyl, trifluoroisopropyl, difluoroisopropyl, and fluoroisopropyl
and pharmaceutically acceptable salts thereof.

In one embodiment R² is OR⁸, and R⁸ is selected from C1-C4 haloalkyl, in particular one of trifluoromethyl, difluoromethyl, fluoromethyl, trifluoroethyl, difluoroethyl, fluoroethyl, trifluoropropyl, difluoropropyl, fluoropropyl, trifluoroisopropyl, difluoroisopropyl, and fluoroisopropyl; or C1-C6 alkyl substituted with C1-C4 haloalkyl, in particular one of trifluoromethyl, difluoromethyl, fluoromethyl, trifluoroethyl, difluoroethyl, fluoroethyl, trifluoropropyl, difluoropropyl, fluoropropyl, trifluoroisopropyl, difluoroisopropyl, and fluoroisopropyl In one embodiment n=0 or 1; and $Z^1$ is selected from methyl; ethyl; propyl; isopropyl; C3 cycloalkyl; C4 cycloalkyl; and C5 cycloalkyl.

In one embodiment n=0 or 1; $Z^1$ is selected from methyl; ethyl; propyl; isopropyl; C3 cycloalkyl; C4 cycloalkyl; and C5 cycloalkyl; and $R^2$ is $OR^8$; and $R^8$ is selected from C1-C4 haloalkyl, in particular one of trifluoromethyl, difluoromethyl, fluoromethyl, trifluoroethyl, difluoroethyl, fluoroethyl, trifluoropropyl, difluoropropyl, fluoropropyl, trifluoroisopropyl, difluoroisopropyl, and fluoroisopropyl; or C1-C6 alkyl substituted with C1-C4 haloalkyl, in particular one of trifluoromethyl, difluoromethyl, fluoromethyl, trifluoroethyl, difluoroethyl, fluoroethyl, trifluoropropyl, difluoropropyl, fluoropropyl, trifluoroisopropyl, difluoroisopropyl, and fluoroisopropyl In one embodiment, the compound according to the present invention has one of the structures as shown hereafter:

| # cpd | Structure |
|---|---|
| 1 | |
| 2 | |
| 3 | 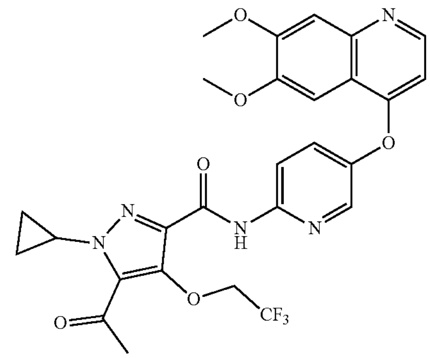 [SMILES: COc1cc2nccc(Oc3ccc(NC(=O)c4nn(C5CC5)c(C(C)=O)c4OCC(F)(F)F)nc3)c2cc1OC] |
| 4 | 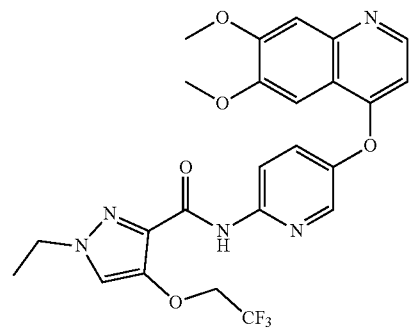 [SMILES: CCn1cc(OCC(F)(F)F)c(C(=O)Nc2ccc(Oc3ccnc4cc(OC)c(OC)cc34)cn2)n1] |
| 5 | 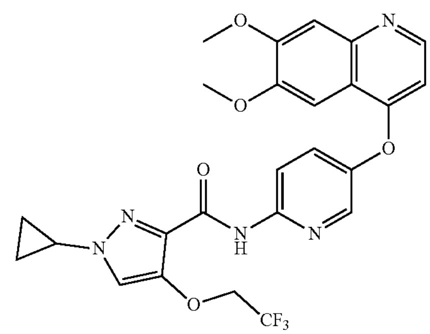 |
| 6 | 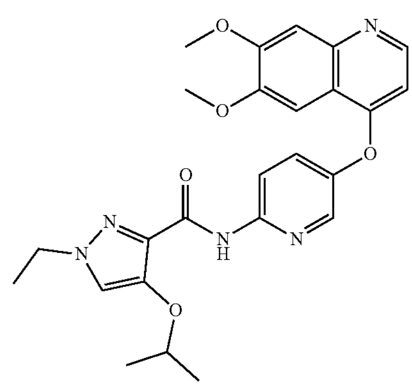 [SMILES: CCn1cc(OC(C)C)c(C(=O)Nc2ccc(Oc3ccnc4cc(OC)c(OC)cc34)cn2)n1] |

-continued

| # cpd | Structure |
|---|---|
| 7 | (structure) |
| 8 | (structure) |
| 9 | (structure) |
| 10 | (structure) |

-continued

| # cpd | Structure |
|---|---|
| 11 | (structure) |
| 12 | (structure) |
| 13 | (structure) |
| 14 | (structure) |

| # cpd | Structure |
|---|---|
| 15 | 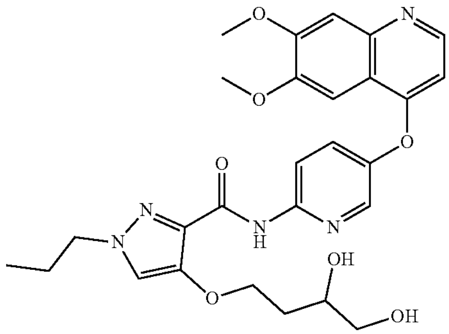 [SMILES: CCCn1cc(OCCC(O)CO)c(C(=O)Nc2ccc(Oc3ccnc4cc(OC)c(OC)cc34)cn2)n1] |
| 16 | 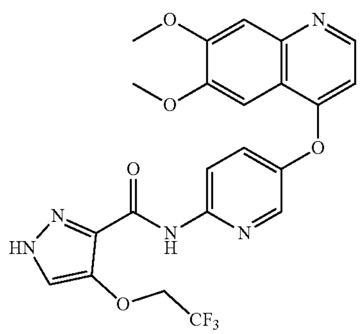 [SMILES: COc1cc2nccc(Oc3ccc(NC(=O)c4n[nH]cc4OCC(F)(F)F)nc3)c2cc1OC] |
| 17 | 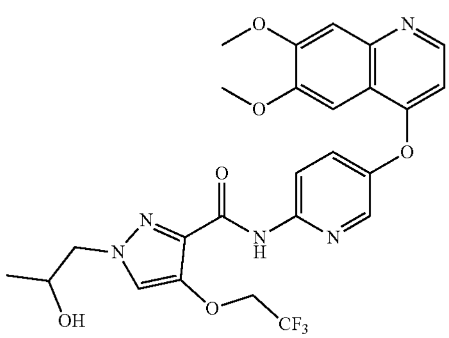 [SMILES: COc1cc2nccc(Oc3ccc(NC(=O)c4nn(CC(C)O)cc4OCC(F)(F)F)nc3)c2cc1OC] |
| 18 | 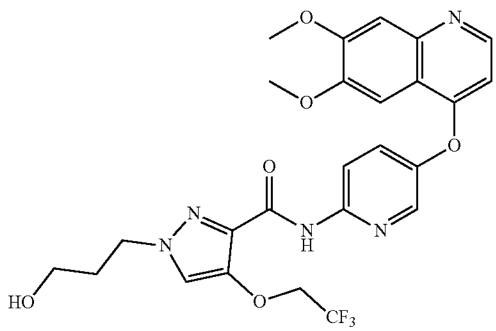 [SMILES: COc1cc2nccc(Oc3ccc(NC(=O)c4nn(CCCO)cc4OCC(F)(F)F)nc3)c2cc1OC] |
| 19 | |
| 20 | |
| 21 | |
| 22 | |

-continued
| # cpd | Structure |
|---|---|
| 23 | 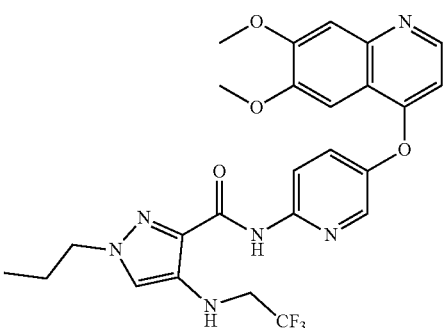 |
| 24 | 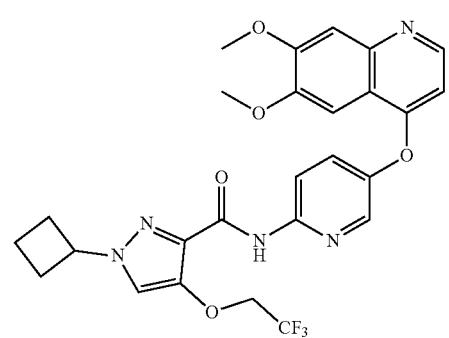 [SMILES: COc1cc2nccc(Oc3ccc(NC(=O)c4nn(C5CCC5)cc4OCC(F)(F)F)nc3)c2cc1OC] |
| 25 | 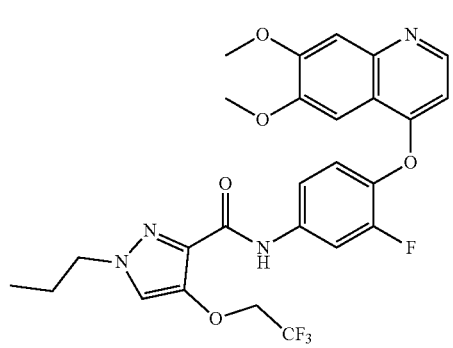 |
| 26 | 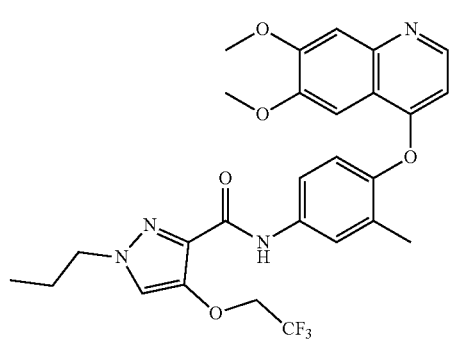 [SMILES: CCCn1cc(OCC(F)(F)F)c(C(=O)Nc2ccc(Oc3ccnc4cc(OC)c(OC)cc34)c(C)c2)n1] |
-continued
| # cpd | Structure |
|---|---|
| 27 | 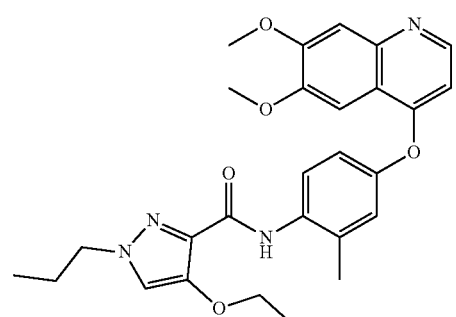 |
| 28 | 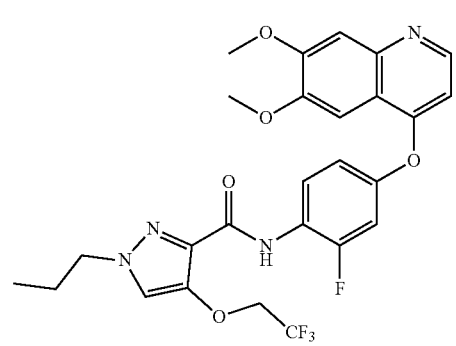 |
| 29 | 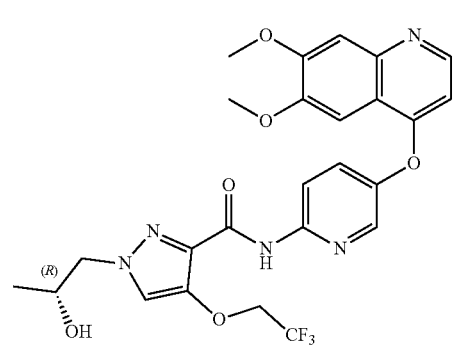 |
| 30 | 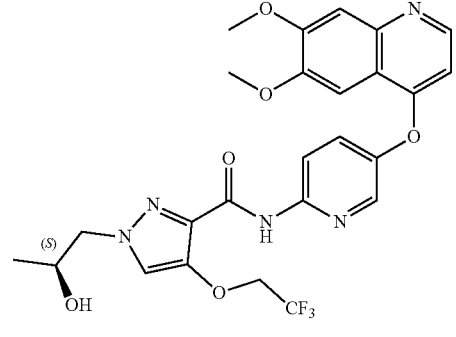 |

| # cpd | Structure |
|---|---|
| 31 | 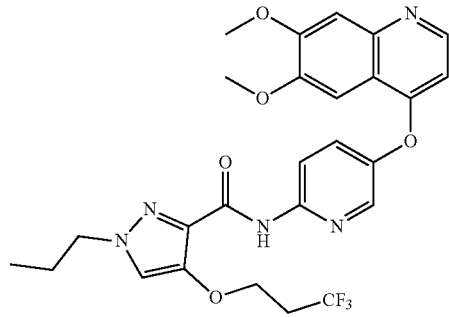 [SMILES: CCCn1cc(OCCC(F)(F)F)c(C(=O)Nc2ccc(Oc3ccnc4cc(OC)c(OC)cc34)cn2)n1] |
| 32 | 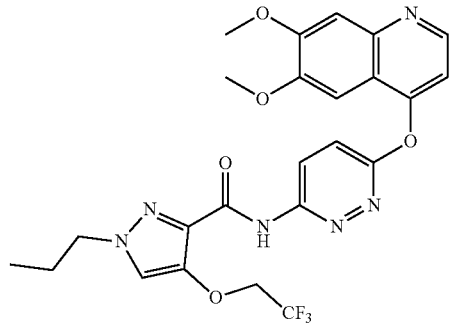 |
| 33 | 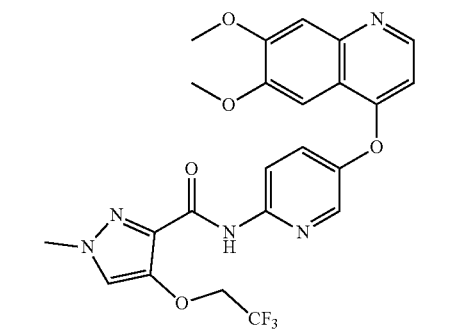 [SMILES: COc1cc2nccc(Oc3ccc(NC(=O)c4nn(C)cc4OCC(F)(F)F)nc3)c2cc1OC] |
| 34 | 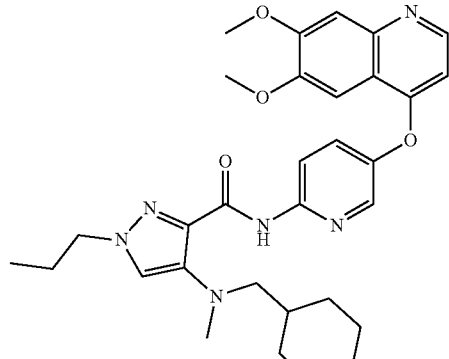 |
| 35 | 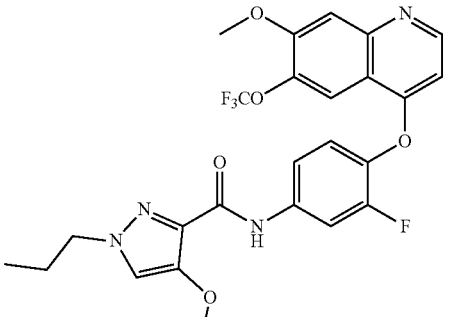 |
| 36 | 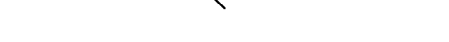 |
| 37 | 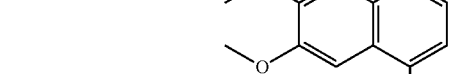 |
| 38 |  |

| # cpd | Structure |
|---|---|
| 39 | (structure) |
| 40 | (structure) |
| 41 | (structure) |
| 42 | (structure) |

| # cpd | Structure |
|---|---|
| 43 | (structure) |
| 44 | (structure) |
| 45 | (structure) |
| 46 | (structure) |

-continued

| # cpd | Structure |
|---|---|
| 47 | 1-cyclopentyl-N-(2-fluoro-4-((6,7-dimethoxyquinolin-4-yl)oxy)phenyl)-4-(2,2,2-trifluoroethoxy)-1H-pyrazole-3-carboxamide |
| 48 | N-(2-fluoro-4-((6,7-dimethoxyquinolin-4-yl)oxy)phenyl)-1-isobutyl-4-(2,2,2-trifluoroethoxy)-1H-pyrazole-3-carboxamide |
| 49 | N-(2-fluoro-4-((6,7-dimethoxyquinolin-4-yl)oxy)phenyl)-1-(2-methoxyethyl)-4-(2,2,2-trifluoroethoxy)-1H-pyrazole-3-carboxamide |
| 50 | N-(2-fluoro-4-((6,7-dimethoxyquinolin-4-yl)oxy)phenyl)-1-methyl-4-(2,2,2-trifluoroethoxy)-1H-pyrazole-3-carboxamide |

-continued

| # cpd | Structure |
|---|---|
| 51 | N-(2-fluoro-4-((6,7-dimethoxyquinolin-4-yl)oxy)phenyl)-1-(2-hydroxyethyl)-4-(2,2,2-trifluoroethoxy)-1H-pyrazole-3-carboxamide |
| 52 | 1-cyclopentyl-N-(3-fluoro-4-((6,7-dimethoxyquinolin-4-yl)oxy)phenyl)-4-(2,2,2-trifluoroethoxy)-1H-pyrazole-3-carboxamide |
| 53 | N-(3-fluoro-4-((6,7-dimethoxyquinolin-4-yl)oxy)phenyl)-1-isobutyl-4-(2,2,2-trifluoroethoxy)-1H-pyrazole-3-carboxamide |
| 54 | N-(3-fluoro-4-((6,7-dimethoxyquinolin-4-yl)oxy)phenyl)-1-(2-methoxyethyl)-4-(2,2,2-trifluoroethoxy)-1H-pyrazole-3-carboxamide |

-continued

| # cpd | Structure |
|---|---|
| 55 | (6,7-dimethoxyquinolin-4-yloxy)-3-fluorophenyl amide of 1-(tetrahydrofuran-3-yl)-4-(2,2,2-trifluoroethoxy)-1H-pyrazole-3-carboxamide |
| 56 | 1-(2-hydroxyethyl)-N-(4-((6,7-dimethoxyquinolin-4-yl)oxy)-3-methylphenyl)-4-(2,2,2-trifluoroethoxy)-1H-pyrazole-3-carboxamide |
| 57 | 1-cyclopentyl-N-(4-((6,7-dimethoxyquinolin-4-yl)oxy)-3-methylphenyl)-4-(2,2,2-trifluoroethoxy)-1H-pyrazole-3-carboxamide |
| 58 | 1-isobutyl-N-(4-((6,7-dimethoxyquinolin-4-yl)oxy)-3-methylphenyl)-4-(2,2,2-trifluoroethoxy)-1H-pyrazole-3-carboxamide |

-continued

| # cpd | Structure |
|---|---|
| 59 | 1-(2-hydroxyethyl)-N-(4-((6,7-dimethoxyquinolin-4-yl)oxy)phenyl)-4-(2,2,2-trifluoroethoxy)-1H-pyrazole-3-carboxamide |
| 60 | 1-cyclopentyl-N-(4-((6,7-dimethoxyquinolin-4-yl)oxy)phenyl)-4-(2,2,2-trifluoroethoxy)-1H-pyrazole-3-carboxamide |
| 61 | 1-(2-methoxyethyl)-N-(4-((6,7-dimethoxyquinolin-4-yl)oxy)phenyl)-4-(2,2,2-trifluoroethoxy)-1H-pyrazole-3-carboxamide |
| 62 | 1-(tetrahydrofuran-3-yl)-N-(4-((6,7-dimethoxyquinolin-4-yl)oxy)phenyl)-4-(2,2,2-trifluoroethoxy)-1H-pyrazole-3-carboxamide |

TABLE-continued

| # cpd | Structure |
|---|---|
| 63 | (6,7-dimethoxyquinolin-4-yloxy)pyridin-2-yl pyrazole-3-carboxamide with 2-aminopropyl N-substituent and 2,2,2-trifluoroethoxy at pyrazole-4 |
| 64 | same scaffold with 2,2-difluoropropyl N-substituent |
| 65 | same scaffold with 2-(cyclobutoxy)ethyl N-substituent |
| 66 | same scaffold with oxetan-3-yl N-substituent |
| 67 | same scaffold with 2-hydroxyethyl N-substituent |
| 68 | same scaffold with 3-aminopropyl N-substituent |
| 69 | same scaffold with cyclohexyl N-substituent |
| 70 | same scaffold with pyrrolidin-3-yl N-substituent |

-continued

| # cpd | Structure |
|---|---|
| 71 | 6,7-dimethoxyquinolin-4-yl ether of pyridine linked to pyrazole-3-carboxamide; pyrazole N1 bears cyclopentylmethyl; pyrazole C4 bears OCH₂CF₃ |
| 72 | 6,7-dimethoxyquinolin-4-yl ether of pyridine linked to pyrazole-3-carboxamide; pyrazole N1 bears (pyrrolidin-3-yl)methyl; pyrazole C4 bears OCH₂CF₃ |
| 73 | 6,7-dimethoxyquinolin-4-yl ether of pyridine linked to pyrazole-3-carboxamide; pyrazole N1 bears (azetidin-3-yl)methyl; pyrazole C4 bears OCH₂CF₃ |
| 74 | 6,7-dimethoxyquinolin-4-yl ether of 2-fluorophenyl linked to pyrazole-3-carboxamide; pyrazole N1 bears pyrrolidin-3-yl; pyrazole C4 bears OCH₂CF₃ |

-continued

| # cpd | Structure |
|---|---|
| 75 | 6,7-dimethoxyquinolin-4-yl ether of 2-fluorophenyl linked to pyrazole-3-carboxamide; pyrazole N1 bears 2-aminoethyl; pyrazole C4 bears OCH₂CF₃ |
| 76 | 6,7-dimethoxyquinolin-4-yl ether of 2-fluorophenyl linked to pyrazole-3-carboxamide; pyrazole N1 bears 2-hydroxypropyl; pyrazole C4 bears OCH₂CF₃ |
| 77 | 6,7-dimethoxyquinolin-4-yl ether of 2-fluorophenyl linked to pyrazole-3-carboxamide; pyrazole N1 bears tetrahydrofuran-3-yl; pyrazole C4 bears OCH₂CF₃ |
| 78 | 6,7-dimethoxyquinolin-4-yl ether of 2-fluorophenyl linked to pyrazole-3-carboxamide; pyrazole N1 bears pyrrolidin-3-yl; pyrazole C4 bears OCH₂CF₃ |

| # cpd | Structure |
|---|---|
| 79 | (6,7-dimethoxyquinolin-4-yl)oxy-phenyl; 3-F; pyrazole-3-carboxamide; N1-(2-aminoethyl); 4-O-CH2CF3 |
| 80 | (6,7-dimethoxyquinolin-4-yl)oxy-phenyl; 3-F; pyrazole-3-carboxamide; N1-(2-hydroxypropyl); 4-O-CH2CF3 |
| 81 | (6,7-dimethoxyquinolin-4-yl)oxy-phenyl; 3-methyl; pyrazole-3-carboxamide; N1-(pyrrolidin-3-yl); 4-O-CH2CF3 |
| 82 | (6,7-dimethoxyquinolin-4-yl)oxy-phenyl; 3-methyl; pyrazole-3-carboxamide; N1-(2-aminoethyl); 4-O-CH2CF3 |
| 83 | (6,7-dimethoxyquinolin-4-yl)oxy-phenyl; 3-methyl; pyrazole-3-carboxamide; N1-((S)-2-hydroxypropyl); 4-O-CH2CF3 |
| 84 | (6,7-dimethoxyquinolin-4-yl)oxy-phenyl; 3-methyl; pyrazole-3-carboxamide; N1-(2-methoxyethyl); 4-O-CH2CF3 |
| 85 | (6,7-dimethoxyquinolin-4-yl)oxy-phenyl; 3-methyl; pyrazole-3-carboxamide; N1-(tetrahydrofuran-3-yl); 4-O-CH2CF3 |
| 86 | (6,7-dimethoxyquinolin-4-yl)oxy-phenyl; pyrazole-3-carboxamide; N1-(pyrrolidin-3-yl); 4-O-CH2CF3 |

-continued

| # cpd | Structure |
|---|---|
| 87 | (6,7-dimethoxyquinolin-4-yloxy)phenyl pyrazole carboxamide with isobutyl N-substituent and 2,2,2-trifluoroethoxy group |
| 88 | (6,7-dimethoxyquinolin-4-yloxy)phenyl pyrazole carboxamide with 2-aminoethyl N-substituent and 2,2,2-trifluoroethoxy group |
| 89 | (6,7-dimethoxyquinolin-4-yloxy)phenyl pyrazole carboxamide with 2-hydroxypropyl N-substituent and 2,2,2-trifluoroethoxy group |
| 90 | (6,7-dimethoxyquinolin-4-yloxy)pyridinyl pyrazole carboxamide with tetrahydropyran-4-yl N-substituent and 2,2,2-trifluoroethoxy group |

| # cpd | Structure |
|---|---|
| 91 | (6,7-dimethoxyquinolin-4-yloxy)pyridinyl pyrazole carboxamide with 1-methylpyrrolidin-3-yl N-substituent and 2,2,2-trifluoroethoxy group |
| 92 | (6,7-dimethoxyquinolin-4-yloxy)pyridinyl pyrazole carboxamide with oxetan-3-ylmethyl N-substituent and 2,2,2-trifluoroethoxy group |
| 93 | (6,7-dimethoxyquinolin-4-yloxy)pyridinyl pyrazole carboxamide with 2-cyclopentylethyl N-substituent and 2,2,2-trifluoroethoxy group |
| 94 | (6,7-dimethoxyquinolin-4-yloxy)-2-fluorophenyl pyrazole carboxamide with 1-methylpyrrolidin-3-yl N-substituent and 2,2,2-trifluoroethoxy group |

TABLE 31-continued
| # cpd | Structure |
|---|---|
| 95 | 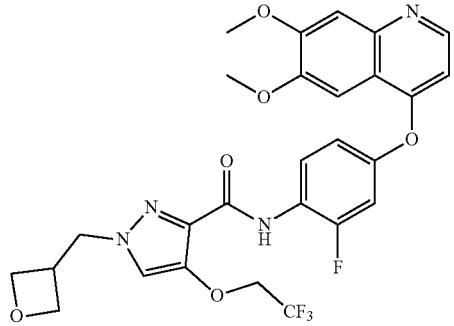 [SMILES: COc1cc2nccc(Oc3ccc(NC(=O)c4nn(CC5COC5)cc4OCC(F)(F)F)c(F)c3)c2cc1OC] |
| 96 | 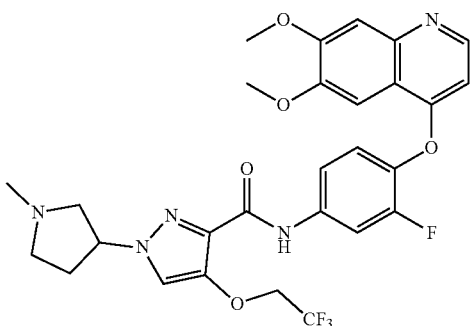 |
| 97 | 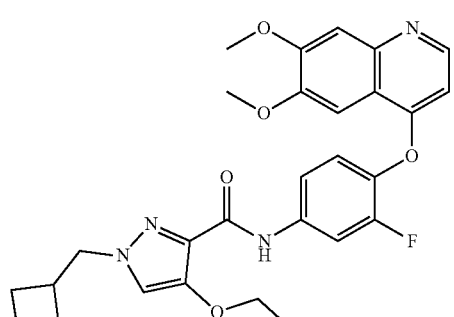 |
| 98 | 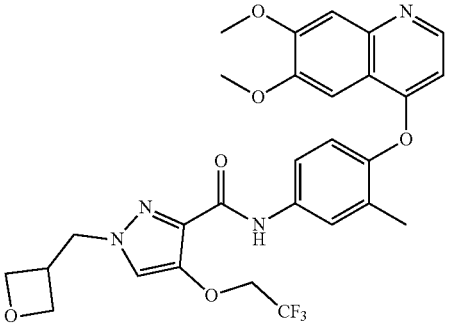 |
TABLE 32-continued
| # cpd | Structure |
|---|---|
| 99 | 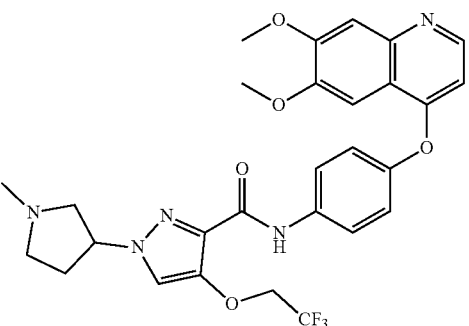 |
| 100 | 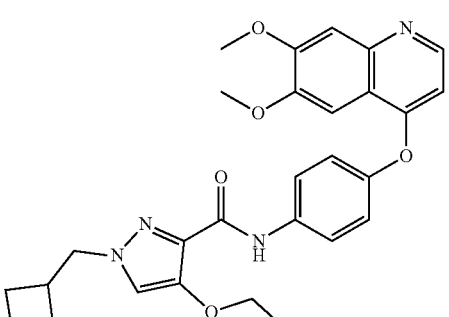 |
| 101 | 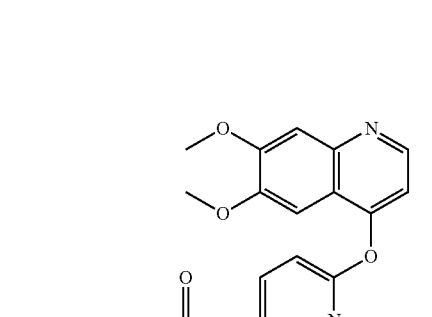 |
| 102 | 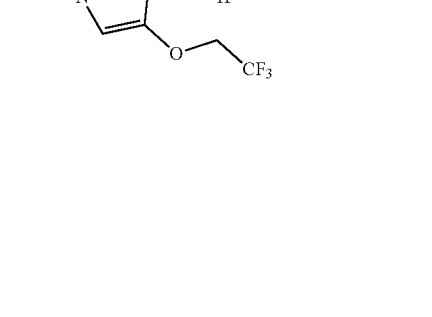 |

| # cpd | Structure |
|---|---|
| 103 | (structure) |
| 104 | (structure) |
| 105 | (structure) |
| 106 | (structure) |
| 107 | (structure) |
| 108 | (structure) |
| 109 | (structure) |
| 110 | (structure) |

-continued

| # cpd | Structure |
|---|---|
| 111 | (chemical structure) |
| 112 | (chemical structure) |
| 113 | (chemical structure) |
| 114 | (chemical structure) |
| 115 | (chemical structure) |
| 116 | (chemical structure) |
| 117 | (chemical structure) |
| 118 | (chemical structure) |

-continued

| # cpd | Structure |
|---|---|
| 119 | (6,7-dimethoxyquinolin-4-yloxy)phenyl pyrazole carboxamide with N-(2-methylamino)ethyl and 2,2,2-trifluoroethoxy substituents |
| 120 | (6,7-dimethoxyquinolin-4-yloxy)pyridazinyl pyrazole carboxamide with 2-(cyclopropoxy)ethyl and 2,2,2-trifluoroethoxy substituents |
| 121 | (6,7-dimethoxyquinolin-4-yloxy)pyridazinyl pyrazole carboxamide with cyclopentyl and 2,2,2-trifluoroethoxy substituents |
| 122 | (6,7-dimethoxyquinolin-4-yloxy)pyridazinyl pyrazole carboxamide with pyrrolidin-3-yl and 2,2,2-trifluoroethoxy substituents |

-continued

| # cpd | Structure |
|---|---|
| 123 | (6,7-dimethoxyquinolin-4-yloxy)pyridazinyl pyrazole carboxamide with oxetan-3-ylmethyl and 2,2,2-trifluoroethoxy substituents |
| 124 | (6,7-dimethoxyquinolin-4-yloxy)pyridazinyl pyrazole carboxamide with isobutyl and 2,2,2-trifluoroethoxy substituents |
| 125 | (6,7-dimethoxyquinolin-4-yloxy)pyridazinyl pyrazole carboxamide with 2-aminoethyl and 2,2,2-trifluoroethoxy substituents |
| 126 | (6,7-dimethoxyquinolin-4-yloxy)pyridazinyl pyrazole carboxamide with 2-methoxyethyl and 2,2,2-trifluoroethoxy substituents |

| # cpd | Structure |
|---|---|
| 127 | 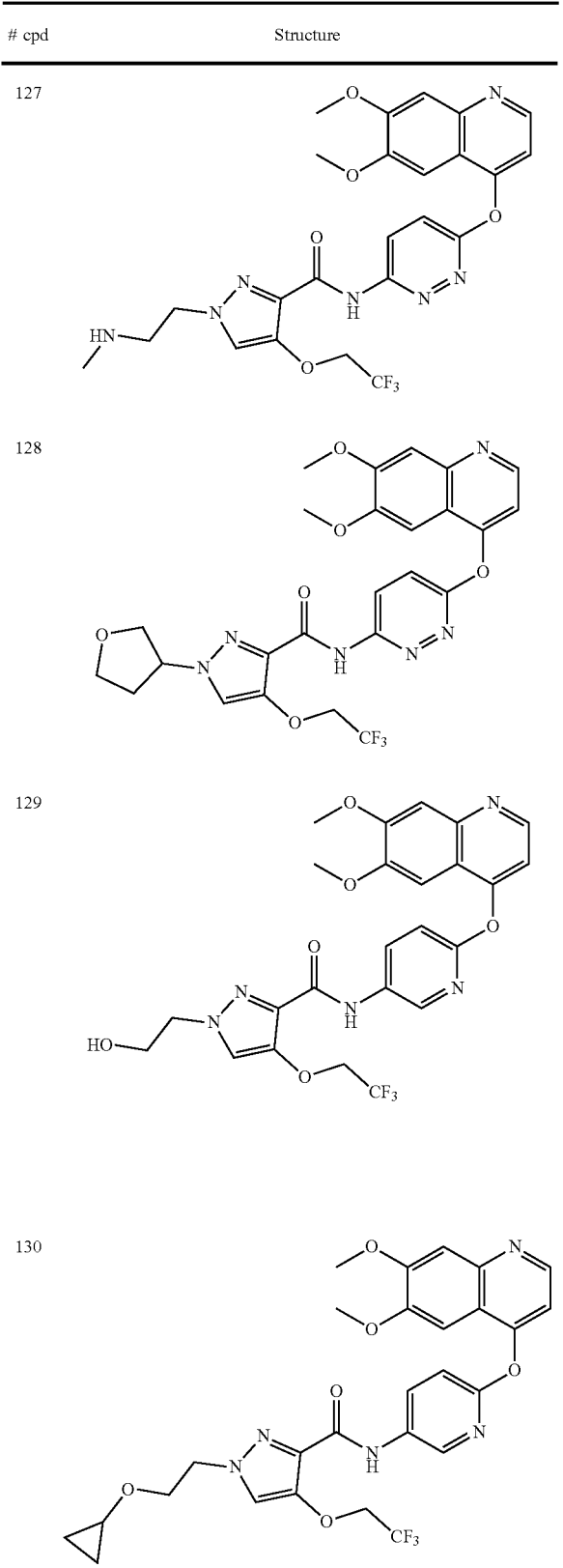 |
| 128 | |
| 129 | |
| 130 | |
| # cpd | Structure |
|---|---|
| 131 | 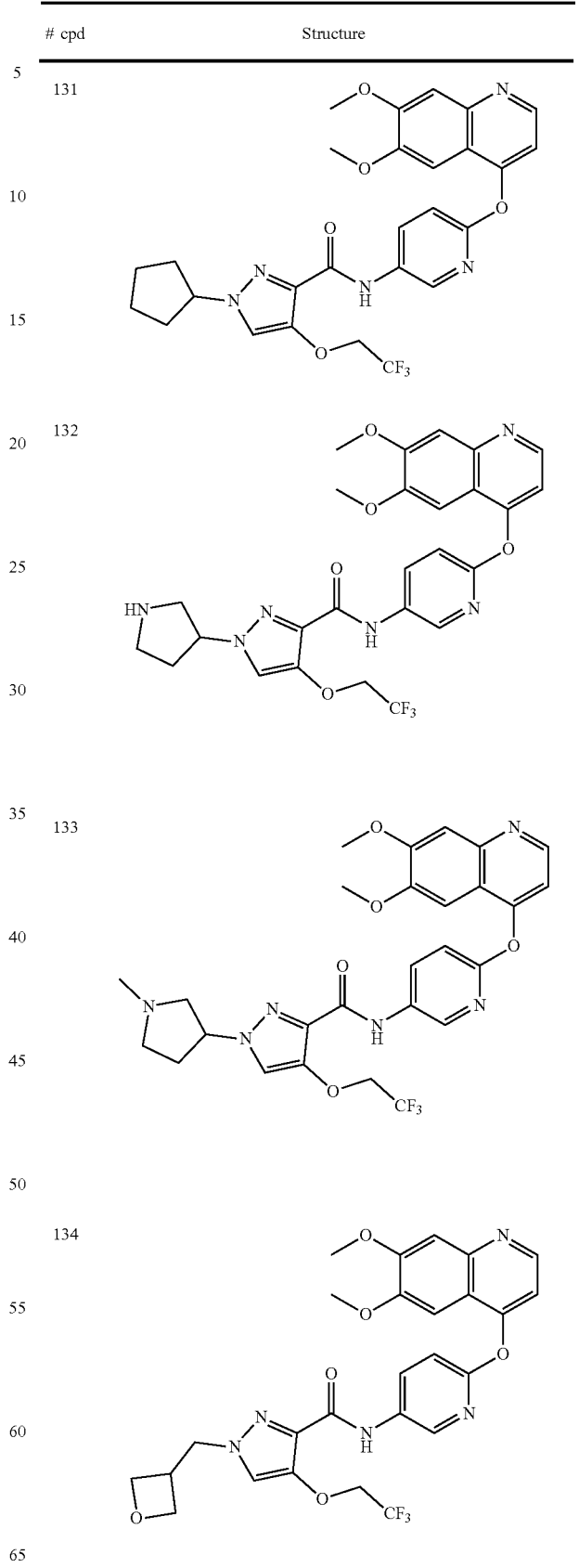 |
| 132 | |
| 133 | |
| 134 | |

| # cpd | Structure |
|---|---|
| 135 | 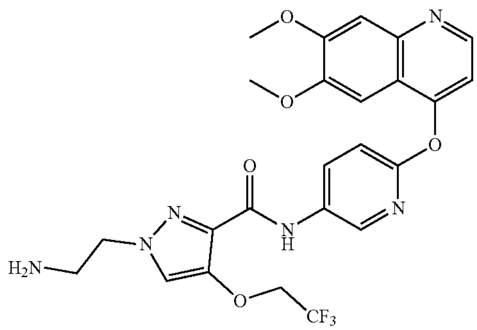 [SMILES: COc1cc2nccc(Oc3ccc(NC(=O)c4nn(CCN)cc4OCC(F)(F)F)cn3)c2cc1OC] |
| 136 | 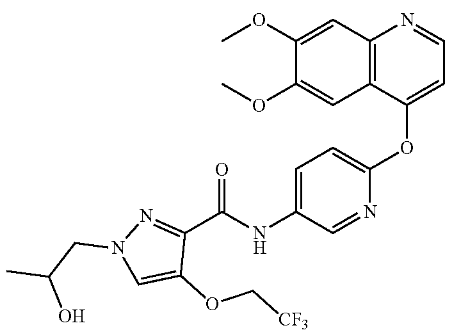 [SMILES: COc1cc2nccc(Oc3ccc(NC(=O)c4nn(CC(C)O)cc4OCC(F)(F)F)cn3)c2cc1OC] |
| 137 | 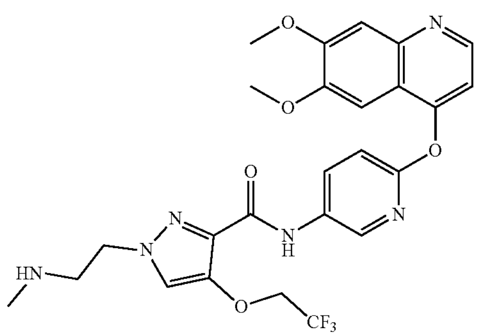 [SMILES: CNCCn1cc(OCC(F)(F)F)c(C(=O)Nc2ccc(Oc3ccnc4cc(OC)c(OC)cc34)nc2)n1] |
| 138 | 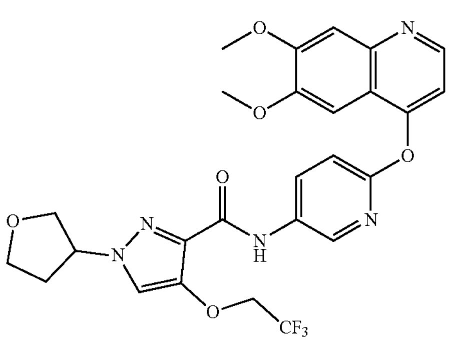 |

| # cpd | Structure |
|---|---|
| 139 | |
| 140 | |
| 141 | |
| 142 | |

| # cpd | Structure |
|---|---|
| 143 | 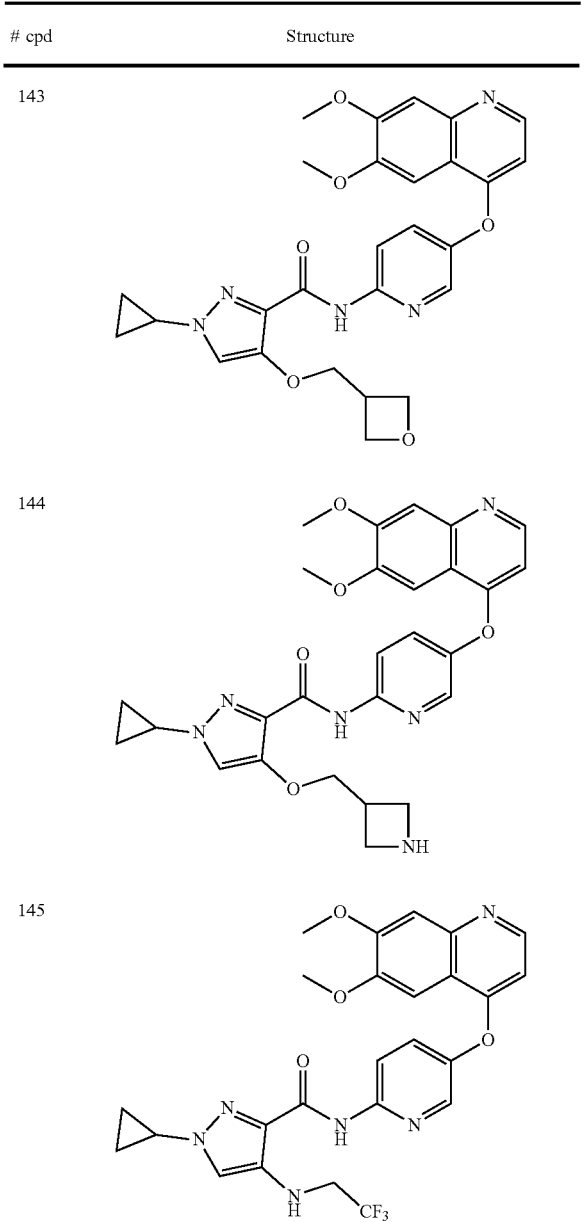 |
| 144 | |
| 145 | |
| 146 | |
| # cpd | Structure |
|---|---|
| 147 | 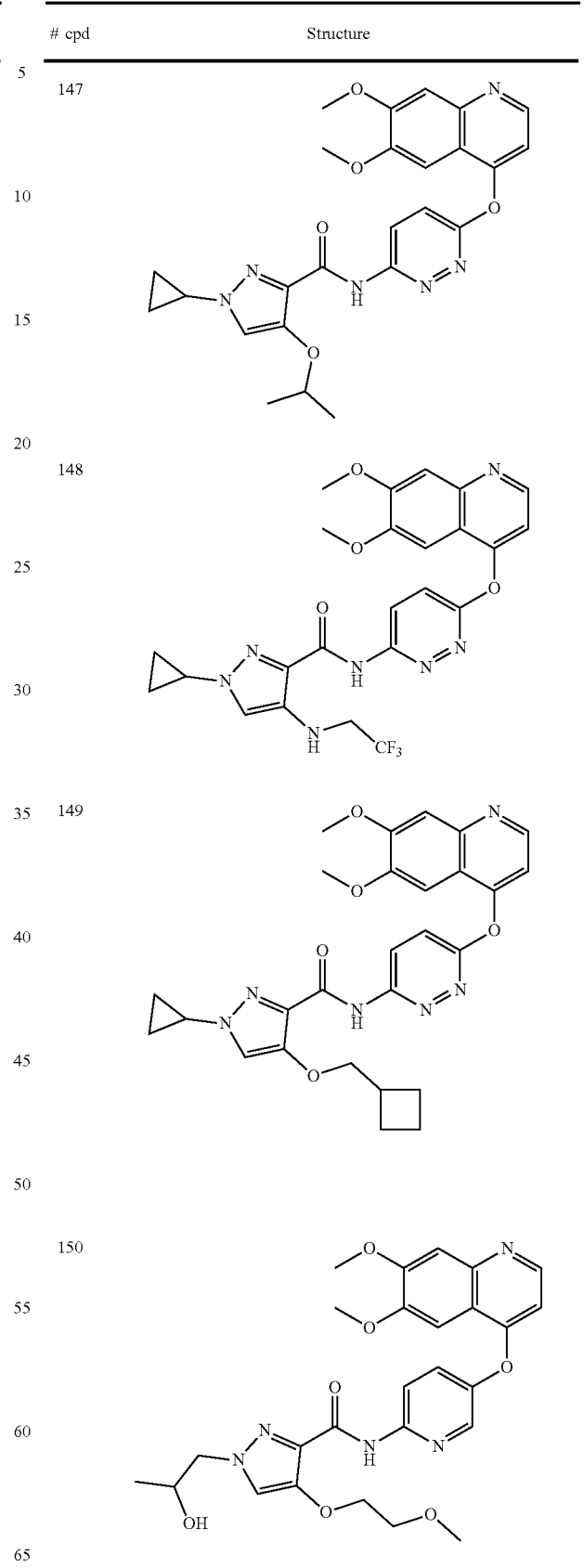 |
| 148 | |
| 149 | |
| 150 | |

| # cpd | Structure |
|---|---|
| 151 | 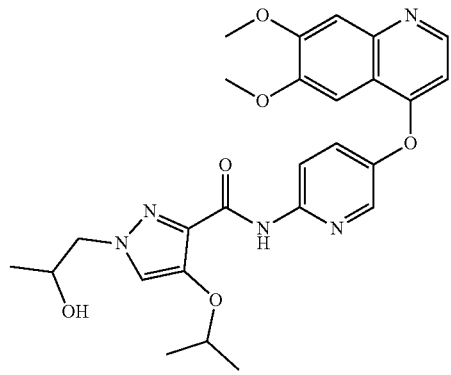 [SMILES: COc1cc2nccc(Oc3ccc(NC(=O)c4nn(CC(C)O)cc4OC(C)C)nc3)c2cc1OC] |
| 152 | 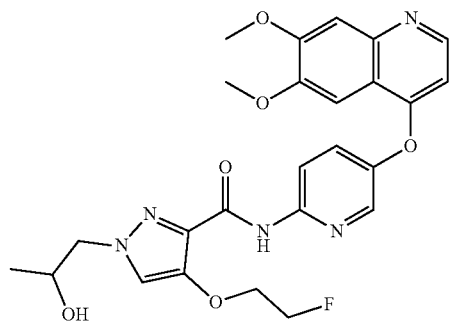 [SMILES: COc1cc2nccc(Oc3ccc(NC(=O)c4nn(CC(C)O)cc4OCCF)nc3)c2cc1OC] |
| 153 | 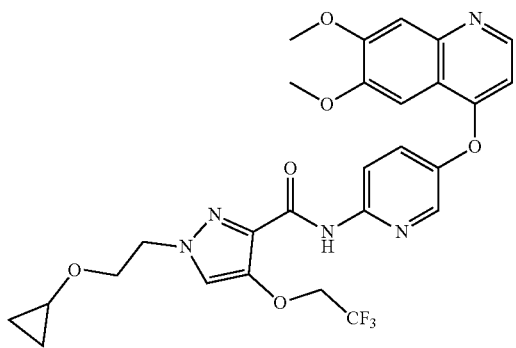 |
| 154 | 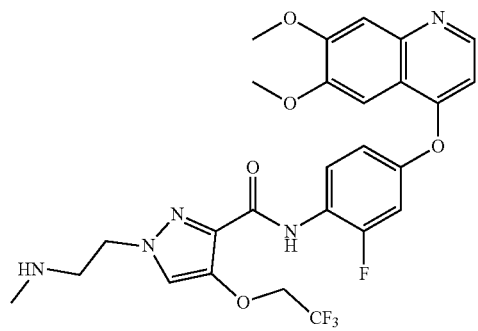 [SMILES: CNCCn1cc(OCC(F)(F)F)c(C(=O)Nc2ccc(Oc3ccnc4cc(OC)c(OC)cc34)cc2F)n1] |
| # cpd | Structure |
|---|---|
| 155 | 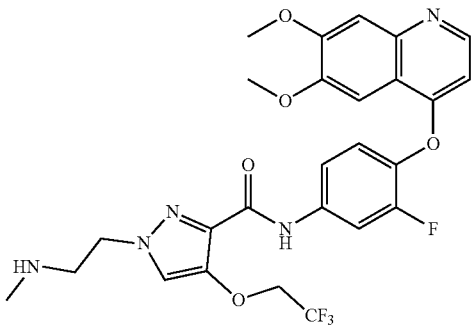 [SMILES: CNCCn1cc(OCC(F)(F)F)c(C(=O)Nc2ccc(Oc3ccnc4cc(OC)c(OC)cc34)c(F)c2)n1] |
| 156 | 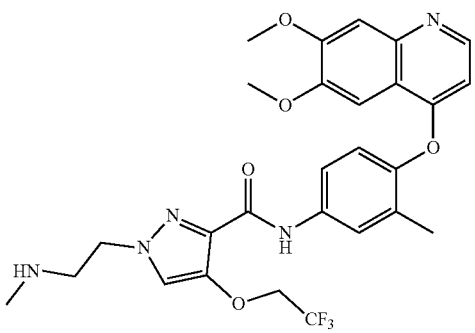 [SMILES: CNCCn1cc(OCC(F)(F)F)c(C(=O)Nc2ccc(Oc3ccnc4cc(OC)c(OC)cc34)c(C)c2)n1] |
| 157 | 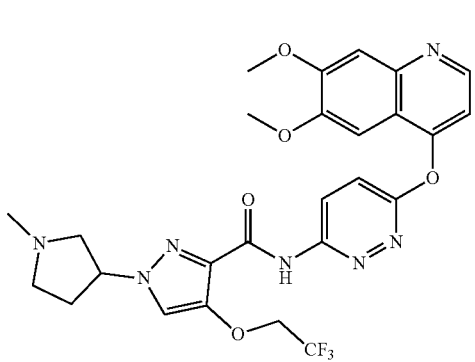 [SMILES: COc1cc2nccc(Oc3ccc(NC(=O)c4nn(C5CCN(C)C5)cc4OCC(F)(F)F)nn3)c2cc1OC] |
| 158 | 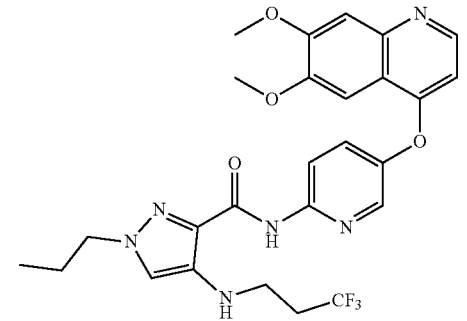 [SMILES: CCCn1cc(NCCC(F)(F)F)c(C(=O)Nc2ccc(Oc3ccnc4cc(OC)c(OC)cc34)cn2)n1] |

-continued

| # cpd | Structure |
|---|---|
| 159 | (structure) |
| 160 | (structure) |
| 161 | (structure) |
| 162 | (structure) |
| 163 | (structure) |
| 164 | (structure) |
| 165 | (structure) |
| 166 | (structure) |

| # cpd | Structure |
|---|---|
| 167 | 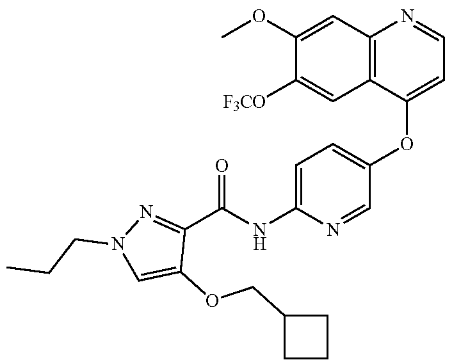 [SMILES: CCCn1cc(OCC2CCC2)c(C(=O)Nc2ccc(Oc3ccnc4cc(OC)c(OC(F)(F)F)cc34)cn2)n1] |
| 168 | 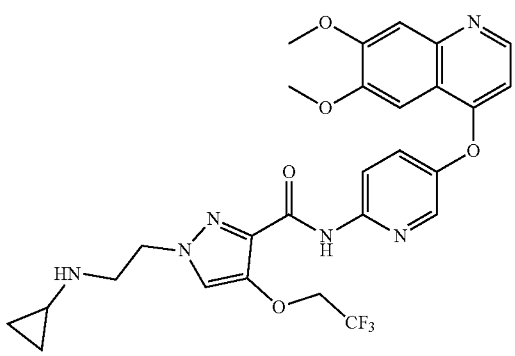 |
| 169 | 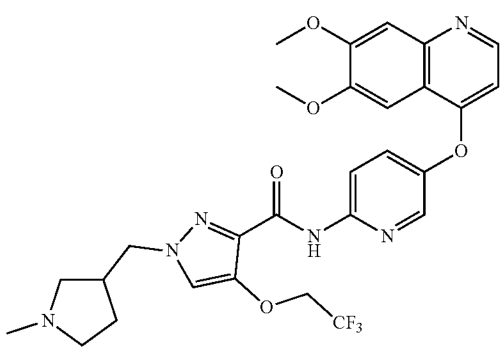 [SMILES: COc1cc2nccc(Oc3ccc(NC(=O)c4nn(CC5CCN(C)C5)cc4OCC(F)(F)F)nc3)c2cc1OC] |
| 170 | 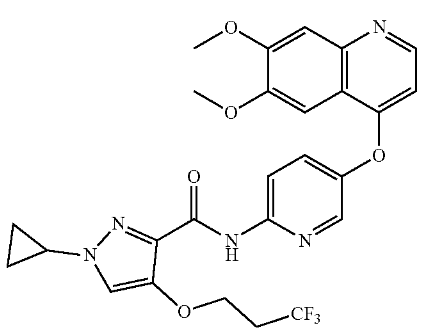 [SMILES: COc1cc2nccc(Oc3ccc(NC(=O)c4nn(C5CC5)cc4OCCC(F)(F)F)nc3)c2cc1OC] |
| 171 | |
| 172 | |
| 173 | |
| 174 | |

-continued

| # cpd | Structure |
|---|---|
| 175 | 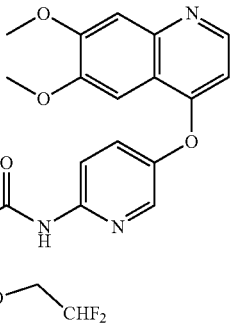 |
| 176 | 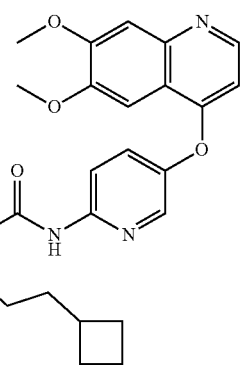 |
| 177 | 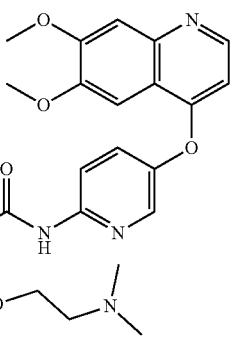 |
| 178 | 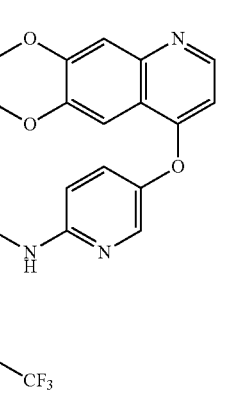 |

-continued

| # cpd | Structure |
|---|---|
| 179 | 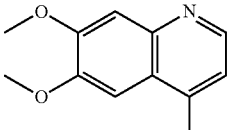 |

In a further aspect, the present invention relates to a composition comprising at least one compound according the present invention, together with at least one pharmaceutically acceptable carrier, excipient and/or diluent.

In one embodiment, the composition according to the present invention further comprises at least one other pharmaceutically active agent.

In a further aspect, the present invention relates to a compound according to the present invention or a composition according to the present invention, for use as a pharmaceutically active agent, preferably for use in a method of treating a disorder.

In a further aspect, the present invention relates to a compound according to the present invention or the composition according to the present invention, for use in the treatment of a disorder associated with, accompanied by, caused by or induced by a Axl/Mer and CSF1R receptor tyrosine kinase, in particular associated with, accompanied by, or caused by Axl/Mer and CSF1R (colony-stimulating factor-1-receptor), preferably associated with, accompanied by, or caused by a hyperfunction of said Axl/Mer and a hyperfunction of said CSF1R.

In one embodiment, said disorder is selected from hyperproliferative disorders, inflammatory disorders and neurodegenerative disorders.

In one embodiment, said hyperproliferative disorder is a cancer, preferably a cancer selected from adenocarcinoma, acoustic neuroma, acute lymphoblastic leukemia, acute myeloid leukemia, adrenocortical carcinoma, aids-related cancers, aids-related lymphoma, anal cancer, appendix cancer, astrocytomas, atypical teratoid/rhabdoid tumor, ampullary carcinoma, basal cell carcinoma, bile duct cancer, bladder cancer, bone cancer, osteosarcoma and malignant fibrous histiocytoma, brain stem glioma, brain tumor, central nervous system atypical teratoid/rhabdoid tumor, craniopharyngioma, ependymoblastoma, ependymoma, medulloblastoma, medulloepithelioma, pineal parenchymal tumors of intermediate differentiation, supratentorial primitive neuroectodermal tumors and pineoblastoma, brain and spinal cord tumors, breast cancer, urachal tumors, burkitt lymphoma, carcinoid tumor, choroidal melanoma, gastrointestinal cancer, central nervous system lymphoma, cervical cancer, corpus cancer, chordoma, chronic lymphocytic leukemia, chronic myelogenous leukemia, chronic myeloproliferative disorders, colon cancer, colorectal cancer, cutaneous t-cell lymphoma, desmoid tumor, mycosis fungoides, endometrial cancer, esophageal cancer, esthesioneuroblastoma, Ewing sarcoma family of tumors, extracranial germ cell tumor, extragonadal germ cell tumor, extrahepatic bile duct cancer, ear tumors, intraocular melanoma, retinoblastoma, gallbladder cancer, gastric cancer, gastrointestinal carcinoid tumor, gastrointestinal stromal tumor, gastrointestinal stromal cell tumor, gynecologic tumors, ovarian germ cell tumor, gestational trophoblastic tumor, glioma, gallbladder carcinomas, hairy cell leukemia, head and neck cancer, heart cancer, hepatocellular cancer, histiocytosis, hypopharyngeal cancer, hematologic neoplasias, islet cell tumors (endocrine pancreas), renal cell cancer, kidney cancer, langerhans cell histiocytosis, laryngeal cancer, leukemia, lip and oral cavity cancer, liver cancer, lung cancer, non-small cell lung cancer, small intestinal tumors, small cell lung cancer, hodgkin lymphoma, non-hodgkin lymphoma, primary central nervous system lymphoma, macroglobulinemia, malignant fibrous histiocytoma of bone and osteosarcoma, melanoma, merkel cell carcinoma, mesothelioma, metastatic squamous neck cancer with occult primary, spinalioms, multiple endocrine neoplasia syndromes, myelodysplastic syndromes, myelodysplastic/myeloproliferative neoplasms, myeloid leukemia, multiple myeloma, myeloproliferative disorders, nasal cavity and paranasal sinus cancer, nasopharyngeal cancer, neuroblastoma, oral cavity cancer, oropharyngeal cancer, osteosarcoma and malignant fibrous histiocytoma of bone, ovarian cancer, ovarian epithelial cancer, ovarian low malignant potential tumor, oligodendroglioma, plasmacytomas, pancreatic cancer, papillomatosis, parathyroid cancer, penile cancer, pharyngeal cancer, pituitary tumor, plasma cell neoplasm/multiple myeloma, pleuropulmonary blastoma, prostate cancer, rectal cancer, renal cell cancer, transitional cell cancer, respiratory tract cancer, rhabdomyosarcoma, salivary gland cancer, sarcoma, skin testis cancer, ewing sarcoma, kaposi sarcoma, uterine sarcoma, non-melanoma skin cancer, melanoma skin cancer, skin carcinoma, small intestine cancer, soft tissue sarcoma, squamous cell carcinoma, squamous neck cancer, stomach cancer, soft tissue tumors, testicular cancer, throat cancer, thymoma and thymic carcinoma, thyroid cancer, transitional cell cancer of the renal pelvis and ureter, trophoblastic tumor, testicle cancer, gestational cancer, urologic tumors, ureter and renal pelvis cancer, urethral cancer, urothelial carcinoma, uterine cancer, vaginal cancer, vulvar cancer, waldenström macroglobulinemia and wilms tumor, tumors that cause effusions in potential spaces of the body, pleural effusions, pericardial effusions, peritoneal effusion aka ascites, giant cell tumor (GCT), GCT of bone, pigmented villonodular synovitis (PVNS), tenosynovial giant cell tumor (TGCT), TGCT of tendon sheath (TGCT-TS).

In one embodiment, said inflammatory disorder is selected from osteoarthritis, inflammatory bowel syndrome, transplant rejection, systemic lupus erythematosis, ulcerative colitis, crohn's disease, chronic obstructive pulmonary disease, emphysema, Kawasaki's Disease, hemophagocytic syndrome (macrophage activation syndrome), multicentric reticulohistiocytosis, atherosclerosis, primary progressive multiple sclerosis, tenpsy Type I diabetes, Type II diabetes, insulin resistance, hyperglycemia, obesity, lipolysis, hypereosinophilia, osteoporosis, increased risk of fracture, Paget's disease, hypercalcemia, infection mediated osteolysis (e.g. osteomyelitis), peri-prosthetic or wear-debris-mediated osteolysis, endometriosis, inflammatory pain, chronic pain, and bone pain.

In one embodiment, said neurodegenerative disorder is selected from Binswanger type dementia, prosencephaly, microcephaly, cerebral palsy, congenital hydrocephalus, abdominal dropsy, progress supranuclear palsy, glaucoma, Wilson disease, Alzheimer's disease and other dementias, Parkinson's disease (PD) and PD-related disorders, multi infarct dementia, Frontotemporal dementia, pseudo-dementia, Prion disease, Motor neuron diseases, Huntington's disease, spinocerebellar ataxia, and spinal muscular atrophy.

In one embodiment, said use is in combination with another pharmaceutically active drug or therapy, in particular radiation therapy, chemotherapy agents, targeted drugs and immune check point inhibitor drugs.

In a further aspect, the present invention relates to a method of treatment of a disease selected from hyperproliferative disorders, inflammatory disorders and/or neurodegenerative disorders, comprising administering a compound according to the present invention, or a composition according to the present invention to a patient in need thereof.

The present invention also relates to the use of a compound or composition according to the present invention as defined above, for the manufacture of a medicament for the treatment of a disease associated with, accompanied by, caused by Axl/Mer and CSF1R. The present invention also relates to a method of treatment of a disease associated with, accompanied by, caused by and/or induced by Axl/Mer and CSF1R, said method comprising the administration of a compound according to the present invention to a patient in need thereof. In one embodiment, the disease associated with, accompanied by, caused by and/or induced by Axl/Mer and CSF1R is a disease selected from hyperproliferative disorders, inflammatory disorders and neurodegenerative disorders, all as defined further above.

Without wishing to be bound by any theory, the present inventors believe that the compounds of the present invention are efficient inhibitors of Axl/Mer and CSF1R and thus, are suitable for the treatment of disorders associated with, accompanied by, caused by Axl/Mer and CSF1R, in particular their hyper-function, and thereby have an effect on one or several of cell survival, proliferation, autophagy, vascular smooth muscle homeostasis, migration, adhesion, angiogenesis, platelet aggregation, thrombus stabilization, erythropoiesis, oligodendrocyte cell survival, osteoclast function, innate immunity, inflammation, phagocytosis of apoptotic cells and/or natural killer cell differentiation.

The compounds of the invention are capable of inhibiting cell proliferation and thus, are suitable for the treatment and/or prevention of Axl/Mer and CSF1R induced hyperproliferative disorders, particularly selected from the group comprising cancer, especially immune-suppressive cancer and refractory cancer, and primary tumor metastases. In a preferred embodiment of the invention, the Axl/Mer and CSF1R induced disorders are associated with Axl/Mer and CSF1R overexpression and/or hyperactivity, e.g. an increased degree of auto-phosphorylation compared to normal tissue. The hyperproliferative disorder may be a cancer, preferably a cancer selected from breast cancer, colon cancer, prostate cancer, lung cancer, gastric cancer, ovarian cancer, endometrial cancer, renal cancer, hepatocellular cancer, thyroid cancer, uterine cancer, esophagus cancer, squamous cell cancer, leukemia, osteosarcoma, melanoma, glioblastoma and neuroblastoma. In an especially preferred embodiment, the disorders are selected from breast cancer, glioblastoma, renal cancer, non-small cell lung cancer (NSCLC), and melanoma.

In an especially preferred embodiment, the disorders are selected from breast cancer, glioblastoma, renal cancer, non-small cell lung cancer (NSCLC), and melanoma. Examples for disorders associated with, accompanied by, caused by and/or induced by Axl/Mer and CSF1R hyper-function are acute lymphoblastic leukemia, acute myeloid leukemia, adrenocortical carcinoma, aids-related cancers, aids-related lymphoma, anal cancer, appendix cancer, astrocytomas, atypical teratoid/rhabdoid tumor, basal cell carcinoma, bile duct cancer, bladder cancer, bone cancer, osteosarcoma and malignant fibrous histiocytoma, brain stem glioma, brain tumor, central nervous system atypical teratoid/rhabdoid tumor, astrocytomas, craniopharyngioma, ependymoblastoma, ependymoma, medulloblastoma, medulloepithelioma, pineal parenchymal tumors of intermediate differentiation, supratentorial primitive neuroectodermal tumors and pineoblastoma, brain and spinal cord tumors, breast cancer, bronchial tumors, burkitt lymphoma, carcinoid tumor, gastrointestinal cancer, central nervous system (CNS) lymphoma, cervical cancer, chordoma, chronic lymphocytic leukemia, chronic myelogenous leukemia, chronic myeloproliferative disorders, colon cancer, colorectal cancer, craniopharyngioma, cutaneous t-cell lymphoma, mycosis fungoides, sezary syndrome, endometrial cancer, ependymoblastoma, ependymoma, esophageal cancer, esthesioneuroblastoma, ewing sarcoma family of tumors, extracranial germ cell tumor, extragonadal germ cell tumor, extrahepatic bile duct cancer, intraocular melanoma, retinoblastoma, gallbladder cancer, gastric (stomach) cancer, gastrointestinal carcinoid tumor, gastrointestinal stromal tumor (gist), gastrointestinal stromal cell tumor, extracranial germ cell tumor, extragonadal germ cell tumor, ovarian germ cell tumor, gestational trophoblastic tumor, glioma, hairy cell leukemia, head and neck cancer, heart cancer, hepatocellular (liver) cancer, histiocytosis, hodgkin lymphoma, hypopharyngeal cancer, intraocular melanoma, islet cell tumors (endocrine pancreas), kaposi sarcoma, renal cell cancer, kidney cancer, langerhans cell histiocytosis, laryngeal cancer, acute lymphoblastic leukemia, acute myeloid leukemia, chronic lymphocytic leukemia, chronic myelogenous leukemia, leukemia, lip and oral cavity cancer, liver cancer, lung cancer, non-small cell lung cancer, small cell lung cancer, aids-related lymphoma, burkitt lymphoma, (cutaneous t-cell lymphoma, hodgkin lymphoma, non-hodgkin lymphoma, primary central nervous system lymphoma, macroglobulinemia, malignant fibrous histiocytoma of bone and osteosarcoma, medulloblastoma, medulloepithelioma, melanoma, melanoma intraocular (eye), merkel cell carcinoma, mesothelioma, metastatic squamous neck cancer with occult primary, mouth cancer, multiple endocrine neoplasia syndromes, multiple myeloma/plasma cell neoplasm, myelodysplastic syndromes, myelodysplastic/myeloproliferative neoplasms, myelogenous leukemia, myeloid leukemia, myeloma (multiple), myeloproliferative disorders, nasal cavity and paranasal sinus cancer, nasopharyngeal cancer, neuroblastoma, non-hodgkin lymphoma, non-small cell lung cancer, oral cancer, oral cavity cancer, oropharyngeal cancer, osteosarcoma and malignant fibrous histiocytoma of bone, ovarian cancer, ovarian epithelial cancer, ovarian germ cell tumor, ovarian low malignant potential tumor, pancreatic cancer, papillomatosis, parathyroid cancer, penile cancer, pharyngeal cancer, pineoblastoma and supratentorial primitive neuroectodermal tumors, pituitary tumor, plasma cell neoplasm/multiple myeloma, pleuropulmonary blastoma, pregnancy and breast cancer, prostate cancer, rectal cancer, renal cell (kidney) cancer, transitional cell cancer, respiratory tract cancer, retinoblastoma, rhabdomyosarcoma, salivary gland cancer, sarcoma, ewing sarcoma, kaposi sarcoma, uterine sarcoma, nonmelanoma skin cancer, melanoma skin cancer, skin carcinoma, small cell lung cancer, small intestine cancer, soft tissue sarcoma, squamous cell carcinoma, squamous neck cancer, stomach (gastric) cancer, supratentorial primitive neuroectodermal tumors, t-cell lymphoma, testicular cancer, throat cancer, thymoma and thymic carcinoma, thyroid cancer, transitional cell cancer of the renal pelvis and ureter, trophoblastic tumor, gestational cancer, ureter and renal pelvis cancer, transitional cell cancer, urethral cancer, uterine cancer, endometrial cancer, uterine sarcoma, vaginal cancer, vulvar cancer, Waldenstrom macroglobulinemia and Wilms tumor.

The compounds of the present invention are efficient inhibitors of Axl/Mer and CSF1R. The inventive compounds are suitable for the use as a pharmaceutically active agent which are suitable for the treatment of disorders associated with, accompanied by, caused by Axl/Mer and CSF1R, in particular a hyper-function thereof. The inventive compounds are thus suitable for the treatment of Axl/Mer and CSF1R induced disorders.

Without wishing to be bound by any theory, the present inventors believe that CSF1 is another chemokine that appears to be a promising target for inhibiting TAM contribution to tumor progression. CSF1 is a potent chemoattractant and is considered the most important growth factor regulating the differentiation of monocytes into macrophages. Thus, the present inventors believe that the inhibition of CSF1R signaling in tumor-promoting TAMs represents an attractive strategy to eliminate or repolarize these cells and it is a possible of new immunotherapy for patients with cancers.

Again without wishing to be bound by any theory, the present inventors believe that CSF1/CSF1R blockade not only decreases the number of TAMs, but also reprograms remaining TAMs to support antigen presentation and bolster T cell activation within the tumor microenvironment. This in-turn leads to reduced immune suppression and elevated interferon responses, which restrain tumor progression (Zhu Y et al., Cancer Res. 2014 Sep. 15; 74(18):5057-69).

In conclusion, dual inhibition CSF1R and Axl/Mer RTK is expected to offer strong anti-cancer efficacy through immune modulation by using distinct signal pathways for immune cells. The present invention to provide compounds which have dual-inhibition capabilities for CSF1R and Axl/Mer RTK. These can then be used as pharmaceutically active agents, with a high relevance especially for cancer therapy via immune system modulation.

The term "optionally substituted" as used herein is meant to indicate that a hydrogen atom where present and attached to a member atom within a group, or several such hydrogen atoms, may be replaced by a suitable group, such as halogen including fluorine, chlorine, $C_1$-$C_3$ alkyl, $C_1$-$C_3$ haloalkyl, e.g. $CH_2F$, $CHF_2$, $CF_3$, $CH_2CF_3$, methylhydroxyl, hydroxyl, COOMe, C(O)H, COOH, alkoxy, in particular C1-C3 alkoxy, e.g. OMe, or $OCF_3$;

In one embodiment, the present invention also relates to pharmaceutically acceptable salts of the compounds according to the present invention.

The present invention also relates to combinations of compounds in accordance with the present invention and another anti-cancer agent together.

Combination of a compound in accordance with the present invention with another anti-cancer agent has a better anti-cancer effect. For example combinations with other anti-cancer agents may restore sensitivity of cell lines which have become resistant to other anti-cancer agents and combinations with other immune checkpoint inhibitor as well as radiation also have a synergistic efficacy. As examples of agents with which the compounds according to the present invention may be combined, as a cytotoxicity drugs (actinomycin, all-trans retinoic acid, azacitidine, azathioprine, bleomycin, bortezomib, carboplatin, capecitabine, cisplatin, chlorambucil, cyclophosphamide, cytarabine, daunorubicin, docetaxel, doxifluridine, doxorubicin, epirubicin, epothilone, etoposide, fluorouracil, gemcitabine, hydroxyurea, idarubicin, imatinib, irinotecan, mechlorethamine, mercaptopurine, methotrexate, mitoxantrone, oxaliplatin, paclitaxel, pemetrexed, teniposide, tioguanine, topotecan, valrubicin, vemurafenib, vinblastine, vincristine, vindesine, vinorelbine), targeted drugs (bevacizumab, rituximab, ipilimumab, bortezomib, imatinib, seliciclib, ado-trastuzumab, afatinib, aldesleukin, axitinib, belinostat, bevacizumab, bortezomib, bosutinib, brentuximab vedotin, cabozantinib, canakinumab, carfilzomib, ceritinib, cetuximab, crizotinib, dabrafenib, dasatinib, erlotinib, everolimus, gefitinib, ibritumomab tiuxetan, ibrutinib, idelalisib, imatinib, lapatinib, lenvatinib, nilotinib, obinutuzumab, ofatumumab, olaparib, palbociclib, panitumumab, panobinostat, pazopanib, pertuzumab, ponatinib, ramucirumab, regorafenib, rituxima, romidepsin, ruxolitinib, siltuximab, sipuleucel-T, sorafenib, temsirolimus, tocilizumab, tofacitinib, tositumomab, trametinib, trastuzumab, vandetanib, vemurafenib, vismodegib, vorinosta, ziv-aflibercept), immune check point inhibitor drugs (lpillmumab, nivolumab, pembrolizumab, atezolezumab, avelumab, bevacixumab, tremelimumab).

Other combinations may also or instead include several compounds in accordance with the present invention together. These are also envisaged and encompassed by combinations in accordance with the present invention.

The term "alkyl" refers to a monovalent straight, branched or cyclic chain, saturated aliphatic hydrocarbon radical having a number of carbon atoms in the specified range. Thus, for example, "$C_1$-$C_6$ alkyl" refers to any of the hexyl alkyl and pentyl alkyl isomers as well as n-, iso-, sec-, and t-butyl, n- and isopropyl, cyclic propyl, ethyl and methyl.

The term "alkenyl" refers to a monovalent straight or branched chain aliphatic hydrocarbon radical containing one carbon-carbon double bond and having a number of carbon atoms in the specified range. Thus, for example, "$C_2$-$C_6$ alkenyl" refers to all of the hexenyl and pentenyl isomers as well as 1-butenyl, 2-butenyl, 3-butenyl, isobutenyl, 1-propenyl, 2-propenyl, and ethenyl (or vinyl).

The term "cycloalkyl", alone or in combination with any other term, refers to a group, such as optionally substituted or non-substituted cyclic hydrocarbon, having from three to eight carbon atoms, unless otherwise defined. Thus, for example, "$C_3$-$C_8$ cycloalkyl" refers to cyclopropyl, cyclobutyl, cyclopentyl, cyclohexyl, cycloheptyl, and cyclooctyl.

The term "haloalkyl" refers to an alkyl group, as defined herein that is substituted with at least one halogen. Examples of straight or branched chained "haloalkyl" groups useful in the present invention include, but are not limited to, methyl, ethyl, propyl, isopropyl, n-butyl, and t-butyl substituted independently with one or more halogens. The term "haloalkyl" should be interpreted to include such substituents such as —$CHF_2$, —$CF_3$, —$CH_2$—$CH_2$—F, —$CH_2$—$CF_3$, and the like. More specifically, the term "$C_1$-$C_4$ haloalkyl" is meant to include, but not to be limited to fluoromethyl, difluoromethyl, trifluoromethyl, fluoroethyl, difluoroethyl, trifluoroethyl, fluoropropyl, difluoropropyl, trifluoropropyl, fluoroisopropyl, difluoroisopropyl, trifluoroisopropyl, fluorobutyl, difluorobutyl, trifluorobutyl, with "butyl" including all the butyl isomers, i. e. n-butyl, iso-butyl, sec-butyl and tert-butyl; and the corresponding chloro-alkyls of any of the foregoing, as well as $C_1$-$C_4$ alkyls in which more than one hydrogen is substituted by a halogen (F, Cl, Br and/or I).

The term "heteroalkyl" refers to an alkyl group where one or more carbon atoms have been replaced with a heteroatom, such as, O, N, or S. For example, if the carbon atom of alkyl group which is attached to the parent molecule is replaced with a heteroatom (e.g., O, N, or S) the resulting heteroalkyl groups are, respectively, an alkoxy group (e.g., —$OCH_3$, etc.), an amine (e.g., —$NHCH_3$, —$N(CH_3)_2$, etc.), or thioalkyl group (e.g., —$SCH_3$, etc.). If a non-terminal carbon atom of the alkyl group which is not attached to the parent molecule is replaced with a heteroatom (e.g., O, N, or S) and the resulting heteroalkyl groups are, respectively, an alkyl ether (e.g., —$CH_2CH_2$—O—$CH_3$, etc.), alkyl amine (e.g., —$CH_2NHCH_3$, —$CH_2N(CH_3)_2$, etc.), or thioalkyl ether (e.g., —$CH_2$—S—$CH_3$).

The term "halogen" refers to fluorine, chlorine, bromine, or iodine.

The term "phenyl" as used herein is meant to indicate an optionally substituted or non-substituted phenyl group.

The term "benzyl" as used herein is meant to indicate an optionally substituted or non-substituted benzyl group.

The term "heteroaryl" refers to (i) optionally substituted 5- and 6-membered heteroaromatic rings and (ii) optionally substituted 9- and 10-membered bicyclic, fused ring systems in which at least one ring is aromatic, wherein the heteroaromatic ring or the bicyclic, fused ring system contains from 1 to 4 heteroatoms independently selected from N, O, and S, where each N is optionally in the form of an oxide and each S in a ring which is not aromatic is optionally S(O) or $S(O)_2$. Suitable 5- and 6-membered heteroaromatic rings include, for example, pyridyl, pyrrolyl, pyrazinyl, pyrimidinyl, pyridazinyl, triazinyl, thienyl, furanyl, imidazolyl, pyrazolyl, triazolyl, tetrazolyl, oxazolyl, isooxazolyl, oxadiazolyl, thiazolyl, isothiazolyl, and thiadiazolyl. Suitable 9- and 10-membered heterobicyclic, fused ring systems include, for example, benzofuranyl, indolyl, indazolyl, naphthyridinyl, isobenzofuranyl, benzopiperidinyl, benzisoxazolyl, benzoxazolyl, chromenyl, quinolinyl, isoquinolinyl, cinnolinyl, quinazolinyl, tetrahydroquinolinyl, tetrahydroisoquinolinyl, isoindolyl, benzodioxolyl, benzo furanyl, imidazo[1,2-a] pyridinyl, benzotriazolyl, dihydroindolyl, dihydroisoindolyl, indazolyl, indolinyl, isoindolinyl, quinoxalinyl, quinazolinyl, 2,3-dihydrobenzo furanyl, and 2,3-dihydrobenzo-1,4-dioxinyl.

The term "heterocyclyl" or "heterocycloalkyl", in particular "$C_3$-$C_{10}$ heterocycloalkyl" refers to (i) optionally substituted 3- to 10-membered, saturated and unsaturated but non-aromatic monocyclic rings containing at least one carbon atom and from 1 to 4 heteroatoms, (ii) optionally substituted bicyclic ring systems containing from 1 to 6 heteroatoms, and (iii) optionally substituted tricyclic ring systems, wherein each ring in (ii) or (iii) is independent of fused to, or bridged with the other ring or rings and each ring is saturated or unsaturated but nonaromatic, and wherein each heteroatom in (i), (ii), and (iii) is independently selected from N, O, and S, wherein each N is optionally in the form of an oxide and each S is optionally oxidized to S(O) or $S(O)_2$. Suitable 3- to 10-membered saturated heterocycloalkyls include, for example, azetidinyl, piperidinyl, morpholinyl, thiomorpholinyl, thiazolidinyl, isothiazolidinyl, oxazolidinyl, isoxazolidinyl, pyrrolidinyl, imidazolidinyl, piperazinyl, tetrahydrofuranyl, tetrahydrothienyl, pyrazolidinyl, hexahydropyrimidinyl, thiazinanyl, thiazepanyl, azepanyl, diazepanyl, tetrahydropyranyl, tetrahydrothiopyranyl, dioxanyl, and azacyclooctyl. Suitable unsaturated heterocyclic rings include those corresponding to the saturated heterocyclic rings listed in the above sentence in which a single bond is replaced with a double bond. It is understood that the specific rings and ring systems suitable for use in the present invention are not limited to those listed in this and the preceding paragraphs. These rings and ring systems are merely representative.

Pharmaceutical Compositions
Pharmaceutically Acceptable Salts

Examples of pharmaceutically acceptable addition salts include, without limitation, the non-toxic inorganic and organic acid addition salts such as the acetate derived from acetic acid, the aconate derived from aconitic acid, the ascorbate derived from ascorbic acid, the benzenesulfonate derived from benzensulfonic acid, the benzoate derived from benzoic acid, the cinnamate derived from cinnamic acid, the citrate derived from citric acid, the embonate derived from embonic acid, the enantate derived from enanthic acid, the formate derived from formic acid, the fumarate derived from fumaric acid, the glutamate derived from glutamic acid, the glycolate derived from glycolic acid, the hydrochloride derived from hydrochloric acid, the hydrobromide derived from hydrobromic acid, the lactate derived from lactic acid, the maleate derived from maleic acid, the malonate derived from malonic acid, the mandelate derived from mandelic acid, the methanesulfonate derived from methane sulphonic acid, the naphthalene-2-sulphonate derived from naphtalene-2-sulphonic acid, the nitrate derived from nitric acid, the perchlorate derived from perchloric acid, the phosphate derived from phosphoric acid, the phthalate derived from phthalic acid, the salicylate derived from salicylic acid, the sorbate derived from sorbic acid, the stearate derived from stearic acid, the succinate derived from succinic acid, the sulphate derived from sulphuric acid, the tartrate derived from tartaric acid, the toluene-p-sulphonate derived from p-toluene sulphonic acid, and the like. Such salts may be formed by procedures well known and described in the art.

Other acids such as oxalic acid, which may not be considered pharmaceutically acceptable, may be useful in the preparation of salts useful as intermediates in obtaining a chemical compound of the invention and its pharmaceutically acceptable acid addition salt.

In another embodiment, the compounds of the invention are used in their respective free base form according to the present invention.

Metal salts of a chemical compound of the invention include alkali metal salts, such as the sodium salt of a chemical compound of the invention containing a carboxy group.

The chemical compounds of the invention may be provided in unsolvated or solvated forms together with a pharmaceutically acceptable solvent(s) such as water, ethanol, and the like. Solvated forms may also include hydrated forms such as the monohydrate, the dihydrate, the hemihydrate, the trihydrate, the tetrahydrate, and the like. In general, solvated forms are considered equivalent to unsolvated forms for the purposes of this invention.

Administration and Formulation

The production of medicaments containing the compounds of the invention, its active metabolites or isomers and salts according to the invention and their application can be performed according to well-known pharmaceutical methods.

While the compounds of the invention, useable according to the invention for use in therapy, may be administered in the form of the raw chemical compound, it is preferred to introduce the active ingredient, optionally in the form of a physiologically acceptable salt in a pharmaceutical composition together with one or more adjuvants, excipients, carriers, buffers, diluents, and/or other customary pharmaceutical auxiliaries. Such salts of the compounds of the invention may be anhydrous or solvated.

In a preferred embodiment, the invention provides medicaments comprising a compound useable according to the invention, or a pharmaceutically acceptable salt or derivative thereof, together with one or more pharmaceutically acceptable carriers therefor, and, optionally, other therapeutic and/or prophylactic ingredients. The carrier(s) must be "acceptable" in the sense of being compatible with the other ingredients of the formulation and not harmful to the recipient thereof.

A medicament of the invention may be those suitable for oral, rectal, bronchial, nasal, topical, buccal, sub-lingual, transdermal, vaginal or parenteral (including cutaneous, subcutaneous, intramuscular, intraperitoneal, intravenous, intraarterial, intracerebral, intraocular injection or infusion) administration, or those in a form suitable for administration by inhalation or insufflation, including powders and liquid aerosol administration, or by sustained release systems. Suitable examples of sustained release systems include semipermeable matrices of solid hydrophobic polymers containing the compound of the invention, which matrices may be in form of shaped articles, e.g. films or microcapsules.

The compounds useable according to the invention, together with a conventional adjuvant, carrier, or diluent, may thus be placed into the form of medicament and unit dosages thereof. Such forms include solids, and in particular tablets, filled capsules, powder and pellet forms, and liquids, in particular aqueous or non-aqueous solutions, suspensions, emulsions, elixirs, and capsules filled with the same, all for oral use, suppositories for rectal administration, and sterile injectable solutions for parenteral use. Such medicament and unit dosage forms thereof may comprise conventional ingredients in conventional proportions, with or without additional active compounds or principles, and such unit dosage forms may contain any suitable effective amount of the active ingredient commensurate with the intended daily dosage range to be employed.

The compounds useable according to the invention can be administered in a wide variety of oral and parenteral dosage forms. It will be obvious to those skilled in the art that the following dosage forms may comprise, as the active component, either a compound(s) useable according to the invention or a pharmaceutically acceptable salt of a compound(s) useable according to the invention.

For preparing a medicament from a compound useable according to the invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavouring agents, solubilizers, lubricants, suspending agents, binders, preservatives, tablet disintegrating agents, or an encapsulating material.

In powders, the carrier is a finely divided solid which is in a mixture with the finely divided active component. In tablets, the active component is mixed with the carrier having the necessary binding capacity in suitable proportions and compacted in the shape and size desired. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as carrier providing a capsule in which the active component, with or without carriers, is surrounded by a carrier, which is thus in association with it. Similarly, cachets and lozenges are included.

Tablets, powders, capsules, pills, cachets, and lozenges can be used as solid forms suitable for oral administration.

For preparing suppositories, a low melting wax, such as a mixture of fatty acid glyceride or cocoa butter, is first melted and the active component is dispersed homogeneously therein, as by stirring. The molten homogenous mixture is then poured into convenient sized moulds, allowed to cool, and thereby to solidify. Compositions suitable for vaginal administration may be presented as pessaries, tampons, creams, gels, pastes, foams or sprays containing in addition to the active ingredient such carriers as are known in the art to be appropriate. Liquid preparations include solutions, suspensions, and emulsions, for example, water or water-propylene glycol solutions. For example, parenteral injection liquid preparations can be formulated as solutions in aqueous polyethylene glycol solution.

The chemical compounds according to the present invention may thus be formulated for parenteral administration (e.g. by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, and may contain formulation agents such as suspending, stabilising and/or dispersing agents. Alternatively, the active ingredient may be in powder form, obtained by aseptic isolation of sterile solid or by lyophilization from solution, for constitution with a suitable vehicle, e.g. sterile, pyrogen-free water, before use.

Aqueous solutions suitable for oral use can be prepared by dissolving the active component in water and adding suitable colorants, flavours, stabilising and thickening agents, as desired. Aqueous suspensions suitable for oral use can be made by dispersing the finely divided active component in water with viscous material, such as natural or synthetic gums, resins, methylcellulose, sodium carboxymethylcellulose, or other well known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavours, stabilisers, buffers, artificial and natural sweeteners, dispersants, thickeners, solubilizing agents, and the like.

In one embodiment of the present invention, the medicament is applied topically or systemically or via a combination of the two routes.

For administration, the compounds of the present invention may, in one embodiment, be administered in a formulation containing 0.001% to 70% per weight of the compound, preferably between 0.01% to 70% per weight of the compound, even more preferred between 0.1% and 70% per weight of the compound. In one embodiment, a suitable amount of compound administered is in the range of from 0.01 mg/kg body weight to 1 g/kg body weight.

Compositions suitable for administration also include lozenges comprising the active agent in a flavoured base, usually sucrose and acacia or tragacanth; pastilles comprising the active ingredient in an inert base such as gelatin and glycerol or sucrose and acacia; and mouthwashes comprising the active ingredient in a suitable liquid carrier.

Solutions or suspensions are applied directly to the nasal cavity by conventional means, for example with a dropper, pipette or spray. The compositions may be provided in single or multi-dose form. In the latter case of a dropper or pipette, this may be achieved by the patient administering an appropriate, predetermined volume of the solution or suspension. In the case of a spray, this may be achieved for example by means of a metering atomising spray pump.

Administration to the respiratory tract may also be achieved by means of an aerosol formulation in which the active ingredient is provided in a pressurised pack with a suitable propellant such as a chlorofluorocarbon (CFC) for example dichlorodifluoromethane, trichlorofluoromethane, or dichlorotetrafluoroethane, carbon dioxide, or other suitable gas. The aerosol may conveniently also contain a surfactant such as lecithin. The dose of drug may be controlled by provision of a metered valve.

Alternatively the active ingredients may be provided in the form of a dry powder, for example a powder mix of the compound in a suitable powder base such as lactose, starch, starch derivatives such as hydroxypropylmethyl cellulose and polyvinylpyrrolidone (PVP). Conveniently the powder carrier will form a gel in the nasal cavity. The powder composition may be presented in unit dose form for example in capsules or cartridges of, e.g., gelatin, or blister packs from which the powder may be administered by means of an inhaler.

In compositions intended for administration to the respiratory tract, including intranasal compositions, the compound will generally have a small particle size for example of the order of 5 microns or less. Such a particle size may be obtained by means known in the art, for example by micronization.

When desired, compositions adapted to give sustained release of the active ingredient may be employed.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packaged tablets, capsules, and powders in vials or ampoules. Also, the unit dosage form can be a capsule, tablet, cachet, or lozenge itself, or it can be the appropriate number of any of these in packaged form. Tablets or capsules for oral administration and liquids for intravenous administration and continuous infusion are preferred compositions.

Further details on techniques for formulation and administration may be found in the latest edition of Remington's Pharmaceutical Sciences (Maack Publishing Co. Easton, Pa.).

The invention is further illustrated by the following figures, tables and Examples which are given to illustrate the invention, not to limit it.

Tables

Reference is now made to the figures and tables, wherein

Table 1 shows activity data in Axl, Mer and CSF1R binding assay for selected compounds of the invention. Inhibition is indicated as Kd with the following key: A=Kd less than 0.1 uM; B=Kd greater than 0.1 uM, but less than 0.5 uM; C=Kd greater than 0.5 uM. "n.d."=not determined Table 2 shows activity data of a CSF1R binding assay for selected compounds of the invention Inhibition is indicated as percent inhibition in percentage figures ("Percent (%)") and with the following additional key, classifying the inhibition figures into different classes ("Range"): A=≥80% inhibition; 80% inhibition>B≥50% inhibition; 50% inhibition>C;

Table 3 shows activity data in a cellular Axl Elisa assay (H1299) for selected compounds of the invention. Inhibition is indicated as $IC_{50}$ with the following key: A=$IC_{50}$ less than 0.5 uM; B=$IC_{50}$ greater than or equal to 0.5 uM, but less than 1.0 uM; C=$IC_{50}$ greater than or equal to 1.0 uM.

Table 4 shows activity data in a cellular CSF1R Elisa assay (THP-1) for selected compounds of the invention. Inhibition is indicated as $IC_{50}$ with the following key: A=$IC_{50}$ less than 0.5 uM; B=$IC_{50}$ greater than or equal to 0.5 uM, but less than 1.0 uM; C=$IC_{50}$ greater than or equal to 1.0 uM.

Table 5 shows CSF1R activity data in a cellular M-NFS-60 viability assay; CSF1R inhibition is indicated as $IC_{50}$ with the following key: A: $IC_{50}$<1.0 µM; B: 1.0 µM≤$IC_{50}$<10 µM; C: $IC_{50}$≥10 µM.

Table 6 shows Axl, Mer and CSF1R activity data in a cellular BaF$_3$ viability assay; inhibition is indicated as $IC_{50}$ with the following key: A: $IC_{50}$<1.0 µM; B: 1.0 µM≤$IC_{50}$<10 µM; C: $IC_{50}$≥10 µM.

Table 7 shows comparison data of selected compounds of the present invention (marked with two asterisks**) vs. selected compounds of WO 2016/166250 (marked with a single asterisk*) in terms of binding activity (Axl and Mer and cellular activity (Axl H1299 Elisa assay).

Table 8 Summarizes compounds 1-179 in terms of their structures and corresponding characteristics.

Figure 2:
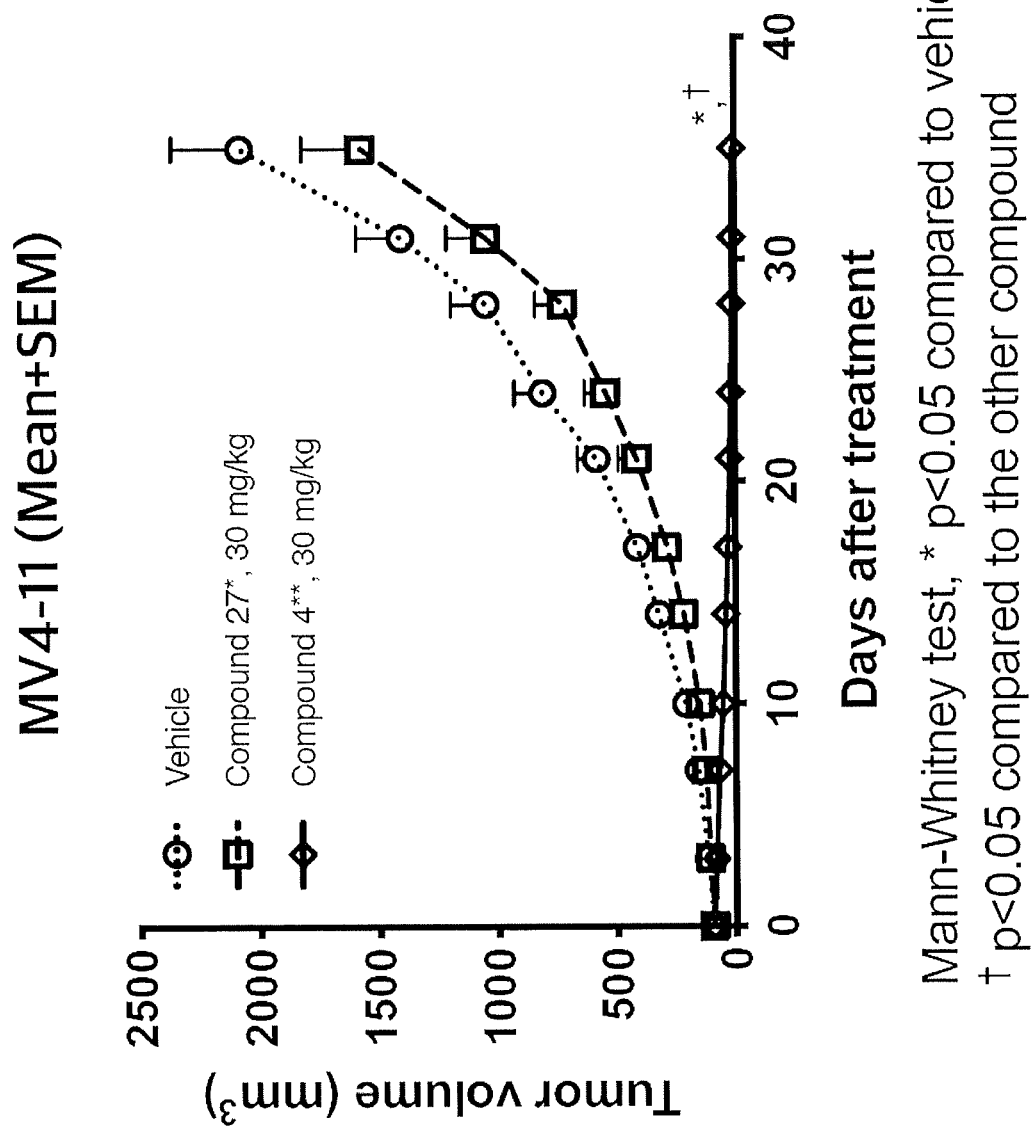

FIGS. 1 and 2 show comparison data of compound 4 of the present invention (marked with two asterisks** and diamond) vs. compound 27 of WO2016/166250 (marked with single asterisk* and open square) in mouse models EMT-6 and MV4-11; EMT-6 measures triple inhibition of Axl, Mer and CSF1R. MV4-11 measures inhibition of Axl.

EXAMPLES

The invention is now further described by reference to the following examples which are intended to illustrate, not to limit the scope of the invention.

Example 1 Kinase Binding Assay for Axl and Mer

Binding Assay Principle

LanthaScreen® Eu Kinase Binding assays were conducted at Life Technologies using the manufacturer's specifications for each kinase indicated.

Briefly, the principle behind this assay is based upon the binding and displacement of an Alexa Fluor 647-labeled tracer to the kinase of interest. Binding of the tracer to the kinase is detected using an EU-labeled anti-tag antibody. Simultaneous binding of both the tracer and antibody to the kinase gives rise to a FRET-signal. Binding of an inhibitor to the kinase competes for binding with the tracer, resulting in a loss of FRET-signal.

Binding Assay Protocol for AXL and Mer

A given compound was diluted in DMSO to make a stock compound solution. The stock compound solution was serially diluted over eight steps in DMSO. Each diluted compound solution in DMSO was diluted in kinase buffer. Afterwards four kinds of working solution were prepared. First, Tracer-Working solution consists of Tracer 236 and Kinase Buffer. Second, Axl, Mer, Tyro3 or Met/anti-GST-AB-Working solution contained one of the kinases Axl, and Mer or anti-GST-AB (=anti glutathione-S-transferase antibody) in Kinase Buffer. Third, anti-GST-AB-Working solution was made with anti-GST-AB and Kinase Buffer. Last, in the DMSO-Working solution DMSO was added to Kinase Buffer to a final concentration to 3%. Each of the four kinds of working solutions were separately added to the assay plate and then incubated for 1 h at room temperature. After incubation, the assay plate was measured with respect to the FRET-Signal with the EnVision (Perkin Elmer) using the program LanthaHTRF-Assay. Data evaluation was done in the Quattro Workflow software. Kd (the equilibrium dissociation constant) values were calculated relative to vehicle (DMSO) control wells.

Table 1 summarizes the results obtained for AXL and Mer kinases binding assays

Example 2: Kinase Binding Assay for CSF1R

Binding Assay Principle

KINOMEscan™ is based on a competition binding assay that quantitatively measures the ability of a compound to compete with an immobilized, active-site directed ligand. The assay is performed by combining three components: DNA-tagged kinase; immobilized ligand; and a test compound. The ability of the test compound to compete with the immobilized ligand is measured via quantitative PCR of the DNA tag.

Binding Assay Protocol for CSF1R

*E. coli* were grown to log-phase and infected with T7 phage and incubated with shaking at 32° C. until lysis. The lysates were centrifuged and filtered to remove cell debris. The remaining kinases were produced in HEK-293 cells and subsequently tagged with DNA for qPCR detection. Streptavidin-coated magnetic beads were treated with biotinylated small molecule ligands for 30 minutes at room temperature to generate affinity resins for kinase assays. The liganded beads were blocked with excess biotin and washed with blocking buffer (SeaBlock (Pierce), 1% BSA, 0.05% Tween 20, 1 mM DTT) to remove unbound ligand and to reduce non-specific binding. Binding reactions were assembled by combining kinases, liganded affinity beads, and test compounds in 1× binding buffer (20% SeaBlock, 0.17×PBS, 0.05% Tween 20, 6 mM DTT). Test compounds were prepared as 111× stocks in 100% DMSO. Kds were determined using an 11-point 3-fold compound dilution series with three DMSO control points. All compounds for Kd measurements are distributed by acoustic transfer (non-contact dispensing) in 100% DMSO. The compounds were then diluted directly into the assays such that the final concentration of DMSO was 0.9%. In case of % inhibition, test compounds were prepared as 40× stocks in 100% DMSO and directly diluted into the assay. All reactions performed in polypropylene 384-well plate. Each was a final volume of 0.02 ml. The assay plates were incubated at room temperature with shaking for 1 hour and the affinity beads were washed with wash buffer (1×PBS, 0.05% Tween 20). The beads were then re-suspended in elution buffer (1×PBS, 0.05% Tween 20, 0.5 µM non-biotinylated affinity ligand) and incubated at room temperature with shaking for 30 minutes. The kinase concentration in the eluates was measured by qPCR.

The CSF1R kinase binding activity results are shown in tables 1 ($K_d$) and 2 (percent inhibition at a concentration of 0.1 uM of compound to be tested).

Data Analysis

Binding constants (Kds) were calculated with a standard dose-response curve using the Hill equation:

$$\text{Response} = \text{Background} + \frac{\text{Signal} - \text{Background}}{1 + (KD^{Hill\ Slope} / Dose^{Hill\ Slope})}$$

The Hill Slope was set to −1.

Curves were fitted using a non-linear least square fit with the Levenberg-Marquardt algorithm.

Binding % inhibition were calculated with as below:

$$\% \text{ inhibition} = 100 - \left[\frac{\text{test compound signal} - \text{positive control signal}}{\text{negative control signal} - \text{positive control signal}}\right] \times 100$$

negative control=DMSO (100% Ctrl)
positive control=control compound (0% Ctrl)

Example 3: Cellular Axl Inhibition Assay

Axl Cellular Assay Principle

Axl is expressed in several of malignant cancer cells; especially H1299 cell endogenously expresses Axl; and an increased phosphorylation of Axl (p-Axl) can be observed, when induced by the Axl ligand, Ga6.

Enzyme-Linked Immunosorbent Assay (ELISA) Using H1299 Cells

The H1299 cells should be 40-80% confluent in the cell culture flask. Then cells are washed with DPBS and trypsinized. After centrifugation, the cell pellet is re-suspended with pre-warmed culture medium (RPMI1640, 10% FBS) and cells are separated by pipetting 6 times up and down with a 10 ml serological pipette. The cell suspension was diluted to a final concentration of $1.25 \times 10^5$ cells/ml. Then 80 µl/well cell suspension is added to the plate. Cell-plates are incubated at 37° C./5% $CO_2$ overnight. Compounds were dissolved by DMSO to 10 mM, and kept in nitrogen cabinet. Prepare the compounds stock plate, the reference compounds concentration starts at 0.50 mM (5 µl+95 µl DMSO), and the tested compounds start at 1.5 mM (6 µl+34 µl DMSO); Then make a 3-fold dilution series (10 doses) compounds. Then dilute compounds by the medium in the mid plate (2 µl compounds+198 µl medium). Transfer 20 µl diluted compounds from mid plate to the cell coated plate. Cell-plates are incubated at 37° C./5% $CO_2$ for 24 h. Add 25 µl of Human Gas6 (1000 ng/ml) to 96-well plate; the final concentration of Human Gas6 is 200 ng/ml. Incubate the plates at 37° C./5% $CO_2$ for 1 h. Remove medium and wash cells once with 300 ul/well ice-cold 1×PBS. Then remove PBS and add 100 µl/well ice-cold 1× Cell Lysis Buffer to 96-well plate. The plate is shaken for 40 min at 4° C. Then plates can be stored at −20° C. After the micro-wells strips have reached room temperature, break off the required number of micro-wells. Place the micro-wells in the strip holder. Unused micro-wells must be resealed and stored at 4° C. immediately. Add 60 µl of cell lysate to the appropriate well. Seal with tape and press firmly onto top of micro-wells. Incubate the plate at 37° C. for 2 h. Gently remove the tape and wash wells 5 times with 1× Wash Buffer, 300 µl each time for each well. Add 100 µl of reconstituted Detection Antibody (green color) to each well. Seal with tape and incubate the plate at 37° C. for 1 h. Repeat wash procedure. Add 100 µl of reconstituted HRP Linked secondary antibody to each well. Seal with tape and incubate the plate at 37° C. for 30 min. Repeat wash procedure. Add 100 µl of TMB Substrate to each well. Seal with tape and incubate the plate at 37° C. for 15 min. Add 100 µl of STOP Solution to each well. Shake gently for a few seconds. Read absorbance at 450 nm within 30 min after adding STOP Solution. Calculations and Formulas: The following calculations and formulas are used for data analysis using XL Fit software: The curve fitting was made using the Sigmoidal Dose-Response Model (Fit model, 205). The data are reported in table 3 (shown further below).

Example 4: Cellular CSF1R Inhibition Assay

CSF1R Cellular Assay Principle

The normal proto-oncogene c-fms encodes the macrophage growth factor (M-CSF, also known as CSF1) receptor involved in growth, survival, and differentiation along the monocyte-macrophage lineage. THP-1 cells act as a model for human monocytes. It confirms that an increased phosphorylation of CSF1R (p-CSF1R) can be observed, when induced by CSF1R ligand, CSF1. M-NFS-60 cells are a mouse myeloid cell line that shows CSF1-dependent proliferation, i.e. it requires CSF1 for growth.

Enzyme-Linked Immunosorbent Assay (ELISA) Using THP-1 Cells

The THP-1 cells should be maintained from $5 \times 10^5$ to $1 \times 10^6$ cells/ml in the cell culture flask. After centrifugation, the supernatant is aspirated. The cell pellet is re-suspended with pre-warmed growth medium (RPMI1640, 10% FBS, 0.05 mM 2-Mercaptoethanol) and cells are separated by pipetting 6 times up and down with a 10 ml serological pipette. The cell suspension has to be diluted to a final concentration of $2 \times 10^5$ cells per 80 µl with pre-warmed growth medium. 80 µl of cell suspension is added to all wells of plates. Cell-plates are incubated at 37° C./5% $CO_2$. Dissolve compound in 100% DMSO to make 10 mM stock solutions (Aliquots stored in the Nitrogen Cabinet). Dilute 10 mM compounds solutions for 2-fold in 100% DMSO to get 5 mM solutions (10 µl+10 µl DMSO), and then make a 3-fold serial dilution (10 µl+20 µl DMSO) for 10 doses. For reference compounds: Dilute 10 mM compounds solutions for 20-fold in 100% DMSO to get 0.5 mM solutions (2 µl+38 µl DMSO), and then make a 3-fold serial dilution (10 µl+20 µl DMSO) for 10 doses. Transfer 2 µl diluted compounds to 198 µl medium to get solution of 50 µM concentration at top point for compounds and 5 µM for reference compounds. Then transfer 20 µl cpd solution into assay plate (Duplicate wells). The plate is incubated at 37° C./5% $CO_2$ for 24 h. The final concentration of DMSO in all wells is 0.2%. Reconstitute human M-CSF at 50 µg/ml in sterile water. (Aliquots stored in −80° C.). 1:1000 dilute human M-CSF by fresh medium to 50 ng/ml. After 24 h compounds treatment, transfer 25 µl diluted human M-CSF (50 ng/ml) to cell plate according to the plate map. The final concentration of human M-CSF in all wells is 10 ng/ml.

The plates is incubated at 37° C./5% $CO_2$ for 5 min. In the beginning the appropriate amount of lysis buffer complete (100 µL/well) is prepared and stored on ice. After 5 min human M-CSF stimulation, wash plates once with 300 µL ice cold PBS. Then 100 µl lysis buffer is added to each well. The plate is shacked for 40 min at 4° C. Plates can now be stored at −20° C. After equilibrate the micro-well strips at room temperature, break off the required number of micro-wells. Place the micro-wells in the strip holder. Unused micro-wells must be resealed and stored at 4° C. immediately. Add 90 µl of cell lysate to the appropriate well. Seal with tape and press firmly onto top of micro-wells. Incubate the plate for 2 h at 37° C. Gently remove the tape and wash wells 4 times with 1× Wash Buffer, 200 µl each time for each well. Add 100 µl of reconstituted Detection Antibody (green color) to each well. Seal with tape and incubate the plate at 37° C. for 1 h. Repeat wash procedure. Add 100 µl of reconstituted HRP-Linked secondary antibody to each well. Seal with tape and incubate the plate for 30 min at 37° C.

Repeat wash procedure. Add 100 µl of TMB Substrate to each well. Seal with tape and incubate the plate for 10 min at 37° C. or 30 min at 25° C. Calculations and Formulas: The following calculations and formulas are used for data analysis using XL Fit software: The curve fitting was made using the Sigmoidal Dose-Response Model (Fit model, 205). The data are reported in table 4 (shown further below).

Cell Titer-Glo (CTG) Assay Using M-NFS-60 Cells

M-NFS-60 cells were cultured in RPMI-1640 medium containing 10% FBS, 0.05 mM 2-Mercaptoethanol, penicillin (100 U/ml)/streptomycin (100 mg/ml) and supplemented with 62 ng/ml recombinant human M-CSF at 37° C./5% $CO_2$. Aliquots of the cells were seeded into a 96-well plate ($2 \times 10^5$ cells in 100 µl/well) and then incubated at 37° C./5% $CO_2$ 1 h. Dissolve compound in 100% DMSO to make 10 mM stock solutions (Aliquots stored in the Nitrogen Cabinet). Dilute 10 mM compounds solutions for 2-fold in 100% DMSO to get 5 mM solutions (10 µl+10 µl DMSO), and then make a 3-fold serial dilution (10 µl+20 µl DMSO) for 10 doses. For reference compounds: Dilute 10 mM compounds solutions for 20-fold in 100% DMSO to get 0.5 mM solutions (2 µl+38 µl DMSO), and then make a 3-fold serial dilution (10 µl+20 µl DMSO) for 8 doses. The 96-well plate was equilibrated at room temperature for 30 min. 50 µl of CellTiter-Glo® Reagent added to each well and mixed for 2 min on an orbital shaker to induce cell lysis. The 96-well plate was incubated at room temperature for 10 min to stabilize luminescent signal. Luminescent was measured at 700 nm by EnVison plate reader. Calculations and Formulas: The following calculations and formulas are used for data analysis using XL Fit software: The curve fitting was made using the Sigmoidal Dose-Response Model (Fit model, 205). The data are reported in table 5 (shown further below).

Example 5: Cellular Axl, Mer and CSF1R Inhibition Measured by $BaF_3$-Viability Assay BaF3 Cell-Based Assay Principle In this system, IL-3-dependent Ba/F3 cells are modified to express an activated recombinant kinase (in the present case Axl, Mer and CSF1R). Following removal of IL-3, the modified cells are dependent on the activity of the recombinant kinase for survival and proliferation. Inhibition of such kinase(s) through test compounds reduces survival and proliferation of the cells.

BaF3 Cell-Based Assay Protocol

Cell lines were maintained in growth media (GM) consisting of RPMI 1640 supplemented with 10% FBS. Cells in logarithmic-phase growth were harvested and 5,000 cells were distributed into each well of a 384-well plate in 50 µl GM. Parental cells (or experimental assays where specified) were further supplemented with 2 ng/ml IL-3 to support cell growth and survival. Fifty nanoliters of the indicated reference standard or experimental compound were added to appropriate wells (in duplicate) and the cells were cultured for 48 h at 37° C./5% $CO_2$. Viability was determined by adding 10 µl Cell Titer Glo and measuring luminescence, which is reported as relative light units (RLU) measured in counts per second. The following calculations and formulas are used for data analysis using GraphPad Prism software: The curve fitting was made using the Dose response curves-Inhibition. The data are reported in table 6 (shown further below).

Example 6: Comparison of Selected Compounds of Present Invention Vs. Selected Compounds of WO 2016/166250 in Terms of Binding Activity (Axl and Mer) and Cellular Activity Table 7 shows the superiority of compounds 4, 10, 16 and 92 of the present invention (marked with **) vs. structurally similar compounds 27, 64, 22 and 48 respectively, of WO 2016/166250 (marked with *) in terms of their binding activity to Axl and Mer and in terms of their cellular activity in the H1299 Elisa assay. The data are extracted from tables 1, 2 and 3 and are reported further below in table 7.

Example 7: EMT-6 and MV4-11 Mouse Models a) EMT-6 Mouse Model
Syngeneic Model

Axl/Mer has been also demonstrated to be constitutive and inducible expressed on multiple immune cells, particularly dendritic cells (DCs) and macrophages, which act as negative feedback to balance the pro-inflammatory signaling. In case of CSF1R, it mediates tumorigenesis in tumor-immune microenvironments and is expressed on myeloid cell tumor-associated macrophages (TAMs); elevated serum CSF1, increased numbers of TAMs in tumors, and high expression of tissue CSF1 and/or CSF1R are associated with poor prognosis in patients with various cancers. Mouse syngeneic tumor models are widely used tools to demonstrate activity of novel anti-cancer immunotherapies. The EMT-6 syngeneic model contains significantly higher amount of myeloid cells and also a higher percentage of TAMs. Therefore, EMT-6 is a suitable model for immune-oncology drug efficacy effects through changes in target immune cells.

EMT-6 Syngeneic Tumor Model Treatment Protocol

BALB/c mice (6-8 week female, Beijing Vital River Laboratory Animal Technology Co., Ltd.) were inoculated subcutaneously at the upper right flank with EMT-6 tumor cells ($1 \times 10^6$) in 0.1 mL of PBS for tumor development. For the study, the treatments were started on day 6 after tumor inoculation, mice were dosed orally with each test compounds or vehicle daily. Tumor volumes were measured every 3 days with a digital caliper, and were calculated using the formula: $V=0.5 a \times b^2$ where a and b are the long and short diameters of the tumor in mm, respectively. Body weight was measured every 3 days. All the procedures related to animal handling, care and the treatment in the study were performed according to the guidelines approved by the Institutional Animal Care and Use Committee (IACUC) of WuXi AppTec following the guidance of the Association for Assessment and Accreditation of Laboratory Animal Care (AAALAC). At the time of routine monitoring, the animals were daily checked for any effects of tumor growth and treatments on normal behavior such as mobility, food and water consumption (by looking only), body weight gain/loss (body weights were measured three times a week), eye/hair matting and any other abnormal effect as stated in the protocol. Death and observed clinical signs were recorded on the basis of the numbers of animals within each subset. The data are reported in FIG. 1 exemplarily for compound 4 of the present invention vs. structurally similar compound 27 of WO 2016/166250 and demonstrate that the compounds according to the present invention delay tumor growth to a significantly larger extent, than other compounds or vehicle.

b) MV4-11 Mouse Model
Xenograft Model

High expression of Axl or Gas6 in acute myeloid leukemia (AML) patients is prognostic for poor survival outcome. AML cells induce expression and secretion of the Axl ligand Gas6 by bone marrow-derived stromal cells (BMDSCs). Gas6 in turn mediates proliferation, survival, and chemoresistance of Axl-expressing AML cells. This Gas6/Axl paracrine axis between AML cells and BMDSCs establishes a chemoprotective tumor cell niche that can be abrogated by Axl-targeting approaches. The Axl/Gas6 axis promotes leukemia cell proliferation and chemoresistance.

MV4-11 Xenograft Tumor Model Treatment Protocol

BALB/c nude mice (6-8 week female, Shanghai SIPPR/BK Laboratory Animal Co., LTD.) were inoculated subcutaneously at the upper right flank with MV4-11 tumor cells ($1\times10^7$) in 0.1 mL of PBS+Matrigel (1:1) for tumor development. For the study, the treatments were started on day 10 after tumor inoculation, mice were dosed orally with each test compounds or vehicle daily. Tumor volumes were measured every 3 days with a digital caliper, and were calculated using the formula: $V=0.5a\times b^2$ where a and b are the long and short diameters of the tumor in mm, respectively. Body weight was measured every 3 days. All the procedures related to animal handling, care and the treatment in the study were performed according to the guidelines approved by the Institutional Animal Care and Use Committee (IACUC) of WuXi AppTec following the guidance of the Association for Assessment and Accreditation of Laboratory Animal Care (AAALAC). At the time of routine monitoring, the animals were daily checked for any effects of tumor growth and treatments on normal behavior such as mobility, food and water consumption (by looking only), body weight gain/loss (body weights were measured three times a week), eye/hair matting and any other abnormal effect as stated in the protocol. Death and observed clinical signs were recorded on the basis of the numbers of animals within each subset. The data are reported exemplarily in FIG. 2 for compound 4 of the present invention vs. structurally similar compound 27 of WO 2016/166250 and demonstrate that the compounds according to the present invention delay tumor growth to a drastically larger extent than other compounds or vehicle.

Data for EMT-6 and MV4-11 are shown in FIG. 1 (EMT-6 syngeneic model efficacy study) and 2 (MV4-11 xenograft model efficacy study).

Example 8: Derivatization of the Dimethoxyquinoline General Scaffold

The presented compounds underwent derivatization according to the methods outlined below (Schemes 1-21). Resulting derivatives were examined for kinase binding, cellular activity and in vivo activity, using the assays described above (Example 1-7), and the results are summarized in Tables 1-7 and FIGS. 1 & 2. The synthesized compounds 1-179 are shown in Table 8, below.

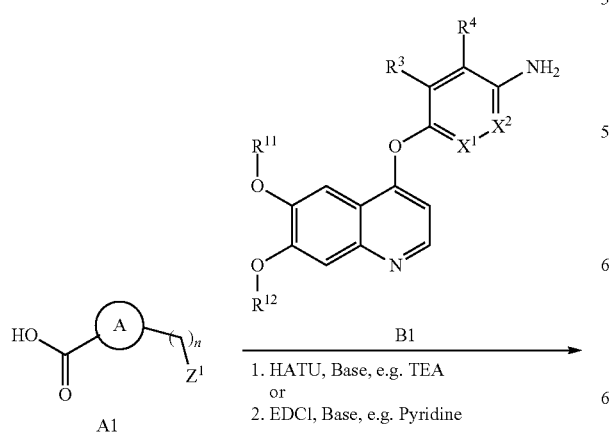

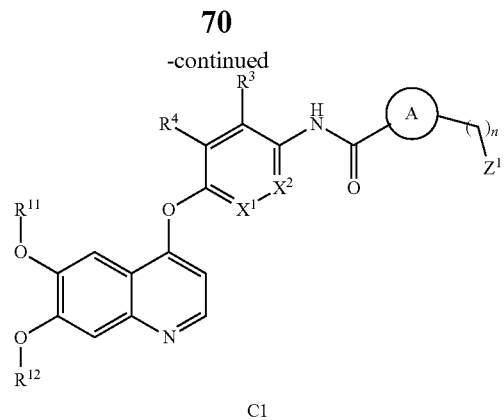

General Procedure for Synthesis of C1

A method to prepare compounds of C1 is shown in Scheme 1. The reaction of A1 and B1 is carried out in the presence of the HATU (O-(7-Azabenzotriazol-1-yl)-N,N,N',N'-tetramethyluronium hexafluorophosphate), TEA in a DMF to give C1. Alternatively, the reaction of A1 and B1 carried out in the presence of the EDCI (1-Ethyl-3-(3-dimethylaminopropyl)carbodiimide) in a pyridine to give C1.

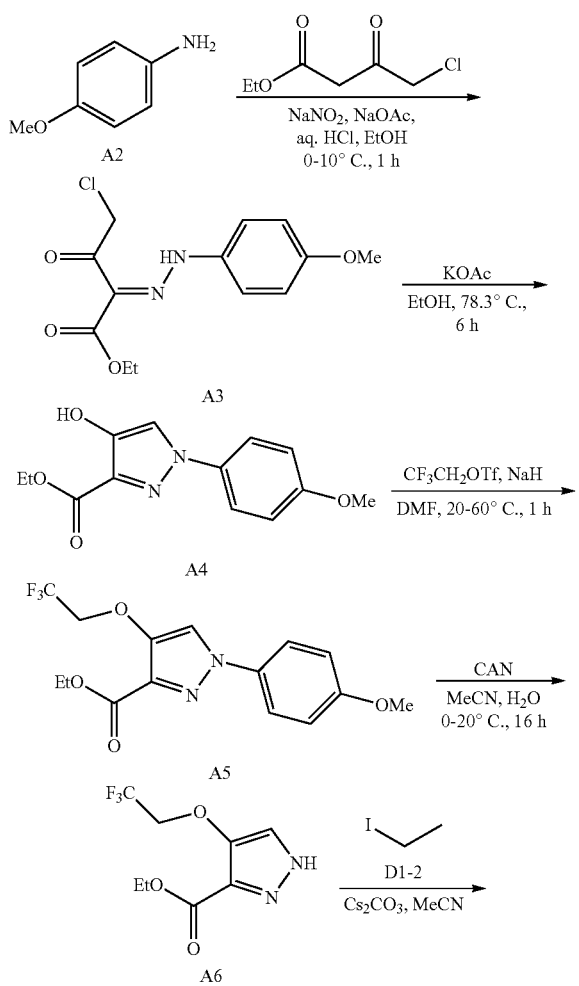

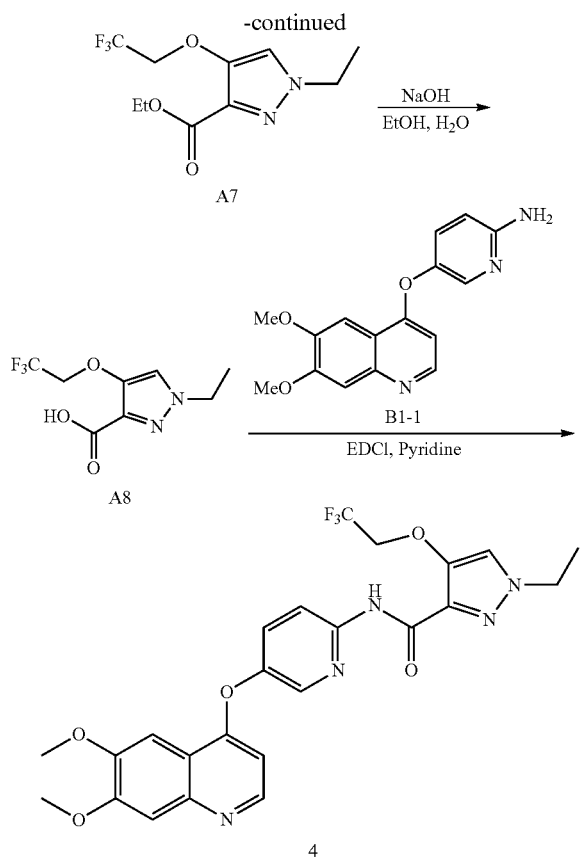

General Procedure for Synthesis of A3

To a HCl (3 M, 180 mL) was added compound A2 (20.0 g, 53.1 mmol) slowly at 10° C., then the mixture was cooled to 0° C., and a solution of NaNO$_2$ (11.8 g, 55.8 mmol) in water (50 mL) was added, the mixture turn to a brown solution (solution A). To a mixture of ethyl 4-chloro-3-oxo-butanoate (28.2 g, 170 mmol) and NaOAc (66.1 g, 812 mmol) in H$_2$O (2000 mL)/EtOH (500 mL) was dropwise added solution A at 0-5° C. Then the mixture was stirred at 10° C. for 1 hour. Yellow powder precipitated out from the reaction mixture. This phenomenon indicated that the reaction worked, and LCMS showed 80% desired MS value. The mixture was filtrated, the filter cake was washed with water (500 mL) and dried under high vacuum to give 35.0 g of compound. A3 (yield: 72.2%) as a yellow powder.

General Procedure for Synthesis of A4

To a solution of compound A3 (35.0 g, 117.17 mmol) in absolute EtOH (300 mL) was added KOAc (23.0 g, 234 mmol). The mixture was heated to reflux at 78.3° C. for 6 hours. The reaction mixture was a yellow solution. LCMS showed 86.7% desired MS value. The mixture was cooled to room temperature, Most EtOH was removed under reduced pressure, the residue was partitioned between EtOAc (800 mL) and H$_2$O (800 mL). The aqueous was extracted with EtOAc (800 mL). The combined organic extract was washed with brine (900 mL×2), dried over anhydrous Na$_2$SO$_4$, filtered and concentrated under reduced pressure to give 27.0 g of compound A4 (yield: 87.9%) as a yellow powder.

General Procedure for Synthesis of A5

To a solution of compound A4 (10.0 g, 38.1 mmol) in DMF (100 mL) was added NaH (3.05 g, 76.3 mmol, 60% dispersion in mineral oil) at 0° C., then the mixture was stirred at 20° C. for 30 minutes, then CF$_3$CH$_2$OTf (17.7 g, 76.3 mmol) was added to the mixture and the reaction mixture was warmed to 60° C. for 2.5 hour. LCMS showed the reaction was completed. The mixture was cooled to room temperature, diluted with water (1000 mL), extracted with EtOAc (1000 mL×3). The combined extract was washed with brine (1500 mL×2), dried over anhydrous Na$_2$SO$_4$ and filtrated, then concentrated under reduced pressure to 46.0 g (crude, containing a little DMF) of compound A5 as a yellow gum General Procedure for Synthesis of A6

To a mixture of compound A5 (40.0 g, 116 mmol) in MeCN (400 mL) was added CAN (191 g, 349 mmol) in H$_2$O (200 mL) at 0° C., then the mixture was allowed to warmed to 20° C. and stirred at 20° C. for 17 hours. TLC (PE/EtOAc=1/2) showed the reaction was completed. The mixture was extracted with EtOAc (500 mL×3), the combined extracts was washed with saturated aqueous NaHCO$_3$ (800 mL×3), the organic phase was dried over anhydrous Na$_2$SO$_4$, filtered, the filtrate was concentrated under reduced pressure to give a residue. The residue was purified by Combi flash (PE/EtOAc=4/1 to 2/1) to give 7.60 g (yield: 27.5%) of compound. A6 as a yellow solid.

General Procedure for Synthesis of A7

To a solution of compound A6 (9.15 g, 38.4 mmol), D1-2 (7.18 g, 42.3 mmol) in MeCN (100 mL) was added Cs$_2$CO$_3$ (31.3 g, 96.1 mmol). The reaction was stirred at 25° C. for 17 hours to give a yellow suspension. LCMS showed the reaction was completed. The reaction mixture was filtered. The filter cake was washed with EtOAc (300 mL). The filtrate was partitioned with EtOAc (300 mL) and water (400 mL). The organic phase was washed with brine (400 mL×2) and dried over anhydrous Na$_2$SO$_4$, filtered and concentrated under reduced pressure to give the crude residue. The residue was purified by Combi Flash (PE/EtOAc=1:0 to 3:1) to give 4.3 g of undesired isomer (yield: 40%) (less polar) as a yellow oil, and 4.9 g of compound A7 (yield: 46%) (more polar) as a yellow gum.

General Procedure for Synthesis of A8

To a solution of compound A7 (4.9 g, 17.5 mmol) in MeOH (33 mL) was added NaOH (2.10 g, 52.5 mmol) in H$_2$O (8 mL). The reaction was stirred at 20° C. for 2 hours to give a yellow solution. TLC showed the reaction was completed. Most MeOH was removed under reduced pressure. The reaction mixture was adjusted to pH=4 with aqueous HCl (1 M). The mixture was extracted with DCM (110 mL×3). The organic layers were washed with brine (150 mL), dried over anhydrous Na$_2$SO$_4$, filtered and concentrated under reduced pressure to give 4.41 g of compound A8 (yield: 100%) as a yellow gum.

General Procedure for Synthesis of 4

To a solution of compound A8 (4.41 g, 17.5 mmol), EDCI (5.03 g, 26.2 mmol) in pyridine (40 mL) was added compound B1-1 (5.30 g, 17.8 mmol). The reaction was stirred at 25° C. for 17 hours to give a yellow solution. LCMS showed the staring material was not consumed completely. The reaction mixture was concentrated under reduced pressure to give a residue. The residue was partitioned between DCM (400 mL) and H$_2$O (300 mL). The organic layer was washed with H$_2$O (200 mL×2), brine (200 mL×2), dried over anhydrous Na$_2$SO$_4$, filtered and concentrated under reduced pressure to give a yellow gum. The crude product was purified by Combi Flash (EtOAc:PE=0:1 to 1:0) and the eluent was concentrated under reduced pressure to give an off-white gum. The product was dissolved in MeCN (30 mL) and H$_2$O (33 mL), and lyophilized to give 5.23 g of compound 7 (yield: 55%, purity: 98.5%) as a white powder.

Scheme 3 - General Synthesis for compound 1

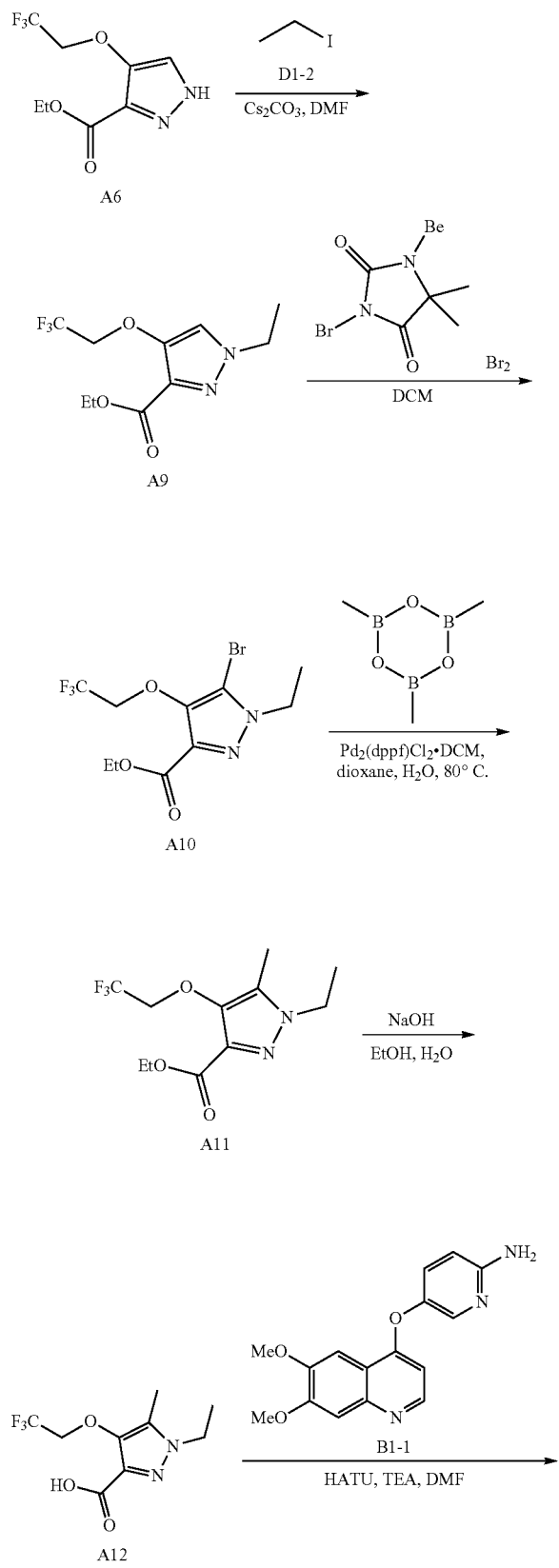

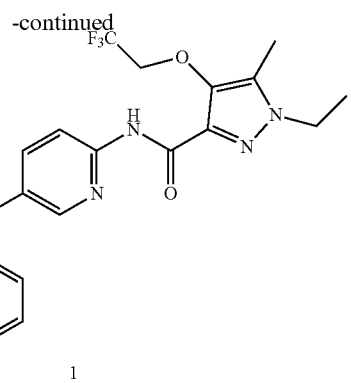

General Procedure for Synthesis A9

A mixture of compound A6 (1.00 g, 4.20 mmol), Cs$_2$CO$_3$ (3.42 g, 10.5 mmol) in DMF (10 mL) was added D1-2 (524 mg, 3.36 mmol). The mixture was stirred at 15° C. for 2 hours to give a yellow mixture. LCMS showed the reaction was completed. The mixture was partitioned between EtOAc (50 mL) and H$_2$O (50 mL). The aqueous phase was extracted with EtOAc (50 mL). The combined organic extract was washed with brine (50 mL×2), dried over anhydrous Na$_2$SO$_4$, filtered and concentrated under reduced pressure to give crude product as yellow oil. The residue was purified by Combi flash (PE:EA=1:0 to 3:1) to give A9 (240 mg, 21.5% yield, more polar, desired product) as a yellow gum. LCMS (Rt=1.080 min) showed the desired MS value.

General Procedure for Synthesis A10

A mixture of A9 (240 mg, 0.902 mmol) in DCM (3 mL) was added 1,3-dibromo-5,5-dimethyl-imidazolidine-2,4-dione (155 mg, 0.541 mmol). The mixture was stirred at 15° C. for 12 hours, LCMS showed starting material was remained, and added Br$_2$ (200 uL), started at 15° C. for 12 hours to give a yellow mixture. TLC showed the reaction was completed. The mixture was partitioned between with DCM (50 mL) and saturated sodium bicarbonate (30 mL), dried over anhydrous Na$_2$SO$_4$ and filtrated, then concentrated under reduced pressure to give A10 (300 mg, 96.4% yield) as a yellow powder. LCMS (Rt=1.243 min) showed the desired MS value.

General Procedure for Synthesis A11

To a mixture of A10 (300 mg, 0.869 mmol), Cs$_2$CO$_3$ (708 mg, 2.17 mmol) in dioxane (3 mL) and H$_2$O (1 mL) was added 2,4,6-trimethyl-1,3,5,2,4,6-trioxatriborinane (327 mg, 2.61 mmol), Pd(dppf)Cl$_2$·CH$_2$Cl$_2$ (71 mg, 0.0869 mmol). The reaction mixture was stirred at 80° C. for 12 hours under N$_2$ atmosphere to give a black mixture. LCMS (Rt=1.186 min) showed the reaction was completed. The mixture was cooled to room temperature and partitioned between DCM (30 mL) and water (20 mL). The aqueous phase was extracted with DCM (30 mL). The combined organic extracts were washed with brine (50 mL×2), concentrated under reduced pressure to give crude product as a brown oil, which was purified by Combi flash (PE/EA=I/O to 3/1) to give A11 (53 mg, 21.8% yield) as a yellow oil.

General Procedure for Synthesis A12

To a mixture of A11 (50 mg, 0.178 mmol) in EtOH (1 mL) was added the solution of NaOH (7.14 mg, 0.178 mmol) in H$_2$O (1 mL). The mixture was stirred at 15° C. for 2 hours to give a brown suspension. TLC showed the reaction was completed. The mixture was concentrated under reduced pressure to remove EtOH. The aqueous phase was diluted with water (30 mL), acidized with HCl (3 M) to pH=4-5 and lyophilized to give A12 (46 mg, crude) as a yellow gum, which was used for next step.

General Procedure for Synthesis 1

To a mixture of A12 (45 mg, 178 mmol), HATU (92.5 mg, 0.243 mmol) in DMF (1 mL) was added B1-1 (48.2 mg, 0.162 mmol), TEA (45 uL) under $N_2$ atmosphere. The mixture was stirred at 60° C. for 12 hours to give a yellow mixture. LCMS showed the reaction was completed. The mixture was cooled to temperature and poured into water (10 mL). The yellow solid precipitated out from the mixture. The mixture was filtrated and the filter cake was washed with water (5 mL) to give a crude product as a brown solid, which was purified by prep-TLC (DCM/MeOH=10/1) and lyophilization to give 1 (42.9 mg, 49.3% yield, 99.1% purity) as a yellow powder.

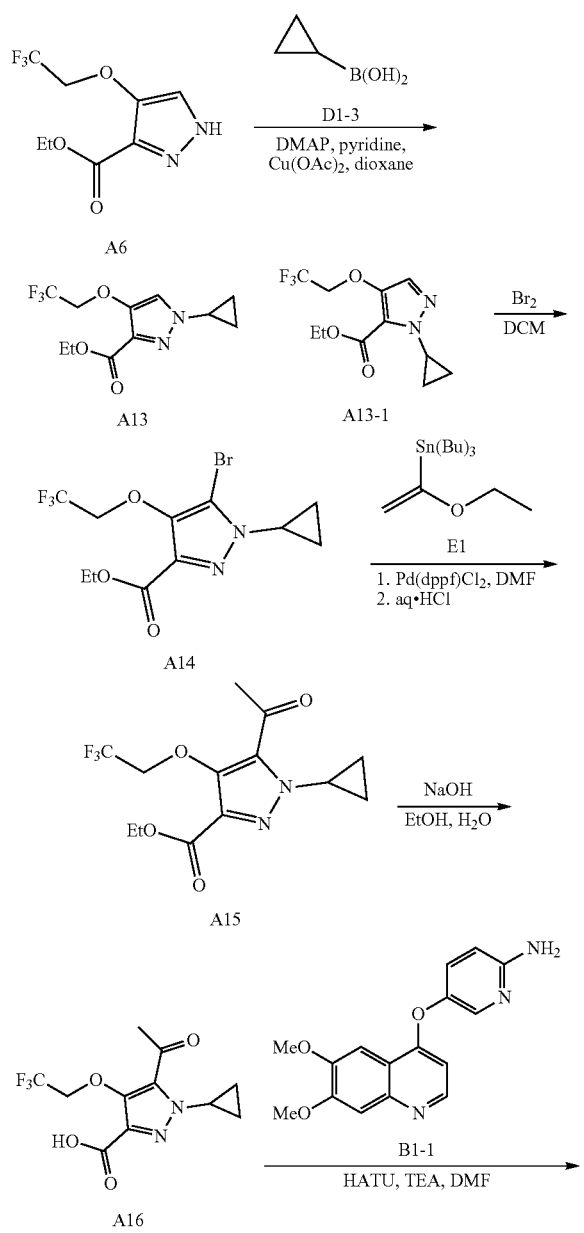

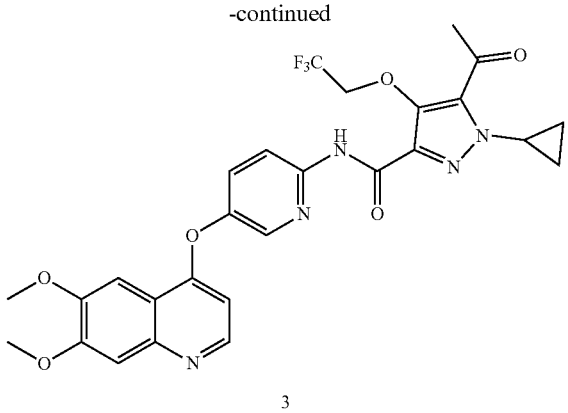

General Procedure for Synthesis A13

The 1$^{st}$ Batch:

To a solution of A6 (200 mg, 0.840 mmol), D1-3 (216 mg, 2.52 mmol), pyridine (79.7 mg, 1.01 mmol), and DMAP (308 mg, 2.52 mmol) in dioxane (5 mL) was added Cu(OAc)$_2$ (229 mg, 1.26 mmol), the mixture was stirred at 100° C. for 17 hours in air. Crude LCMS (Rt: 1.490 min, 1.636 min) showed the reaction was completed.

The 2$^{nd}$ Batch:

To a solution of A6 (500 mg, 2.10 mmol), D1-3 (541 mg, 6.30 mmol), pyridine (199 mg, 2.52 mmol), and DMAP (770 mg, 6.30 mmol) in dioxane (10 mL) was added Cu(OAc)$_2$ (572 mg, 3.15 mmol), the mixture was stirred at 100° C. for 17 hours in air. Crude LCMS and TLC (PE/EtOAc=3/1) showed the reaction was completed.

the each batch mixture were combined and poured into water (100 mL), extracted with EA (50 mL×3), the combined extracts was washed with aqueous NH$_3$·H$_2$O (50 mL×3, 14%) and brine (100 mL), dried over anhydrous Na$_2$SO$_4$, filtered, the filtration was concentrated under reduced pressure to give a residue. the residue was purified by Combi flash to give 510 mg of A13 (total yield: 20%) as a yellow gum and 320 mg of A13-1 as a white powder.

General Procedure for Synthesis A14

The 1$^{st}$ Batch:

To a solution of A13 (100 mg, 0.359 mmol, 1 eq) in DCM (5 mL) was added Br$_2$ (57 mg, 0.36 mmol, 1 eq), the mixture was stirred at 15° C. for 17 hours to give a brown solution. crude LCMS (RT: 0.977 min) showed the reaction was not completed, then additional Br$_2$ (104 mg) was added into above mixture, the resulting mixture was stirred at 15° C. for 24 hours to give a brown solution, TLC (PE/EtOAc=3/1) showed the reaction was completed.

The 2$^{nd}$ Batch:

To a solution of A13 (410 mg, 1.47 mmol) in DCM (5 mL) was added Br$_2$ (236 mg, 1.47 mmol), the mixture was stirred at 15° C. for 17 hours to give a brown solution. TLC (plate 1, PE/EtOAc=3/1) showed the reaction was not completed, then Br$_2$ (500 mg) was added into above mixture, the mixture was stirred at 30° C. for 1 hours, TLC (plate 2, PE/EtOAc=3/1) showed the reaction was completed Two combined batches mixture was poured into DCM (50 mL) and washed with saturated aqueous NaHCO$_3$ (50 mL×3), dried over anhydrous Na$_2$SO$_4$, filtered, the filtrate was concentrated under reduced pressure to give a residue, the residue was purified by Combi flash (PE/EtOAc=10/1 to 2/1) to give 450 mg (yield: 86%) of A14 as a white powder.

General Procedure for Synthesis A15

To a solution of A14 (450 mg, 1.26 mmol), E1 (1.37 g, 3.78 mmol) and LiCl (53 mg, 1.3 mmol) in DMF (5 mL) was added Pd(dppf)Cl$_2$ (184 mg, 0.252 mmol), the mixture purged with N$_2$ for three times and stirred at 100° C. for 17 hours to give a brown suspension. Crude LCMS (Rt: 1.233 min) and TLC (PE/EtOAc=3/1) showed the reaction was completed, then the mixture was treated with aqueous HCl (10 mL, 1M) to give a brown suspension, TLC (PE/EtOAc=3/1) and LCMS showed the reaction was completed. the pH value of the mixture was adjusted to 8 with saturated aqueous NaHCO$_3$, extracted with EtOAc (30 mL×3), the combined extracts was washed with brine (50 mL), dried over anhydrous Na$_2$SO$_3$, filtered, the filtrate was concentrated under reduced pressure to give a residue. The residue was purified by Combi flash (PE/EtOAc=10/1) to give 100 mg (yield: 26%) of A15 as a yellow powder.

General Procedure for Synthesis A16

To a solution of A15 (100 mg, 0.327 mmol) in EtOH (3 mL) was added NaOH (26 mg, 0.65 mmol) in H$_2$O (1 mL), the mixture stirred at 15° C. for 3 hours to give a yellow powder. TLC (EtOAc) showed the reaction was completed. The pH value of the mixture was adjusted to 5, the mixture was concentrated under reduced pressure to give a residue, the residue was dried in vacuum. Then the crude compound was treated with aqueous NaOH (1M, 20 mL) to from the Na salt, then extracted with EtOAc (10 mL×2) to removed the impurity, the pH value of water phase was adjusted to 5 with aqueous HCl (3M), extracted with DCM (30 mL×3), dried over anhydrous Na$_2$SO$_4$, filtered, the filtrate was concentrated under reduced pressure to 60 mg (yield: 63%) of A16 as a white powder.

General Procedure for Synthesis 3

To a solution of A16 (60 mg, 0.21 mmol), B1-1 (61 mg, 0.21 mmol) and TEA (104 mg, 1.03 mmol) in DMF (1 mL) was added HATU (156 mg, 0.411 mmol), the mixture was stirred at 15° C. for 17 hours to give a suspension. Crude LCMS and HPLC showed the reaction worked well. The mixture was filtered, the filter cake was washed with MeCN (2 mL) to give the product (about: 60 mg, HNMR: containing DMF (7%). The product was lyophilized to give 36 mg (yield: 31%) of 3 as a white powder.

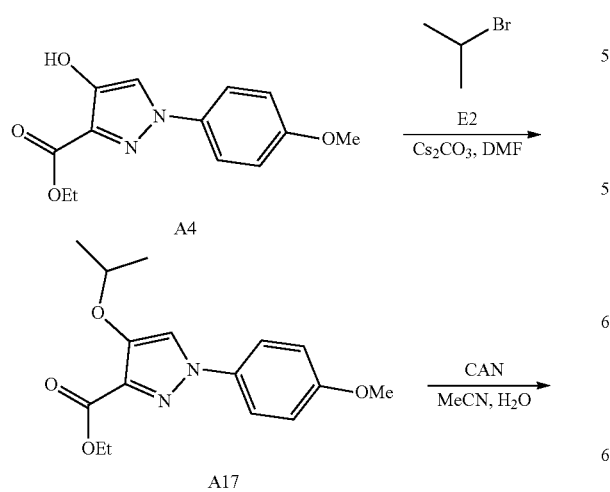

Scheme 5 - General synthesis for compound 6

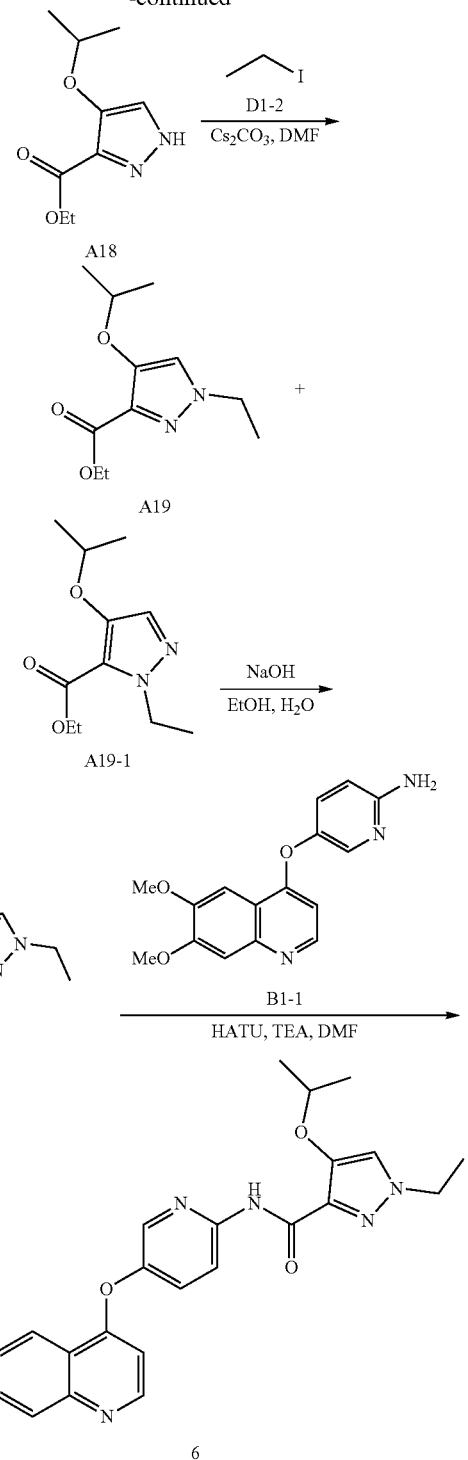

General Procedure for Synthesis A17

The mixture of A4 (10.0 g, 38.0 mmol) and Cs$_2$CO$_3$ (24.8 g, 76.3 mmol) in DMF (20 mL) was stirred at 25° C. for 30 minutes. To the resulting mixture was added E2 (9.38 g, 76.3 mmol, 7.2 mL). The mixture was stirred at 25° C. for 16 hours to form a brown mixture. LCMS showed the reaction was completed. The mixture was partitioned between EtOAc (200 mL) and H$_2$O (200 mL). The aqueous phase was extracted with EtOAc (200 mL×2). The combined organic extract was washed with brine (500 mL×2), dried over anhydrous Na$_2$SO$_4$, filtered and concentrated under reduced pressure to give A17 (10.50 g, yield: 90.5%) as a brown solid.

General Procedure for Synthesis A18

To a solution of A17 (10.5 g, 34.5 mmol) in MeCN (100 mL) was added the solution of CAN (56.7 g, 104 mmol) in H$_2$O (100 mL) at 0° C. The mixture was stirred at 25° C. for 16 hours to from a brown solution. LCMS showed the reaction was completed. To the mixture was added EtOAc (500 mL) and saturated NaHCO$_3$ (500 mL). The mixture was filtered. The filtrate was separated. The aqueous was extracted with EtOAc (500 mL×2). The combined organic extract was washed with brine (800 mL×2), dried over anhydrous Na$_2$SO$_4$, filtered and concentrated under reduced pressure to give a residue, which was purified by Combi flash (PE/EtOAc=I/O to 4/1) to give A18 (2.40 g, yield: 22.2%, LCMS: 63.2%) as dark yellow oil.

General Procedure for Synthesis A19

To a mixture of A18 (1.00 g, 5.04 mmol) and Cs$_2$CO$_3$ (3.29 g, 10.1 mmol) in DMF (10 mL) was added D1-2 (944 mg, 6.05 mmol, 0.48 mL). The mixture was stirred at 20° C. for 4 hours to form a brown mixture. LCMS showed the reaction was completed. The mixture was cooled to room temperature. The mixture was partitioned between EtOAc (30 mL) and H$_2$O (30 mL). The aqueous phase was extracted with EtOAc (30 mL×2). The combined organic extract was washed with brine (80 mL×3), dried over anhydrous Na$_2$SO$_4$, filtered and concentrated under reduced pressure to give a residue, which was purified by Combi flash (eluent: PE/EtOAc=3/1) to give A19 (300 mg, yield: 26.4%, more polar) and A19-1 (450 mg, yield: 39.4%, less polar) as yellow oil.

General Procedure for Synthesis A20

To a mixture of A19 (300 mg, 1.33 mmol) in EtOH (8 mL) and H$_2$O (4 mL) was added NaOH (159 mg, 3.98 mmol). The mixture was stirred at 15° C. for 2 hours. LCMS showed compound 2 was remained. The mixture was stirred for another 1 hour to form a yellow solution. TLC (eluent: EtOAc) showed the reaction was completed. Most of EtOH was removed under reduced pressure. The aqueous solution was diluted with H$_2$O (5 mL) and adjusted pH=3-4 by HCl (2 M, aq.), and then extracted with DCM (10 mL×3). The organic extract was dried over anhydrous Na$_2$SO$_4$, filtered and concentrated under reduced pressure to give A20 (230 mg, yield: 87.5%) as yellow gum.

General Procedure for Synthesis 6

To a mixture of A20 (240 mg, 1.21 mmol) and B1-1 (300 mg, 1.01 mmol) in DMF (6 mL) was added HATU (575 mg, 1.51 mmol) and TEA (306 mg, 3.03 mmol, 0.42 mL). The mixture was stirred at 15° C. for 17 hours. LCMS showed the reaction was not completed. The mixture was warmed up to 60° C. and stirred for another 3 hours. LCMS showed the reaction was not completed. The mixture was stirred at 60° C. for another 17 hours to form a brown mixture. LCMS showed the reaction was completed. The mixture was partitioned between EtOAc (20 mL) and H$_2$O (20 mL). The aqueous phase was extracted with EtOAc (20 mL×2). The combined organic extract was washed with brine (50 mL×3), dried over anhydrous Na2SO4, filtered and concentrated under reduced pressure to give a residue, which was purified by Combi flash (eluent: PE/EtOAc=1/1 to 7/3) and lyophilization to give impure product. The impure product was further purified by prep-TLC (eluent: PE/EtOAc=1/9) to give 50 mg of the product, which still contain impurity from LCMS. H NMR showed pure. Then the sample was further purified by prep-HPLC (0.05% NH4HCO3). Most of MeCN was removed by lyophilization to give 6 (25.4 mg, yield: 5.3%, LCMS: 100%) as a white powder.

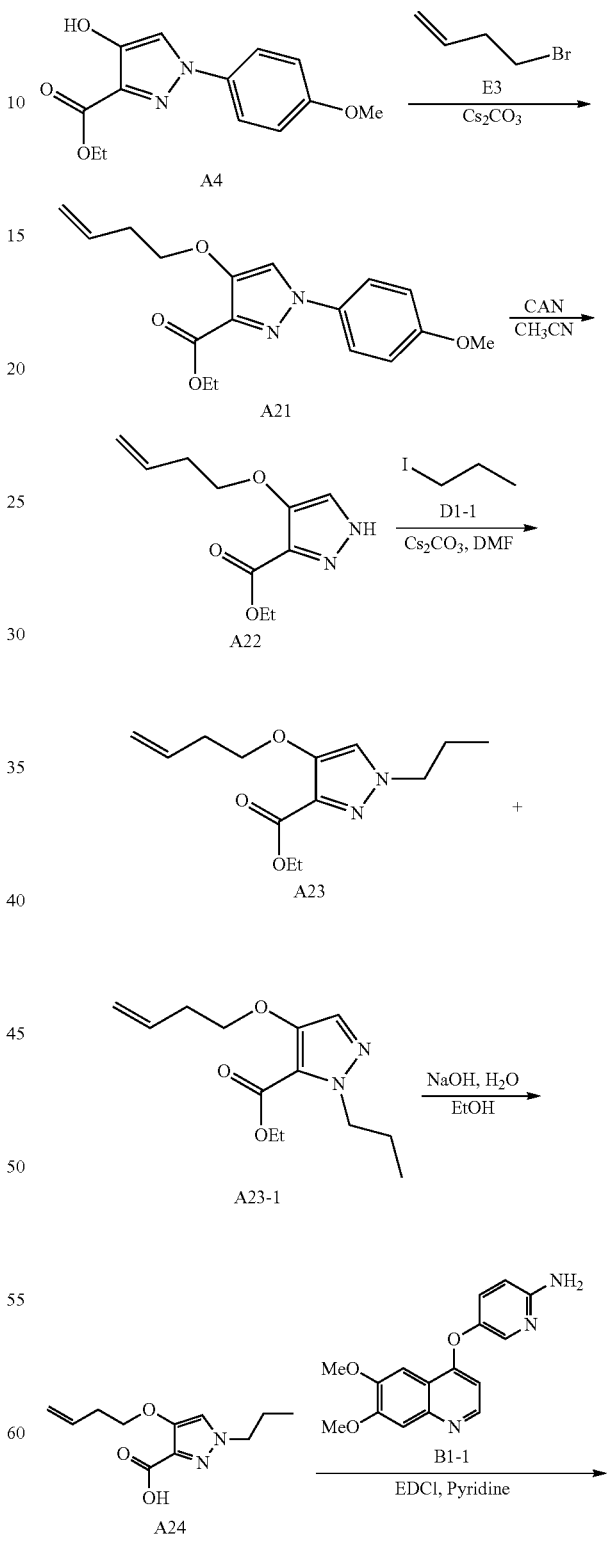

Scheme 6 - General synthesis for compound 15

-continued

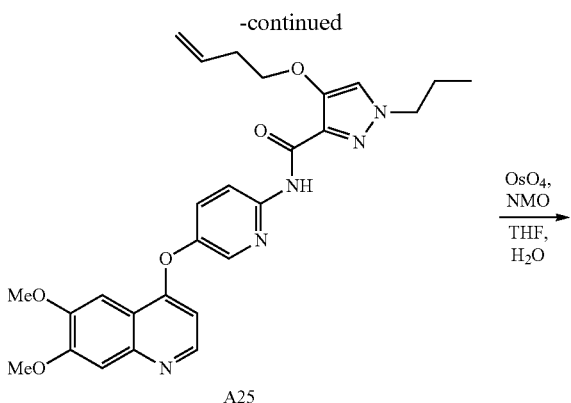

A25

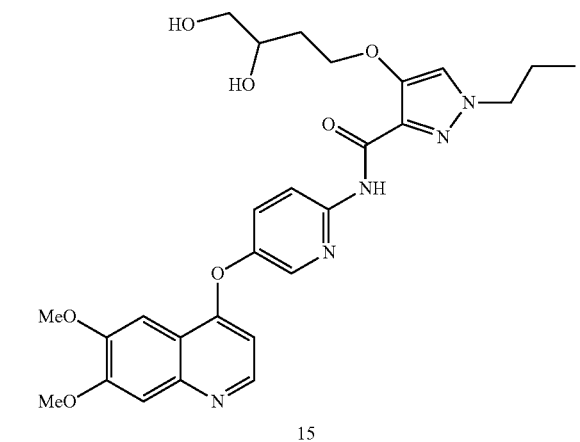 [SMILES: CCCn1cc(OCCC(O)CO)c(C(=O)Nc2ccc(Oc3ccnc4cc(OC)c(OC)cc34)cn2)n1]

15

General Procedure for Synthesis A21

To a mixture of A4 (25 g, 95.3 mmol) in DMF (150 mL) was added Cs$_2$CO$_3$ (77.7 g, 238 mmol), E3 (25 g, 185 mmol, 18.8 mL. The mixture was stirred at 25° C. for 17 hours to give a brown mixture. LCMS showed the reaction was not completed, and new 10 g of E3 was added into the above mixture, the mixture was stirred at 25° C. for 3 hours. LCMS (Rt=1.622 min) showed the reaction was completed. The mixture was filtered, the filter cake was washed with EtOAc (500 mL), the filtrate was washed with water (400 mL), the aqueous phase was extracted with EtOAc (150 mL×2), the combined extracts were washed with water (500 mL×3), brine (500 mL), dried over anhydrous Na$_2$SO$_4$, filtered and concentrated under reduced pressure to give A21 (18 g, 40.9 mmol) as brown oil. The crude product was used for next step without purification.

General Procedure for Synthesis A22

To a mixture of A21 (18 g, 56.9 mmol) in MeCN (150 mL) was added CAN (93.6 g, 170 mmol, 85.1 mL) in H$_2$O (150 mL) at 0-5° C. The mixture was stirred at 25° C. for 17 hours to give a brown mixture. LCMS (Rt=1.244 min) showed the reaction was completed. The mixture was partitioned between EtOAc (300 mL) and water (300 mL), the aqueous phase was extracted with EtOAc (150 mL×2), the combined extracts were washed with saturated NaHCO$_3$ (500 mL×3), brine (500 mL), dried over anhydrous Na$_2$SO$_4$, filtered and concentrated under reduced pressure to give a crude product, which was purified by Combi flash (PE/EA=10:1 to 2:1) to give A22 (1.4 g, crude) as brown gum.

General Procedure for Synthesis A23

To a solution of A22 (1.2 g, 5.71 mmol), D1-1 (1.46 g, 8.56 mmol) in DMF (15 mL) was added Cs$_2$CO$_3$ (3.72 g, 11.4 mmol). The reaction was stirred under N2 atmosphere at 20° C. for 17 hours to give a yellow suspension. LCMS (Rt=1.526 min) showed the reaction was completed. The reaction mixture was partitioned between EtOAc (300 mL) and H$_2$O (500 mL). The separated aqueous phase was extracted with EtOAc (100 mL). The combined organic layers were washed with H$_2$O (200 mL×2), brine (100 mL), dried over anhydrous Na$_2$SO$_4$, filtered and concentrated under reduced pressure to give a residue. The residue was purified by Combi flash (Petroleum ether/Ethyl acetate=1/0 to 3/1) to give 310 mg (yield: 19.4%, purity: 90%, more polar) of A23 as yellow brown oil, and 430 mg (yield: 29.8%, purity: 99.7%, less polar) of A23-1 as yellow oil.

General Procedure for Synthesis A24

To a solution of A23 (310 mg, 1.23 mmol) in MeOH (3 mL) was added a solution of NaOH (147 mg, 3.69 mmol) in H$_2$O (4 mL). The reaction was stirred at 20° C. for 2 hours to give a yellow solution. TLC showed the reaction was completed. The reaction mixture was adjusted to pH=5 with aqueous HCl solution (1 M). The mixture was extracted with EtOAc (100 mL×2). The organic layers were washed with brine (60 mL), dried over anhydrous Na2SO4, filtered and concentrated under reduced pressure to give 300 mg (crude) of A24 as yellow oil.

General Procedure for Synthesis A25

To a solution of A24 (150 mg, 0.669 mmol), B1-1 (199 mg, 0.669 mmol) in pyridine (3 mL) was added EDCI (192 mg, 1.00 mmol) under N$_2$ atmosphere. The reaction was stirred under N$_2$ atmosphere at 20° C. for 17 hours to give a yellow mixture. LCMS (Rt=1.459 min) showed the reaction was completed. The reaction mixture was partitioned between EtOAc (100 mL) and water (100 mL). The aqueous phase was extracted with EtOAc (60 mL×3). The combined extracts was washed with 0.5 M aqueous NaOH solution (70 mL), H$_2$O (70 mL), 0.5 M aqueous HCl solution (70 mL), H$_2$O (70 mL), brine (60 mL), dried over anhydrous Na$_2$SO$_4$, filtered and concentrate under reduced pressure to give 170 mg (yield: 50.5%) of A25 as a yellow gum.

General Procedure for Synthesis 15

To a solution of A25 (170 mg, 0.338 mmol) in THF (3 mL) was added NMO (79 mg, 0.675 mmol), OsO$_4$ (26 mg, 0.101 mmol) in H$_2$O (2 mL). The reaction was stirred at 20° C. for 17 hours to give a yellow mixture. LCMS showed the reaction was completed. The reaction mixture was added a solution of Na$_2$SO$_3$ (400 mg) in H$_2$O (4 mL), and stirred at 25° C. for 20 minutes. After filtration, the filtrate was partitioned between EtOAc (100 mL) and H$_2$O (20 mL). The aqueous layer was extracted with EtOAc (50 mL×2). The combined organic layers were washed with H$_2$O (40 mL×2), brine (40 mL), dried over anhydrous Na$_2$SO$_4$, filtered and concentrated under reduced pressure to give a residue. After prep-HPLC (0.01% NH$_4$HCO$_3$) purification, the eluent was lyophilized to give 47.9 mg (yield: 26.4%, purity: 100%) of 15 as a white powder.

Scheme 7 - General synthesis for compound 17 and 19

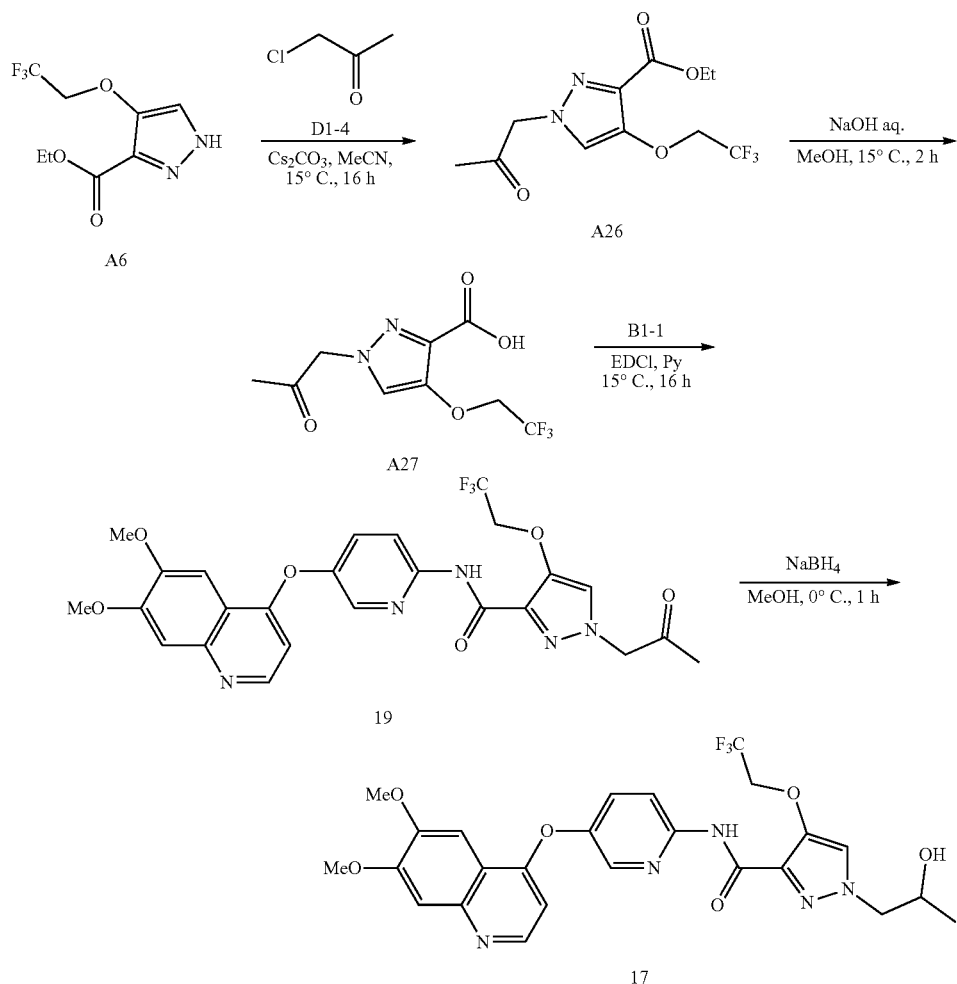

General Procedure for Synthesis A26

To a solution of A6 (0.4 g, 1.68 mmol, 1 eq) in CH3CN (20 mL) was added $Cs_2CO_3$ (821 mg, 2.52 mmol, 1.5 eq) and D1-4 (186 mg, 2.02 mmol, 1.2 eq). The resulting mixture was stirred at 15° C. for 16 hours to give yellow suspension. LCMS and TLC (PE/EtOAc=1/1) showed the reaction was completed. The reaction mixture was quenched by addition $H_2O$ (50 mL) and extracted with EtOAc (50 mL×2). The combined organic layers were washed with brine (10 mL×2), dried over $Na_2SO_4$, filtered and concentrated under reduced pressure to give a residue. The residue was purified by column chromatography ($SiO_2$, PE/EtOAc=1/1) to afford A26 (184 mg, 37.2% yield) as a white solid.

General Procedure for Synthesis A27

To a solution of A26 (184 mg, 0.625 mmol, 1 eq) in MeOH (12 mL) and $H_2O$ (2 mL) was added NaOH (75 mg, 1.88 mmol, 3 eq). The resulting mixture was stirred at 15° C. for 2 hours to give yellow solution. LCMS showed the reaction was completed. The reaction mixture was concentrated under reduced pressure to give a residue, then diluted with $H_2O$ (10 mL) and extracted with EtOAc (10 mL). The water layers were adjust to pH=4 with 0.5 M HCl (5 mL), then concentrated under reduced pressure to give A27 (300 mg, crude, contains much NaCl salt) as a white solid. The product was used for next step directly without further purification.

General Procedure for Synthesis 19

To a solution of B1-1 (160 mg, 0.538 mmol, 1 eq) in pyridine (3 mL) was added A27 (158 mg, 0.592 mmol, 1.1 eq) and EDCI (155 mg, 0.807 mmol, 1.5 eq). The resulting mixture was stirred at 15° C. for 16 hours to give yellow solution. LCMS showed the reaction was completed and desired product was formed. The reaction mixture was concentrated under reduced pressure to give a residue. The residue was added $H_2O$ (20 mL) and extracted with EtOAc (20 mL×2). The combined organic layers were washed with brine (10 mL×2), dried over $Na_2SO_4$, filtered and concentrated under reduced pressure to give a residue, which was purified by column chromatography ($SiO_2$, PE/EtOAc=0/1) to afford 19 (185 mg, 63% yield) as a white solid.

General Procedure for Synthesis 17

To a solution of 19 (185 mg, 0.339 mmol, 1 eq) in MeOH (5 mL) was added $NaBH_4$ (25.7 mg, 0.678 mmol, 2 eq) in one portion, the resulting mixture was stirred at 0° C. for 1 hour to give colorless solution. LCMS showed the reaction was completed. The reaction mixture was quenched by addition $H_2O$ (1 mL) and concentrated under reduced pressure to give a residue. Then the residue diluted with H₂O (20 mL) and extracted with EtOAc (20 mL×2). The combined organic layers were washed with brine (10 mL×2), dried over Na₂SO₄, filtered and concentrated under reduced pressure to give a residue. The residue was dissolved in CH₃CN (2 mL) and H₂O (5 mL), then lyophilized to afford the product. HNMR and HPLC showed the product with impurity, then the impure product was further purified by prep-HPLC (column: Waters Xbridge 150*255 mobile phase: [water (0.05% ammonia hydroxide v/v)-ACN]; B %: 40%-75%, 7 min). The fraction was concentrated and lyophilized to give 17 (89.9 mg, 48.4% yield, 100% purity) as a white solid.

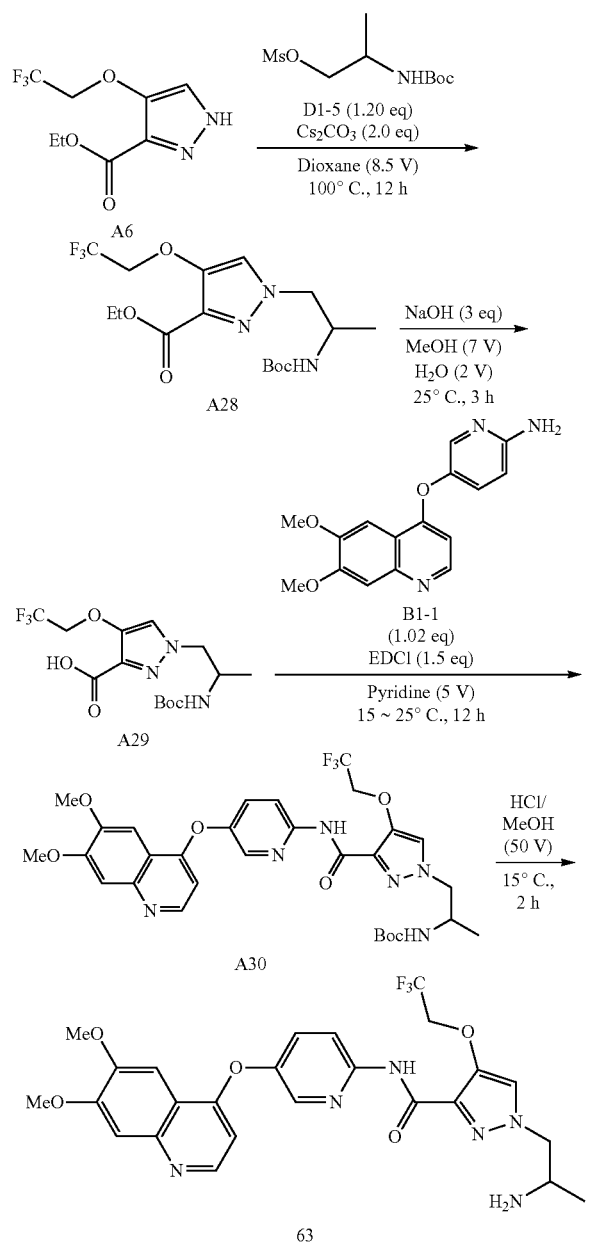

General Procedure for Synthesis A28

A mixture of D1-5 (2.55 g, 10.1 mmol, 564 uL, 1.20 eq), A6 (2.00 g, 8.40 mmol, 1.00 eq) and Cs₂CO₃ (5.47 g, 16.80 mmol, 2.00 eq) in dioxane (17.0 mL) was heated to 100° C. for 12 h. LCMS (A28: RT=1.24 min) showed compound A6 was consumed completely and one main peak with desired m/z was detected. The mixture was concentrated and the filtrate was concentrated. The residue was purified by column chromatography (SiO₂, petroleum ether/ethyl acetate=3/1 to 1/1) (TLC: petroleum ether/ethyl acetate=1/1, A28: Rf=0.35). A28 (1.8 g, 4.55 mmol, 54.2% yield) was obtained as yellow solid.

General Procedure for Synthesis A29

To a solution of compound A28 (1.80 g, 4.55 mmol, 1 eq) in MeOH (12.6 mL) was added dropwise a solution of NaOH (364 mg, 9.11 mmol, 2.0 eq) in H₂O (3.60 mL) at 15~25° C. The mixture was stirred at 15~25° C. for 12 h. TLC (petroleum ether/ethyl acetate=1/1, A28: Rf=0.35, A29: Rf=0.01) showed compound A28 was consumed completely. The mixture was concentrated. The pH value of the residue was adjusted to 5~6 with 4 M HCl (15.0 mL). The mixture was extracted with a solution of DCM and IPA (3/1, 20 mL×4). The combined organic layers were dried over anhydrous Na₂SO₄, filtered and concentrated. Compound A29 (1.39 g, 3.78 mmol, 83.1% yield) was obtained as yellow solid.

General Procedure for Synthesis A30

To a solution of compound A29 (200 mg, 544 umol, 1.00 eq) and compound B1-1 (165 mg, 555 umol, 1.02 eq) in pyridine (5 V) was added EDCI (156 mg, 816 umol, 1.50 eq). The mixture was stirred for at 15~25° C. 12 h under N₂. LCMS (A30: RT=1.04 min) showed compound A29 was consumed completely and one main peak with desired m/z was detected. The reaction mixture was concentrated. Compound A30 (200 mg, 309 umol, 56.8% yield) was obtained as brown oil.

General Procedure for Synthesis 63

A solution of Formula A30 (1.00 eq) in HCl/MeOH (50 mL) was stirred at 15° C. for 2 h. LCMS showed compound A30 was consumed completely and one main peak with desired m/z was detected. The mixture was concentrated under reduced pressure to give a residue. The crude product was purified by reversed-phase HPLC (0.1% HCl condition) (HPLC). Compound 63 (168 mg, 92.4% yield, 99.2% purity) was obtained as yellow solid.

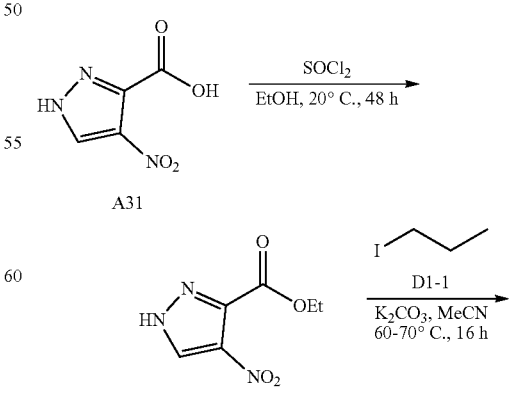

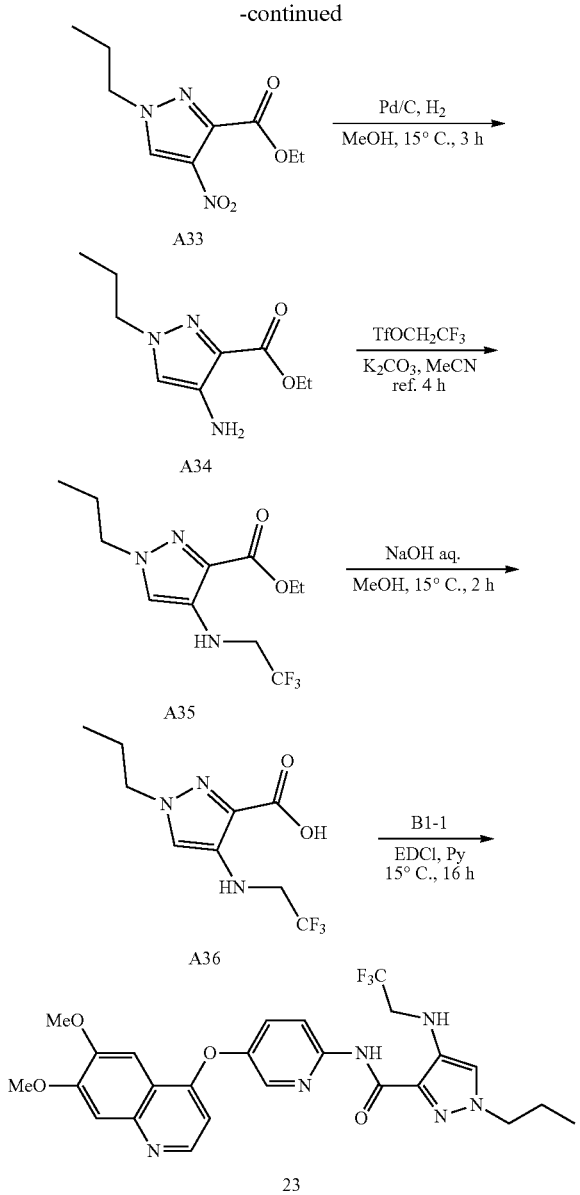

General Procedure for Synthesis A32

To a mixture of A31 (10 g, 63.7 mmol, 1 eq) in EtOH (150 mL) was added SOCl₂ (8.33 g, 70.0 mmol, 5.08 mL, 1.1 eq) slowly at 20° C. (r.t.) and the resulting mixture was stirred at 20° C. for 48 hours to afford a colorless solution. The reaction was not monitored by TLC or LCMS as it is a general reaction. The mixture was concentrated directly and then re-evaporated with 100 mL of toluene to afford A32 (12.4 g, crude) as a white solid.

General Procedure for Synthesis A33

To a mixture of compound A32 (12.4 g, 66.9 mmol, 1 eq) and K₂CO₃ (23.1 g, 167 mmol, 2.5 eq) in MeCN (120 mL) was added D1-1 (28.5 g, 167 mmol, 16.4 mL, 2.5 eq) and the resulting mixture was heated to 60-70° C. for 16 hours to afford a white mixture. TLC showed two new spots. The mixture was partitioned between EtOAc (100 mL) and H₂O (100 mL). The aqueous phase was extracted with EtOAc (100 mL×2). The combined organic extract was dried over anhydrous Na₂SO₄, filtered and concentrated under reduced pressure to give crude product. The crude product was purified by combi flash (PE/EtOAc=1/0 to 4/1 to 3/1) to afford compound A33 (9.5 g, 62.4% yield) as a yellow oil.

General Procedure for Synthesis A34

To a solution of A33 (2 g, 8.8 mmol, 1 eq) in MeOH (20 mL) was added wet Pd/C (200 mg, 10% purity) under N₂ atmosphere. The suspension was degassed under vacuum and purged with H₂ several times. The mixture was stirred under H2 (15 psi) at 15° C. for 3 hours to give black suspension. LCMS showed the reaction was completed. The reaction mixture was filtered over a pad of Celite and the filtrate was concentrated to obtain A34 (1.55 g, 88.8% yield, 99.4% purity) as a yellow oil.

General Procedure for Synthesis A35

To a solution of A34 (200 mg, 1.01 mmol, 1 eq) in CH₃CN (10 mL) was added 2,2,2-trifluoroethyl trifluoromethanesulfonate (353 mg, 1.52 mmol, 1.5 eq), K₂CO₃ (308 mg, 2.23 mmol, 2.2 eq) and Et₃N (154 mg, 1.52 mmol, 0.2 mL, 1.5 eq). The resulting mixture was heated at 90° C. (oil bath) and stirred for 4 hours to give yellow suspension. LCMS showed the reaction was completed, TLC (PE: EtOAc=3:1) showed part of the starting material remain, one new spot was formed. The reaction mixture was quenched by addition H₂O (30 mL) and extracted with EtOAc (30 mL×2). The combined organic layers were washed with brine (10 mL×2), dried over Na₂SO₄, filtered and concentrated under reduced pressure to give a residue. The residue was purified by column chromatography (SiO₂, PE:EtOAc=3:1) to give compound A35 (110 mg, 38.9% yield) as a white solid.

General Procedure for Synthesis A36

To a solution of A35 (110 mg, 0.394 mmol, 1 eq) in MeOH (8 mL) and H₂O (2 mL) was added NaOH (78.8 mg, 1.97 mmol, 5 eq). The resulting mixture was stirred at 15° C. for 2 hours to give colorless solution. LCMS showed the reaction was completed. The reaction mixture was adjust to pH~4 with 0.5 M HCl and stirred for 30 min, then concentrated under reduced pressure to give A36 (121 mg, crude) as a white solid.

General Procedure for Synthesis 23

To a solution of B1-1 (95 mg, 0.32 mmol, 1 eq) and A36 (88.3 mg, 0.35 mmol, 1.1 eq) in pyridine (2 mL) was added EDCI (92 mg, 0.48 mmol, 1.5 eq). The resulting mixture was stirred at 15° C. for 16 hours to give yellow suspension. LCMS showed most of the starting material was consumed and desired product was formed. The reaction mixture was concentrated under reduced pressure to give a residue, and then diluted with H₂O (20 mL), extracted with EtOAc (20 mL×2). The combined organic layers were washed with brine (10 mL×2), dried over Na₂SO₄, filtered and concentrated under reduced pressure to give a residue. The residue was purified by column chromatography (SiO₂, PE:EtOAc=1:1) to give product, which was dissolved in CH₃CN (2 mL) and H₂O (3 mL) and lyophilized to give 23 (56.5 mg, 33.3% yield, 100% purity) as a white powder.

Scheme 10 - General synthesis for compound 34

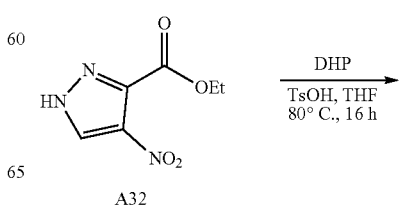

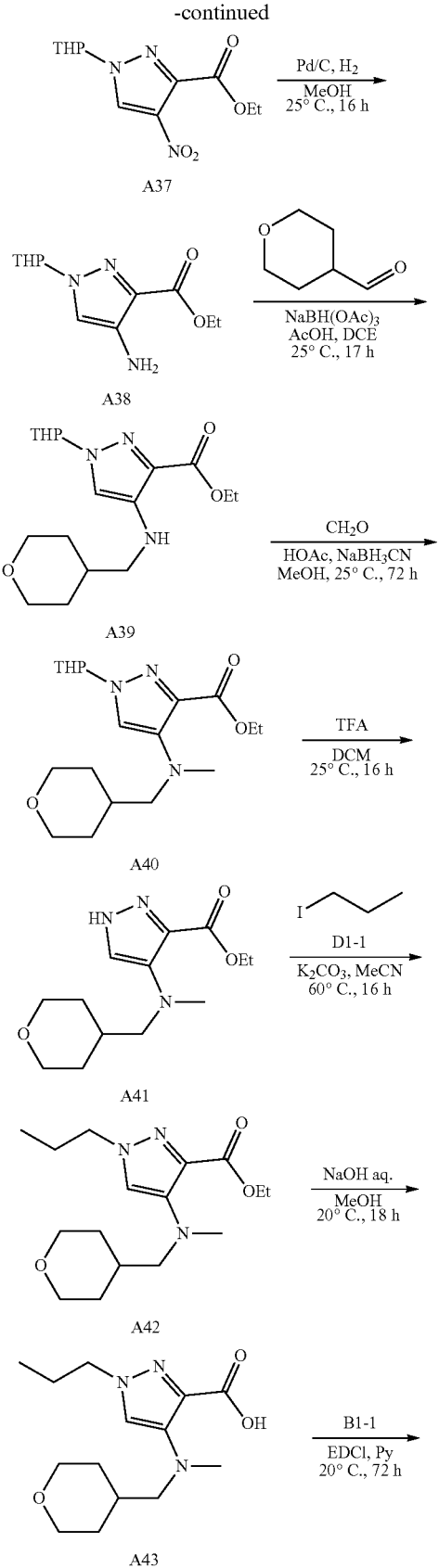

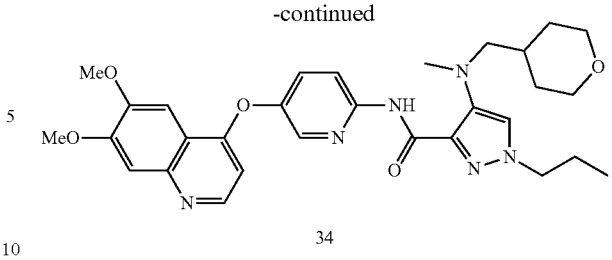

34

General Procedure for Synthesis A37

To a mixture of A32 (5.45 g, 29.4 mmol, 1 eq) and 3,4-dihydro-2H-pyran (7.43 g, 88.3 mmol, 8.07 mL, 3 eq) in THF (40 mL) was added TsOH (507 mg, 2.94 mmol, 0.1 eq). The resulting mixture was stirred at 80° C. for 16 hours to give a yellow solution. TLC (PE/EtOAc=3/1) showed the reaction was completed. The reaction mixture was quenched with $H_2O$ (100 mL) and extracted with EtOAc (50 mL×2). The organic layer were washed with brine (20 mL×3), dried over anhydrous $Na_2SO_4$, filtered and concentrated under reduced pressure to give a residue. The residue was purified by silica gel column chromatography ($SiO_2$, PE/EtOAc=3:1) to give 7.01 g (yield: 88.4%) of A37 as a yellow oil.

General Procedure for Synthesis A38

To a solution of A37 (7.01 g, 26.0 mmol, 1 eq) in MeOH (70 mL) was added wet Pd/C (1.5 g, 10% purity, 50% in water) under $N_2$. The suspension was degassed under vacuum and purged with $H_2$ several times. The mixture was stirred under $H_2$ (15 psi) at 25° C. for 16 hours to give a black suspension. TLC (PE/EtOAc=2/1) showed the reaction was completed. The reaction mixture was filtered by a pad of celite and the filtrate was concentrated to give 5.84 g (yield: 93.7%) of A38 as a purple oil.

General Procedure for Synthesis A39

To a mixture of A38 (4.20 g, 17.6 mmol, 1 eq) in DCE (25 mL), was added tetrahydropyran-4-carbaldehyde (2.20 g, 19.3 mmol, 1.1 eq), NaBH(OAc)$_3$ (9.30 g, 43.9 mmol, 2.5 eq) and HOAc (1.05 g, 17.6 mmol, 1.0 mL, 1 eq). The resulting mixture was stirred at 25° C. for 17 hours to give a purple suspension. TLC (PE/EtOAc=2/1) showed the reaction was completed. The mixture was concentrated under reduced pressure to give 5.53 g (crude) of A39 as purple oil.

General Procedure for Synthesis A40

To a solution of A39 (5.53 g, 16.4 mmol, 1 eq) in MeOH (50 mL), was added polyformaldehyde (2.46 g, 16.39 mmol), HOAc (984 mg, 16.4 mmol, 937 uL, 1 eq) and NaBH$_3$CN (1.03 g, 16.4 mmol, 1 eq). The resulting mixture was stirred at 25° C. for 72 hours to give a light red solution. TLC (PE/EtOAc=1/1) showed the reaction was completed. The reaction mixture was concentrated under reduced pressure to give a residue. The residue was dissolved in EtOAc (50 mL). Sat. Na$_2$CO$_3$ (40 mL) was added to the solution. The aqueous was extracted with EtOAc (20 mL). The combined organic layer were washed with brine (15 mL×2), dried over anhydrous Na$_2$SO$_4$, filtered and concentrated under reduced pressure to give 5.38 g (crude) of A40 as brown oil.

General Procedure for Synthesis A41

To a solution of A40 (5.38 g, 15.3 mmol, 1 eq) in DCM (90 mL) was added TFA (46.2 g, 405 mmol, 30 mL, 26.5 eq). The resulting mixture was stirred at 25° C. for 16 hours to give a brown mixture. TLC (PE/EtOAc=1/1) showed a little starting material was still remained. LCMS (Rt=0.665 min) showed 83% of desired compound MS. The reaction mixture was concentrated under reduced pressure. The residue was dissolved in EtOAc (50 mL). Sat. Na$_2$CO$_3$ (100 mL) was added to the solution. The aqueous phase was extracted with EtOAc (30 mL). The combined organic layer extract was washed with brine (20 mL×3), dried over anhydrous Na$_2$SO$_4$, filtered and concentrated under reduced pressure to give a residue. The residue was purified by Combi flash (PE/EtOAc=1/1) to give 1.98 g (yield: 48.4%) of A41 as a brown gum.

General Procedure for Synthesis A42

To a solution of A41 (520 mg, 1.95 mmol, 1 eq) and D1-1 (827 mg, 4.86 mmol, 475 uL, 2.5 eq) in MeCN (10 mL) was added K$_2$CO$_3$ (672 mg, 4.86 mmol, 2.5 eq) at 25° C., then the mixture was stirred at 60° C. for 16 hours to give an off-white suspension. TLC (PE/EtOAc=1/1) showed two new spots. LCMS (Rt=0.711 min) showed the reaction was completed. The mixture was concentrated in vacuum, and the residue was quenched by water (30 mL). The resulting solution was extracted with EtOAc (20 mL×3). The combined organic layers were washed with brine (10 mL×2), dried over anhydrous Na$_2$SO$_4$, filtered and concentrated in vacuum to give a residue. The residue was purified by Combi flash (PE/EtOAc=3/1 to 2/1 to 1/1) to give 280 mg (yield: 46.5%) of A42 as a yellow oil.

General Procedure for Synthesis A43

To a solution of A42 (280 mg, 0.905 mmol, 1 eq) in MeOH (4 mL), was added NaOH (3 M, 603 uL, 2 eq) in H$_2$O (0.6 mL), and the mixture was stirred at 20° C. for 18 hours to give a colorless mixture. TLC (PE/EtOAc=1/1) showed a new spot. LCMS (Rt=0.518 min) showed the reaction was completed. The reaction mixture was concentrated under reduced pressure to give a residue. The residue was quenched by addition H$_2$O (10 mL), and then extracted with EtOAc (20 mL). Then 2 N hydrochloric acid was added to that aqueous phase to adjust pH=1 by aq. HCl. The aqueous phase was extracted with DCM (10 mL×8). The combined organic layers were washed with brine (10 mL×3), dried over anhydrous Na$_2$SO$_4$, filtered and concentrated in vacuum to give 90 mg (crude) of A43 as a light yellow solid. LCMS showed 81% purity. The aqueous phase still contained product from LCMS. Then toluene (10 mL×5) was added to the aqueous phase. The aqueous phase was concentrated under reduced pressure to give 130 mg (crude, contain NaCl salt) of A43 as a white solid. LCMS showed 98% of desired MS value.

General Procedure for Synthesis 34

To a solution of A43 (130 mg, 0.457 mmol, 3 eq) and B1-1 (45 mg, 0.15 mmol, 1 eq) in pyridine (1.5 mL), was added EDCI (44 mg, 0.23 mmol, 1.5 eq). The resulting mixture was stirred at 20° C. for 16 hours to give a yellow mixture. TLC (EtOAc) showed a new spot. LCMS showed 4.9% of desired compound MS. The mixture was stirred at 20° C. for another 8 hours. Then additional EDCI (44 mg, 0.23 mmol, 1.5 eq) was added. The mixture was stirred at 20° C. for 48 hours. LCMS (Rt=0.773 min) showed 7.2% of desired compound MS. The mixture was partitioned between DCM (50 mL) and water (30 mL). The aqueous phase was extracted with DCM (20 mL×3). The combined extracts were washed with saturated brine (10 mL×2), dried over anhydrous Na$_2$SO$_4$, filtered and concentrated under reduced pressure to give a residue. The residue was purified by prep-TLC [(PE/EtOAc=1/1)/(DCM/MeOH=10/1)=1/1] to give 34 (3.7 mg, yield: 4.2%, purity: 97.5%) as a white powder.

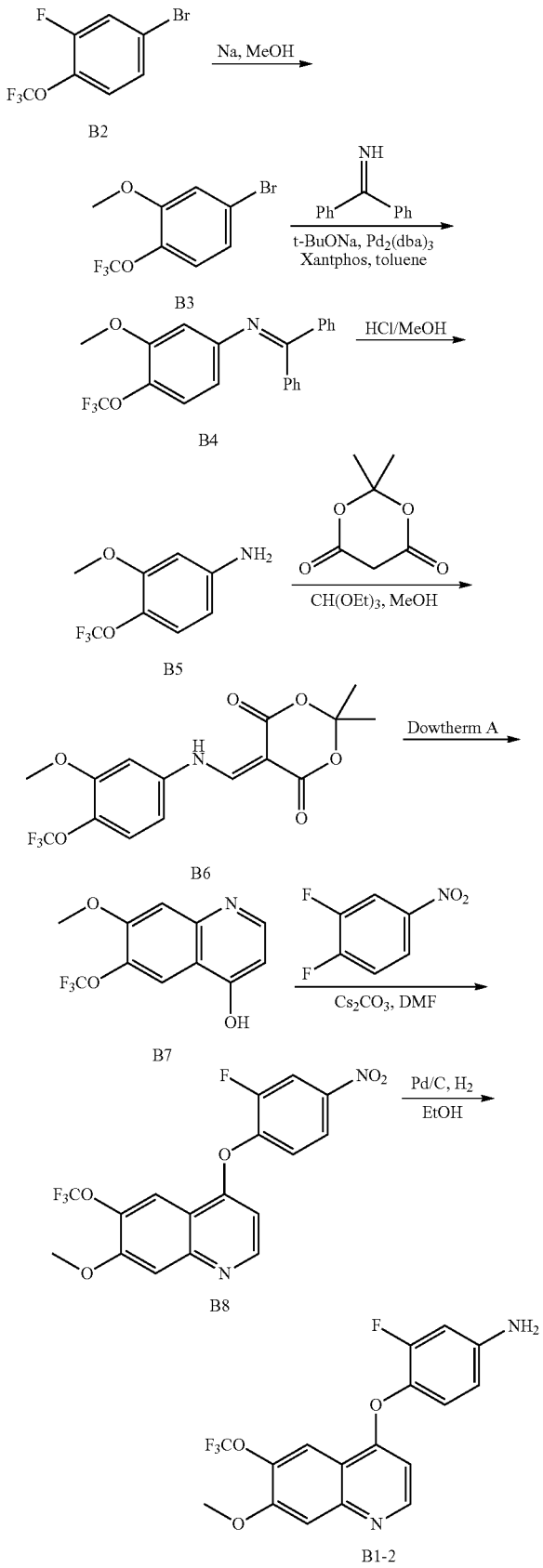

Scheme 11 - General synthesis for compound 35

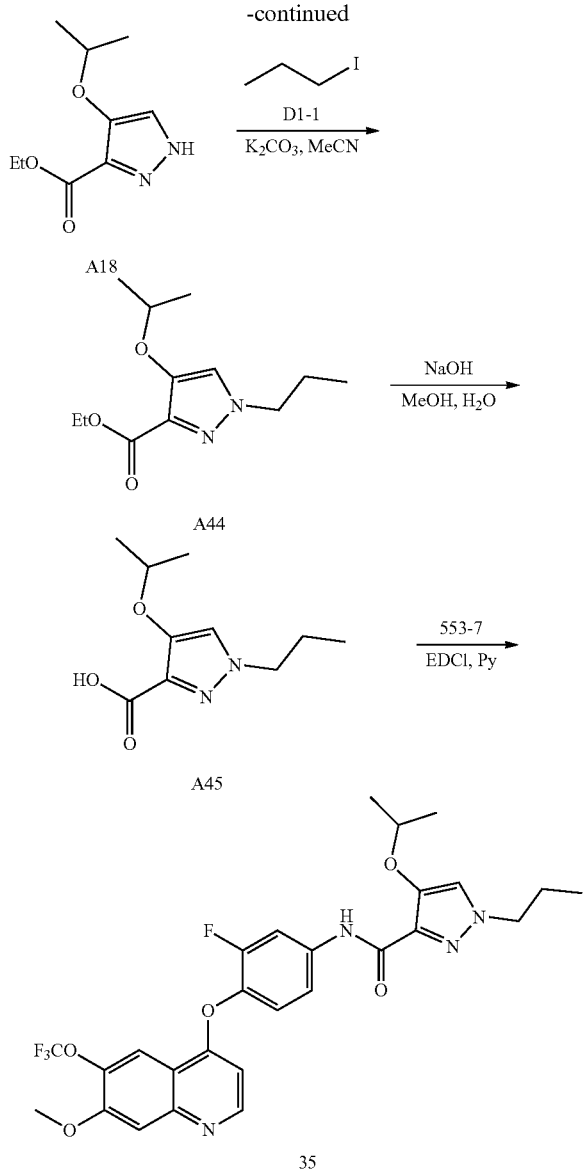

General Procedure for Synthesis B3

A suspension of Na (2.66 g, 116 mmol, 3 eq) in MeOH (40 mL) was stirred at 25° C. for 30 min. Then B2 (10 g, 38.6 mmol, 1 eq) was added into the above mixture. The reaction was stirred at 80° C. for 17 hours to give a yellow suspension. TLC showed starting material was not consumed completely. The mixture was cooled to room temperature. The mixture was adjusted pH to 1-2 by aqueous HCl (4 M), extracted with EtOAc (200 mL×2). The combined extract was washed with brine (200 mL×2), dried over anhydrous $Na_2SO_4$ and filtered, then concentrated under reduced pressure to give B3 (8.3 g, yield: 79%) as yellow oil.

General Procedure for Synthesis B4

To a solution of B3 (7.1 g, 26.2 mmol, 1 eq) and diphenylmethanimine (5.7 g, 31.4 mmol, 1.2 eq) in toluene (150 mL) was added $Pd_2(dba)_3$ (599 mg, 0.655 mmol, 0.025 eq), BINAP (1.22 g, 1.96 mmol, 0.075 eq) and t-BuONa (3.52 g, 36.7 mmol, 1.4 eq) under $N_2$. The resulting mixture was heated at 90° C. and stirred for 12 hours to give red solution. TLC showed desired product was formed. The reaction mixture was quenched by addition $H_2O$ (150 mL) and extracted with EtOAc (150 mL×2). The combined organic layers were washed with brine (50 mL×2), dried over $Na_2SO_4$, filtered and concentrated under reduced pressure to give a residue. The residue was purified by column chromatography ($SiO_2$, PE/EtOAc=20:1) to obtain 6 g crude product, which was triturated with PE/EtOAc=40 mL/2 mL to give 4.65 g of B4 as a light yellow solid.

General Procedure for Synthesis B5

To a solution of B4 (5.4 g, 14.5 mmol, 1 eq) in HO/MeOH (4M) (20 mL) was stirred at 20° C. for 30 min to give white suspension. LCMS showed the reaction was completed. The reaction mixture was concentrated under reduced pressure to give a residue. Then diluted with $H_2O$ (50 mL) and basified with sat. $NaHCO_3$ solution to pH=~9, extracted with EtOAc (50 mL). The combined organic layers were washed with brine (10 mL), dried over $Na_2SO_4$, filtered and concentrated under reduced pressure to give a residue. The residue was purified by column chromatography ($SiO_2$, PE/EtOAc=3/1) to give B5 (2.5 g, yield: 83%) as a yellow oil.

General Procedure for Synthesis B6

A mixture of 2,2-dimethyl-1,3-dioxane-4,6-dione (1.83 g, 12.7 mmol, 1.05 eq) and diethoxymethoxyethane (1.97 g, 13.3 mmol, 1.1 eq) was heated at 50° C. and stirred for 1.5 hours. Then a solution of B5 (2.5 g, 12.1 mmol, 1 eq) in MeOH (10 mL) was added to the mixture. The mixture was stirred at 50° C. for 1 hour to give yellow suspension. The mixture was cooled to room temperature and added EtOH (20 mL). The resulting mixture was stirred at 0° C. for 30 min. White powder was observed. The mixture was filtered. The filter cake was washed with EtOH (20 mL) and dried over high vacuum to give 1.3 g as a white solid, However LCMS and H NMR showed it is not the desired product. The filtrate was extracted with EtOAc (50 mL). The combined organic layers were washed with brine (20 mL), dried over $Na_2SO_4$, filtered and concentrated under reduced pressure to give a residue. The residue was purified by silica column (PE/EtOAc=3/1) to obtain B6 (550 mg, crude) as a yellow solid. H NMR showed the mixture of desired product and B5.

General Procedure for Synthesis B7

To a solution of B6 (550 mg, 1.00 mmol, 1 eq) in Dowtherm A (4 mL) was heated at 210° C. and stirred for 1 hour under $N_2$ to give brown solution. TLC showed the reaction was completed. The reaction was cooled to room temperature and quenched by addition $H_2O$ (20 mL) and extracted with EtOAc (20 mL×2). The combined organic layers were washed with brine (10 mL×2), dried over $Na_2SO_4$, filtered and concentrated under reduced pressure to give a residue. The residue was purified by column chromatography (SiO2, DCM:MeOH=10:1) to give B7 (30 mg, yield: 11%, purity: 98%) as a yellow solid.

General Procedure for Synthesis B8

To a solution of B7 (30 mg, 0.116 mmol, 1 eq) and 1,2-difluoro-4-nitro-benzene (18.4 mg, 0.116 mmol, 1 eq) in DMF (1 mL) was added $Cs_2CO_3$ (56.6 mg, 0.174 mmol, 1.5 eq). The resulting mixture was heated at 40° C. and stirred for 2 hrs to give red solution. LCMS showed the reaction was completed. The reaction was quenched by addition $H_2O$ (20 mL) and extracted with EtOAc (20 mL×2). The combined organic layers were washed with brine (10 mL×2), dried over $Na_2SO_4$, filtered and concentrated under reduced pressure to give a residue. The residue was purified by prep-TLC (PE:EtOAc=1:1) to give B8 (30 mg, yield: 65%) as a yellow solid.

General Procedure for Synthesis B1-2

To a solution of B8 (30 mg, 0.075 mmol, 1 eq) in EtOH (5 mL) was added Pd/C (wet) in 50% water (20 mg, 10% purity) under $N_2$. The suspension was degassed under vacuum and purged with $H_2$ several times. The mixture was stirred under $H_2$ (15 psi) at 20° C. for 12 hours to give black suspension. LCMS and TLC showed part of the starting material remain and one new spot was formed. The reaction mixture was filtered and the filter was concentrated. The residue was purified by prep-TLC (PE:EtOAc=1:1) to give B1-2 (20 mg, yield: 72%, purity: 100%) as an off-white solid.

General Procedure for Synthesis A44

To a suspension of A18 (1.43 g, 7.21 mmol, 1 eq), $K_2CO_3$ (2.49 g, 18 mmol, 2.5 eq) in MeCN (143 mL) was added D1-1 (3.07 g, 18 mmol, 2.5 eq) at 25° C. The reaction was stirred at 60° C. for 17 hours to give a yellow suspension. LCMS showed the reaction was completed. The reaction mixture was worked up after combining with the pilot reaction from 100 mg of A18. The reaction mixture was partitioned between EtOAc (200 mL) and $H_2O$ (200 mL). The organic layer was washed with brine (200 mL×2), dried over anhydrous $Na_2SO_4$, filtered and concentrated under reduced pressure to give black oil. The crude product was purified by combi flash (EtOAc:PE=0:1 to 1:4) to give A44 (0.8 g, yield: 43%, purity: 95%) as yellow oil.

General Procedure for Synthesis A45

To a solution of A44 (0.8 g, 3.33 mmol, 1 eq) in MeOH (10 mL) was added NaOH (400 mg, 9.99 mmol, 3 eq) in $H_2O$ (3 mL). The reaction was stirred at 25° C. for 1.5 hours to give a yellow solution. LCMS showed the starting material was not consumed completely. The reaction was stirred at 25° C. for 17 hours to give a yellow solution. LCMS showed the starting material was consumed completely. The reaction was adjusted to pH=4, and extracted with EtOAc (200 mL). The organic layer was washed with brine (150 mL), dried over anhydrous $Na_2SO_4$, filtered and concentrated under reduced pressure to give A45 (710 mg, crude) as yellow oil.

General Procedure for Synthesis 35

To a solution of B1-2 (20 mg, 1 eq) and A45 (17.3 mg, 0.081 mmol, 1.5 eq) in pyridine (0.5 mL) was added EDCI (15.6 mg, 0.081 mmol, 1.5 eq). The resulting mixture was stirred at 20° C. for 12 hrs to give yellow solution. LCMS showed the reaction was completed. The reaction mixture concentrated under reduced pressure to give a residue. The residue was purified by prep-HPLC (column: Waters Xbridge 150*50 10 u; mobile phase: [water (0.05% ammonia hydroxide v/v)-ACN]; B %: 55%-85%, 7.8 min), then concentrated and lyophilized to give 35 (11.8 mg, yield: 38%, purity: 100%) as a white powder.

Scheme 12 - General synthesis for compound 44

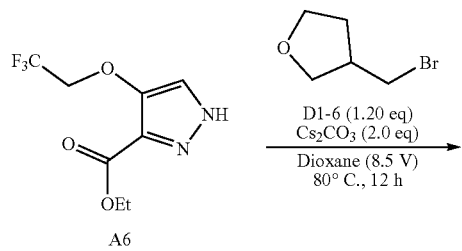

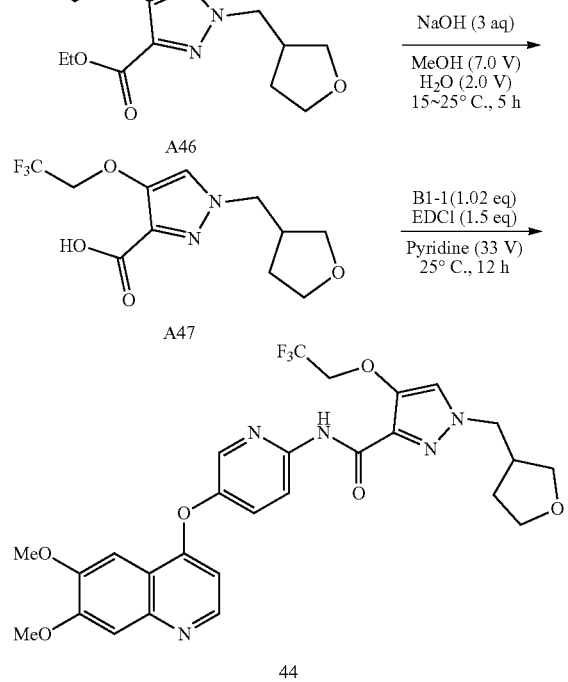

General Procedure for Synthesis A46

A mixture of D1-6 (831.50 mg, 5.04 mmol, 1.20 eq), A6 (1.00 g, 4.20 mmol, 1.00 eq) and $Cs_2CO_3$ (2.74 g, 8.40 mmol, 2.00 eq) in dioxane (8.5 mL) was heated to 80° C. for 12 h. TLC (petroleum ether/ethyl acetate=1/1, A6: Rf=0.42, A46: Rf=0.36) showed A6 was consumed. The mixture was concentrated and the filtrate was concentrated. The residue was purified by column chromatography ($SiO_2$, petroleum ether/ethyl acetate=3/1 to 1/1) (TLC: petroleum ether/ethyl acetate=1/1, A46: Rf=0.36). A46 (0.82 g, 2.54 mmol, 60.60% yield) was obtained as yellow oil.

General Procedure for Synthesis A47

To a solution of A46 (0.82 g, 2.54 mmol, 1.00 eq) in MeOH (5.7 mL) was added dropwise a solution of NaOH (305 mg, 7.63 mmol, 3.00 eq) in $H_2O$ (1.64 mL) at 15~25° C. The mixture was stirred at 15~25° C. for 5 h. TLC (petroleum ether/ethyl acetate=1/1, A46: Rf=0.34, A47: Rf=0.01) showed A46 was consumed completely. The mixture was concentrated. The pH value of the residue was adjusted to 5~6 with 4 M HCl (15.0 mL). The mixture was extracted with a solution of DCM and IPA (3/1, 20 mL×4). The combined organic layers were dried over anhydrous $Na_2SO_4$, filtered and concentrated. A47 (0.68 g, 2.31 mmol, 90.83% yield) was obtained as yellow oil.

General Procedure for Synthesis 44

To a solution of A47 (0.15 g, 510 umol, 1.00 eq) in pyridine (5 mL) was added EDCI (147 mg, 765 umol, 1.50 eq) stir for 15 min. The B1-1 (155 mg, 520 umol, 1.02 eq) was added the mixture. The mixture was stirred at 25° C. for 12 h. LC-MS (44: RT=0.84 min) showed A47 was consumed completely and one main peak with desired mass was detected. HPLC (ET24988-44-P1A, compound 44: RT=2.55 min) showed one main peak was detected. The mixture was concentrated under reduced pressure to give a residue. The residue was purified by reversed-phase HPLC (0.1% HCl condition). 44 (0.08 g, 134 umol, 26.3% yield, 96.2% purity) was obtained as a yellow solid.

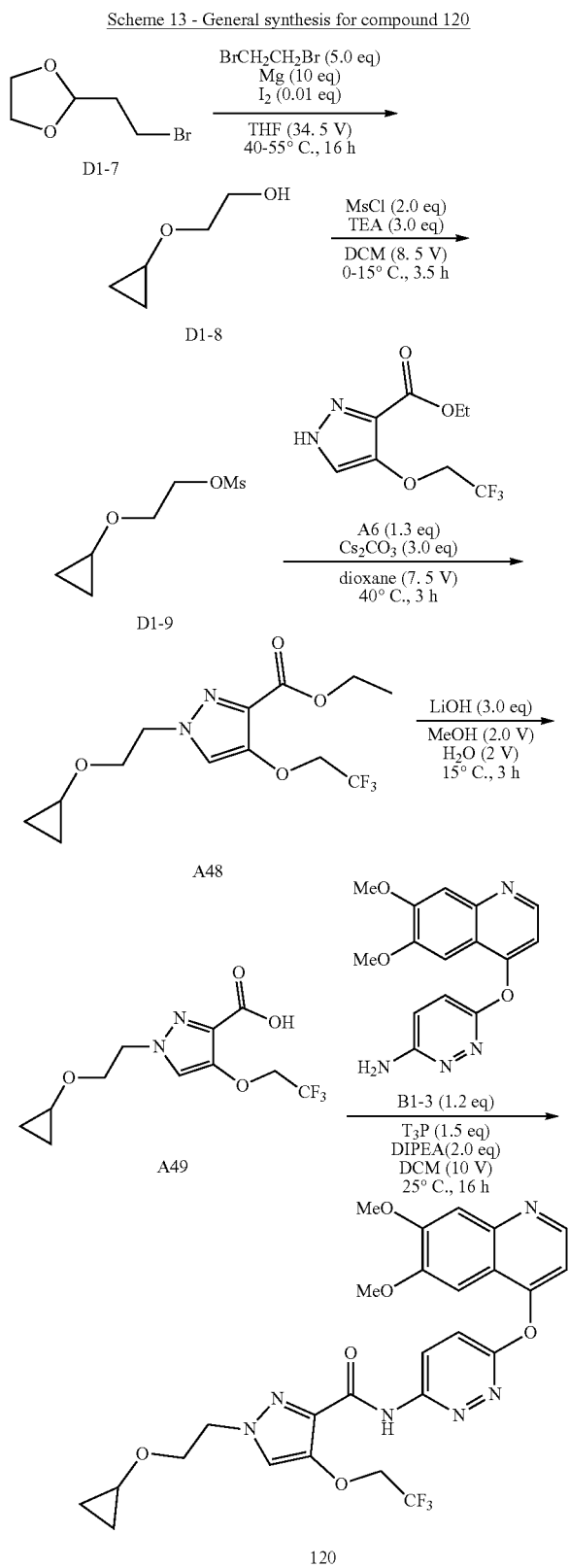

Scheme 13 - General synthesis for compound 120

General Procedure for Synthesis D1-8

To a suspension of Mg (67.1 g, 2.76 mol, 10 eq) and $I_2$ (701 mg, 2.76 mmol, 0.01 eq) in THF (350 mL) was added slowly 1,2-dibromoethane (259 g, 1.38 mol, 5.0 eq) in THF (1 L) slowly at a rate as to keep the internal temperature between 40-55° C. After the addition, a solution of D1-7 (50 g, 276 mmol, 1 eq) in THF (375 mL) was added drop-wise. The reaction mixture was kept at 40-55° C. for 16 h. TLC (petroleum ether/ethyl acetate=2/1, D1-8: Rf=0.27) indicated D1-7 was consumed completely and many new spots formed. The reaction was quenched with saturated $NH_4Cl$ (3 L) slowly at 0° C. The mixture was extracted and the aqueous phase was extracted with DCM/i-PrOH (v/v=10/1, 2.5 L and 1 L). The combined organic layers were dried over $Na_2SO_4$, filtered and concentrated. The residue was purified by column chromatography ($SiO_2$, petroleum ether/ethyl acetate=10/1 to 3/1). D1-8 (14 g, 137 mmol, 49.6% yield) was obtained as yellow oil, which was used into next step without further purification.

General Procedure for Synthesis D1-9

To the solution of D1-8 (7 g, 68.5 mmol, 1.0 eq) and TEA (20.8 g, 206 mmol, 3.0 eq) in DCM (60 mL) was added MsCl (15.7 g, 137.1 mmol, 2.0 eq) slowly drop-wise at 0° C. for 0.5 h. The mixture was stirred at 25° C. for 3 h. TLC (petroleum ether/ethyl acetate=2/1, PMA, D1-8: Rf=0.27) showed D1-8 was consumed completely. The reaction mixture was quenched by addition of aqueous $NH_4Cl$ (5 mL), extracted with $CH_2Cl_2$ (30 mL, 15 mL). The organic phases were combined and dried over $Na_2SO_4$, filtered and concentrated. The residue was purified by column chromatography ($SiO_2$, petroleum ether/ethyl acetate=20/1 to 1/1). D1-9 (11.5 g, crude) was obtained as red oil, which was used into next step without further purification.

General Procedure for Synthesis A48

To the solution of D1-9 (21.3 g, 89.43 mmol, 1.0 eq) and $Cs_2CO_3$ (87.42 g, 268.30 mmol, 3.0 eq) in dioxane (150 mL) was added A6 (20.95 g, 116.26 mmol, 1.3 eq) at 15° C. The mixture was stirred at 40° C. for 3 h. TLC (petroleum ether/ethyl acetate=1/1, A47: Rf=0.3) showed D1-9 was consumed completely. The reaction mixture was added water (5 mL) and extracted with EtOAc (5 mL). The residue was purified by column chromatography ($SiO_2$, petroleum ether/ethyl acetate=20/1 to 3/1). A48 (15.2 g, crude) was obtained as red oil, which was used into the next step without further purification.

General Procedure for Synthesis A49

To the solution of A48 (15.5 g, 48.1 mmol, 1.0 eq) in MeOH (30 mL) and $H_2O$ (30 mL) was added $LiOH \cdot H_2O$ (6.05 g, 144 mmol, 3 eq) at 15° C. The mixture was stirred at 15° C. for 3 h. TLC (petroleum ether/ethyl acetate=1/1, A47: Rf=0.3) showed A47 was consumed completely. The reaction mixture was concentrated to remove MeOH. The pH value was adjusted to 2-3 with HCl solution (1M, 18 mL). The mixture was extracted with DCM (100 mL). The organic phase was dried over $Na_2SO_4$. The mixture was filtered and the filtrate was concentrated to get product. A49 (14 g, 47.6 mmol, 98.9% yield) was obtained as a light red solid, which was used into next step without further purification.

General Procedure for Synthesis 120

To the solution of A49 (200 mg, 679 umol, 1 eq) in DCM (2 mL) was added B1-3 (243 mg, 815 umol, 1.2 eq) and DIPEA (175 mg, 1.36 mmol, 2.0 eq) at 25° C. To the mixture was added T3P (648 mg, 1.02 mmol, 50% purity in EtOAc solution, 1.5 eq) at 15° C. The mixture was stirred at 25° C. for 16 h. LCMS (120: RT=1.01 min) showed that 12.9% of 120 was detected. The mixture was washed with water (2 mL). The organic phase was concentrated to get a residue. The residue was purified by prep-HPLC (column: Waters Xbridge Prep OBD C18 150*40 mm*10 um; mobile phase: [water (10 mM NH4HCO3)-ACN]; B %: 30%-50%, 8 min).

120 (40 mg, 68.7 umol, 10.1% yield, 98.6% purity) was obtained as an off-white solid.

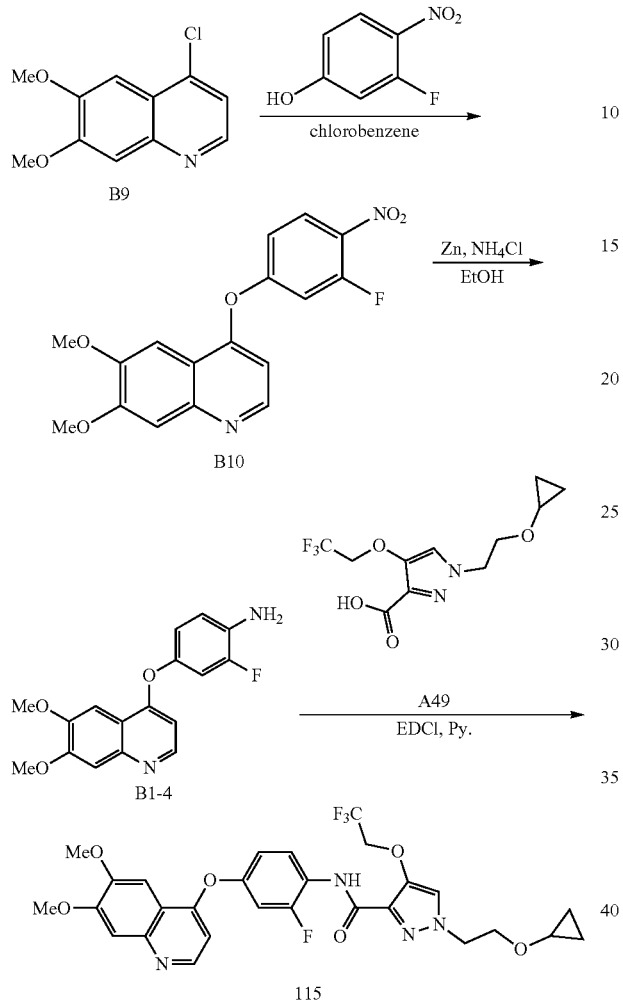

General Procedure for Synthesis B10

A mixture of B9 (500 mg, 2.24 mmol, 1 eq) and 3-fluoro-4-nitro-phenol (703 mg, 4.47 mmol, 2 eq) in chlorobenzene (10 mL) was stirred at 131° C. for 12 hours to give an off-white suspension. LCMS (Rt=1.045-1.107 min) showed ~25% of 545-1 and ~75% of desired MS value. The reaction mixture were filtered, filtrate cake was washed with toluene (10 mL) and dried under vacuum to give a crude compound. The crude compound was basified with 10% aq·NaOH, and the suspension was stirred for 1 hour at room temperature. The mixture was filtered, filtrate cake was dried in high vacuum to give B10 (300 mg, 37.6% yield, 96.5% purity) as a yellow solid.

General Procedure for Synthesis B1-4

To a mixture of B10 (300 mg, 0.871 mmol, 1 eq) and NH$_4$Cl (466 mg, 8.71 mmol, 10 eq) in EtOH (10 mL) was added Zn (570 mg, 8.71 mmol, 10 eq). The reaction mixture was stirred at 20° C. for 12 hours to give a black mixture. LCMS (Rt=0.997 min) showed the reaction was completed. The mixture was filtered and the filtrate was concentrated under reduced pressure to give B1-4 (270 mg, 99% yield) as a yellow solid. The crude product was used for the next step without further purification.

General Procedure for Synthesis 115

To a solution of compound A49 (1.00 eq) and B1-4 (1.02 eq) in pyridine (5 V) was added EDCI (1.50 eq) at 15~25° C. under N$_2$. The mixture was stirred for at 15~25° C. 12 h under N$_2$. LCMS showed A49 was consumed completely and one main peak with desired m/z was detected. The mixture was concentrated under reduced pressure to give a residue. The crude product was purified by reversed-phase HPLC. 115 (128 mg, 60.7% yield, 95.6% purity) was obtained as a white solid.

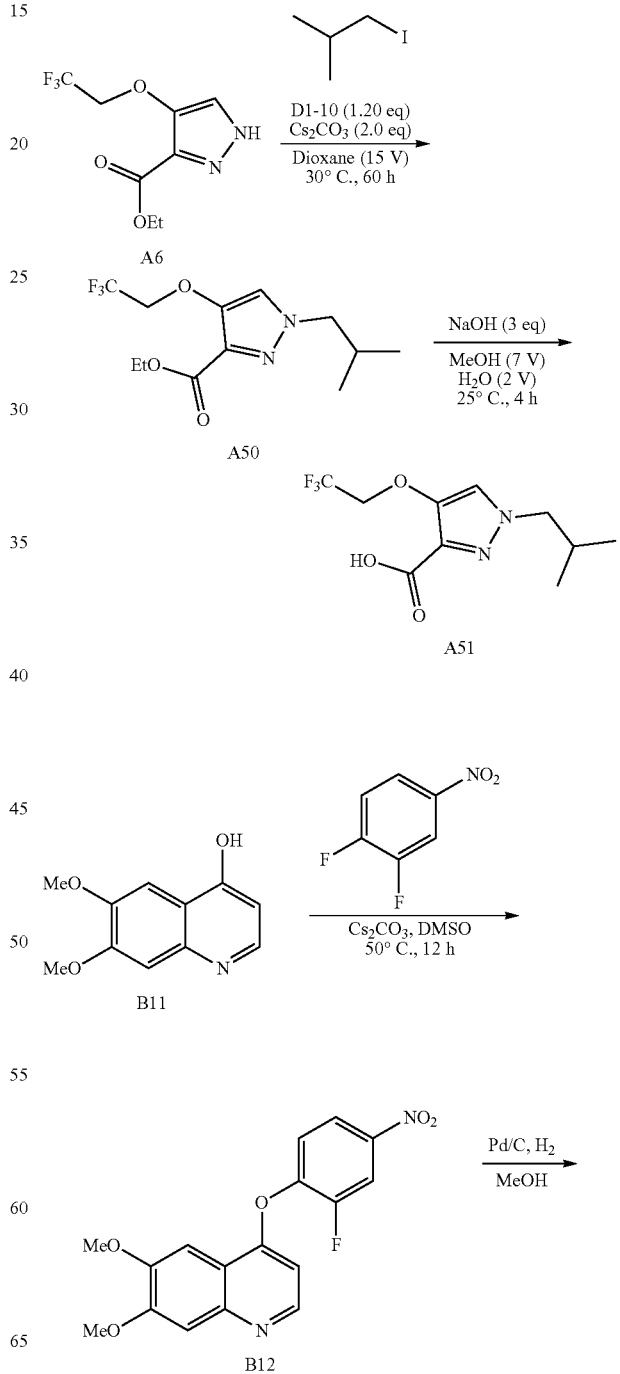

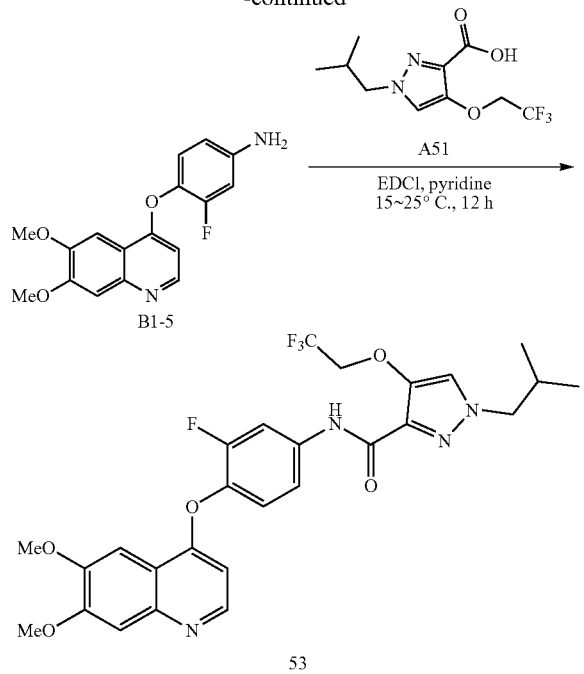

General Procedure for Synthesis A50

A mixture of compound A6 (3.00 g, 12.6 mmol, 1.00 eq), D1-10 (2.78 g, 15.1 mmol, 1.74 mL, 1.20 eq) and $Cs_2CO_3$ (8.21 g, 25.2 mmol, 2.00 eq) in dioxane (45 mL) was heated to 30° C. for 60 h. LCMS (A49: RT=1.16 min) showed A6 was consumed completely and the desired MS was detected. The mixture was filtered and the filtrate was concentrated. The residue was purified by column chromatography ($SiO_2$, petroleum ether/ethyl acetate=3/1 to 1/1) (TLC: petroleum ether/ethyl acetate=1/1, A49: Rf=0.50). A50 (2.5 g, 8.50 mmol, 67.4% yield) was obtained as yellow solid.

General Procedure for Synthesis A51

To a solution of A49 (2.5 g, 8.50 mmol, 1 eq) in MeOH (17.5 mL) and $H_2O$ (5 mL) was added NaOH (1.02 g, 25.5 mmol, 3 eq). The mixture was stirred at 25° C. for 4 hr. TLC (petroleum ether/ethyl acetate=3/1, A49: Rf=0.30, A50: Rf=0.00) indicated A49 was consumed completely and one major new spot with larger polarity was detected. The reaction mixture was added ethyl acetate (20 mL) and $H_2O$ (10 mL) to stirred at 15~25° C. for 10 min. The mixture was separated. The pH value of the aqueous layer was adjusted to 5~6 with 4M HCl (10.0 mL). The mixture was extracted with a solution of DCM and IPA (3/1, 30 mL×4). The combined organic layers were dried over anhydrous $Na_2SO_4$, filtered and concentrated. A51 (2 g, 7.51 mmol, 88.4% yield) was obtained as a light yellow oil General Procedure for Synthesis B12

To a mixture of B11 (1 g, 4.87 mmol, 1 eq) and 1,2-difluoro-4-nitro-benzene (1.55 g, 9.75 mmol, 1.08 mL, 2 eq) in DMSO (10 mL) was added $Cs_2CO_3$ (3.18 g, 9.75 mmol, 2 eq). The reaction mixture was stirred at 50° C. for 12 hours to give a brown mixture. LCMS showed the reaction was completed. The mixture was allowed to 20° C., diluted with EtOAc (100 mL), washed with water (50 mL×3) and brine (80 mL), dried over anhydrous $Na_2SO_4$, filtered and concentrated to give a crude compound. The crude compound was purified by flash silica gel chromatography (ISCO®; 20 g SepaFlash® Silica Flash Column, Eluent of 10%~50%~100% Ethyl acetate/Petroleum ether gradient @ 30 mL/min) to afford B12 (1 g, 59% yield, 98.9% purity) as a yellow solid.

General Procedure for Synthesis B1-5

To a mixture of B12 (1 g, 2.90 mmol, 1 eq) in MeOH (20 mL) was added Pd/C (200 mg, 10% purity, 50% $H_2O$) under $N_2$. The suspension was degassed under vacuum and purged with H2 twice. The mixture was stirred under $H_2$ (15 psi) at 20° C. for 12 hours to give a black mixture. LCMS showed the reaction was completed. The mixture was filtered and the filtrate was concentrated under reduced pressure to give B1-5 (560 mg, 61.3% yield) as an off-white solid. The product was used for the next step without further purification.

General Procedure for Synthesis 53

To a solution of A50 (1.00 eq) and B1-5 (1.02 eq) in pyridine (7 V) was added EDCI (1.50 eq) at 15~25° C. under $N_2$. The mixture was stirred for at 15~25° C. 12 h under $N_2$. LCMS showed A51 was consumed completely and one main peak with desired m/z was detected. The mixture was concentrated under reduced pressure to give a residue. The crude product was purified by reversed-phase HPLC. 53 (199 mg, 61.7% yield, 98.3% purity) was obtained as a yellow solid.

Scheme 16 - General synthesis for compound 58

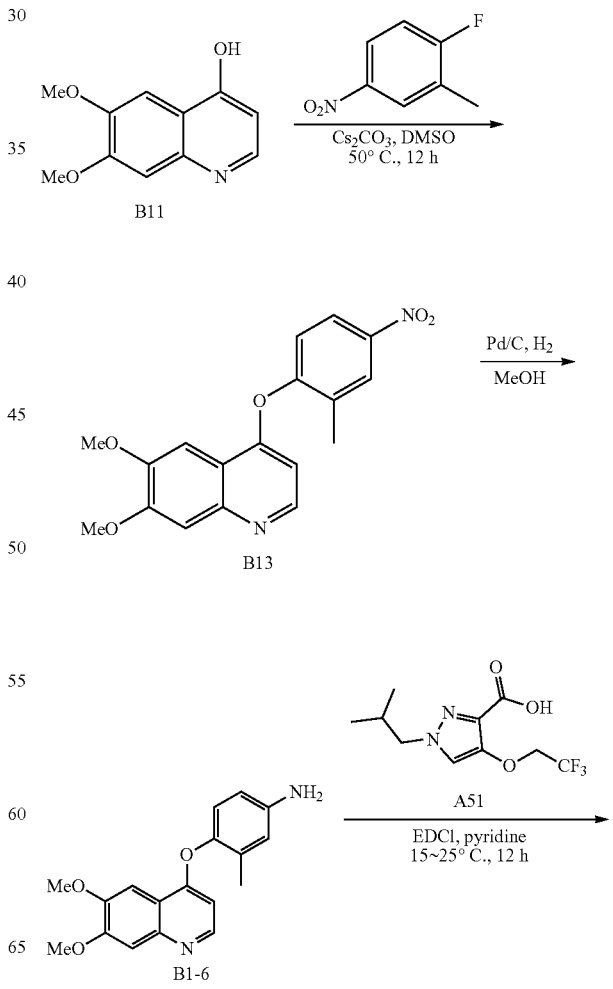

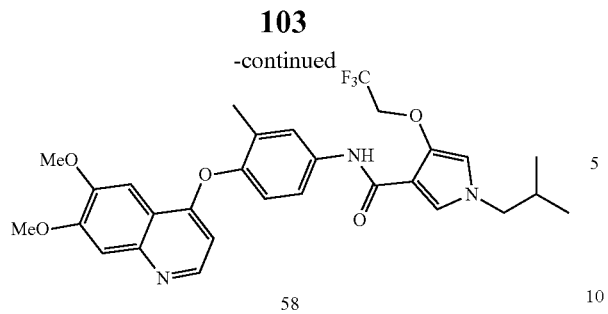

58

General Procedure for Synthesis B13

To a mixture of B11 (500 mg, 2.44 mmol, 1 eq) and 1-fluoro-2-methyl-4-nitro-benzene (756 mg, 4.87 mmol, 2 eq) in DMSO (5 mL) was added Cs$_2$CO$_3$ (1.59 g, 4.87 mmol, 2 eq). The reaction mixture was stirred at 50° C. for 12 hours to give a black mixture. LCMS showed the reaction was completed. The mixture was diluted with EtOAc (100 mL), washed with water (30 mL×3) and brine (30 mL), concentrated under reduced pressure to give a crude compound. The crude compound was purified by flash silica gel chromatography (ISCO®; 12 g SepaFlash® Silica Flash Column, Eluent of 5-70% Ethyl acetate/Petroleum ether gradient @ 30 mL/min) to afford B13 (190 mg, 22.4% yield, 98% purity) as a yellow solid.

General Procedure for Synthesis B1-6

To a mixture of B13 (190 mg, 558.28 umol, 1 eq) in MeOH (10 mL) was added Pd/C (38 mg, 10% purity, 50% H$_2$O) under N$_2$. The suspension was degassed under vacuum and purged with H2 two times. The mixture was stirred under H$_2$ (15 psi) at 20° C. for 12 hours to give a black mixture. LCMS (Rt=0.670 min) showed the reaction was completed. The reaction mixture was filtered and filtrate was concentrated under reduced pressure to give B1-6 (150 mg, crude) as a yellow oil. The crude compound was used for the next step without further purification.

General Procedure for Synthesis 58

To a solution of A51 (1.00 eq) and B1-6 (1.02 eq) in pyridine (7 V) was added EDCI (1.50 eq) at 15~25° C. under N$_2$. The mixture was stirred for at 15~25° C. 12 h under N$_2$. LCMS showed A51 was consumed completely and one main peak with desired m/z was detected. The mixture was concentrated under reduced pressure to give a residue. The crude product was purified by reversed-phase HPLC. 58 (168 mg, 52.4% yield, 98.2% purity) was obtained as a white solid.

Scheme 17 - General synthesis for compound 176

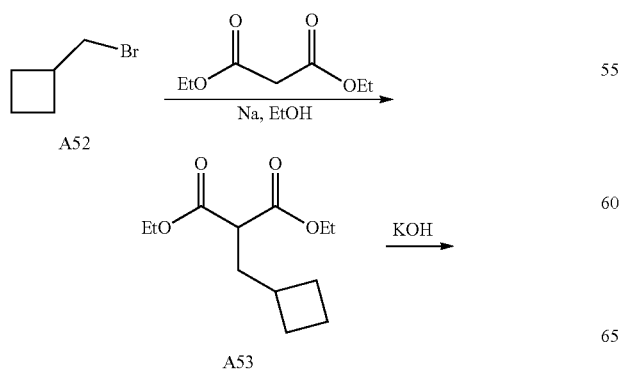

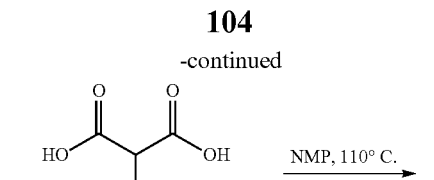

A54

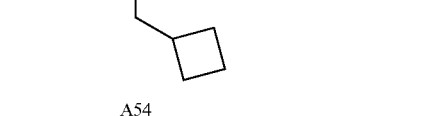

A55

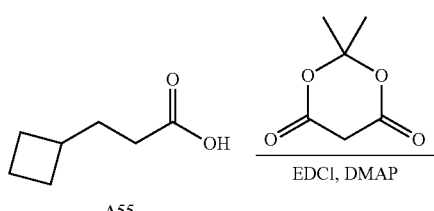

A56

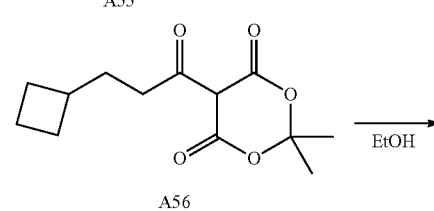

A57

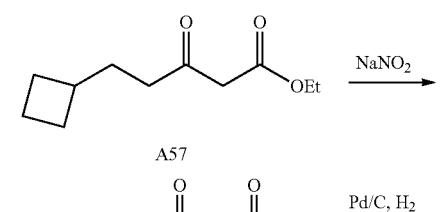

A58

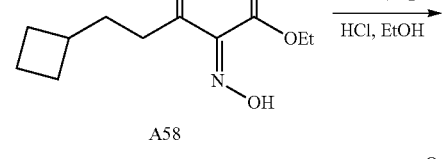

A59

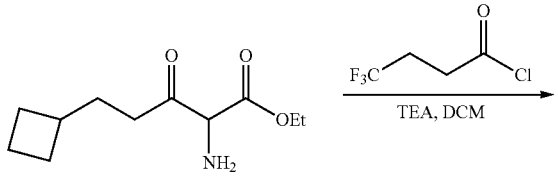

A60

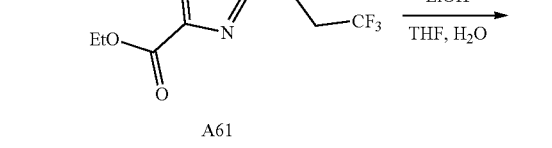

A61

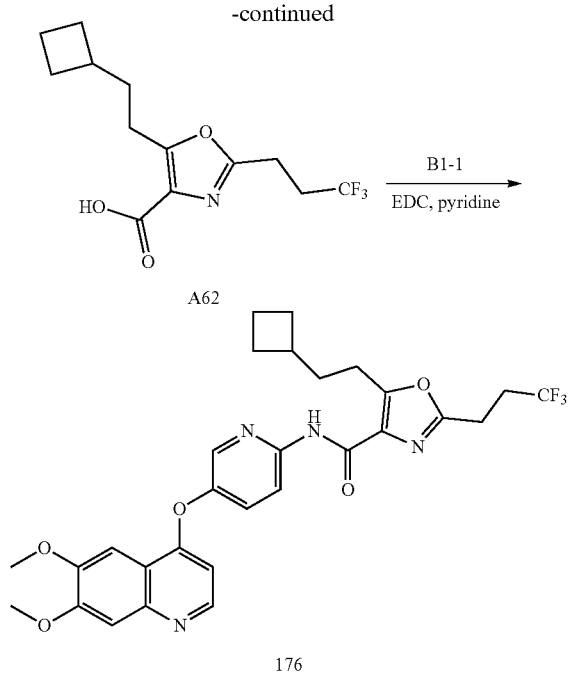

General Procedure for Synthesis A53

To EtOH (25 mL) was added Na (339.38 mg, 14.76 mmol, 349.88 uL, 1.1 eq), after Na disappeared, diethyl propanedioate (3.01 g, 18.79 mmol, 2.84 mL, 1.4 eq) was added into the above mixture, and the mixture was stirred at 100° C. for 30 min. To the reaction mixture was added a solution of A52 (2.00 g, 13.42 mmol, 1.50 mL, 1 eq) in EtOH (10 mL) dropwised over 10 min, and then the mixture was stirred for 17 hr. TLC indicated that one major new spot with lower polarity was detected. The reaction mixture was concentrated under reduced pressure to remove the solvent. The residue was diluted with water (50 mL) and extracted with EtOAc (50 mL*2). The combined organic layers were washed with HCl (1N) (25 mL*2), dried over Na$_2$SO$_4$, filtered and concentrated under reduced pressure to give a residue. The residue was purified by flash silica gel chromatography (Eluent of 0-2% Ethyl acetate/Petroleum ether gradient) to give 2.6 g (yield: 84.87%) of A53 as colorless oil.

General Procedure for Synthesis A54

To the solution of A53 (2.6 g, 11.39 mmol, 1 eq) in H$_2$O (10 mL) and EtOH (10 mL) was added KOH (2.56 g, 45.56 mmol, 4 eq), and the mixture was stirred at 15° C. for 1.5 hr. TLC indicated the reaction was completed. The reaction mixture was concentrated under reduced pressure to remove the solvent. The residue was diluted with water (20 mL) and adjust pH to 3-5 by HCl (1N), and then it was extracted with EtOAc (20 mL*3). The combined organic layers were washed with aqueous NaCl (20 mL*3), dried over Na$_2$SO$_4$, filtered and concentrated under reduced pressure to give 1.7 g (yield: 86.69%) of A54 as a white solid.

General Procedure for Synthesis A55

A solution of A54 (1.7 g, 9.87 mmol, 1 eq) in NMP (2 mL) was stirred at 110° C. for 2 hr. TLC indicated that material was remained, and one major new spot with lower polarity was detected. Then the mixture was heated to 120° C. for 17 hr, and TLC indicated that material was still remained. The reaction mixture was diluted with water (30 mL) and it was extracted with EtOAc (30 mL*2). The combined organic layers were washed with aqueous NaCl (30 mL*2), dried over Na$_2$SO$_4$, filtered and concentrated under reduced pressure to give 1.01 g (yield: 79.81%) of A55 as a white solid.

General Procedure for Synthesis A56

To the solution of A55 (1.01 g, 7.88 mmol, 1 eq) and 2,2-dimethyl-1,3-diozane-4,6-dione (1.25 g, 8.67 mmol, 1.1 eq) in DCM (15 mL) was added DMAP (1.44 g, 11.82 mmol, 1.5 eq), after cooling the mixture to 0° C., EDCI (2.11 g, 11.03 mmol, 1.4 eq) was added. The mixture was stirred at 15° C. for 17 hr. TLC indicated that the reaction was completed and one major new spot with lower polarity was detected. The mixture was treated with 50 ml of water and the mixture was extracted with EtOAc (50 mL×2). The combined organic layer was washed with 1N HCl (20 mL×2), dried over magnesium sulfate, and concentrated under reduced pressure to give 1.9 g (yield: 94.82%) of A56 as yellow oil.

General Procedure for Synthesis A57

A solution of A56 (1.9 g, 7.47 mmol, 1 eq) in EtOH (40 mL) was stirred at 80° C. for 4 hr. TLC indicated that the reaction was completed. The reaction mixture concentrated under reduced pressure to give 1.47 g (yield: 99.23%) of A57 as yellow oil.

General Procedure for Synthesis A58

A solution of NaNO$_2$ (767.36 mg, 11.12 mmol, 1.5 eq) in H$_2$O (12 mL) was added dropwise to the solution of A57 (1.47 g, 7.41 mmol, 1 eq) in CH$_3$COOH (4 mL) and H$_2$O (12 mL) under 0° C. The stirring mixture was maintained at 0° C. for 2 h and then at 15° C. for 2.5 h. Then, water (10 ml) was added and the mixture was stirred for 17 hr. TLC indicated the reaction was completed. The reaction mixture was diluted with water (10 mL) and it was extracted with EtOAc (30 mL*2). The combined organic layers were washed with sat. aq. NaHCO$_3$ (15 mL*2), brine (15 mL*2), dried over Na$_2$SO$_4$, filtered and concentrated under reduced pressure to give 1.42 g (yield: 84.27%) of A58 as yellow oil.

General Procedure for Synthesis A59

To the solution of A58 (3.1 g, 13.64 mmol, 1 eq) in EtOH (50 mL) were added wet Pd/C (0.4 g) and conc. HCl (227.82 mg, 6.25 mmol, 223.36 uL). The suspension was degassed and purged with H$_2$ for 3 times. The mixture was stirred under H$_2$ (15 Psi) at 40° C. for 17 hr. TLC indicated the reaction was completed. The suspension was filtered through a pad of Celite and the pad was washed with EtOH (10 mL×3). The combined filtrates were concentrated to dryness to 3.3 g (yield: 96.87%, HCl) of A59 as a white solid.

General Procedure for Synthesis A60

To the solution of A59 (1.00 g, 4.00 mmol, 1 eq, HCl) in DCM (5 mL) was added TEA (1.22 g, 12.01 mmol, 1.67 mL, 3 eq), and then 4,4,4-trifluorobutanoyl chloride (1.29 g, 8.01 mmol, 2 eq) was added dropwise at 0° C. After addition, the mixture was stirred at 20° C. for 1 hr to give a yellow mixture. TLC indicated the reaction was completed. The reaction mixture was diluted with water (50 mL) and it was extracted with EtOAc (50 mL*2). The combined organic layers were washed with sat. aq. NaHCO$_3$ (20 mL*2), NaCl (20 mL*2), dried over Na$_2$SO$_4$, filtered and concentrated under reduced pressure to give a residue. The residue was purified by flash silica gel chromatography (Eluent of 0-20% Ethyl acetate/Petroleum ether) to afford 0.32 g (yield: 23.69%) of A60 as yellow oil.

General Procedure for Synthesis A61

To the solution of A60 (0.32 g, 948.62 umol, 1 eq) in DCM (10 mL) were added PPh$_3$ (497.62 mg, 1.90 mmol, 2 eq), I$_2$ (481.53 mg, 1.90 mmol, 382.17 uL, 2 eq) and TEA (383.96 mg, 3.79 mmol, 528.15 uL, 4 eq). The mixture was stirred at 20° C. for 2 hr. TLC indicated the reaction was completed. The reaction mixture was diluted with water (20 mL) and it was extracted with EtOAc (10 mL*3). The combined organic layers were washed with aqueous NaCl (10 mL*3), dried over $Na_2SO_4$, filtered and concentrated under reduced pressure to give a residue. The residue was purified by flash silica gel chromatography (Silica Flash Column, Eluent of 0-20% Ethyl acetate/Petroleum ether gradient) to afford 0.22 g (yield: 72.63%) of A61 as yellow oil.

General Procedure for Synthesis A62

To a solution of compound A61 (0.29 g, 908.18 umol, 1 eq) in THF (8 mL) and $H_2O$ (2 mL) was added LiOH·$H_2O$ (57.17 mg, 1.36 mmol, 1.5 eq), and the mixture was stirred at 20° C. for 17 hr to give a yellow mixture. And then the mixture was stirred at 50° C. for another 6 hr. LCMS showed the reaction was completed. The residue was diluted with water (20 mL) and then lyophilized to afford 0.325 g (crude) of A62 as a white solid.

General Procedure for Synthesis 176

To the solution of A62 (0.15 g, crude) in pyridine (2 mL) were added B1-1 (153.11 mg, 514.99 umol, 1 eq) and EDCI (148.09 mg, 772.49 umol, 1.5 eq). The mixture was stirred at 15° C. for 17 hr to give a yellow mixture. LCMS showed 7% of desired product was detected. The reaction mixture was diluted with water (30 mL) and it was extracted with EtOAc (10 mL*3). The combined organic layers were washed with aqueous NaCl (10 mL*3), dried over $Na_2SO_4$, filtered and concentrated under reduced pressure to give a residue. The residue was purified by prep-TLC (DCM: MeOH=20:1) to afford 5 mg (yield: 1.46%) of 176 as a white solid.

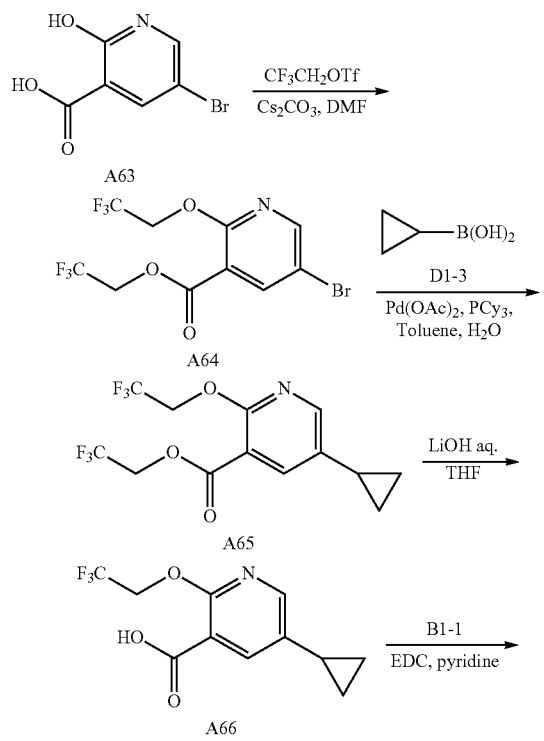

Scheme 18 - General synthesis for compound 178

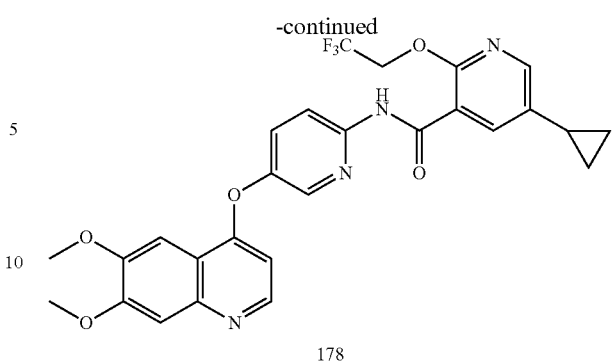

General Procedure for Synthesis A64

To a mixture of A63 (2 g, 9.17 mmol, 1 eq) in DMF (20 mL) were added $Cs_2CO_3$ (7.47 g, 22.9 mmol, 2.5 eq) and 2,2,2-trifluoroethyl trifluoromethanesulfonate (4.26 g, 18.3 mmol, 2 eq) at 0° C., the mixture was stirred at 15° C. for 1 hour to give a pale mixture. LCMS showed the desired product was observed. The mixture was poured into ice-water (30 mL). The aqueous phase was extracted with ethyl acetate (20 mL×3). The combined organic phase was washed with brine (50 mL×5), dried with anhydrous $Na_2SO_4$, filtered and concentrated in vacuum to afford crude product. The crude product was purified by combi flash (PE/EtOAc=I/O to 3/1) to afford A63 (1.49 g, 42.5% yield) as a white solid.

General Procedure for Synthesis A65

To a mixture of A64 (1.49 g, 3.90 mmol, 1 eq) and D1-3 (1.00 g, 11.70 mmol, 3 eq) in $H_2O$ (2 mL) and toluene (20 mL) were added $K_3PO_4$ (2.07 g, 9.75 mmol, 2.5 eq), $PCy_3$ (109 mg, 390 umol, 126 uL, 0.1 eq) and $Pd(OAc)_2$ (87.5 mg, 390 umol, 0.1 eq), and the mixture was stirred at 80° C. under $N_2$ protection for 5 hours to give a yellow mixture. LCMS showed the desired product was observed. The mixture was partitioned between EtOAc (15 mL) and water (10 mL). The aqueous phase was extracted with EtOAc (10 mL×2). The combined organic extract was washed with brine (10 mL), dried over $Na_2SO_4$, filtered, concentrated under reduced pressure to give crude product. The crude product was purified by combi flash (PE/EtOAc=I/O to 5/1 to 3/1) to afford A65 (150 mg, 11.2% yield) as a yellow solid.

General Procedure for Synthesis A66

To a mixture of A65 (150 mg, 437 umol, 1 eq) in THF (2 mL) and $H_2O$ (1 mL) was added LiOH·$H_2O$ (36.6 mg, 874 umol, 2 eq), and the mixture was stirred at 15° C. for 1 hours to give a yellow mixture. LCMS showed the reactant was consumed. The mixture was acidified with 1N HCl to pH=4-5, and then it was partitioned between DCM (15 mL) and water (10 mL). The aqueous phase was extracted with DCM (10 mL×2). The combined organic extract was washed with brine (10 mL), dried over $Na_2SO_4$, filtered, concentrated under reduced pressure to afford A66 (70 mg, 61.3% yield) as a yellow gum.

General Procedure for Synthesis 178

To a mixture of A66 (70 mg, 268 umol, 1 eq) and B1-1 (71.7 mg, 241 umol, 0.9 eq) in pyridine (2 mL) was added EDCI (102 mg, 535 umol, 2 eq), and the mixture was stirred at 15° C. for 16 hours to give a yellow mixture. LCMS showed the reaction was completed. The mixture was concentrated under reduced pressure to give a crude product. The crude product was purified by prep-HPLC (Waters Xbridge BEH C18 100*25 mm*5 um; mobile phase: [water (0.05% ammonia hydroxide v/v)-ACN]; B %: 45%-75%, 9.5 min) to afford 178 (35.1 mg, 24.2% yield) as a white powder.

I₂ (1.16 g, 4.58 mmol, 1.1 eq) in THF (5 mL) was added. The reaction was further stirred for 30 min at −78° C., then warmed to 20° C. for 17 hours to give a yellow mixture.

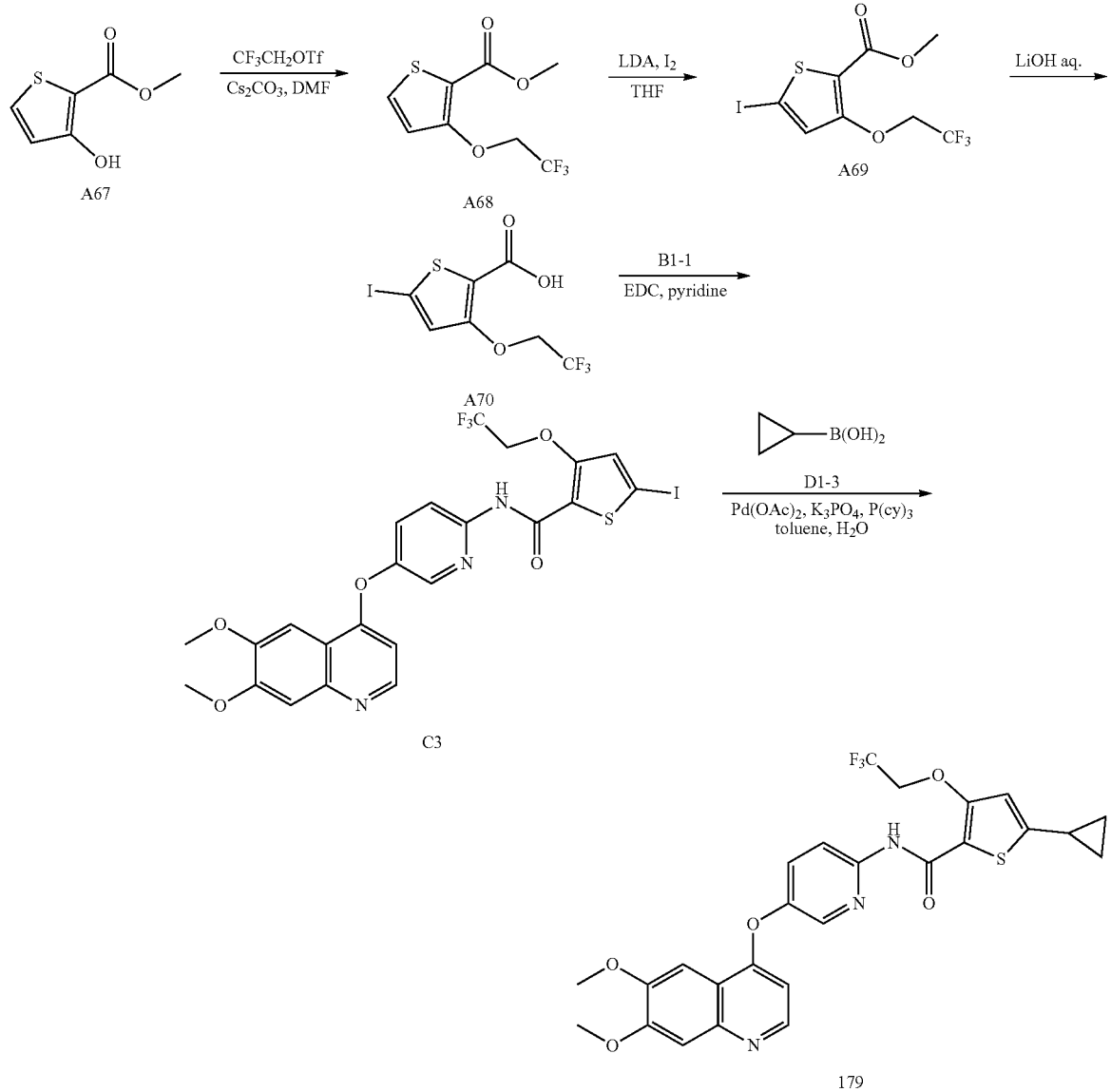

General Procedure for Synthesis A68

To a suspension of A67 (4 g, 25.3 mmol, 1 eq) and 2, 2, 2-trifluoroethyl trifluoromethanesulfonate (6.46 g, 27.8 mmol, 1.1 eq) in DMF (30 mL) was added Cs₂CO₃ (12.4 g, 37.9 mmol, 1.5 eq). The reaction was stirred at 60-70° C. for 16 hours to give a light yellow suspension. TLC showed the reaction was completed. The mixture was partitioned between water (100 mL) and EtOAc (100 mL). The organic layer was washed with brine (100 mL×3), dried over anhydrous Na₂SO₄, filtered and concentrated under reduced pressure to give A68 (6.1 g, crude) as a white powder.

General Procedure for Synthesis A69

To a solution of A68 (1 g, 4.16 mmol, 1 eq) in THF (5 mL) was added LDA (2 M, 2.29 mL, 1.1 eq) at −78° C. under N2. The reaction mixture was stirred for 5 min, and a solution of LCMS showed most of starting material was still remained. The mixture was quenched with water (5 mL), and 1 N HCl (1 mL) was added. The mixture was partitioned between EtOAc (80 mL) and H₂O (80 mL). The organic layer was washed with saturated brine (80 mL×3), dried over anhydrous Na₂SO₄, filtered, and concentrated under reduced pressure to give a residue. The residue was purified by combi flash (PE/EtOAc=1/0 to 10/1) to give A69 (70 mg, 4.6% yield) as yellow gum General Procedure for Synthesis A70

To a solution of A69 (170 mg, 0.464 mmol, 1 eq) in THF (3 mL) was added LiOH (22 mg, 0.928 mmol, 2 eq) in H₂O (1 mL). The reaction was stirred at 20° C. for 1.5 hours to give a yellow mixture. LCMS showed the starting material was not consumed completely. LiOH (20 mg) was added.

The reaction was stirred at 20° C. for 17 hours to give a yellow mixture. LCMS showed the starting material was not consumed completely. LiOH (20 mg) was added. The reaction was stirred at 40° C. for 5 hours to give a yellow mixture. TLC showed the reaction was completed. The reaction was adjusted to pH=4 with 1 N HCl at 0-10° C., extracted with DCM (30 mL×3). The combined organic layer was dried over anhydrous $Na_2SO_4$, filtered and concentrated under reduced pressure to give A70 (130 mg, 79.5% yield) as a yellow gum General Procedure for Synthesis C3

To a mixture of A70 (120 mg, 0.341 mmol, 1 eq) and B1-1 (101 mg, 0.341 mmol, 1 eq) in pyridine (2 mL) was added EDCI (131 mg, 0.682 mmol, 2 eq). The reaction was stirred at 20° C. for 17 hours to give a yellow mixture. LCMS showed the reaction was completed. The reaction mixture was concentrated under reduced pressure to give a residue. The residue was partitioned between EtOAc (20 mL) and $H_2O$ (20 mL). The aqueous layer was extracted with EtOAc (20 mL×2). The combined organic layer was washed with brine (30 mL), dried over anhydrous $Na_2SO_4$, filtered and concentrated under reduced pressure to give a yellow gum. The crude product was purified by prep-TLC (EtOAc/PE=1/3 first, then DCM/MeOH=30:1) to give C3 (150 mg, 69.7% yield, 100% purity) as off-white powder.

General Procedure for Synthesis 179

To a mixture of C3 (130 mg, 0.206 mmol, 1 eq), D1-3 (28 mg, 0.329 mmol, 1.6 eq), P(cy)$_3$ (8 mg, 0.021 mmol, 0.1 eq) and $K_3PO_4$ (153 mg, 0.721 mmol, 3.5 eq) in toluene (2 mL) and $H_2O$ (0.2 mL) was added Pd(OAc)$_2$ (5 mg, 0.021 mmol, 0.1 eq). The reaction was stirred at 100° C. for 2 hours under $N_2$ to give a yellow mixture. LCMS showed the starting material was not consumed completely. The reaction was stirred at 100° C. for 2 hours under $N_2$ to give a yellow mixture. LCMS showed the starting material was not consumed completely. cyclopropylboronic acid (30 mg), and $K_3PO_4$ (150 mg) were added into the reaction mixture. The reaction was stirred at 100° C. for 1 hour under $N_2$ to give a yellow mixture. LCMS showed the starting material was not consumed completely. The mixture was partitioned between EtOAc (30 mL) and $H_2O$ (30 mL). The aqueous layer was extracted with EtOAc (20 mL×2). The combined organic layer was washed with brine (20 mL), dried over anhydrous $Na_2SO_4$, filtered, and concentrated under reduced pressure to give a residue. The crude product was purified by prep-TLC (DCM/MeOH=40/1) to give yellow gum. LCMS showed impure. The yellow gum was purified by prep-HPLC (column: Waters Xbridge C18 150*50 mm*10 um; mobile phase: [water (0.04% $NH_3H_2O$+10 mM $NH_4HCO_3$)-ACN]; B %: 50%-80%, 11 min). LCMS showed impure. The eluent was concentrated under reduced pressure to give yellow oil. The oil was purified by prep-TLC (EtOAc/PE=1/2) to give a yellow gum. LCMS showed impure. The yellow gum was purified by prep-HPLC (column: Welch Xtimate C18 100*25 mm*3 um; mobile phase: [water (0.05% ammonia hydroxide v/v)-ACN]; B %: 64%-64%, 12 min). The eluent was concentrated under reduced pressure to give a residue. The residue was partitioned between MeCN (5 mL) and $H_2O$ (5 mL) and lyophilized to give 179 (12.2 mg, 10.9% yield, 100% purity) as a white powder.

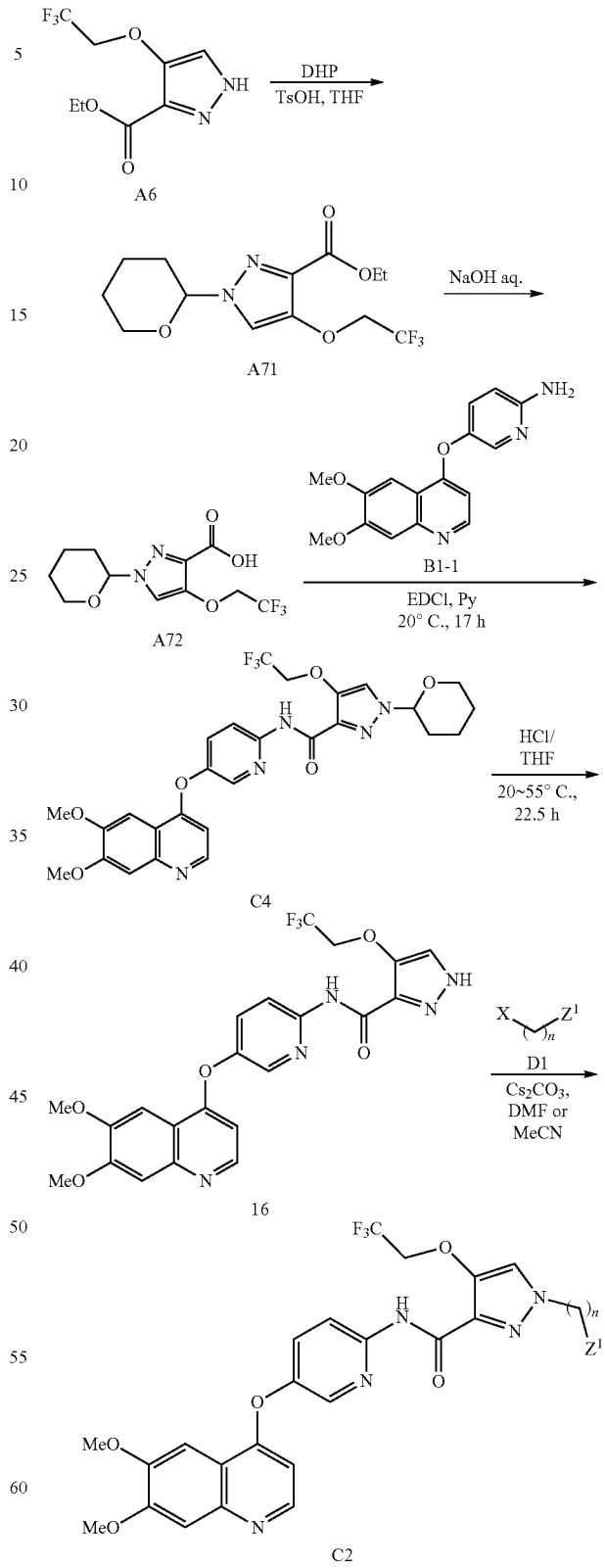

Scheme 20 - General Synthetic route II

General Procedure for Synthesis A71

To a solution of A6 (10 g, 42.0 mmol, 1 eq) and 3,4-dihydro-2H-pyran (10.6 g, 126 mmol, 11.5 mL, 3 eq) in THF (100 mL) was added p-TsOH (723 mg, 4.20 mmol, 0.1 eq). The resulting mixture was stirred at 80° C. for 3 hrs to give yellow solution. TLC (PE:EtOAc=3:1) showed the reaction was completed. The reaction mixture was concentrated under reduced pressure to give a residue. Then diluted with H₂O (100 mL) and extracted with EtOAc (100 mL×2). The combined organic layers were washed with brine (60 mL×2), dried over Na₂SO₄, filtered and concentrated under reduced pressure to give a residue. The residue was purified by column chromatography (SiO2, PE:EtOAc=3:1) to give A71 (13 g, 94.6% yield, 98.5% purity) as a yellow oil.

General Procedure for Synthesis A72

To a solution of A71 (13 g, 40.3 mmol, 1 eq) in MeOH (60 mL) and THF (60 mL) was added NaOH (3 M, 40.3 mL, 3 eq). The resulting mixture was heated at 60° C. and stirred for 1 hr to give red solution. LCMS showed the reaction was completed. The reaction mixture was concentrated under reduced pressure to give a residue. Then diluted with H₂O (50 mL) and and extracted with EtOAc (100 mL×2). The water layers were adjust to pH-5 and extracted with DCM (100 mL×2), washed with brine (30 mL×2), dried over Na₂SO₄, filtered and concentrated under reduced pressure to give A72 (9.9 g, 83.4% yield, 100% purity) as a yellow solid.

General Procedure for Synthesis C4

To a mixture of compound A72 (8.28 g, 28.2 mmol, 1.5 eq), compound B1-1 (5.58 g, 18.8 mmol, 1 eq) in pyridine (15 mL) was added EDCI (7.20 g, 37.5 mmol, 2 eq). The reaction was stirred at 20° C. for 17 hours to give a yellow mixture. LCMS showed the starting material was not consumed completely. The reaction mixture was concentrated under reduced pressure to give a residue. The residue was partitioned between EtOAc (200 mL) and H₂O (200 mL). The organic layer was washed with H₂O (200 mL×2), brine (200 mL), dried over anhydrous Na₂SO₄, filtered and concentrated under reduced pressure to give a yellow gum. The crude product was purified by combi flash (EtOAc/PE=0/1 to 7/2) to give C4 (6.29 g, yield: 57%, purity: 98%) as yellow gum.

General Procedure for Synthesis 16

To a solution of C4 (6.29 g, 11 mmol, 1 eq) in DCM (20 mL) was added TFA (10 mL, 135 mmol, 12.3 eq) at 0° C. The reaction was stirred at 20° C. for 17 hours to give a yellow solution. LCMS showed the starting material was not consumed completely. The mixture was concentrated under reduced pressure to give a residue. The residue was dissolved in THF (20 mL). HCl (2 M, 11 mL, 2 eq) was added. The reaction was stirred at 20° C. for 2 hours to give a yellow solution. LCMS showed the starting material was not consumed completely. HCl (2 M, 11 mL, 2 eq) was added. The reaction was stirred at 20° C. for 2 hours to give a yellow solution. TLC showed the starting material was not consumed completely. THF (25 mL) and HCl (2 M, 25 mL) were added. The reaction was stirred at 50° C. for 17 hours to give a yellow solution. LCMS showed the starting material was not consumed completely. The reaction was stirred at 55° C. for 1.5 hours to give a yellow solution. LCMS showed the starting material was not consumed completely. After filtration, the filter cake was washed with H₂O (10 mL×2), and partitioned between NaHCO₃ (300 mL), DCM (300 mL), MeOH (50 mL). The aqueous layer was extracted with DCM (300 mL). The combined organic layers were dried over anhydrous Na₂SO₄, filtered and concentrated under reduced pressure to give a yellow powder. The crude product was triturated with EtOAc/PE (1/1, 40 mL) to give 16 (4.26 g, yield: 79%, purity: 100%) as a white powder.

General Procedure for Synthesis C2

A method to prepare compounds of C2 is shown in Scheme 8. The reaction of 16 and D1 is carried out in the presence of a Cs₂CO₃ in a solvent like DMF or MeCN to give C2. In addition, many of the D1 alkyl reagents are commercially available.

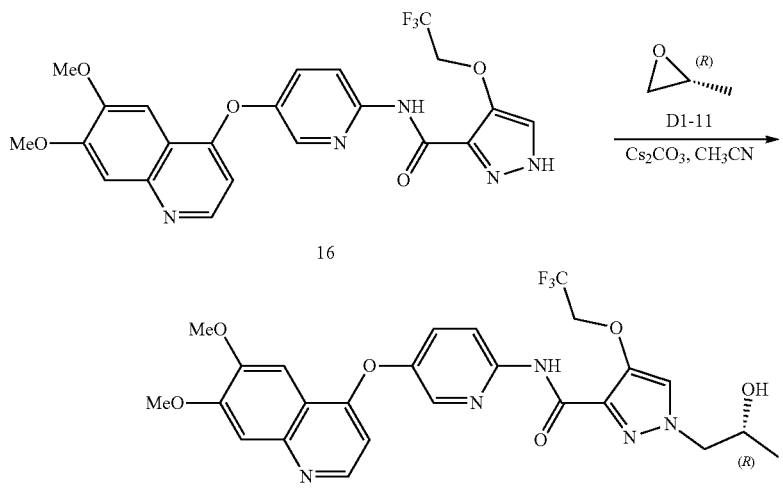

Scheme 21 - General synthesis for compound 29

To a solution of 16 (20 mg, 0.409 mmol, 1 eq) and D1-11 (2.37 mg, 0.409 mmol, 2.86 uL, 1 eq) in CH₃CN (2 mL) was added Cs₂CO₃ (20 mg, 0.613 mmol, 1.5 eq). The resulting mixture was stirred at 20° C. for 16 hours to give yellow solution. TLC (PE:EtOAc=0:1) showed little of the starting material was remained and desired product was formed. The reaction mixture was quenched by addition H₂O (5 mL) and extracted with EtOAc (5 mL). The combined organic layers were washed with brine (3 mL), dried over Na₂SO₄, filtered and concentrated under reduced pressure to give a residue. The residue was purified by TLC (PE:EtOAc=0:1), then dissolved in CH₃CN (1 mL) and H₂O (1 mL), lyophilized to afford 29 (14 mg, 62.6% yield, 100% purity) as a white powder.

REFERENCES

The Role of TAM Family Receptors in Immune Cell Function: Implications for Cancer Therapy. Paolino M, Penninger J M., Cancers (Basel). 2016 Oct. 21; 8(10). pii: E97.

Diversification of TAM receptor tyrosine kinase function. Zagórska A, Través P G, Lew E D, Dransfield I, Lemke G., Nat Immunol. 2014 October; 15(10):920-8.

TAM receptor tyrosine kinases as emerging targets of innate immune checkpoint blockade for cancer therapy. Akalu Y T, Rothlin C V, Ghosh S., Immunol Rev. 2017 March; 276(1):165-177.

Ligand Activation of TAM Family Receptors-Implications for Tumor Biology and Therapeutic Response. Davra V, Kimani S G, Calianese D, Birge R B., Cancers (Basel). 2016 Nov. 29; 8(12). pii: E107.

Development of monocytes, macrophages, and dendritic cells. Geissmann F, Manz M G, Jung S, Sieweke M H, Merad M, Ley K., Science. 2010 Feb. 5; 327(5966):656-61.

CSF1/CSF1R blockade reprograms tumor-infiltrating macrophages and improves response to T-cell checkpoint immunotherapy in pancreatic cancer models. Zhu Y, Knolhoff B L, Meyer M A, Nywening T M, West B L, Luo J, Wang-Gillam A, Goedegebuure S P, Linehan D C, DeNardo D G., Cancer Res. 2014 Sep. 15; 74(18):5057-69.

The invention is now further exemplarily described by tables 1-7 which show activity data of selected compounds in binding assays of example 1-2 (tables 1-2), in cellular ELISA assays of examples 3-4 (tables 3 and 4), in cellular viability assays of examples 4 and 5 (Tables 5 and 6), and comparison data of examples 6-7, Table 7, Example 8 and FIGS. 1 and 2; and the structure of compounds 1-179 including ¹H-NMR-data is shown in table 8.

TABLE 1

Axl, Mer and CSF1R kinase binding activity

| # cpds | Axl | Mer | CSF1R |
|---|---|---|---|
| 1 | A | A | A |
| 2 | A | A | B |
| 3 | A | A | B |
| 4 | A | A | A |
| 5 | A | A | A |
| 6 | A | A | A |
| 7 | A | A | A |
| 8 | A | A | A |
| 9 | A | A | A |
| 10 | A | A | A |
| 11 | A | A | A |
| 12 | A | A | A |
| 13 | A | A | A |
| 14 | A | A | A |
| 15 | A | A | n.d. |
| 16 | A | A | n.d. |
| 17 | A | A | n.d. |
| 18 | A | A | n.d. |
| 19 | A | A | n.d. |
| 20 | A | A | n.d. |
| 21 | A | A | n.d. |
| 22 | A | A | n.d. |
| 23 | A | A | n.d. |
| 24 | A | A | n.d. |
| 25 | A | A | n.d. |
| 26 | A | A | n.d. |
| 27 | A | A | n.d. |
| 28 | A | A | n.d. |
| 29 | A | A | n.d. |
| 30 | A | A | n.d. |
| 31 | A | A | n.d. |
| 32 | A | A | n.d. |
| 33 | A | A | n.d. |
| 34 | C | B | n.d. |
| 35 | C | C | n.d. |
| 36 | A | A | n.d. |
| 37 | B | A | n.d. |
| 38 | A | A | n.d. |
| 39 | A | A | n.d. |
| 40 | A | A | n.d. |
| 41 | A | A | n.d. |
| 42 | A | A | n.d. |
| 43 | A | A | n.d. |
| 44 | A | A | n.d. |
| 45 | A | A | n.d. |
| 46 | A | A | n.d. |
| 47 | A | A | n.d. |
| 48 | A | A | n.d. |
| 49 | A | A | n.d. |
| 50 | A | A | n.d. |
| 51 | A | A | n.d. |
| 52 | A | A | n.d. |
| 53 | A | A | n.d. |
| 54 | A | A | n.d. |
| 55 | A | A | n.d. |
| 56 | B | A | n.d. |
| 57 | A | A | n.d. |
| 58 | A | A | n.d. |
| 59 | A | A | n.d. |
| 60 | A | A | n.d. |
| 61 | A | A | n.d. |
| 62 | A | A | n.d. |
| 63 | A | A | n.d. |
| 64 | A | A | n.d. |
| 65 | A | A | n.d. |
| 66 | A | A | n.d. |
| 67 | A | A | n.d. |
| 68 | A | A | n.d. |
| 69 | A | A | n.d. |
| 70 | A | A | n.d. |
| 71 | A | A | n.d. |
| 72 | A | A | n.d. |
| 73 | B | B | n.d. |
| 74 | B | B | n.d. |
| 75 | B | B | n.d. |
| 76 | A | A | n.d. |
| 77 | A | A | n.d. |
| 78 | A | B | n.d. |
| 79 | A | A | n.d. |
| 80 | A | A | n.d. |
| 81 | C | B | n.d. |
| 82 | C | B | n.d. |
| 83 | A | A | n.d. |
| 84 | A | A | n.d. |
| 85 | A | A | n.d. |
| 86 | B | B | n.d. |
| 87 | A | A | n.d. |
| 88 | B | B | n.d. |
| 89 | A | A | n.d. |
| 90 | A | A | n.d. |
| 91 | A | A | n.d. |
| 92 | A | A | n.d. |
| 93 | A | A | n.d. |
| 94 | A | A | n.d. |
| 95 | A | A | n.d. |
| 96 | A | A | n.d. |
| 97 | A | A | n.d. |
| 98 | B | A | n.d. |
| 99 | A | A | n.d. |
| 100 | A | A | n.d. |
| 101 | A | A | n.d. |

TABLE 1-continued

Axl, Mer and CSF1R kinase binding activity

| # cpds | Axl | Mer | CSF1R |
|---|---|---|---|
| 102 | A | A | n.d. |
| 103 | A | A | n.d. |
| 104 | A | A | n.d. |
| 105 | A | A | n.d. |
| 106 | A | A | n.d. |
| 107 | A | A | n.d. |
| 108 | A | A | n.d. |
| 109 | A | A | n.d. |
| 110 | A | A | n.d. |
| 111 | A | A | n.d. |
| 112 | A | A | n.d. |
| 113 | A | A | n.d. |
| 114 | A | A | n.d. |
| 115 | A | A | n.d. |
| 116 | A | A | n.d. |
| 117 | A | A | n.d. |
| 118 | A | A | n.d. |
| 119 | B | B | n.d. |
| 120 | A | A | n.d. |
| 121 | A | A | n.d. |
| 122 | B | B | n.d. |
| 123 | A | A | n.d. |
| 124 | A | A | n.d. |
| 125 | C | C | n.d. |
| 126 | A | A | n.d. |
| 127 | C | C | n.d. |
| 128 | A | A | n.d. |
| 129 | B | B | n.d. |
| 130 | A | A | n.d. |
| 131 | A | A | n.d. |
| 132 | C | C | n.d. |
| 133 | B | B | n.d. |
| 134 | A | A | n.d. |
| 135 | C | C | n.d. |
| 136 | A | A | n.d. |
| 137 | C | C | n.d. |
| 138 | A | A | n.d. |
| 139 | A | A | n.d. |
| 140 | C | B | n.d. |
| 141 | C | C | n.d. |
| 142 | A | A | n.d. |
| 143 | A | A | n.d. |
| 144 | B | B | n.d. |
| 145 | A | A | n.d. |
| 146 | A | A | n.d. |
| 147 | A | A | n.d. |
| 148 | A | A | n.d. |
| 149 | A | A | n.d. |
| 150 | A | A | n.d. |
| 151 | A | A | n.d. |
| 152 | A | A | n.d. |
| 153 | A | A | n.d. |
| 154 | A | A | n.d. |
| 155 | A | B | n.d. |
| 156 | B | B | n.d. |
| 157 | B | B | n.d. |
| 158 | A | A | n.d. |
| 159 | C | C | n.d. |
| 160 | C | C | n.d. |
| 161 | A | A | n.d. |
| 162 | A | A | n.d. |
| 163 | A | A | n.d. |
| 164 | A | A | n.d. |
| 165 | B | C | n.d. |
| 166 | A | A | n.d. |
| 167 | A | A | n.d. |
| 168 | A | A | n.d. |
| 169 | A | A | n.d. |
| 170 | A | A | n.d. |
| 171 | A | B | n.d. |
| 172 | C | C | n.d. |
| 173 | A | A | n.d. |
| 174 | C | C | n.d. |
| 175 | A | A | n.d. |
| 176 | B | B | n.d. |
| 177 | A | B | n.d. |
| 178 | A | A | n.d. |
| 179 | B | B | n.d. |

Activity range: A indicates < 0.1 uM, B indicates 0.1 ≤ Kd < 0.5 uM, C indicates ≥ 0.5 uM; n.d. = not determined

TABLE 2

CSF1R kinase binding activity (%, @ 0.1 uM)

| # cpds | Range | Percent (%) |
|---|---|---|
| 1 | A | 96 |
| 2 | A | 89 |
| 3 | B | 71 |
| 4 | A | 98 |
| 5 | A | 97 |
| 6 | A | 97 |
| 7 | A | 97 |
| 8 | A | 94 |
| 9 | A | 92 |
| 10 | A | 98 |
| 11 | A | 88 |
| 12 | A | 98 |
| 13 | A | 98 |
| 14 | A | 98 |
| 15 | A | 87 |
| 16 | A | 99 |
| 17 | A | 97 |
| 18 | A | 97 |
| 19 | A | 97 |
| 20 | A | 99 |
| 21 | A | 95 |
| 22 | A | 93 |
| 23 | A | 94 |
| 24 | A | 96 |
| 25 | A | 87 |
| 26 | A | 94 |
| 27 | B | 58 |
| 28 | A | 90 |
| 29 | A | 99 |
| 30 | A | 99 |
| 31 | A | 95 |
| 32 | A | 95 |
| 33 | A | 98 |
| 35 | C | 6 |
| 36 | A | 95 |
| 37 | A | 97 |
| 38 | A | 87 |
| 39 | A | 97 |
| 40 | A | 94 |
| 41 | A | 97 |
| 42 | A | 95 |
| 43 | A | 94 |
| 44 | A | 82 |
| 45 | A | 93 |
| 46 | A | 96 |
| 47 | A | 91 |
| 48 | A | 82 |
| 49 | B | 66 |
| 50 | B | 80 |
| 51 | A | 82 |
| 52 | B | 71 |
| 53 | B | 71 |
| 54 | A | 81 |
| 55 | B | 60 |
| 56 | C | 0 |
| 57 | A | 97 |
| 58 | B | 76 |
| 59 | A | 82 |
| 60 | B | 75 |
| 61 | B | 76 |
| 62 | B | 54 |
| 63 | A | 96 |
| 64 | A | 95 |

TABLE 2-continued

CSF1R kinase binding activity (%, @ 0.1 uM)

| # cpds | Range | Percent (%) |
|---|---|---|
| 65 | A | 96 |
| 66 | A | 96 |
| 67 | A | 96 |
| 68 | A | 98 |
| 69 | A | 89 |
| 70 | B | 79 |
| 71 | A | 88 |
| 72 | A | 96 |
| 73 | A | 97 |
| 74 | C | 39 |
| 75 | B | 57 |
| 76 | A | 94 |
| 77 | B | 76 |
| 78 | C | 11 |
| 79 | C | 12 |
| 80 | B | 64 |
| 81 | C | 46 |
| 82 | C | 35 |
| 83 | A | 97 |
| 84 | A | 97 |
| 85 | B | 78 |
| 86 | C | 11 |
| 87 | B | 71 |
| 88 | C | 21 |
| 89 | B | 56 |
| 90 | A | 95 |
| 91 | A | 99 |
| 92 | A | 100 |
| 93 | A | 89 |
| 94 | B | 65 |
| 95 | B | 61 |
| 96 | B | 57 |
| 97 | B | 56 |
| 98 | B | 60 |
| 99 | A | 94 |
| 100 | C | 36 |
| 101 | C | 45 |
| 102 | A | 87 |
| 103 | C | 29 |
| 104 | C | 46 |
| 105 | A | 91 |
| 106 | A | 95 |
| 107 | A | 90 |
| 108 | A | 96 |
| 109 | A | 98 |
| 110 | A | 98 |
| 111 | A | 89 |
| 112 | A | 97 |
| 113 | A | 82 |
| 114 | C | 27 |
| 115 | A | 94 |
| 116 | A | 93 |
| 117 | A | 94 |
| 118 | A | 93 |
| 119 | C | 9 |
| 120 | A | 95 |
| 121 | A | 98 |
| 122 | C | 19 |
| 123 | B | 72 |
| 124 | A | 95 |
| 125 | C | 38 |
| 126 | B | 78 |
| 127 | C | 38 |
| 128 | A | 94 |
| 129 | C | 24 |
| 130 | C | 41 |
| 131 | C | 21 |
| 132 | C | 16 |
| 133 | C | 9 |
| 134 | C | 18 |
| 135 | C | 4 |
| 136 | C | 23 |
| 137 | C | 6 |
| 138 | C | 9 |
| 139 | C | 37 |
| 140 | C | 38 |
| 141 | C | 23 |
| 142 | A | 92 |
| 143 | A | 95 |
| 144 | B | 73 |
| 145 | A | 94 |
| 146 | C | 43 |
| 147 | A | 85 |
| 148 | B | 60 |
| 149 | B | 76 |
| 150 | B | 74 |
| 151 | A | 97 |
| 152 | A | 96 |
| 153 | A | 95 |
| 154 | C | 47 |
| 155 | C | 22 |
| 156 | C | 49 |
| 157 | A | 81 |
| 158 | A | 91 |
| 159 | B | 64 |
| 160 | C | 25 |
| 161 | C | 14 |
| 162 | A | 91 |
| 163 | A | 93 |
| 164 | B | 73 |
| 165 | C | 5 |
| 166 | A | 84 |
| 167 | C | 0 |
| 168 | A | 95 |
| 169 | A | 93 |
| 170 | A | 90 |
| 171 | B | 60 |
| 172 | C | 36 |
| 173 | B | 69 |
| 174 | C | 25 |
| 175 | A | 97 |
| 176 | C | 40 |

Activity range: A indicates ≥ 80%, B indicates 80 > % inhibition 50%, C indicates < 50%

TABLE 3

Cellular Axl activity by H1299 Elisa

| # cpds | Axl |
|---|---|
| 1 | A |
| 2 | A |
| 3 | A |
| 4 | A |
| 5 | A |
| 6 | A |
| 7 | A |
| 8 | A |
| 9 | A |
| 10 | A |
| 11 | A |
| 12 | A |
| 13 | A |
| 14 | A |
| 15 | C |
| 16 | A |
| 17 | A |
| 18 | A |
| 19 | A |
| 20 | A |
| 21 | A |
| 22 | A |
| 23 | A |
| 24 | A |
| 25 | A |
| 26 | A |
| 27 | A |
| 28 | A |
| 29 | A |

TABLE 3-continued

Cellular Axl activity by H1299 Elisa

| # cpds | Axl |
|---|---|
| 30 | A |
| 31 | A |
| 32 | A |
| 33 | A |
| 34 | C |
| 35 | C |
| 36 | A |
| 37 | C |
| 38 | A |
| 39 | A |
| 40 | A |
| 41 | A |
| 42 | A |
| 43 | A |
| 44 | A |
| 45 | B |
| 46 | A |
| 47 | A |
| 48 | A |
| 49 | A |
| 50 | A |
| 51 | A |
| 52 | A |
| 53 | A |
| 54 | A |
| 55 | A |
| 56 | C |
| 57 | A |
| 58 | A |
| 59 | A |
| 60 | A |
| 61 | A |
| 62 | A |
| 63 | A |
| 64 | A |
| 65 | A |
| 66 | A |
| 67 | A |
| 68 | A |
| 69 | A |
| 70 | A |
| 71 | A |
| 72 | C |
| 73 | C |
| 74 | A |
| 75 | A |
| 76 | A |
| 77 | A |
| 78 | A |
| 79 | A |
| 80 | A |
| 81 | C |
| 82 | C |
| 83 | A |
| 84 | A |
| 85 | A |
| 86 | A |
| 87 | A |
| 88 | B |
| 89 | A |
| 90 | A |
| 91 | A |
| 92 | A |
| 93 | A |
| 94 | A |
| 95 | A |
| 96 | A |
| 97 | A |
| 98 | C |
| 99 | A |
| 100 | B |
| 101 | A |
| 102 | C |
| 103 | A |
| 104 | B |
| 105 | A |
| 106 | A |
| 107 | A |
| 108 | A |
| 109 | A |
| 110 | A |
| 111 | A |
| 112 | A |
| 113 | A |
| 114 | A |
| 115 | A |
| 116 | A |
| 117 | B |
| 118 | A |
| 119 | C |
| 120 | B |
| 121 | A |
| 122 | C |
| 123 | A |
| 124 | A |
| 125 | C |
| 126 | A |
| 127 | C |
| 128 | A |
| 129 | C |
| 130 | C |
| 131 | A |
| 132 | C |
| 133 | C |
| 134 | A |
| 135 | C |
| 136 | C |
| 137 | C |
| 138 | A |
| 139 | A |
| 140 | C |
| 141 | C |
| 142 | A |
| 143 | A |
| 144 | C |
| 145 | A |
| 146 | A |
| 147 | A |
| 148 | A |
| 149 | A |
| 150 | A |
| 151 | A |
| 152 | B |
| 153 | A |
| 154 | B |
| 155 | A |
| 156 | C |
| 157 | C |
| 158 | A |
| 159 | C |
| 160 | C |
| 161 | A |
| 162 | A |
| 163 | A |
| 164 | A |
| 165 | A |
| 166 | A |
| 167 | A |
| 168 | A |
| 169 | C |
| 170 | A |
| 171 | A |
| 172 | C |

TABLE 3-continued

Cellular Axl activity by H1299 Elisa

| # cpds | Axl |
|---|---|
| 173 | A |
| 174 | C |
| 175 | A |
| 176 | A |
| 177 | A |
| 178 | A |
| 179 | A |

Activity range: A indicates < 0.5 uM, B indicates 0.5 ≤ IC50 < 1 uM, C indicates ≥ 1 uM

TABLE 4

Cellular CSF1R activity by THP-1 Elisa assay

| # cpds | CSF1R |
|---|---|
| 1 | A |
| 2 | A |
| 3 | A |
| 4 | A |
| 5 | A |
| 6 | A |
| 7 | A |
| 8 | A |
| 9 | A |
| 10 | A |
| 11 | B |
| 12 | A |
| 13 | A |
| 14 | A |
| 15 | C |
| 16 | A |
| 17 | A |
| 18 | A |
| 19 | A |
| 20 | A |
| 21 | A |
| 22 | A |
| 23 | A |
| 24 | A |
| 25 | B |
| 26 | A |
| 27 | C |
| 28 | B |
| 29 | A |
| 30 | A |
| 31 | A |
| 32 | A |
| 33 | A |
| 34 | C |
| 35 | C |
| 36 | A |
| 37 | A |
| 38 | B |
| 39 | A |
| 40 | A |
| 41 | A |
| 42 | A |
| 43 | A |
| 44 | A |
| 45 | A |
| 46 | B |
| 47 | B |
| 48 | B |
| 49 | C |
| 50 | B |
| 51 | A |
| 52 | C |
| 53 | B |
| 54 | C |
| 55 | C |
| 56 | A |
| 57 | B |
| 58 | C |
| 59 | A |
| 60 | B |
| 61 | C |
| 62 | C |
| 63 | B |
| 64 | A |
| 65 | A |
| 66 | A |
| 67 | A |
| 68 | A |
| 69 | A |
| 70 | B |
| 71 | A |
| 72 | A |
| 73 | A |
| 74 | C |
| 75 | C |
| 76 | C |
| 77 | C |
| 78 | C |
| 79 | C |
| 80 | C |
| 81 | C |
| 82 | C |
| 83 | A |
| 84 | B |
| 85 | B |
| 86 | C |
| 87 | B |
| 88 | C |
| 89 | B |
| 90 | A |
| 91 | A |
| 92 | A |
| 93 | A |
| 94 | C |
| 95 | C |
| 96 | C |
| 97 | C |
| 98 | C |
| 99 | B |
| 100 | C |
| 101 | C |
| 102 | A |
| 103 | C |
| 104 | C |
| 105 | A |
| 106 | A |
| 107 | A |
| 108 | A |
| 109 | A |
| 110 | A |
| 111 | B |
| 112 | B |
| 113 | A |
| 114 | C |
| 115 | B |
| 116 | B |
| 117 | A |
| 118 | B |
| 119 | C |
| 120 | B |
| 121 | A |
| 122 | C |
| 123 | C |
| 124 | B |
| 125 | C |
| 126 | C |
| 127 | C |
| 128 | A |
| 129 | C |
| 130 | C |
| 131 | C |
| 132 | C |
| 133 | C |
| 134 | C |

TABLE 4-continued

Cellular CSF1R activity by THP-1 Elisa assay

| # cpds | CSF1R |
|---|---|
| 135 | C |
| 136 | C |
| 137 | C |
| 138 | C |
| 139 | C |
| 140 | C |
| 141 | C |
| 142 | A |
| 143 | A |
| 144 | C |
| 145 | A |
| 146 | C |
| 147 | B |
| 148 | C |
| 149 | C |
| 150 | C |
| 151 | A |
| 152 | A |
| 153 | A |
| 154 | C |
| 155 | C |
| 156 | C |
| 157 | B |
| 158 | A |
| 159 | C |
| 160 | C |
| 161 | C |
| 162 | A |
| 163 | B |
| 164 | C |
| 165 | C |
| 166 | C |
| 167 | C |
| 168 | A |
| 169 | A |
| 170 | A |
| 171 | C |
| 172 | C |
| 173 | C |
| 174 | C |
| 175 | A |
| 176 | C |
| 177 | C |
| 178 | A |
| 179 | A |

Activity range: A indicates < 0.5 uM, B indicates 0.5 ≤ IC50 < 1 uM, C indicates ≥ 1 uM

TABLE 5

Cellular CSF1R activity by M-NFS-60 viability assay

| # cpds | CSF1R |
|---|---|
| 1 | A |
| 2 | A |
| 3 | C |
| 4 | A |
| 5 | A |
| 6 | A |
| 7 | A |
| 8 | A |
| 9 | A |
| 10 | A |
| 11 | A |
| 12 | A |
| 13 | A |
| 14 | A |
| 15 | B |
| 16 | A |
| 17 | A |
| 18 | A |
| 19 | A |
| 20 | A |
| 21 | A |
| 22 | A |
| 23 | A |
| 24 | A |
| 25 | B |
| 26 | B |
| 27 | B |
| 28 | B |
| 29 | A |
| 30 | A |
| 31 | A |
| 32 | B |
| 33 | A |
| 34 | B |
| 35 | B |
| 36 | A |
| 37 | A |
| 38 | A |
| 39 | A |
| 40 | A |
| 41 | A |
| 42 | A |
| 43 | A |
| 44 | A |
| 45 | B |
| 46 | B |
| 47 | A |
| 48 | A |
| 49 | B |
| 50 | B |
| 51 | A |
| 52 | A |
| 53 | A |
| 54 | A |
| 55 | B |
| 56 | A |
| 57 | A |
| 58 | B |
| 59 | A |
| 60 | B |
| 61 | B |
| 62 | B |
| 63 | B |
| 64 | B |
| 65 | B |
| 66 | B |
| 67 | B |
| 68 | B |
| 69 | B |
| 70 | B |
| 71 | B |
| 72 | B |
| 73 | B |
| 74 | B |
| 75 | B |
| 76 | B |
| 77 | B |
| 78 | B |
| 79 | B |
| 80 | B |
| 81 | B |
| 82 | B |
| 83 | B |
| 84 | B |
| 85 | B |
| 86 | B |
| 87 | B |
| 88 | B |
| 89 | B |
| 90 | A |
| 91 | A |
| 92 | A |
| 93 | A |
| 94 | B |
| 95 | B |
| 96 | B |

TABLE 5-continued

Cellular CSF1R activity by M-NFS-60 viability assay

| # cpds | CSF1R |
|---|---|
| 97 | B |
| 98 | B |
| 99 | B |
| 100 | B |
| 101 | B |
| 102 | B |
| 103 | B |
| 104 | C |
| 105 | A |
| 106 | A |
| 107 | B |
| 108 | A |
| 109 | A |
| 110 | A |
| 111 | B |
| 112 | B |
| 113 | B |
| 114 | B |
| 115 | B |
| 116 | B |
| 117 | A |
| 118 | B |
| 119 | B |
| 120 | B |
| 121 | A |
| 122 | B |
| 123 | B |
| 124 | B |
| 125 | C |
| 126 | B |
| 127 | C |
| 128 | B |
| 129 | C |
| 130 | B |
| 131 | B |
| 132 | C |
| 133 | B |
| 134 | C |
| 135 | C |
| 136 | B |
| 137 | B |
| 138 | B |
| 139 | B |
| 140 | B |
| 141 | C |
| 142 | B |
| 143 | B |
| 144 | C |
| 145 | A |
| 146 | B |
| 147 | B |
| 148 | B |
| 149 | B |
| 150 | B |
| 151 | A |
| 152 | A |
| 153 | A |
| 154 | B |
| 155 | B |
| 156 | B |
| 157 | B |
| 158 | B |
| 159 | C |
| 160 | C |
| 161 | B |
| 162 | B |
| 163 | B |
| 164 | C |
| 165 | B |
| 166 | B |
| 167 | B |
| 168 | A |
| 169 | A |
| 170 | A |
| 171 | C |
| 172 | C |
| 173 | B |
| 174 | C |
| 175 | A |
| 176 | B |
| 177 | B |
| 178 | A |
| 179 | A |

Activity range: A indicates < 1.0 uM, B indicates 1.0 ≤ IC50 < 10 uM, C indicates ≥ 10 uM

TABLE 6

Cellular Axl and Mer activity by Ba/F3 assay

| # cpds | Axl | Mer | CSF1R |
|---|---|---|---|
| 4 | A | A | A |
| 5 | A | A | A |
| 7 | A | A | A |
| 10 | A | A | A |
| 12 | A | A | A |
| 15 | A | B | B |
| 16 | A | A | A |
| 17 | A | A | A |
| 18 | A | A | A |
| 29 | A | A | A |
| 30 | A | A | A |
| 35 | C | C | B |

Activity range: A indicates < 1.0 uM, B indicates 1.0 ≤ IC50 < 10 uM, C indicates ≥ 10 uM

TABLE 7

Comparison data by Binding and Cellular assay

| | Binding activity | | Cellular activity |
|---|---|---|---|
| | Axl | Mer | Axl (H1299) |
| # Cpds | (Kd, nM) | (Kd, nM) | (IC50, nM) |
| Compound 22* | 104 | 73 | >3000 |
| Compound 16** | 19 | 12 | 44 |
| Compound 27* | 64 | 11 | 190 |
| Compound 4** | 1.1 | 1.6 | 3.4 |
| Compound 48* | 19 | 3.7 | 183 |
| Compound 92** | 1.4 | 1.3 | 3.9 |
| Compound 64* | 60 | 3.2 | 337 |
| Compound 10** | 3.2 | 0.2 | 5.2 |

*: Compounds of WO2016/166250

**: Compounds of present invention

TABLE 8

Summarizes compounds 1-179 in terms of their structures and corresponding characteristics.

| # cpd | Structure | Characterization Data |
|---|---|---|
| 1 | 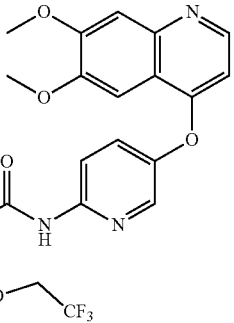 | yellow powder; $^1$H-NMR (DMSO-d6, 400 MHz): δ 9.59 (1H, s), 8.50 (1H, d, J = 5.2 Hz), 8.40 (1H, d, J = 2.8 Hz), 8.31 (1H, d, J = 9.2 Hz), 7.87 (1H, dd, J = 8.8, 2.4 Hz), 7.54 (1H, s), 7.42 (1H, s), 6.55 (1H, d, J = 5.2 Hz), 4.73 (2H, q, J = 9.2 Hz), 4.15 (2H, q, J = 7.2 Hz), 3.95 (3H, s), 3.94 (3H, s), 2.24 (3H, s), 1.38 (3H, t, J = 7.2 Hz); LCMS: 99.1%, MS (ESI): m/z 532.1 [M + H]+. |
| 2 | 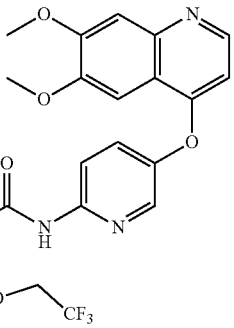 | white powder; $^1$H-NMR (DMSO-d6, 400 MHz): δ 9.60 (1H, s), 8.51 (1H, d, J = 5.2 Hz), 8.41 (1H, d, J = 2.8 Hz), 8.32 (1H, d, J = 9.2 Hz), 7.87 (1H, dd, J = 9.2, 2.8 Hz), 7.54 (1H, s), 7.42 (1H, s), 6.55 (1H, d, J = 5.2 Hz), 4.73 (2H, q, J = 9.2 Hz), 4.54-4.65 (1H, m), 3.96 (3H, s), 3.95 (3H, s), 2.25 (3H, s), 1.43 (6H, d, J = 6.4 Hz); LCMS: 96.9%, MS (ESI): m/z 546.1 [M + H]+. |
| 3 | 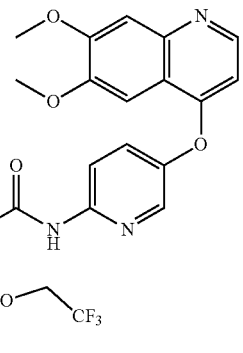 | white powder; $^1$H-NMR (DMSO-d6, 400 MHz): δ 10.25 (1H, brs), 8.49 (1H, d, J = 5.2 Hz), 8.43 (1H, d, J = 3.2 Hz), 8.28 (1H, |
| 4 | 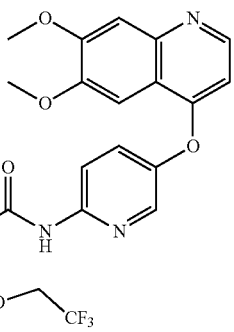 | white powder; $^1$H-NMR (DMSO-d6, 400 MHz): 9.53 (1H, brs), 8.50 (1H, d, J = 5.2 Hz), 8.40 (1H, d, J = 3.2 Hz), 8.32 (1H, d, J = 8.8 Hz), 7.99 (1H, s), 7.86 (1H, dd, J = 8.8, 2.8 Hz), 7.54 (1H, s), 7.42 (1H, s), 6.55 (1H, d, J = 5.2 Hz), 4.78 (2H, q, J = 8.8 Hz), 4.18 (2H, q, J = 7.2 Hz), 3.96 (3H, s), 3.95 (6H, s), 1.43 (3H, t, J = 7.2 Hz); LCMS: 100%, MS (ESI): m/z 518.1 [M + H]+. |

TABLE 8-continued

Summarizes compounds 1-179 in terms of their structures and corresponding characteristics.

| # cpd | Structure | Characterization Data |
|---|---|---|
| 5 | 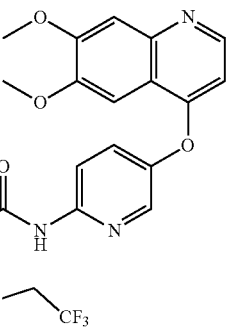 | white powder; ¹H-NMR (DMSO-d6, 400 MHz): δ 9.58 (1H, brs), 8.50 (1H, d, J = 5.2 Hz), 8.40 (1H, d, J = 2.8 Hz), 8.31 (1H, d, J = 8.8 Hz), 8.04 (1H, s), 7.86 (1H, dd, J = 8.8, 2.8 Hz), 7.54 (1H, s), 7.42 (1H, s), 6.55 (1H, d, J = 5.2 Hz), 4.76 (2H, q, J = 8.8 Hz), 3.95 (3H, s), 3.94 (3H, s), 3.78-3.87 (1H, m), 1.11-1.18 (2H, m), 0.99-1.07 (2H, m); LCMS: 98.4%, MS (ESI): m/z 530.1 [M + H]+. |
| 6 | 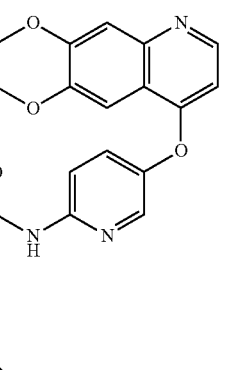 | white powder; ¹H-NMR (DMSO-d6, 400 MHz): δ 9.58 (1H, brs), 8.49 (1H, d, J = 5.2 Hz), 8.39 (1H, d, J = 3.2 Hz), 8.36 (1H, d, J = 8.8 Hz), 7.82-7.89 (2H, m), 7.54 (1 H, s), 7.41 (1H, s), 6.55 (1H, d, J = 5.2 Hz), 4.35-4.46 (1H, m), 4.15 (2H, q, J = 7.2 Hz), 3.95 (3H, s), 3.94 (3H, s), 1.41 (3H, t, J = 7.2 Hz), 1.36 (6 H, d, J = 6.0 Hz); LCMS: 100%, MS (ESI): m/z 478.1 [M + H]+. |
| 7 | 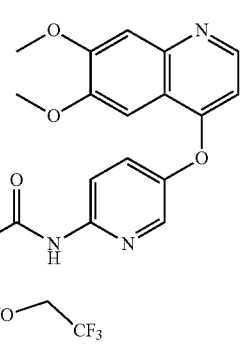 | white powder; ¹H-NMR (DMSO-d6, 400 MHz): 9.51 (1H, brs), 8.51 (1H, d, J = 5.2 Hz), 8.40 (1H, d, J = 2.8 Hz), 8.32 (1H, d, J = 9.2 Hz), 7.97 (1H, s), 7.87 (1H, dd, J = 9.2, 2.4 Hz), 7.54 (1H, s), 7.42 (1H, s) 6.55 (1H, d, J = 5.2 Hz), 4.78 (2H, q, J = 8.8 Hz), 4.11 (2H, t, J = 6.4 Hz), 3.95 (3H, s), 3.94 (3H, s), 1.81-1.86 (2H, m), 0.86 (3H, t, J = 7.6 Hz); LCMS: 100%, MS (ESI): m/z 532.1 [M + H]+. |
| 8 | 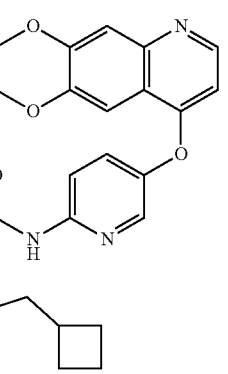 | white powder; ¹H-NMR (DMSO-d6, 400 MHz): 9.59 (1H, brs), 8.49 (1H, d, J = 5.2 Hz), 8.34-8.39 (2H, m), 7.83-7.88 (2H, m), 7.53 (1H, s), 7.41 (1H, s), 6.55 (1H, d, J = 5.2 Hz), 4.15 (2H, q, J = 7.2 Hz), 4.03 (2H, d, J = 6.8 Hz), 3.95 (3H, s), 3.94 (3H, s), 2.72-2.84 (1H, m), 2.05-2.11 (2H, m), 1.87-1.98 (4H, m), 1.41 (3H, t, J = 7.2 Hz); LCMS: 100%, MS (ESI): m/z 504.1 [M + H]+. |

TABLE 8-continued

Summarizes compounds 1-179 in terms of their structures and corresponding characteristics.

| # cpd | Structure | Characterization Data |
|---|---|---|
| 9 | 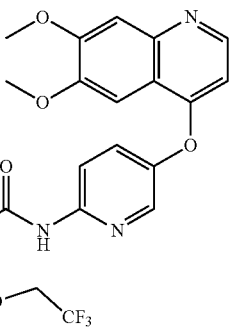 | white powder; ¹H-NMR (DMSO-d6, 400 MHz): 9.56 (1H, brs), 8.48 (1H, d, J = 5.2 Hz), 8.38 (1H, d, J = 2.8 Hz), 8.30 (1H, d, J = 9.2 Hz), 7.96 (1H, s), 7.85 (1H, dd, J = 9.2, 2.8 Hz), 7.52 (1H, s), 7.40 (1H, s), 6.53 (1H, d, J = 4.8 Hz), 4.75 (2H, q, J = 8.8 Hz), 4.20-4.35 (2H, m), 3.94 (3H, s), 3.93 (3H, s), 2.65-2.90 (2H, m), 2.10-2.35 (6H, m); LCMS: 100%, MS (ESI): m/z 583.1 [M + Na]+. |
| 10 | 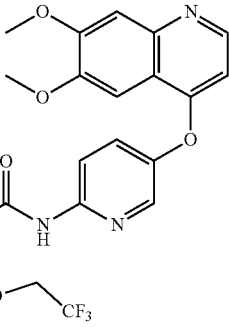 | white powder; ¹H-NMR (DMSO-d6, 400 MHz): 9.54 (1H, brs), 8.50 (1H, d, J = 5.2 Hz), 8.40 (1H, d, J = 2.8 Hz), 8.32 (1H, d, J = 9.2 Hz), 7.95 (1H, s), 7.87 (1H, dd, J = 8.8, 2.8 Hz), 7.54 (1H, s), 7.42 (1H, s), 6.56 (2H, d, J = 4.8 Hz), 4.79 (2H, q, J = 8.8 Hz), 4.31 (2H, t, J = 5.2 Hz), 3.95 (3H, s), 3.94 (3H, s), 3.75 (2H, d, J = 5.2 Hz), 3.26 (3H, s); LCMS: 100%, MS (ESI): m/z 548.1 [M + H]+. |
| 11 | 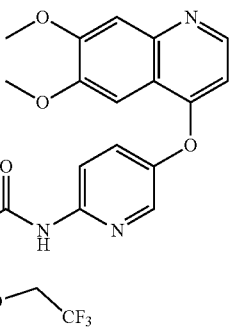 | white powder; ¹H-NMR (DMSO-d6, 400 MHz): δ 9.57 (1H, brs), 8.50 (1H, d, J = 5.2 Hz), 8.40 (1H, d, J = 3.2 Hz), 8.32 (1H, d, J = 9.2 Hz), 7.94 (1H, s), 7.86 (1H, d, J = 8.8, 2.8 Hz), 7.53 (1H, s), 7.42 (1H, s), 6.55 (1H, d, J = 5.2 Hz), 4.76 (2H, q, J = 8 8 Hz), 4.19 (2H, q, J = 6.0 Hz), 3.95 (3H, s), 3.94 (3H, s), 2.90 (2H, q, J = 6.0 Hz), 2.29 (3H, s); LCMS: 100%, MS (ESI): m/z 569.1 [M + Na]+ |
| 12 | 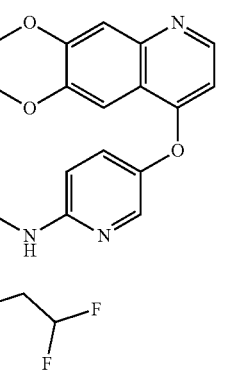 | white powder; ¹H-NMR (DMSO-d6, 400 MHz): δ 9.48 (1H, brs), 8.50 (1H, d, J = 5.2 Hz), 8.38 (1H, d, J = 3.2 Hz), 8.31 (1H, d, J = 8.8 Hz), 7.91 (1H, s), 7.85 (1H, dd, J = 9.2, 2.8 Hz), 7.53 (1H, s), 7.41 (1H, s), 6.20-6.70 (2H, m), 4.25-4.44 (2H, m), 4.08 (2H, t, J = 7.2 Hz), 3.94 (3H, s), 3.93 (3H, s), 1.75-1.90 (2H, m), 0.85 (2H, t, J = 7.6 Hz); LCMS: 100%, MS (ESI): m/z 514.1 [M + H]+. |

TABLE 8-continued

Summarizes compounds 1-179 in terms of their structures and corresponding characteristics.

| # cpd | Structure | Characterization Data |
|---|---|---|
| 13 | 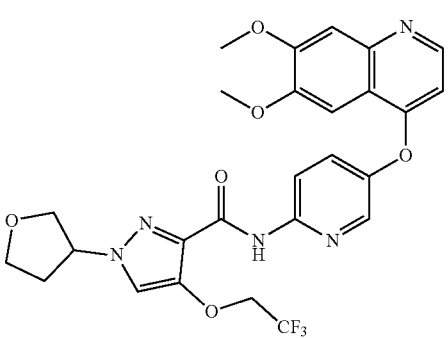 | white powder; ¹H-NMR (400 MHz, DMSO-d6) δ 9.61 (1H, brs), 8.50 (1H, d, J = 4.8 Hz), 8.40 (1H, d, J = 2.4 Hz), 8.31 (1H, d, J = 9.6 Hz), 8.02 (1H, s), 7.87 (1H, dd, J = 8.8, 2.8 Hz), 7.54 (1H, s), 7.42 (1H, s), 6.56 (2H, d, J = 5.6 Hz), 5.02-5.08 (1H, m), 4.79 (2H, q, J = 8.8 Hz), 3.90-4.05 (9H, m), 3.81-3.83 (1H, m), 2.30-2.38 (2H, m); LCMS: 100%, MS (ESI): m/z 560.1 [M + H]+. |
| 14 | 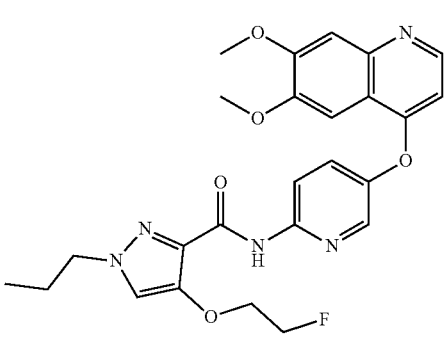 [SMILES: CCCn1cc(OCCF)c(C(=O)Nc2ccc(Oc3ccnc4cc(OC)c(OC)cc34)cn2)n1] | white powder; ¹H-NMR (DMSO-d6, 400 MHz): δ 9.52 (1H, s), 8.49 (1H, d, J = 5.2 Hz), 8.39 (1H, d, J = 2.8 Hz), 8.34 (1H, d, J = 9.2 Hz), 7.84-7.89 (2H, m), 7.54 (1H, s), 7.41 (1H, s), 6.55 (1H, d, J = 5.2 Hz), 4.69-4.85 (2H, m), 4.25-4.36 (2H, m), 4.09 (2H, t, J = 6.8 Hz), 3.95 (6H, d, J = 2.8 Hz), 1.79-1.88 (2H, m), 0.86 (3H, t, J = 7.6 Hz); LCMS: 96.7%, MS (ESI): m/z 496.1 [M + H]+. |
| 15 | 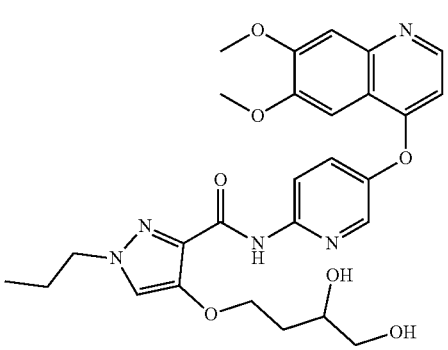 [SMILES: CCCn1cc(OCCC(O)CO)c(C(=O)Nc2ccc(Oc3ccnc4cc(OC)c(OC)cc34)cn2)n1] | white powder; ¹H-NMR (DMSO-d6, 400 MHz): δ 9.55 (1H, brs), 8.49 (1H, d, J = 5.2 Hz), 8.31-8.41 (2H, m), 7.80-7.90 (2H, m), 7.54 (1H, S), 7.41 (1H, s), 6.55 (1H, d, J = 5.2 Hz), 4.68 (1H, d, J = 4.8 Hz), 4.59 (1H, t, J = 5.6 Hz), 4.14 (2H, t, J = 6.0 Hz), 4.08 (2H, t, J = 6.8 Hz), 3.95 (3H, s), 3.94 (3H, s), 3.64-3.73 (1H, m), 3.35-3.44 (2H, m), 1.95-2.07 (1H, m), 1.79-1.89 (2H, m), 1.64-1.77 (1H, m), 0.86 (3H, t, J = 7.2 Hz); LCMS: 100%, MS (ESI): m/z 538.2 [M + H]+. |
| 16 | 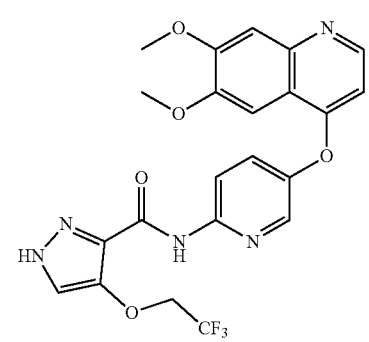 [SMILES: COc1cc2nccc(Oc3ccc(NC(=O)c4n[nH]cc4OCC(F)(F)F)nc3)c2cc1OC] | white powder; ¹H-NMR (DMSO-d6, 400 MHz) δ 13.84 (1H, brs), 13.40 (1H, brs), 9.61 (1H, brs), 9.29 (1H, brs), 8.50 (1H, d, J = 5.2 Hz), 8.40 (1H, s), 8.33 (1H, d, J = 8.8 Hz), 7.93 (1H, s), 7.87 (1H, d, J = 8.8 Hz), 7.77 (1H, s), 7.54 (1H, s), 7.42 (1H, s), 6.55 (1H, d, J = 5.2 Hz), 5.01 (1H, d, J = 8.0 Hz), 4.77 (1H, q, J = 8.8 Hz), 3.95 (3H, s), 3.94 (3H, s); LCMS: 100%, MS (ESI): m/z 490.0 [M + H]+. |

TABLE 8-continued

Summarizes compounds 1-179 in terms of their structures and corresponding characteristics.

| # cpd | Structure | Characterization Data |
|---|---|---|
| 17 | 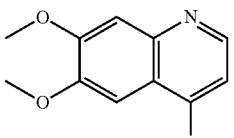 | white solid; $^1$H-NMR (CDCl3, 400 MHz) δ 9.30 (1H, s), 8.48-8.53 (2H, m), 8.27-8.29 (m, 1H), 7.62 (1H, dd, J = 8.8 Hz), 7.56 (1H, s), 7.43 (1H, s), 7.41 (1H, s), 6.46 (1H, d, J = 6.4 Hz), 4.49 (2H, q, J = 8.4 Hz), 4.28-4.34 (1H, m), 4.16-4.20 (1H, m), 4.07 (6H, s), 3.88-4.04 (1H, m), 1.29 (3H, d, J = 6.4 Hz); LCMS: 100.0%, MS (ESI): m/z 548.1 [M + H]+. |
| 18 | 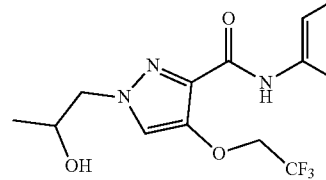 | off-white powder; $^1$H-NMR (DMSO-d6, 400 MHz) δ 9.54 (1H, s), 8.50 (1H, d, J = 5.2 Hz), 8.40 (1H, d, J = 3.2 Hz), 8.32 (1H, d, J = 8.8 Hz), 7.96 (1H, s), 7.86 (1H, dd, J = 9.2, 3.2 Hz), 7.54 (1H, s), 7.42 (1H, s), 6.55 (1H, d, J = 5.6 Hz), 4.77 (2H, q, J = 9.2 Hz), 4.67 (1H, t, J = 4.8 Hz), 4.20 (2H, t, J = 6.8 Hz), 3.95 (3H, s), 3.94 (3H, s), 3.42 (2H, q, J = 5.6 Hz), 1.92-2.05 (2H, m); LCMS: 100%, MS (ESI): m/z 548.1 [M + H]+. |
| 19 | 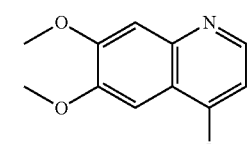 | yellowish powder; $^1$H-NMR (CDCl3, 400 MHz) δ 9.29 (1H, s), 8.53 (1H, d, J = 5.2 Hz), 8.48 (1H, d, J = 9.2 Hz), 8.27 (1H, d, J = 2.4 Hz), 7.61 (1H, dd, J = 8.8 Hz, 2.8 Hz), 7.56 (1H, s), 7.45 (1H, s), 7.38 (1H, s), 6.47 (1H, d, J = 5.2 Hz), 4.94 (2H, s), 4.57 (2H, q, J = 8.4 Hz), 4.07 (6H, s), 2.25 (3H, s); LCMS: 100.0%, MS (ESI): m/z 546.0 [M + H]+. |
| 20 | 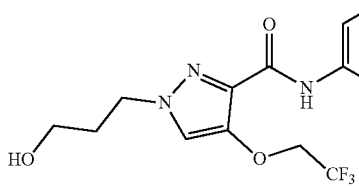 | white powder; $^1$H-NMR (DMSO-d6, 400 MHz) δ 10.33 (1H, s), 8.54 (1H, s), 8.51 (1H, d, J = 5.2 Hz), 8.44 (1H, d, J = 2.8 Hz), 8.31 (1H, d, J = 8.8 Hz), 7.89 (1H, dd, J = 9.2, 3.2 Hz), 7.54 (1H, s), 7.42 (1H, s), 6.57 (1H, d, J = 5.2 Hz), 4.89 (2H, q, J = 8.4 Hz), 3.95 (3H, s), 3.94 (3H, s), 3.22 (2H, q, J = 7.2 Hz), 1.19-1.21 (3H, m); LCMS: 97.6%, MS (ESI): m/z 546.1 [M + H]+. |

TABLE 8-continued

Summarizes compounds 1-179 in terms of their structures and corresponding characteristics.

| # cpd | Structure | Characterization Data |
|---|---|---|
| 21 | 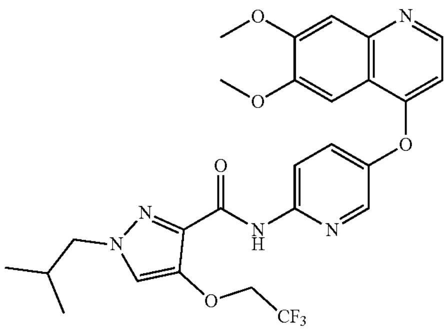 | white powder; ¹H-NMR (CDCl3, 400 MHz) δ 9.36 (1H, s), 8.53 (1H, d, J = 5.2 Hz), 8.49 (1H, d, J = 8.8 Hz), 8.29 (1H, d, J = 2.8 Hz), 7.61 (1H, dd, J = 8.8, 2.8 Hz), 7.56 (1H, s), 7.45 (1H, s), 7.31 (1H, s), 6.47 (1H, d, J = 5.2 Hz), 4.56 (2H, t, J = 8.4 Hz), 4.07 (6H, s), 3.90 (2H, d, J = 7.2 Hz), 2.21-2.27 (1H, m), 0.95 (6H, d, J = 6.8 Hz); LCMS: 100.0%, MS (ESI): m/z 546.1 [M + H]+. |
| 22 | 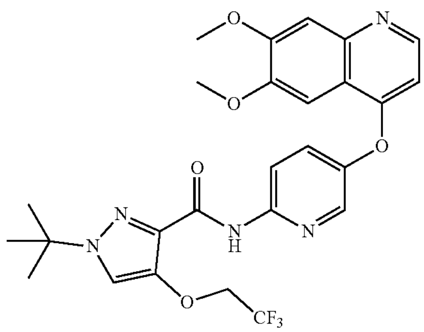 [SMILES: COc1cc2nccc(Oc3ccc(NC(=O)c4nn(C(C)(C)C)cc4OCC(F)(F)F)nc3)c2cc1OC] | white powder; 1H-NMR (CDCl3, 400 MHz) δ 9.37 (1H, s), 8.50-8.53 (2H, m), 8.29 (1H, d, J = 2.8 Hz), 7.61 (1H, dd, J = 9.2, 2.8 Hz), 7.57 (1H, s), 7.45-7.46 (2H, m), 6.47 (1H, d, J = 5.6 Hz), 4.56 (2H, q, J = 8.4 Hz), 4.07-4.08 (6H, m), 1.62 (6H, s); LCMS: 100.0%, MS (ESI): m/z 546.1 [M + H]+. |
| 23 | 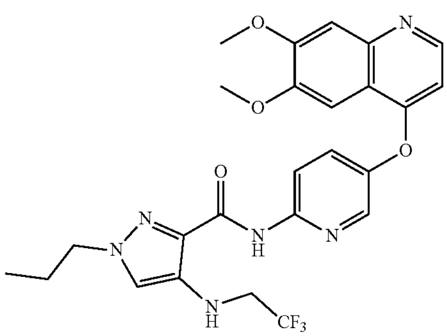 [SMILES: CCCn1cc(NCC(F)(F)F)c(C(=O)Nc2ccc(Oc3ccnc4cc(OC)c(OC)cc34)cn2)n1] | white powder; ¹H-NMR (CDCl3, 400 MHz) δ 9.24 (1H, s), 8.53 (1H, d, J = 5.2 Hz), 8.44 (1H, d, J = 9.2 Hz), 8.27 (1H, d, J = 2.4 Hz), 7.59 (1H, dd, J = 9.2, 2.8 Hz), 7.56 (1H, s), 7.45 (1H, s), 6.97 (1H, s), 6.47 (2H, d, J = 5.6 Hz), 5.72 (1H, t, J = 7.0 Hz), 4.07-4.08 (6H, m), 4.03 (2H, t, J = 7.0 Hz), 3.62-3.68 (2H, m), 1.87-1.94 (2H, m), 0.95 (2H, t, J = 7.6 Hz); LCMS: 100.0%, MS (ESI): m/z 531.1 [M + H]+. |
| 24 | 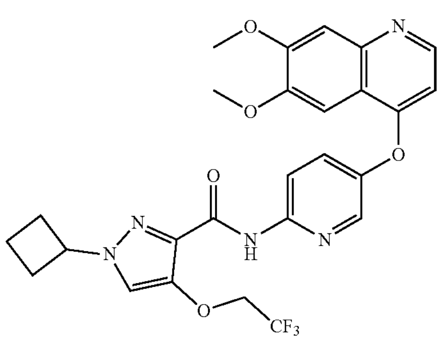 [SMILES: COc1cc2nccc(Oc3ccc(NC(=O)c4nn(C5CCC5)cc4OCC(F)(F)F)nc3)c2cc1OC] | white powder; ¹H-NMR (DMSO-d6, 400 MHz): δ 9.58 (1H, s), 8.50 (1H, d, J = 5.2 Hz), 8.40 (1H, d, J = 3.2 Hz), 8.32 (1H, d, J = 9.2 Hz), 8.08 (1H, s), 7.87 (1H, dd, J = 9.2, 3.2 Hz), 7.54 (1H, s), 7.42 (1H, s), 6.56 (1H, d, J = 4.8 Hz), 4.82-4.91 (1H, m), 4.78 (2H, q, J = 8.8 Hz), 3.95 (3H, s), 3.95 (3H, s), 2.31-2.47 (4H, m), 1.75-1.89 (2H, m); LCMS: 100%, MS (ESI): m/z 544.1 [M + H]+. |

TABLE 8-continued

Summarizes compounds 1-179 in terms of their structures and corresponding characteristics.

| # cpd | Structure | Characterization Data |
|---|---|---|
| 25 | 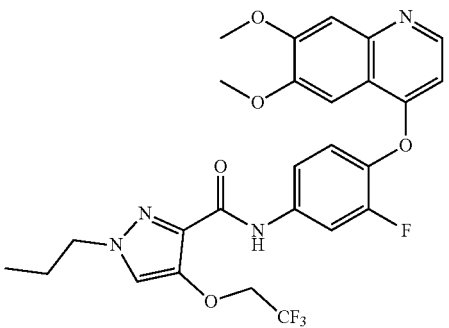 | white foam; $^1$H-NMR (DMSO-d6, 400 MHz): δ 10.24 (1H, s), 8.48 (1H, d, J = 4.8 Hz), 8.03 (1H, dd, J = 13.6, 2.0 Hz), 7.92 (1H, s), 7.74 (1H, dd, J = 7.6, 2.0 Hz), 7.53 (1H, s), 7.47-7.40 (2H, m), 6.46 (1H, d, J = 5.6 Hz), 4.70 (2H, q, J = 8.8 Hz), 4.10 (2H, t, J = 6.8 Hz), 3.95 (6H, s), 1.89-1.80 (2H, m), 0.87 (3H, t, J = 7.2 Hz); LCMS: 100.0%, MS (ESI): m/z 549.1 [M + H]+. |
| 26 | 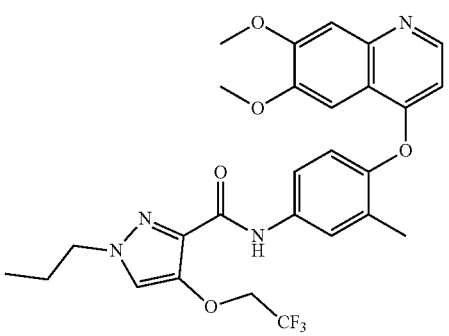 [SMILES: CCCn1cc(OCC(F)(F)F)c(C(=O)Nc2ccc(Oc3ccnc4cc(OC)c(OC)cc34)c(C)c2)n1] | white powder; $^1$H-NMR (DMSO-d6, 400 MHz): δ 9.89 (1H, s), 8.44 (1H, d, J = 5.2 Hz), 7.91 (1H, s), 7.87 (1H, d, J = 2.4 Hz), 7.72 (1H, dd, J = 8.8, 2.4 Hz), 7.57 (1H, s), 7.39 (1H, s), 7.16 (1H, d, J = 8.4 Hz), 6.29 (1H, d, J = 5.2 Hz), 4.70 (2H, q, J = 8.8 Hz), 4.09 (2H, t, J = 6.8 Hz), 3.95 (6H, s), 2.1 (3H, s), 1.89-1.80 (2H, m), 0.87 (3H, t, J = 7.2 Hz); LCMS: 100.0%, MS (ESI): m/z 545.1 [M + H]+. |
| 27 | 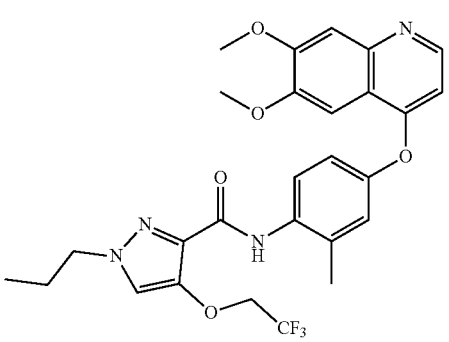 [SMILES: CCCn1cc(OCC(F)(F)F)c(C(=O)Nc2ccc(Oc3ccnc4cc(OC)c(OC)cc34)cc2C)n1] | white powder; $^1$H-NMR (DMSO-d6, 400 MHz): δ 9.21 (1H, s), 8.48 (1H, d, J = 5.2 Hz), 7.92 (1H, s), 7.81 (1H, d, J = 8.8 Hz), 7.50 (1H, s), 7.40 (1H, s), 7.20 (1H, d, J = 2.8 Hz), 7.12 (1H, dd, J = 8.4, 2.4 Hz), 6.50 (1H, d, J = 5.2 Hz), 4.74 (2H, q, J = 9.2 Hz), 4.08 (2H, t, J = 6.8 Hz), 3.94 (3H, s), 3.93 (3H, s), 2.8 (3H, s), 1.89-1.78 (2H, m), 0.87 (3H, t, J = 7.2 Hz); LCMS: 100.0%, MS (ESI): m/z 545.1 [M + H]+. |
| 28 | 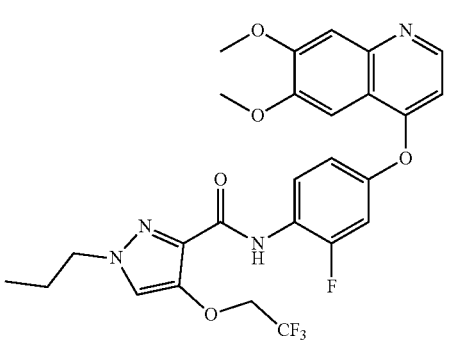 [SMILES: CCCn1cc(OCC(F)(F)F)c(C(=O)Nc2ccc(Oc3ccnc4cc(OC)c(OC)cc34)cc2F)n1] | white powder; $^1$H-NMR (DMSO-d6, 400 MHz): δ 9.4 (1H, s), 8.52 (1H, d, J = 5.2 Hz), 8.05 (1H, t, J = 9.2 Hz), 7.94 (1H, s), 7.48 (1H, s), 7.42-7.35 (2H, m), 7.14 (2H, dd, J = 10.4, 1.6 Hz), 6.59 (1H, d, J = 5.2 Hz), 4.74 (2H, q, J = 8.8 Hz), 4.09 (2H, t, J = 6.8 Hz), 3.93 (3H, s), 3.94 (3H, s), 1.9-1.76 (2H, m), 0.87 (3H, t, J = 7.2 Hz); LCMS: 100.0%, MS (ESI): m/z 549.1 [M + H]+. |

TABLE 8-continued

Summarizes compounds 1-179 in terms of their structures and corresponding characteristics.

| # cpd | Structure | Characterization Data |
|---|---|---|
| 29 | 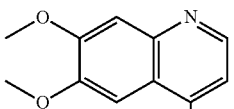 | (R), white powder; ¹H-NMR (CDCl3, 400 MHz) δ 9.30 (1H, s), 8.49-8.51 (2H, m), 8.28 (1H, d, J = 2.8 Hz), 7.61 (1H, dd, J = 9.2, 2.8 Hz), 7.56 (1H, s), 7.44 (1H, s), 7.42 (1H, s), 6.46 (1H, d, J = 5.2 Hz), 4.52 (1H, q, J = 8.0 Hz), 4.19-4.20 (1H, m), 4.17-4.19 (1H, m), 4.07 (6H, s), 4.01-4.04 (1H, m), 1.28 (3H, d, J = 6.4 Hz); LCMS: 100.0%, MS (ESI): m/z 548.1 [M + H]+. |
| 30 | 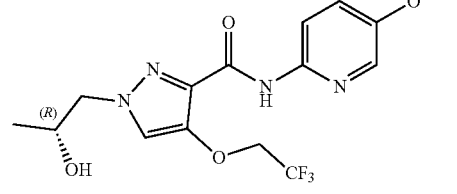 | (S), white powder; ¹H-NMR (CDCl3, 400 MHz) δ 9.30 (1H, s), 8.49-8.51 (2H, m), 8.28 (1H, d, J = 2.8 Hz), 7.61 (1H, dd, J = 8.8, 2.8 Hz), 7.56 (1H, s), 7.45 (1H, s), 7.42 (1H, s), 6.46 (1H, d, J = 5.2 Hz), 4.51 (1H, q, J = 8.4 Hz), 4.19-4.20 (1H, m), 4.17-4.19 (1H, m), 4.07 (6H, s), 4.02-4.04 (1H, m), 1.29 (3H, d, J = 6.4 Hz); LCMS: 100.0%, MS (ESI): m/z 548.1 [M + H]+. |
| 31 | 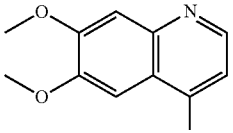 | yellow powder; ¹H-NMR (CDCl3, 400 MHz): δ 9.34 (1H, s), 8.49-8.55 (2H, m), 8.26 (1H, d, J = 2.8 Hz), 7.54-7.61 (2H, m), 7.46 (1H, s), 7.20 (1H, s), 6.47 (1H, d, J = 5.2 Hz), 4.28 (2H, t, J = 6.8 Hz), 4.03-4.11 (8H, m), 2.74 (2H, m), 1.93 (2H, m), 0.95 (3H, t, J = 7.6 Hz); LCMS: 100%, MS (ESI): m/z 546.1 [M + H]+. |
| 32 | 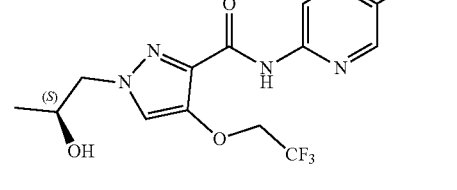 | yellow powder; ¹H-NMR (400 MHz, CDCl3): δ 9.69 (s, 1H), 8.80 (d, J = 9.6 Hz, 1H), 8.64 (d, J = 5.2 Hz, 1H), 7.39-7.46 (m, 3H), 7.31 (s, 1H), 6.92 (d, J = 5.2 Hz, 1 H), 4.51 (q, J = 8.4 Hz, 2H), 4.00-4.10 (m, 8H), 1.89-1.96 (m, 2H), 0.94 (t, J = 7.6 Hz, 3H); LCMS: 100%, MS (ESI): m/z 533.1 [M + H]+. |

TABLE 8-continued

Summarizes compounds 1-179 in terms of their structures and corresponding characteristics.

| # cpd | Structure | Characterization Data |
|---|---|---|
| 33 | 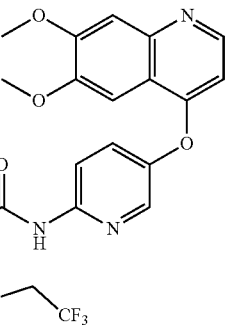 | white powder; $^1$H-NMR (400 MHz, DMSO-d6) δ ppm 9.51 (1H, s), 8.50 (1H, d, J = 5.2 Hz), 8.39 (1H, d, J = 2.8 Hz), 8.31 (1H, d, J = 8.8 Hz), 7.91 (1H, s), 7.86 (1H, dd, J = 8.8, 2.8 Hz), 7.54 (1H, s), 7.41 (1H, s), 6.55 (1H, d, J = 5.2 Hz), 4.77 (2H, q, J = 8.8 Hz), 3.94-3.97 (6H, m), 3.90 (3H, s); LCMS: 100%, MS (ESI): m/z 504.0 [M + H]+. |
| 34 | 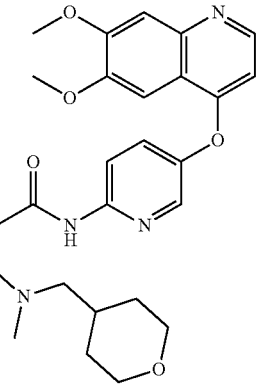 | white powder; $^1$H-NMR (400 MHz, CDCl3): δ 10.83 (1H, s), 8.47-8.63 (2H, m), 8.24 (1H, d, J = 2.4 Hz), 7.53-7.62 (2H, m), 7.45 (1H, s), 7.33 (1H, s), 6.48 (1H, d, J = 5.2 Hz), 4.12 (2H, t, J = 7.2 Hz), 4.07 (3H, s), 4.06 (3H, s), 3.92-4.03 (2H, m), 3.31-3.41 (2H, m), 2.89 (2H, d, J = 7.2 Hz), 2.78 (3H, s), 1.91-1.99 (2H, m), 1.82-1.91 (1H, m), 1.73-1.82 (3H, m), 1.33-1.41 (2H, m), 0.95 (2H, t, J = 7.2 Hz); LCMS: 100%, MS (ESI): m/z 561.2 [M + H]+. |
| 35 | 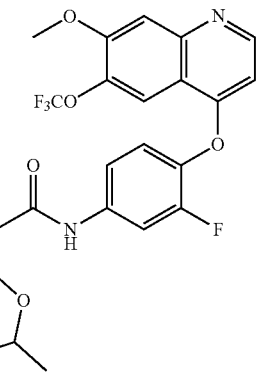 | white powder; $^1$H-NMR (CDCl3, 400 MHz): δ 9.17 (1H, s), 8.31 (1H, s), 8.04 (1H, d, J = 11.6 Hz), 7.46-7.50 (2H, m), 7.36-7.40 (1H, m), 7.18 (1H, s), 6.34-6.36 (2H, m), 4.35-4.42 (1H, m), 4.11 (2H, t, J = 7.2 Hz), 3.74 (3H, s), 1.89-1.99 (2H, m), 1.47 (6H, d, J = 6.0 Hz), 0.96 (3H, t, J = 7.2 Hz); LCMS: 100.0%, MS (ESI): m/z 563.1 [M + H]+. |
| 36 | 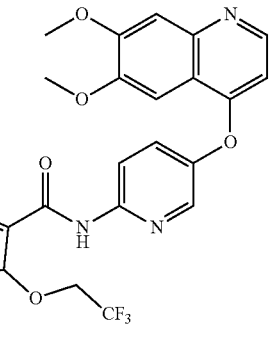 | white solid; $^1$H-NMR (CDCl3, 400 MHz): δ 9.28 (s, 1H), 8.45 (d, J = 4.2 Hz, 1H), 8.42 (d, J = 9.2 Hz, 1H), 8.21 (d, J = 2.4 Hz, 1H), 7.53 (dd, J = 3.2, 9.2 Hz, 1H), 7.49 (s, 1H), 7.40 (br.s, 1H), 7.24 (s, 1H), 6.40 (d, J = 5.2 Hz, 1H), 4.48 (q, J = 8.4 Hz, 2H), 4.03 (t, J = 7.2 Hz, 2H), 4.00 (s, 6H), 1.77-1.85 (m,2H), 1.24-1.33 (m,2H), 0.90 (t, J = 7.6 Hz, 3H); LCMS: 96.8%, MS (ESI): m/z 546.1 [M + H]+. |

TABLE 8-continued

Summarizes compounds 1-179 in terms of their structures and corresponding characteristics.

| # cpd | Structure | Characterization Data |
|---|---|---|
| 37 | 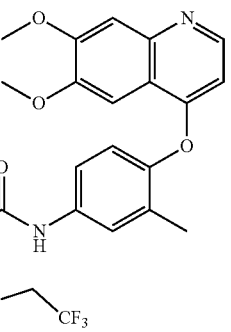 | white solid; $^1$H-NMR (CDCl3, 400 MHz): δ 8.56 (s, 1H), 8.39 (d, J = 5.2 Hz, 1H), 7.63 (d, J = 2.4 Hz, 1H), 7.55 (s, 1H), 7.49 (dd, J = 2.4, 8.8 Hz, 1H), 7.40 (s, 1H), 7.19 (s, 1H), 7.03 (d, J = 8.8 Hz, 1H), 6.25 (d, J = 5.2 Hz, 1H), 4.49 (q, J = 8.4 Hz, 2H), 4.00 (s, 3H), 3.99 (s, 3H), 3.85 (s, 3H), 2.13 (s, 3H); LCMS: 95.6%, MS (ESI): m/z 517.2 [M + H]+. |
| 38 | 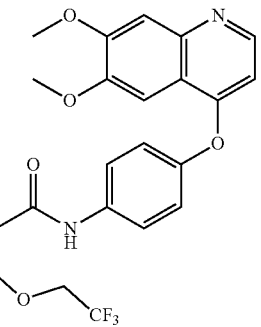 | white solid; $^1$H-NMR (CDCl3, 400 MHz): δ 8.69 (s, 1H), 8.50 (d, J = 5.2 Hz, 1H), 7.78 (d, J = 8.8 Hz, 2H), 7.58 (s, 1H), 7.45 (s, 1H), 7.33 (s, 1H), 7.21 (d, J = 8.8 Hz, 2H), 6.49 (d, J = 5.2 Hz, 1H), 4.57 (q, J = 8.4 Hz, 2H), 4.07-4.10 (m, 8H), 1.91-1.97 (m, 2H), 0.97 (t, J = 7.2 Hz, 3H); LCMS: 95.7%, MS (ESI): m/z 531.1 [M + H]+. |
| 39 | 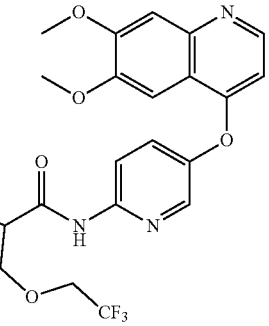 | white solid; $^1$H-NMR (CDCl3, 400 MHz): δ 9.27 (s, 1H), 8.48-8.54 (m, 2H), 8.29 (d, J = 2.4 Hz, 1H), 7.62 (m, 1H), 7.56 (s, 1H), 7.48 (s, 2H), 6.48 (d, J = 5.2 Hz, 1H), 4.56 (q, J = 8.4 Hz, 2H), 4.41 (t, J = 6.4 Hz, 2H), 4.08 (s, 6H), 3.04 (t, J = 6.4 Hz, 2H); LCMS: 94.1%, MS (ESI): m/z 543.2 [M + H]+. |
| 40 | 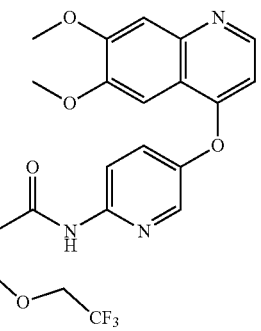 | yellow solid; $^1$H-NMR (CDCl3, 400 MHz): δ 9.46 (s, 1H), 8.64 (d, J = 9.2 Hz, 1H), 8.53 (t, J = 6.0 Hz, 1H), 8.33 (d, J = 2.8 Hz, 1H), 8.20 (s, 1H), 7.63-7.71 (m, 2H), 7.37 (s, 1H), 6.75 (d, J = 6.4 Hz, 1H), 4.63 (q, J = 7.2 Hz, 1H), 4.55 (q, J = 8.4 Hz, 2H), 4.19 (s, 3H), 4.13 (s, 3H), 2.16-2.28 (m, 2H), 2.01-2.12 (m, 2H), 1.87-1.98 (m, 2H), 1.73-1.80 (m, 2H); LCMS: 96.4%, MS (ESI): m/z 558.2 [M + H]+. |

TABLE 8-continued

Summarizes compounds 1-179 in terms of their structures and corresponding characteristics.

| # cpd | Structure | Characterization Data |
|---|---|---|
| 41 | 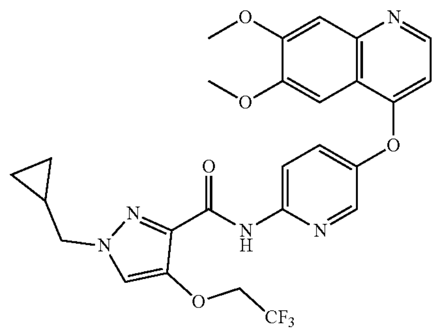 [SMILES: COc1cc2nccc(Oc3ccc(NC(=O)c4nn(CC5CC5)cc4OCC(F)(F)F)nc3)c2cc1OC] | yellow solid; ¹H-NMR (CDCl3, 400 MHz): δ 9.51 (s, 1H), 8.65 (d, J = 9.2 Hz, 1H), 8.53-8.56 (m, 1H), 8.34 (d, J = 2.8 Hz, 1H), 8.22 (s, 1H), 7.67-7.70 (m, 2H), 7.47 (s, 1H), 6.76 (d, J = 6.4 Hz, 1H), 4.58 (q, J = 8.0 Hz, 2H), 4.21 (s, 3H), 4.14 (s, 3H), 4.01 (d, J = 7.2 Hz, 2H), 1.28-1.35 (m, 1H), 0.73-0.78 (m, 2H), 0.44-0.48 (m, 2H); LCMS: 98.0%, MS (ESI): m/z 544.3 [M + H]+. |
| 42 | 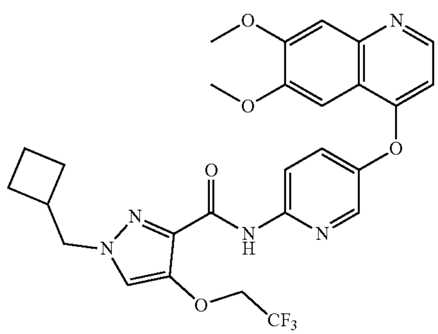 [SMILES: COc1cc2nccc(Oc3ccc(NC(=O)c4nn(CC5CCC5)cc4OCC(F)(F)F)nc3)c2cc1OC] | off-white solid; ¹H-NMR (DMSO-d6, 400 MHz): δ 9.59 (s, 1H), 8.83 (d, J = 6.4 Hz, 1H), 8.51 (d, J = 2.8 Hz, 1H), 8.39 (d, J = 8.8 Hz, 1H), 8.00 (dd, J = 2.4, 8.8 Hz, 1H), 7.96 (s, 1H), 7.77 (s, 1H), 7.61 (s, 1H), 7.01 (d, J = 6.4 Hz, 1H), 4.78 (q, J = 8.8 Hz, 2H), 4.17 (d, J = 7.6 Hz, 2H), 4.04 (s, 3H), 4.03 (s, 3H), 2.76-2.83 (m, 1H), 2.00-2.02 (m, 2H), 1.79-1.87 (m, 4H); LCMS: 98.6%, MS (ESI): m/z 558.3 [M + H]+. |
| 43 | 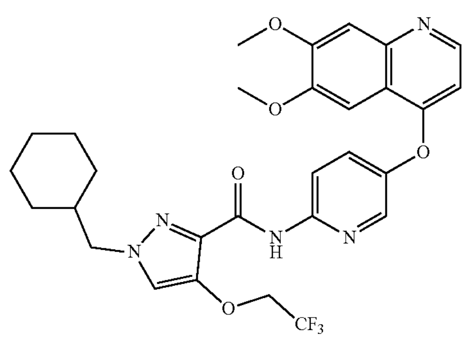 [SMILES: COc1cc2nccc(Oc3ccc(NC(=O)c4nn(CC5CCCCC5)cc4OCC(F)(F)F)nc3)c2cc1OC] | yellow solid; ¹H-NMR (CDCl3, 400 MHz): δ 9.44 (s, 1H), 8.63 (d, J = 8.8 Hz 1H), 8.54 (d, J = 6.4 Hz, 1H), 8.34 (d, J = 2.8 Hz, 1H), 8.20 (s, 1H), 7.66 -7.69 (m, 2H), 7.31 (s, 1H), 6.75 (d, J = 6.4 Hz, 1H), 4.56 (q, J = 8.4 Hz, 2H), 4.20 (s, 3H), 4.14 (s, 3H), 3.94 (d, J = 7.2 Hz, 2H), 1.93-1.94 (m, 1H), 1.75-1.80 (m, 3H), 1.59-1.66 (m, 2H), 1.21-1.30 (m, 3H), 0.99-1.02 (m, 2H); LCMS: 96.3%, MS (ESI): m/z 586.3 [M + H]+. |
| 44 | 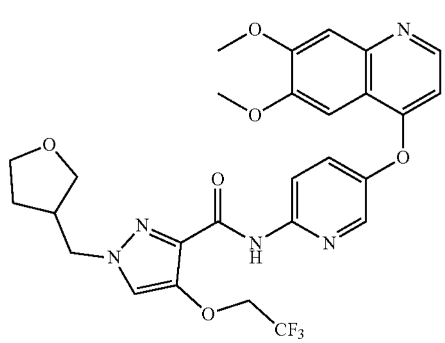 [SMILES: COc1cc2nccc(Oc3ccc(NC(=O)c4nn(CC5CCOC5)cc4OCC(F)(F)F)nc3)c2cc1OC] | yellow solid; ¹H-NMR (CDCl3, 400 MHz): δ 9.68 (s, 1H), 8.67 (d, J = 9.2 Hz, 1H), 8.55 (s, 1H), 8.33 (s, 1H), 8.19 (s, 1H), 7.72 (d, J = 7.2 Hz, 1H), 7.64 (s, 1H), 7.36 (s, 1H), 6.75 (d, J = 6.0 Hz, 1H), 4.55 (q, J = 8.4 Hz, 2H), 4.18 (s, 3H), 4.12 (s, 3H), 4.10 (s, 2H), 3.92-3.99 (s, 1H), 3.75-3.82 (m, 2H), 3.56-3.63 (m, 1H), 2.89-2.94 (m, 1H), 2.08-2.12 (m, 1H), 1.66-1.70 (m, 1H); LCMS: 96.2%, MS (ESI): m/z 574.2 [M + H]+. |

TABLE 8-continued

Summarizes compounds 1-179 in terms of their structures and corresponding characteristics.

| # cpd | Structure | Characterization Data |
|---|---|---|
| 45 | 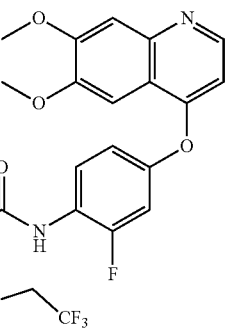 | white solid; ¹H-NMR (CDCl3, 400 MHz): δ 8.88 (d, J = 2.4 Hz, 1H), 8.68 (t, J = 8.8 Hz, 1H), 8.43 (d, J = 6.4 Hz, 1H), 8.08 (d, J = 3.6 Hz, 1H), 7.55 (s, 1H), 7.24 (s, 1H), 7.01-7.03 (m, 2H), 6.68-6.69 (m, 1H), 4.42-4.48 (q, J = 8.0 Hz, 2H), 4.10 (s, 3H), 4.04 (s, 3H), 3.88 (s, 3H); LCMS: 97.1%, MS (ESI): m/z 521.2 [M + H]+. |
| 46 | 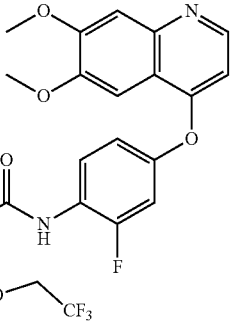 | white solid; ¹H-NMR (CDCl3, 400 MHz): δ 8.96 (d, J = 2.4 Hz, 1H), 8.75-8.80 (m, 1H), 8.51 (d, J = 8.0 Hz, 1H), 8.17 (s, 1H), 7.64 (s, 1H), 7.49 (s, 1H), 7.09-7.14 (m, 2H), 6.79 (d, J = 4.0 Hz, 1H), 4.52 (q, J = 8.00 Hz, 2H), 4.31-4.34 (m, 2H) 4.20 (s, 3H) 4.12-4.13 (m, 5H), 2.41 (s, 1H); LCMS: 97.4%, MS (ESI): m/z 551.2 [M + H]+. |
| 47 | 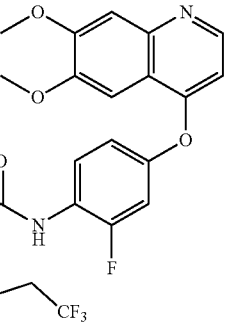 | yellow solid; ¹H-NMR (CDCl3, 400 MHz): δ 9.00 (br s, 1H), 8.75 (t, J = 8.0 Hz, 1H), 8.51 (s, 1H), 8.17 (s, 1H), 7.63 (s, 1H), 7.36 (s, 1H), 7.10 (d, J = 8.8 Hz, 2H), 6.78 (s, 1H), 4.66 (q, J = 7.2 Hz, 1H), 4.54 (q, J = 8.4 Hz, 2H), 4.18 (s, 3H), 4.12 (s, 3H), 2.16-2.25 (m, 2H), 1.99-2.10 (m, 2H), 1.85-1.97 (m, 2H), 1.72-1.82 (m, 2H); LCMS: 96.2%, MS (ESI): m/z 575.2 [M + H]+. |
| 48 | 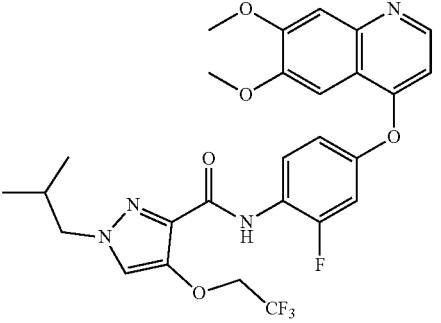 [SMILES: COc1cc2nccc(Oc3ccc(NC(=O)c4nn(CC(C)C)cc4OCC(F)(F)F)c(F)c3)c2cc1OC] | white solid; ¹H-NMR (CDCl3, 400 MHz): δ 8.91 (d, J = 2.4 Hz, 1H), 8.68 (t, J = 8.8 Hz, 1H), 8.44 (d, J = 4.8 Hz, 1H), 8.11 (s, 1H), 7.55 (s, 1H), 7.23 (s, 1H), 7.03 (s, 1H), 7.01 (s, 1H), 6.69 (d, J = 6.8 Hz, 1H), 4.46 (q, J = 8.4 Hz, 2H), 4.11 (s, 3H), 4.04 (s, 3H), 3.85 (d, J = 7.2 Hz, 2H), 2.14-2.21 (m, 1H), 0.90 (s, 3H), 0.88 (s, 3H); LCMS: 100%, MS (ESI): m/z 563.2 [M + H]+. |

TABLE 8-continued

Summarizes compounds 1-179 in terms of their structures and corresponding characteristics.

| # cpd | Structure | Characterization Data |
|---|---|---|
| 49 | 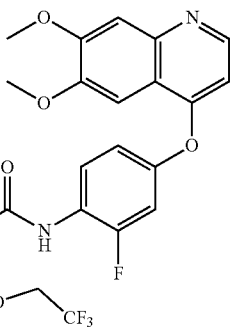 | yellow solid; $^1$H-NMR (CDCl3, 400 MHz): δ 8.97 (d, J = 2.4 Hz, 1H), 8.77 (t, J = 8.8 Hz, 1H), 8.52-8.53 (m, 1H), 8.18 (s, 1H), 7.63 (s, 1H), 7.44 (s, 1H), 7.09-7.11 (m, 2H), 6.77 (d, J = 3.6 Hz, 1H), 4.52 (q, J = 8.0 Hz, 2H), 4.32 (t, J = 4.8 Hz, 2H), 4.18 (s, 3H), 4.12 (s, 3H), 3.78 (t, J = 4.8 Hz, 2H), 3.38 (s, 3H); LCMS: 100%, MS (ESI): m/z 565.3 [M + H]+. |
| 50 | 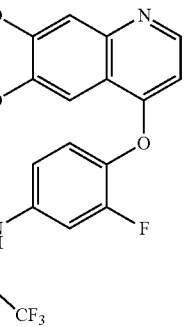 | white solid; $^1$H-NMR (CDCl3, 400 MHz): δ 8.62 (s, 1H), 8.43 (d, J = 5.2 Hz, 1H), 7.82 (dd, J = 2.4, 12.0 Hz, 1H), 7.53 (s, 1H), 7.38 (s, 2H), 7.24-7.30 (m, 2H), 6.37 (d, J = 5.2 Hz, 1H), 4.48 (q, J = 8.4 Hz, 2H), 4.00 (s, 3H), 3.99 (s, 3H), 3.86 (s, 3H); LCMS: 98.2%, MS (ESI): m/z 521.2 [M + H]+. |
| 51 | 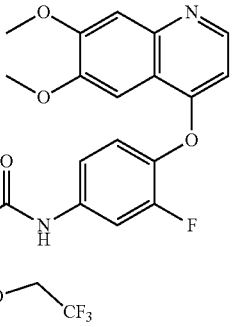 | gray solid; $^1$H-NMR (CDCl3, 400 MHz): δ 8.69 (s, 1H), 8.43 (d, J = 8.0 Hz, 1H), 8.06 (s, 1H), 7.90 (dd, J = 12.10, 2.4 Hz, 1H), 7.59 (s, 1H), 7.38-7.40 (m, 2H), 7.24 (t, J = 8.0 Hz, 1H), 6.65 (d, J = 8.0 Hz, 1H), 4.45 (q, J = 8.0 Hz, 2H), 4.20-4.23 (m, 2H), 4.10 (s, 3H), 4.00-4.02 (m, 5H); LCMS: 95.6%, MS (ESI): m/z 551.2 [M + H]+. |
| 52 | 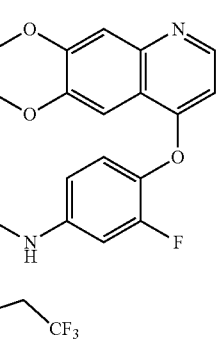 | yellow solid; $^1$H-NMR (CDCl3, 400 MHz): δ 8.79 (s, 1H), 8.52 (t, J = 6.0 Hz, 1H), 8.18 (s, 1H), 7.99 (dd, J = 2.4, 12.4 Hz, 1H), 7.67 (s, 1H), 7.48 (d, J = 8.8 Hz, 1H), 7.37 (s, 1H), 7.32 (t, J = 8.4 Hz, 1H), 6.74 (d, J = 6.0 Hz, 1H), 4.64 (q, J = 7.2 Hz, 1H), 4.55 (q, J = 8.4 Hz, 2H), 4.18 (s, 3H), 4.13 (s, 3H), 2.16-2.28 (m, 2H), 1.99-2.09 (m, 2H), 1.86-1.96 (m, 2H), 1.74-1.83 (m, 2H); LCMS: 99.2%, MS (ESI): m/z 575.2 [M + H]+. |

TABLE 8-continued

Summarizes compounds 1-179 in terms of their structures and corresponding characteristics.

| # cpd | Structure | Characterization Data |
|---|---|---|
| 53 | 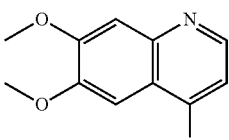 | yellow solid; $^1$H-NMR (CDCl3, 400 MHz): δ 8.71 (s, 1H), 8.40-8.48 (m, 1H), 8.10 (s, 1H), 7.92 (dd, J = 2.0, 12.0 Hz, 1H), 7.59 (s, 1H), 7.41 (d, J = 8.0 Hz, 1H), 7.22-7.26 (m, 2H), 6.67 (d, J = 5.2 Hz, 1H), 4.48 (q, J = 8.4 Hz, 2H), 4.11 (s, 3H), 4.05 (s, 3H), 3.84 (d, J = 7.6 Hz, 2H), 2.12-2.22 (m, 1H), 0.90 (s, 3H), 0.88 (s, 3H); LCMS: 98.3%, MS (ESI): m/z 563.2 [M + H]+. |
| 54 | 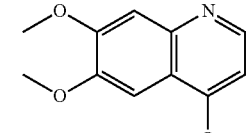 | white solid; $^1$H-NMR (CDCl3, 400 MHz): δ 8.77 (s, 1H), 8.52 (t, J = 3.2 Hz, 1H), 8.19 (s, 1H), 7.99 (dd, J = 2.4, 12.0 Hz, 1H), 7.67 (s, 1H), 7.42-7.49 (m, 2H), 7.32 (t, J = 8.4 Hz, 1H), 6.74 (d, J = 6.0 Hz, 1H), 4.54 (q, J = 8.4 Hz, 2H), 4.30 (t, J = 4.8 Hz, 2H), 4.19 (s, 3H), 4.13 (s, 3H), 3.77 (t, J = 4.8 Hz, 2H), 3.39 (s, 3H); LCMS: 97.6%, MS (ESI): m/z 565.2 [M + H]+. |
| 55 | 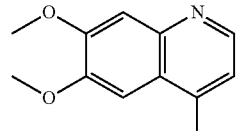 | yellow solid; $^1$H-NMR (CDCl3, 400 MHz): δ 8.79 (s, 1H), 8.54 (d, J = 6.0 Hz, 1H), 8.18 (s, 1H), 8.01 (d, J = 2.0, 12.0 Hz, 1H), 7.68 (s, 1H), 7.47-7.50 (m, 2H), 7.34 (t, J = 8.4 Hz, 1H), 6.78 (d, J = 6.0 Hz, 1H), 4.99-5.02 (m, 1H), 4.55 (q, J = 8.4 Hz, 2H), 4.16-4.22 (m, 5H), 4.14 (s, 1H), 4.03-4.07 (m, 1H), 3.94-4.01 (m, 1H), 2.53-2.62 (m, 1H), 2.30-2.38 (m, 1H); LCMS: 94.1%, MS (ESI): m/z 577.2 [M + H]+. |
| 56 | 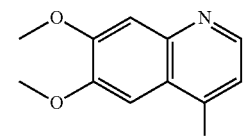 | yellow solid; $^1$H-NMR (CDCl3, 400 MHz): δ 8.70 (s, 1H), 8.47 (t, J = 8.0 Hz, 1H), 8.16 (s, 1H), 7.78 (s, 1H), 7.67-7.70 (m, 2H), 7.49 (s, 1H), 7.17 (d, J = 8.0 Hz, 1H), 6.62 (d, J = 4.0 Hz, 1H), 4.55 (q, J = 8.4 Hz, 2H), 4.29-4.32 (m, 2H), 4.19 (s, 3H), 4.14-4.19 (m, 3H), 4.09-4.12 (m, 2H), 2.21 (s, 3H); LCMS: 99.1%, MS (ESI): m/z 547.2 [M + H]+. |

TABLE 8-continued

Summarizes compounds 1-179 in terms of their structures and corresponding characteristics.

| # cpd | Structure | Characterization Data |
|---|---|---|
| 57 | 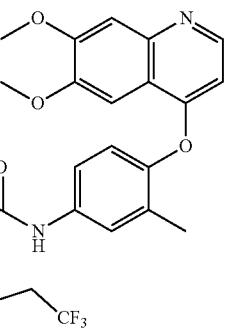 | yellow solid; ¹H-NMR (CDCl3, 400 MHz): δ 8.71 (s, 1H), 8.47 (t, J = 6.4 Hz, 1H), 8.16 (s, 1H), 7.79 (d, J = 2.0 Hz, 1H), 7.65-7.68 (m, 2H), 7.37 (s, 1H) 7.15 (d, J = 8.8 Hz, 1H), 6.62 (d, J = 6.4 Hz, 1H), 4.64 (q, J =6.8 Hz, 1H), 4.55 (q, J = 8.4 Hz, 2H), 4.18 (s, 3H), 4.13 (s, 3H), 2.20-2.23 (m, 5H), 2.04-2.05 (m, 2H), 1.91-1.92 (m, 2H), 1.76-1.79 (m, 2H); LCMS: 98.4%, MS (ESI): m/z 571.2 [M + H]+. |
| 58 | 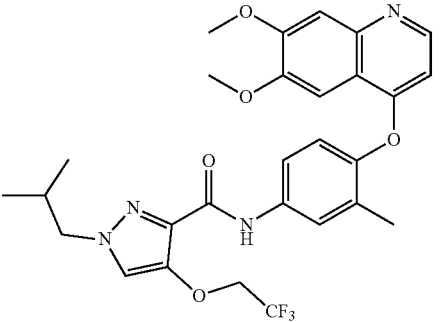 | white solid; ¹H-NMR (CDCl3, 400 MHz): δ 8.63 (s, 1H), 8.36-8.42 (m, 1H), 8.10 (s, 1H), 7.71 (d, J = 2.4 Hz, 1H), 7.58-7.60 (m, 2H), 7.24 (s, 1H), 7.07 (d, J = 8.8 Hz, 1H), 6.54 (d, J = 6.4 Hz, 1H), 4.49 (q, J = 8.4 Hz, 2H), 4.10 (s, 3H), 4.05 (s, 3H), 3.84 (d, J = 7.2 Hz, 2H), 2.12-2.22 (m, 4H), 0.90 (s, 3H), 0.88 (s, 3H); LCMS: 98.2%, MS (ESI): m/z 559.3 [M + H]+. |
| 59 | 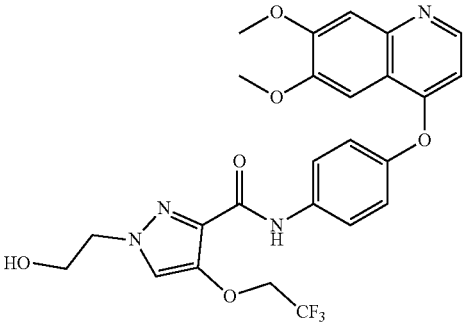 | yellow solid; ¹H-NMR (CDCl3, 400 MHz): δ 8.75 (s, 1H), 8.40-8.50 (m, 1H), 8.13 (s, 1H), 7.88 (d, J = 8.4 Hz, 2H), 7.66 (s, 1H), 7.48 (s, 1H), 7.25 (s, 1H), 6.73 (d, J = 4.4 Hz, 1H), 4.50 (q, J = 8.4 Hz, 2H), 4.29-4.30 (m, 2H), 4.18 (s, 3H), 4.10-4.12 (m, 5H), 1.26 (s, 1H); LCMS: 98.2%, MS (ESI): m/z 533.2 [M + H]+. |
| 60 | 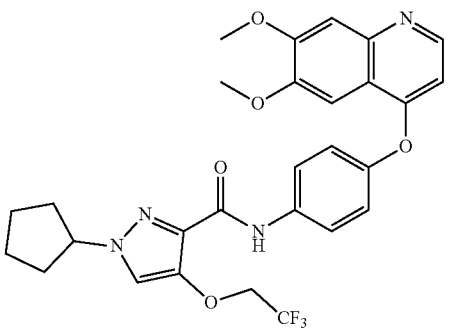 [SMILES: COc1cc2nccc(Oc3ccc(NC(=O)c4nn(C5CCCC5)cc4OCC(F)(F)F)cc3)c2cc1OC] | yellow solid; ¹H-NMR (CDCl3, 400 MHz): δ 8.76 (s, 1H), 8.48 (t, J = 6.4 Hz, 1H), 8.16 (s, 1H), 7.89 (d, J = 8.8 Hz, 2H), 7.66 (s, 1H), 7.37 (s, 1H), 7.22-7.30 (m, 2 H), 6.74 (d, J = 6.4 Hz, 1H), 4.65 (q, J = 7.2 Hz, 1H), 4.56 (q, J = 8.4 Hz, 2H), 4.18 (s, 3H), 4.12 (s, 3H), 2.15 2.27 (m, 2H), 1.98-2.10 (m, 2H), 1.84-1.97 (m, 2H), 1.70-1.84 (m, 2H); LCMS: 95.0%, MS (ESI): m/z 557.2 [M + H]+. |

TABLE 8-continued

Summarizes compounds 1-179 in terms of their structures and corresponding characteristics.

| # cpd | Structure | Characterization Data |
|---|---|---|
| 61 | 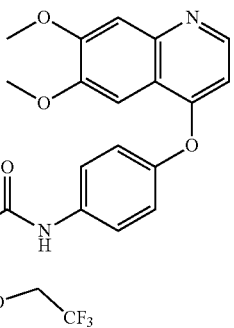 | white solid; $^1$H-NMR (CDCl3, 400 MHz): δ 8.75 (s, 1H), 8.48-8.49 (m, 1H), 8.17 (s, 1H), 7.88 (d, J = 8.8 Hz, 2H), 7.66 (s, 1H), 7.45 (s, 1H), 7.24 (d, J = 8.8 Hz, 2H), 6.74 (d, J = 6.4 Hz, 1H), 4.55 (q, J = 8.0 Hz, 2H), 4.30 (t, J = 5.2 Hz, 2H), 4.18 (s, 3H), 4.12 (s, 3H), 3.77 (t, J = 5.2 Hz, 2H), 3.39 (s, 3H); LCMS: 98.4%, MS (ESI): m/z 547.2 [M + H]+. |
| 62 | 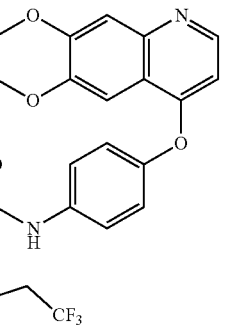 | yellow solid; $^1$H-NMR (CDCl3, 400 MHz): δ 8.67 (s, 1H), 8.38-8.47 (m, 1H), 8.08 (s, 1H), 7.81 (d, J = 8.4 Hz, 2H), 7.58 (s, 1H), 7.38 (s, 1H), 7.18 (s, 1H), 7.16 (s, 1H), 6.64-6.70 (m, 1H), 4.88-4.96 (m, 1H), 4.48 (q, J = 8.4 Hz, 2H), 4.07-4.13 (m, 5H), 4.04 (s, 1H), 3.95-3.99 (m, 1H), 3.85-3.91 (m, 1H), 2.43-2.53 (m, 1H), 2.24-2.28 (m, 1H); LCMS: 94.4%, MS (ESI): m/z 559.2 [M + H]+. |
| 63 | 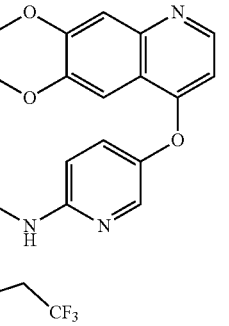 | HCl salt, yellow solid; $^1$H-NMR (MeOD, 400 MHz): δ 8.77 (d, J = 6.8 Hz, 1H), 8.59 (d, J = 2.4 Hz, 1H), 8.49 (d, J = 9.2 Hz, 1H), 8.21 (dd, J = 9.2, 2.8 Hz, 1H), 7.92 (s, 1H), 7.86 (s, 1H), 7.54 (s, 1H), 7.15 (d, J = 6.8 Hz, 1H), 4.69 (q, J = 8.4 Hz, 2H), 4.40-4.56 (m, 2H), 4.15 (s, 3H), 4.11 (s, 3H), 3.88-3.98 (m, 1H), 1.38 (d, J = 6.4 Hz, 3H); LCMS: 99.2%, MS (ESI): m/z 547.2 [M + H]+. |
| 64 | 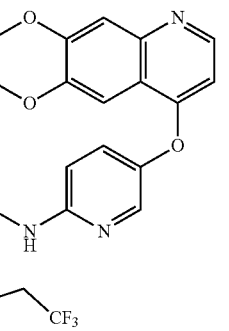 | yellow solid; $^1$H-NMR (MeOD, 400 MHz): δ 8.72 (d, J = 6.8 Hz, 1H), 8.40-8.59 (m, 2H), 8.02 (dd, J = 2.8, 9.2 Hz, 1H), 7.86 (s, 1H), 7.84 (s, 1H), 7.50 (s, 1H), 7.07 (d, J = 6.8 Hz, 1H), 4.63-4.70 (m, 4H), 4.14 (s, 3H), 4.10 (s, 3H), 1.67 (t, J = 18.8 Hz, 3H); LCMS: 96.9%, MS (ESI): m/z 568.3 [M + H]+. |

TABLE 8-continued

Summarizes compounds 1-179 in terms of their structures and corresponding characteristics.

| # cpd | Structure | Characterization Data |
|---|---|---|
| 65 | 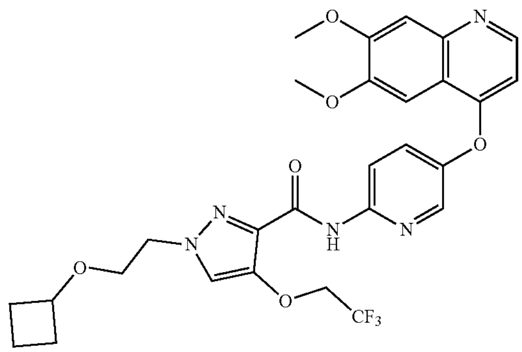 [SMILES: COc1cc2nccc(Oc3ccc(NC(=O)c4nn(CCOC5CCC5)cc4OCC(F)(F)F)nc3)c2cc1OC] | white solid; $^1$H-NMR (CDCl3, 400 MHz): δ 9.34 (s, 1H), 8.49-8.54 (m, 2H), 8.26-8.29 (m, 1H), 7.61 (dd, J = 2.4, 8.8 Hz, 1H), 7.58 (s, 1H), 7.46 (s, 2H), 6.47 (d, J = 5.2 Hz, 1H), 4.55 (q, J = 8.4 Hz, 2H), 4.25 (t, J = 4.8 Hz, 2H), 4.08 (s, 6H), 3.88-3.93 (m, 1H), 3.70 (t, J = 4.8 Hz, 2H), 2.16-2.20 (m, 2H), 1.83-1.90 (m, 2H), 1.68-1.72 (m, 1H), 1.49-1.54 (m, 1H); LCMS: 100%, MS (ESI): m/z 588.3 [M + H]+. |
| 66 | 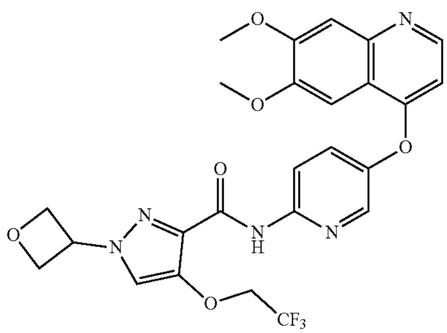 [SMILES: COc1cc2nccc(Oc3ccc(NC(=O)c4nn(C5COC5)cc4OCC(F)(F)F)nc3)c2cc1OC] | white solid; $^1$H-NMR (MeOD, 400 MHz): δ 8.43-8.46 (m, 2H), 8.33 (d, J = 2.4 Hz, 1H), 7.90 (s, 1H), 7.78 (dd, J = 2.4, 9.2 Hz, 1H), 7.63 (s, 1H), 7.36 (s, 1H), 6.60 (d, J = 5.2 Hz, 1H), 5.56 (q, J = 6.8 Hz, 1H), 5.05-5.10 (m, 4H), 4.65 (q, J = 8.4 Hz, 2H), 4.02 (s, 3H), 4.01 (s, 3H); LCMS: 97.0%, MS (ESI): m/z 546.1 [M + H]+. |
| 67 | 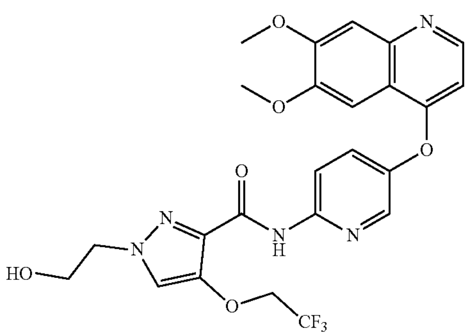 | white solid; $^1$H-NMR (MeOD, 400 MHz): δ 8.76 (d, J = 6.4 Hz, 1H), 8.56 (d, J = 2.4 Hz, 1H), 8.36 (d, J = 9.2 Hz, 1H), 8.21 (dd, J = 2.8, 9.2 Hz, 1H), 7.86 (s, 1H), 7.80 (s, 1H), 7.52 (s, 1H), 6.15 (d, J = 6.8 Hz, 1H), 4.64 (q, J = 8.4 Hz, 2H), 4.31 (t, J = 4.8 Hz, 2H), 4.14 (s, 3H), 4.10 (s, 3H), 3.97 (t, J = 4.2 Hz, 2H); LCMS: 99.4%, MS (ESI): m/z 534.2 [M + H]+. |
| 68 | 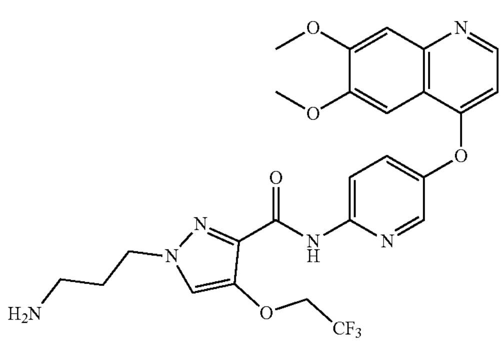 [SMILES: COc1cc2nccc(Oc3ccc(NC(=O)c4nn(CCCN)cc4OCC(F)(F)F)nc3)c2cc1OC] | HCl salt, white solid; $^1$H-NMR (DMSO-d6, 400 MHz): δ 9.68 (s, 1H), 8.85 (d, J = 6.4 Hz, 1H), 8.53 (d, J = 2.8 Hz, 1H), 8.39 (d, J = 9.2 Hz, 1H), 8.14 (s, 2H), 8.01-8.04 (m, 2H), 7.77 (d, J = 10.8 Hz, 2H), 7.04 (d, J = 6.4 Hz, 1H), 4.78 (q, J = 8.8 Hz, 2H), 4.27 (t, J = 6.4 Hz, 3H), 4.04 (s, 6H), 2.80-2.82 (m, 2H), 2.13-2.17 (m, 2H); LCMS: 98.4%, MS (ESI): m/z 547.1 [M + H]+. |

TABLE 8-continued

Summarizes compounds 1-179 in terms of their structures and corresponding characteristics.

| # cpd | Structure | Characterization Data |
|---|---|---|
| 69 | 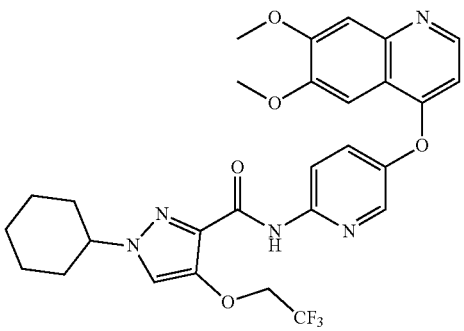 [SMILES: COc1cc2nccc(Oc3ccc(NC(=O)c4nn(C5CCCCC5)cc4OCC(F)(F)F)nc3)c2cc1OC] | yellow solid; $^1$H-NMR (CDCl3, 400 MHz): δ 9.44 (s, 1H), 8.62 (d, J = 9.2 Hz, 1H), 8.53 (d, J = 6.4 Hz, 1H), 8.33 (d, J = 2.4 Hz, 1H), 8.19 (s, 1H), 7.64-7.67 (m, 2H), 7.36 (s, 1H), 6.75 (d, J = 6.4 Hz, 1H), 4.54 (q, J = 8.4 Hz, 2H), 4.19 (s, 3H), 4.13 (s, 3H), 4.05-4.09 (m, 1H), 2.17-2.21 (m, 2H), 1.94-1.98 (m, 2H), 1.71-1.81 (m, 3H), 1.41-1.52 (m, 2H), 1.25-1.35 (m, 1H); LCMS: 96.7%, MS (ESI): m/z 572.2 [M + H]+. |
| 70 | 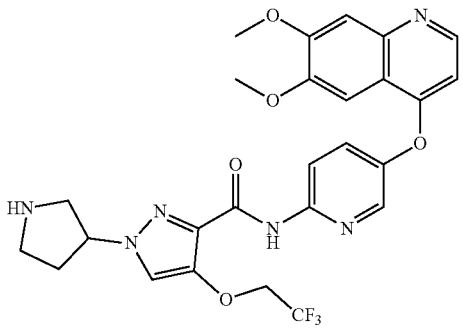 [SMILES: COc1cc2nccc(Oc3ccc(NC(=O)c4nn(C5CCNC5)cc4OCC(F)(F)F)nc3)c2cc1OC] | HCl salt, yellow solid; $^1$H-NMR (MeOD, 400 MHz): δ 8.77 (d, J = 6.8 Hz, 1H), 8.59-8.64 (m, 2H), 8.26 (dd, J = 9.2, 2.8 Hz, 1H), 7.96 (s, 1H), 7.86 (s, 1H), 7.54 (s, 1H), 7.17 (d, J = 6.4 Hz, 1H), 5.34 (br t, J = 6.4 Hz, 1H), 4.68 (q, J = 8.4 Hz, 2H), 4.14 (s, 3H), 4.10 (s, 3H), 3.98 (d, J = 12.8 Hz, 1H), 3.66-3.79 (m, 2H), 3.48-3.61 (m, 1H), 2.55-2.69 (m, 1H), 2.33-2.45 (m, 1H); LCMS: 97.1%, MS (ESI): m/z 559.2 [M + H]+. |
| 71 | 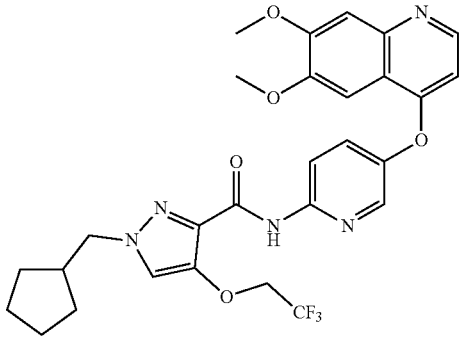 [SMILES: COc1cc2nccc(Oc3ccc(NC(=O)c4nn(CC5CCCC5)cc4OCC(F)(F)F)nc3)c2cc1OC] | off-white solid; $^1$H-NMR (CDCl3, 400 MHz): δ 9.44 (s, 1H), 8.62 (d, J = 9.2 Hz, 1H), 8.53 (s, 1H), 8.33 (d, J = 2.8 Hz, 1H), 8.20 (s, 1H), 7.66-7.68 (m, 2H), 7.34 (s, 1H), 6.74 (d, J = 6.4 Hz, 1H), 4.55 (q, J = 8.4 Hz, 2H), 4.19 (s, 3H), 4.13 (s, 3H), 4.04 (d, J = 7.2 Hz, 2H), 2.42-2.50 (m, 1H), 1.61-1.77 (m, 6H), 1.26-1.29 (m, 2H).; LCMS: 97.5%, MS (ESI): m/z 572.2 [M + H]+. |
| 72 | 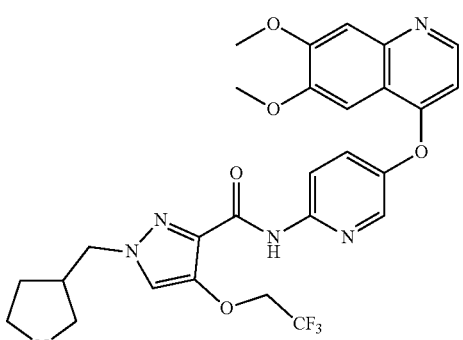 | HCl salt, white solid; $^1$H-NMR (MeOD, 400 MHz): δ 8.78 (d, J = 6.8 Hz, 1H), 8.60 (d, J = 2.8 Hz, 1H), 8.45 (d, J = 9.2 Hz, 1H), 8.23 (dd, J = 2.8, 9.2 Hz, 1H), 7.92 (s, 1H), 7.87 (s, 1H), 7.56 (s, 1H), 7.18 (d, J = 6.8 Hz, 1H), 4.69 (q, J = 8.4 Hz, 2H), 4.38-4.40 (m, 2H), 4.16 (s, 3H), 4.12 (s, 3H), 3.47-3.52 (m, 2H), 3.35-3.38 (m, 1H), 3.19-3.24 (m, 1H), 3.06-3.08 (m, 1H), 2.22-2.26 (m, 1H), 1.87-1.93 (m, 1H); LCMS: 98.2%, MS (ESI): m/z 573.2 [M + H]+. |

TABLE 8-continued

Summarizes compounds 1-179 in terms of their structures and corresponding characteristics.

| # cpd | Structure | Characterization Data |
|---|---|---|
| 73 | 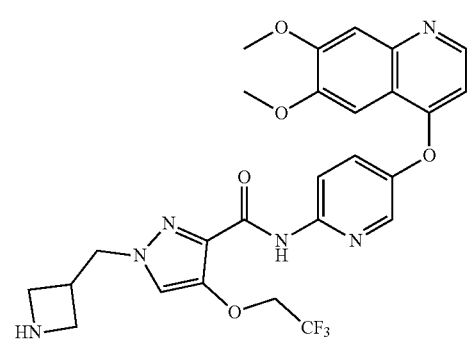 [SMILES: COc1cc2nccc(Oc3ccc(NC(=O)c4nn(CC5CNC5)cc4OCC(F)(F)F)nc3)c2cc1OC] | HCl salt, white solid; $^1$H-NMR (DMSO-d6, 400 MHz): δ 9.73 (s, 1H), 9.41 (s, 1H), 8.84 (d, J = 6.8 Hz, 1H), 8.53 (d, J = 2.8 Hz, 1H), 8.39 (d, J = 9.2 Hz, 1H), 8.00-8.04 (m, 2H), 7.82 (s, 1H), 7.78 (s, 1H), 7.03 (d, J = 6.8 Hz, 1H), 4.79 (q, J = 8.8 Hz, 2H), 4.47 (d, J = 7.2 Hz, 1H), 3.99-4.05 (m, 8H), 3.82-3.90 (m, 2H), 3.23-3.31 (m, 1H); LCMS: 99.0%, MS (ESI): m/z 559.2 [M + H]+. |
| 74 | 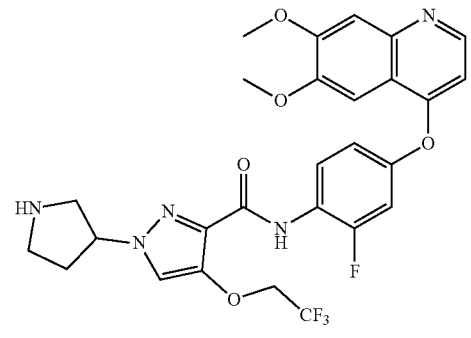 [SMILES: COc1cc2nccc(Oc3ccc(NC(=O)c4nn(C5CCNC5)cc4OCC(F)(F)F)c(F)c3)c2cc1OC] | HCl salt, white solid; $^1$H-NMR (MeOD, 400 MHz): δ 8.71 (d, J = 6.8 Hz, 1H), 8.46 (t, J = 8.8 Hz, 1H), 7.95 (s, 1H), 7.83 (s, 1H), 7.51 (s, 1H), 7.45 (dd, J = 10.8, 2.4 Hz, 1H), 7.31 (br d, J = 8.8 Hz, 1H), 7.04 (d, J = 6.8 Hz, 1H), 5.31 (br t, J = 6.4 Hz, 1H), 4.72 (q, J = 8.4 Hz, 2H), 4.13 (s, 3H), 4.10 (s, 3H), 3.90 (d, J = 12.8 Hz, 1H), 3.53-3.76 (m, 3H), 2.66 (s, 1H), 2.57-2.65 (m, 1H), 2.34-2.43 (m, 1H); LCMS: 97.7%, MS (ESI): m/z 576.2 [M + H]+. |
| 75 | 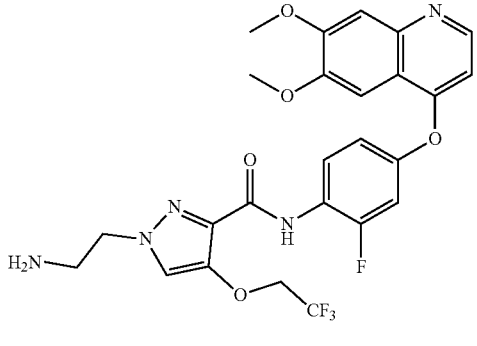 | HCl salt, off-white solid; $^1$H-NMR (D$_2$O, 400 MHz): δ 8.43 (d, J = 6.8 Hz, 1H), 7.86 (t, J = 8.8 Hz, 1H), 7.65 (s, 1H), 7.55 (s, 1H), 7.23 (s, 1H), 7.11 (d, J = 10.4 Hz, 1H), 7.05 (d, J = 9.2 Hz, 1H), 6.87 (d, J = 6.8 Hz, 1H), 4.46 (q, J = 8.0 Hz, 2H), 4.38 (s, 2H), 3.90 (s, 3H), 3.85 (s, 3H), 3.42 (t, J = 5.2 Hz, 2H); LCMS: 99.0%, MS (ESI): m/z 550.2 [M + H]+. |
| 76 | 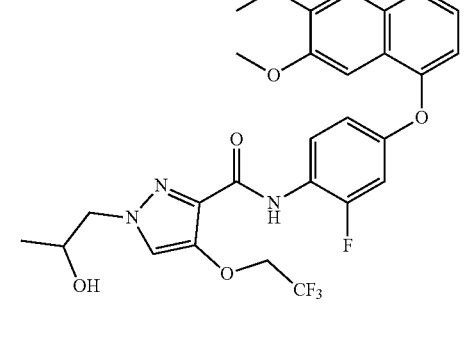 | yellow solid; $^1$H-NMR (MeOD, 400 MHz): δ 8.60 (d, J = 6.8 Hz, 1H), 8.28 (t, J = 8.8 Hz, 1H), 7.73 (s, 1H), 7.66 (s, 1H), 7.39 (s, 1H), 7.31 (dd, J = 1.6,10.8 Hz, 1H), 7.17 (d, J = 8.4 Hz, 1H), 6.93 (d, J = 6.8 Hz, 1H), 4.56 (q, J = 8.4 Hz, 2H), 4.07-4.12 (m, 2H), 4.03 (s, 3H), 3.99 (s, 3H), 3.94-3.98 (m, 1H), 1.12 (d, J = 6.0 Hz, 3H); LCMS: 98.6%, MS (ESI): m/z 565.2 [M + H]+. |

TABLE 8-continued

Summarizes compounds 1-179 in terms of their structures and corresponding characteristics.

| # cpd | Structure | Characterization Data |
|---|---|---|
| 77 | 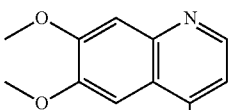 | yellow solid; ¹H-NMR (CDCl3, 400 MHz): δ 8.95 (s, 1H), 8.75 (t, J = 8.8 Hz, 1H), 8.51 (s, 1H), 8.16 (s, 1H), 7.62 (s, 1H), 7.43 (s, 1H), 7.09-7.11 (m, 2H), 6.77 (s, 1H), 4.98-5.06 (m, 1H), 4.52 (q, J = 8.0 Hz, 2H), 4.07-4.21 (m, 8H), 4.03-4.05 (m, 1H), 3.94-3.96 (m, 1H), 2.51-2.60 (m, 1H), 2.31-2.35 (m, 1H); LCMS: 97.7%, MS (ESI): m/z 577.2 [M + H]+. |
| 78 | 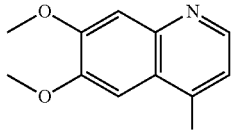 | HCl salt, white solid; ¹H-NMR (MeOD, 400 MHz): δ 8.72 (d, J = 6.4 Hz, 1H), 8.11-8.14 (m, 1H), 7.89 (s, 1H), 7.86 (s, 1H), 7.76-7.74 (m, 1H), 7.47-7.56 (m, 2H), 7.01 (d, J = 6.8 Hz, 1H), 5.29 (s, 1H), 4.64-4.87 (m, 2H), 4.14 (s, 3H), 4.11 (s, 3H), 3.93-3.97 (m, 1 H), 3.68-3.71 (m, 2H), 3.54-3.57 (m, 1H), 2.59-2.64 (m, 1H), 2.40-2.41 (m, 1H); LCMS: 95.7%, MS (ESI): m/z 576.2 [M + H]+. |
| 79 | 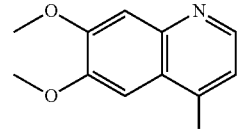 | HCl salt, white solid; ¹H-NMR (DMSO-d6, 400 MHz): δ 10.71 (s, 1H), 8.83 (d, J = 6.4 Hz, 1H), 8.57 (s, 3H, NH2.HCl), 8.21 (dd, J = 2.4, 13.2 Hz, 1H), 7.99 (s, 1H), 7.92 (d, J = 9.6 Hz, 1H), 7.81 (s, 1H), 7.77 (s, 1H), 7.62 (t, J = 9.2 Hz, 1H), 6.98 (d, J = 6.4 Hz, 1H), 4.70 (q, J = 8.8 Hz, 2H), 4.47 (t, J = 5.6 Hz, 2H), 4.05 (s, 3H), 4.04 (s, 3H), 3.35 (d, J = 5.6 Hz, 2H); LCMS: 98.8%, MS (ESI): m/z 550.2 [M + H]+. |
| 80 | 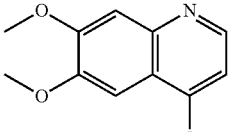 | yellow solid; ¹H-NMR (MeOD, 400 MHz): δ 8.71 (d, J = 6.8 Hz, 1H), 8.09 (dd, J = 2.4, 12.8 Hz, 1H), 7.87 (s, 1H), 7.73 (s, 1H), 7.65-7.68 (m, 1H), 7.31 (t, J = 8.8 Hz, 1H), 7.48 (s, 1H), 7.02 (d, J = 6.4 Hz, 1H), 4.63 (q, J = 8.4 Hz, 2H), 4.20-4.24 (m, 2H), 4.15 (s, 3H), 4.12 (s, 3H), 4.08 (q, J = 8.4 Hz, 1H), 1.23 (d, J = 6.0 Hz, 3H); LCMS: 98.2%, MS (ESI): m/z 565.2 [M + H]+. |

TABLE 8-continued

Summarizes compounds 1-179 in terms of their structures and corresponding characteristics.

| # cpd | Structure | Characterization Data |
|---|---|---|
| 81 | 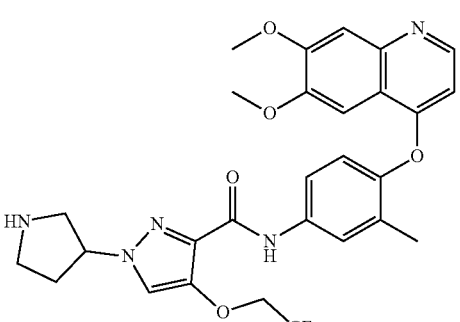 | HCl salt, white solid; ¹H-NMR (MeOD, 400 MHz): δ 8.68 (d, J = 6.8 Hz, 1H), 7.89-7.92 (m, 3H), 7.85 (dd, J = 1.8, 8.8 Hz, 1H), 7.54 (s, 1H), 7.31 (d, J = 8.8 Hz, 1H), 6.85 (d, J = 6.8 Hz, 1H), 5.32 (t, J = 6.0 Hz, 1H), 4.68 (q, J = 8.4 Hz, 2H), 4.15 (s, 3H), 4.13 (s, 3H), 3.97 (d, J = 12.8 Hz, 1H), 3.71-3.77 (m, 2H), 3.53-3.63 (m, 1H), 2.61-2.66 (m, 1H), 2.41-2.43 (m, 1H), 2.25 (s, 3H); LCMS: 98.5%, MS (ESI): m/z 572.2 [M + H]+. |
| 82 | 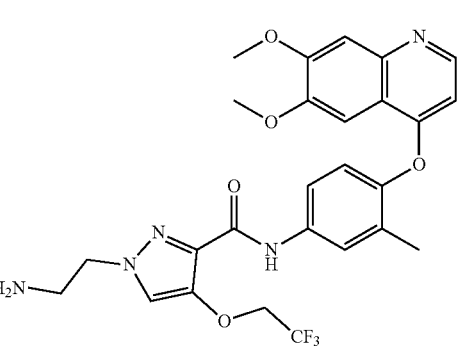 | HCl salt, white solid; ¹H-NMR (DMSO-d6, 400 MHz): δ 10.33 (s, 1H), 8.78 (d, J = 6.8 Hz, 1H), 8.54 (s, 3H, NH2.HCl), 7.99 (d, J = 2.0 Hz, 1H), 7.98 (s, 1H), 7.87 (dd, J = 2.4, 8.8 Hz, 1H), 7.80 (s, 1H), 7.79 (s, 1H), 7.33 (d, J = 8.8 Hz, 1H), 6.74 (d, J = 6.4 Hz, 1H), 4.71 (q, J = 8.8 Hz, 2H), 4.46 (t, J = 5.6 Hz, 2H), 4.05 (s, 3H), 4.04 (s, 3H), 3.49 (q, J = 5.2 Hz, 2H), 2.15 (s, 3H); LCMS: 98.9%, MS (ESI): m/z 546.2 [M + H]+. |
| 83 | 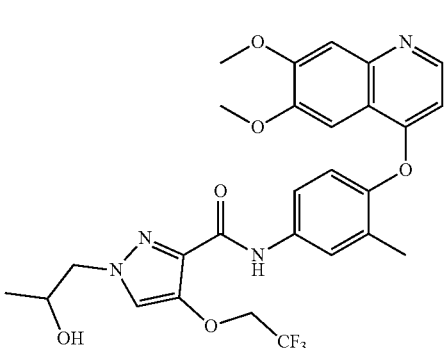 | yellow solid; ¹H-NMR (CDCl3, 400 MHz): δ 8.65 (s, 1H), 8.39 (s, 1H), 8.04 (s, 1H), 7.67 (s, 1H), 7.61-7.62 (m, 2H), 7.44 (s, 1H), 7.07 (d, J = 8.8 Hz, 1H), 6.55 (s, 1H), 4.43 (q, J = 8.4 Hz, 2H), 4.24 (br.s., 1H), 4.09-4.14 (m, 4H), 4.05 (s, 3H), 3.98-3.99 (m, 1H), 2.64 (s, 1H), 2.11 (s, 3H), 1.22 (d, J = 6.0 Hz, 3H); LCMS: 97.1%, MS (ESI): m/z 561.2 [M + H]+. |
| 84 | 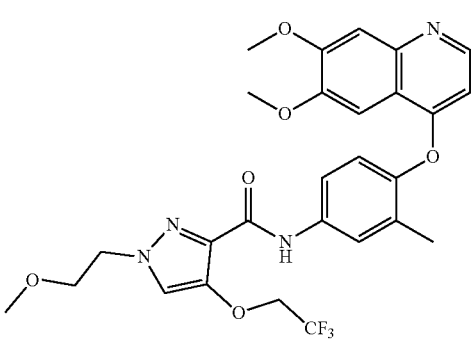 | white solid; ¹H-NMR (CDCl3, 400 MHz): δ 8.62 (s, 1H), 8.40 (s, 1H), 8.09 (s, 1H), 7.71 (d, J = 1.6 Hz, 1H), 7.58-7.60 (m, 2H), 7.38 (s, 1H), 7.07 (d, J = 8.4 Hz, 1H), 6.54 (d, J = 6.0 Hz, 1H), 4.47 (q, J = 8.0 Hz, 2H), 4.22 (t, J = 5.2 Hz, 2H), 4.10 (s, 3H), 4.05 (S, 3H), 3.69 (t, J = 4.8 Hz, 2H), 3.31 (s, 3H), 2.12 (s, 3H); LCMS: 98.9%, MS (ESI): m/z 561.2 [M + H]+. |

TABLE 8-continued

Summarizes compounds 1-179 in terms of their structures and corresponding characteristics.

| # cpd | Structure | Characterization Data |
|---|---|---|
| 85 | 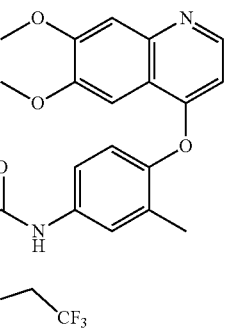 | yellow solid; $^1$H-NMR (CDCl3, 400 MHz): δ 8.62 (s, 1H), 8.41 (t, J = 6.0 Hz, 1H), 8.08 (s, 1H), 7.70 (d, J = 2.4 Hz, 1H), 7.61 (s, 1H), 7.58 (s, 1H), 7.39 (s, 1H), 7.07 (d, J = 8.8 Hz, 1H), 6.54 (d, J = 6.0 Hz, 1H), 4.90-4.93 (m, 1H), 4.48 (q, J = 8.4 Hz, 2H), 4.12-4.13 (m, 1H), 4.09 (s, 3H), 4.07 (s, 1H), 4.05 (s, 3H), 3.95-3.99 (m, 1H), 3.85-3.91 (m, 1H), 2.45-2.52 (m, 1H), 2.25-2.28 (m, 1H), 2.10 (s, 3H); LCMS: 98.2%, MS (ESI): m/z 573.3 [M + H]+. |
| 86 | 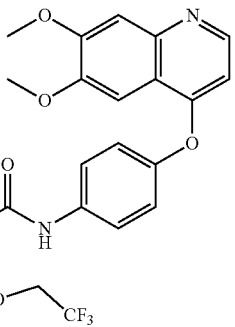 | HCl salt, yellow solid; $^1$H-NMR (MeOD, 400 MHz): δ 8.68 (d, J = 6.8 Hz, 1H), 8.00 (m, J = 9.2 Hz, 2H), 7.89 (s, 1H), 7.85 (s, 1H), 7.48 (s, 1H), 7.40 (m, J = 8.8 Hz, 2H), 6.95 (d, J = 6.8 Hz, 1H), 5.29 (t, J = 6.4 Hz, 1H), 4.67 (q, J = 8.4 Hz, 2H), 4.13 (s, 3H), 4.10 (s, 3H), 3.94 (d, J = 12.8 Hz, 1H), 3.64-3.75 (m, 2H), 3.48-3.59 (m, 1H), 2.56-2.67 (m, 1H), 2.34-2.43 (m, 1H); LCMS: 98.1%, MS (ESI): m/z 558.2 [M + H]+. |
| 87 | 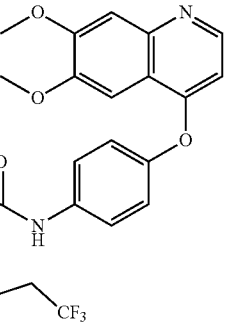 | white solid; $^1$H-NMR (CDCl3, 400 MHz): δ 8.78 (s, 1H), 8.50 (t, J = 6.0 Hz, 1H), 8.18 (s, 1H), 7.89-7.91 (m, 1H), 7.67 (s, 1H), 7.33 (s, 1H), 7.24-7.27 (m, 2H), 6.75 (d, J = 6.8 Hz, 1H), 4.58 (q, J = 8.4 Hz, 2H), 4.19 (s, 3H), 4.13 (s, 3H), 3.94 (s, 1H), 3.92 (s, 1H), 2.19-2.31 (m, 1H), 0.99 (s, 3H), 0.97 (s, 3H); LCMS: 99.6%, MS (ESI): m/z 545.3 [M + H]+. |
| 88 | 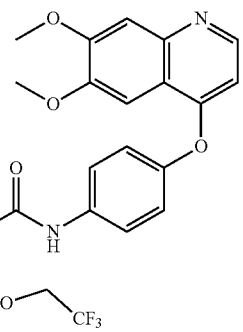 | HCl salt, white solid; $^1$H-NMR (DMSO-d6, 400 MHz): δ 10.41 (s, 1H), 8.79 (d, J = 6.4 Hz, 1H), 8.46 (s, 3H, NH2.HCl), 8.06 (d, J = 8.8 Hz, 2H), 7.98 (s, 1H), 7.74 (d, J = 8.8 Hz, 2H), 7.41 (d, J = 9.2 Hz, 2H), 6.85 (d, J = 6.4 Hz, 1H), 4.71 (q, J = 9.2 Hz, 2H), 4.45 (t, J = 5.6 Hz, 2H), 4.04 (s, 6H), 3.35 (d, J = 5.2 Hz, 2H); LCMS: 100%, MS (ESI): m/z 532.2 [M + H]+. |

TABLE 8-continued

Summarizes compounds 1-179 in terms of their structures and corresponding characteristics.

| # cpd | Structure | Characterization Data |
|---|---|---|
| 89 | 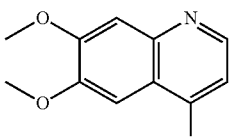 | yellow solid; ¹H-NMR (MeOD, 400 MHz): δ 8.68 (d, J = 6.8 Hz, 1H), 7.95 (d, J = 8.8 Hz, 2H), 7.86 (s, 1H), 7.73 (s, 1H), 7.50 (s, 1H), 7.39 ( d, J = 8.8 Hz, 2H), 6.96 (d, J = 6.8 Hz, 1H), 4.63 (q, J = 8.4 Hz, 2H), 4.19-4.26 (m, 2H), 4.14 (s, 3H), 4.09 (s, 3H), 4.03-4.08 (m, 1H), 1.23 (d, J = 6.0 Hz, 3H); LCMS: 97.6%, MS (ESI): m/z 547.2 [M + H]+. |
| 90 | 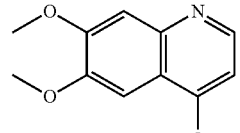 | white solid; ¹H-NMR (MeOD, 400 MHz): δ 8.43-8.46 (m, 2H), 8.32 (d, J = 2.8 Hz, 1H), 7.83 (s, 1H), 7.78 (dd, J = 2.8, 9.2 Hz, 1H), 7.64 (s, 1H), 7.37 (s, 1H), 6.60 (d, J = 5.6 Hz, 2H), 4.65 (q, J = 8.8 Hz, 2H), 4.0-4.50 (m, 1H), 4.07-4.10 (m, 2H), 4.02 (s, 6H), 3.55-3.62 (m, 2H), 2.09-2.17 (m, 4H); LCMS: 97.1%, MS (ESI): m/z 574.2 [M + H]+. |
| 91 | 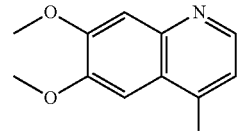 | yellow solid; ¹H-NMR (CDCl3, 400 MHz): δ 9.33 (s, 1H), 8.53 (t, J = 5.2 Hz, 1H), 8.49 (s, 1H), 8.28 (d, J = 2.8 Hz, 1H), 7.60 (dd, J = 2.8, 9.2 Hz, 1H), 7.57 (s, 1H), 7.56 (s, 1H), 7.45 (s, 1H), 6.47 (d, J = 5.6 Hz, 1H), 4.83-4.93 (m, 1H), 4.55 (q, J = 8.4 Hz, 2H), 4.07-4.08 (m, 6H), 2.95-3.00 (m, 2H), 2.80-2.82 (m, 1H), 2.45-2.48 (m, 2H), 2.43 (s, 3H), 2.15-2.17 (m, 1H), 1.62 (s, 2H); LCMS: 95.2%, MS (ESI): m/z 573.3 [M + H]+. |
| 92 | 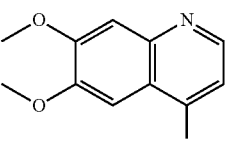 | white solid; ¹H-NMR (MeOD, 400 MHz): δ 8.41-8.48 (m, 2H), 8.32 (d, J = 2.8 Hz, 1H), 7.74-7.81 (m, 2H), 7.64 (s, 1H), 7.37 (s, 1H), 6.59 (d, J = 5.6 Hz, 1H), 4.80-4.85 (m, 2H), 4.63 (q, J = 8.4 Hz, 2H), 4.57 (q, J = 6.4 Hz, 2H), 4.50 (d, J = 7.2 Hz, 2H), 4.01 (s, 3H), 4.00 (s, 3H), 3.53-3.60 (m, 1H); LCMS: 99.4%, MS (ESI): m/z 560.1 [M + H]+. |

TABLE 8-continued

Summarizes compounds 1-179 in terms of their structures and corresponding characteristics.

| # cpd | Structure | Characterization Data |
|---|---|---|
| 93 | 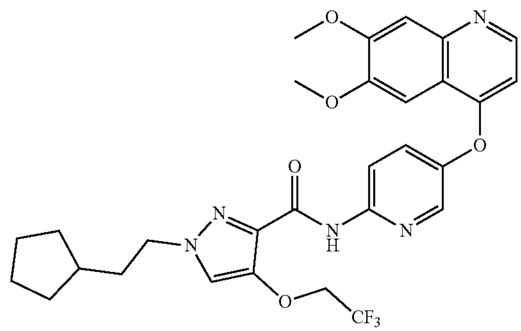 [SMILES: COc1cc2nccc(Oc3ccc(NC(=O)c4nn(CCC5CCCC5)cc4OCC(F)(F)F)nc3)c2cc1OC] | yellow solid; $^1$H-NMR (MeOD, 400 MHz): δ 8.70 (d, J = 6.8 Hz, 1H), 8.54 (d, J = 9.2 Hz, 1H), 8.44 (d, J = 2.8 Hz, 1H), 7.91 (dd, J = 2.8, 8.8 Hz, 1H), 7.87 (s, 1H), 7.78 (s, 1H), 7.46 (s, 1H), 7.03 (d, J = 6.8 Hz, 1H), 4.65 (q, J = 8.4 Hz, 1H), 4.21 (t, J = 7.2 Hz, 2H), 4.13 (s, 3H), 4.10 (s, 3H), 1.94 (q, J = 7.2 Hz, 2H), 1.75-1.85 (m, 3H), 1.60-1.71 (m, 2H), 1.49-1.60 (m, 2H), 1.13-1.25 (m, 2H); LCMS: 100%, MS (ESI): m/z 586.3 [M + H]+. |
| 94 | 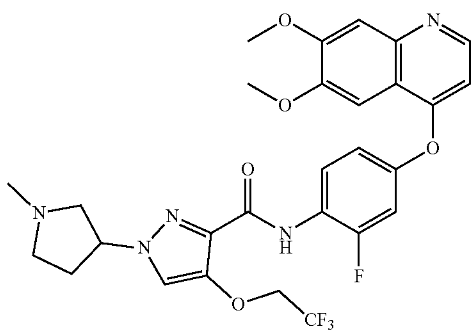 [SMILES: COc1cc2nccc(Oc3ccc(NC(=O)c4nn(C5CCN(C)C5)cc4OCC(F)(F)F)c(F)c3)c2cc1OC] | yellow solid; $^1$H-NMR (CDCl3, 400 MHz): δ 8.89 (s, 1H), 8.57-8.62 (m, 1H), 8.53 (d, J = 5.2 Hz, 1H), 7.59 (s, 1H), 7.53 (s, 1H), 7.44 (s, 1H), 6.99-7.05 (m, 2H), 6.54 (d, J = 5.2 Hz, 1H), 4.89-4.93 (m, 1H), 4.54 (q, J = 8.0 Hz, 2H), 4.07 (s, 3H), 4.06 (s, 3H), 2.96-3.03 (m, 2H), 2.73-2.78 (m, 1H), 2.40-2.52 (m, 5H), 2.08-2.14 (m, 1H), 1.55-1.70 (m, 2H); LCMS: 95.5%, MS (ESI): m/z 590.3 [M + H]+. |
| 95 | 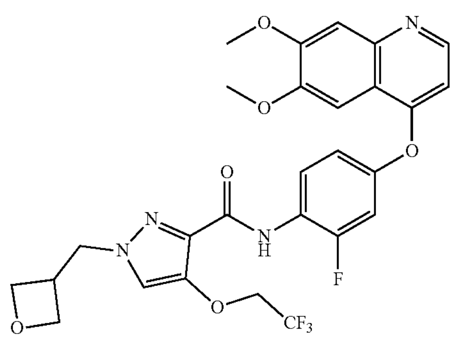 | white solid; $^1$H-NMR (MeOD, 400 MHz): δ 8.45 (d, J = 5.2 Hz, 1H), 8.34 (t, J = 8.8 Hz, 1H), 7.77 (s, 1H), 7.59 (s, 1H), 7.36 (s, 1H), 7.22 (dd, J = 11.2, 2.4 Hz, 1H), 7.12 (d, J = 8.8 Hz, 1H), 6.64 (d, J = 5.6 Hz, 1H), 4.84 (t, J = 7.2 Hz, 2H), 4.64 (q, J = 8.8 Hz, 2H), 4.58 (t, J = 6.0 Hz, 2H), 4.50 (d, J = 7.2 Hz, 2H), 4.02 (s, 3H), 4.00 (s, 3H), 3.50-3.63 (m, 1H); LCMS: 100%, MS (ESI): m/z 577.1 [M + H]+. |
| 96 | 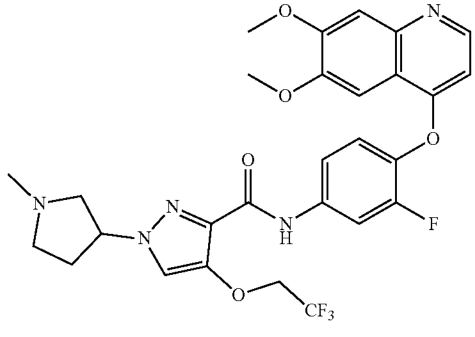 [SMILES: COc1cc2nccc(Oc3ccc(NC(=O)c4nn(C5CCN(C)C5)cc4OCC(F)(F)F)cc3F)c2cc1OC] | yellow solid; $^1$H-NMR (CDCl3, 400 MHz): δ 8.74 (s, 1H), 8.51 (d, J = 5.2 Hz, 1H), 7.89 (dd, J = 2.0, 12.0 Hz, 1H), 7.60 (s, 1H), 7.59 (s, 1H), 7.44 (s, 1H), 7.36-7.42 (m, 1H), 7.23-7.25 (m, 1H), 6.44 (d, J = 5.2 Hz, 1H), 4.86-4.90 (m, 1H), 4.55 (q, J = 8.4 Hz, 2H), 4.08 (s, 3H), 4.06 (s, 3H), 2.97-3.06 (m, 2H), 2.73-2.77 (m, 1H), 2.40-2.52 (m, 5H), 2.12-2.16 (m, 1H), 1.55-1.73 (m, 2H); LCMS: 98.3%, MS (ESI): m/z 590.3 [M + H]+. |

TABLE 8-continued

Summarizes compounds 1-179 in terms of their structures and corresponding characteristics.

| # cpd | Structure | Characterization Data |
|---|---|---|
| 97 | 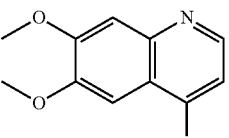 | white solid; ¹H-NMR (MeOD, 400 MHz): δ 8.43 (d, J = 5.2 Hz, 1H), 7.94 (dd, J = 12.8, 2.0 Hz, 1H), 7.74 (s, 1H), 7.64 (s, 1H), 7.55 (br d, J = 8.8 Hz, 1H), 7.33-7.39 (m, 2H), 6.52 (d, J = 5.6 Hz, 1H), 4.83 (t, J = 7.2 Hz, 2H), 4.54-4.65 (m, 4H), 4.49 (d, J = 7.6 Hz, 2H), 4.02 (s, 6H), 3.50-3.63 (m, 1H); LCMS: 100%, MS (ESI): m/z 577.2 [M + H]+. |
| 98 | 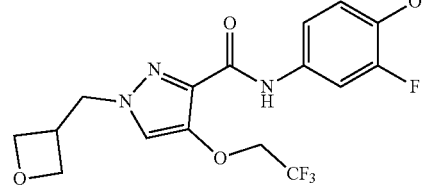 | yellow solid; ¹H-NMR (CDCl3, 400 MHz): δ 8.64 (s, 1H), 8.45 (d, J = 5.6 Hz, 1H), 7.69 (d, J = 2.4 Hz, 1H), 7.62 (s, 1H), 7.57 (s, 1H), 7.54 (d, J = 2.0 Hz, 1H), 7.43 (s, 1H), 7.10 (d, J = 8.4 Hz, 1H), 6.30 (d, J = 5.2 Hz, 1H), 4.84-4.88 (m, 1H), 4.55 (q, J = 8.4 Hz, 2H), 4.07 (s, 3H), 4.05 (s, 3H), 2.96-3.01 (m, 2H), 2.74-2.78 (m, 1H), 2.50-2.60 (m, 1H), 2.42-2.45 (m, 4H), 2.09-2.19 (m, 4H); LCMS: 97.0%, MS (ESI): m/z 586.3 [M + H]+. |
| 99 | 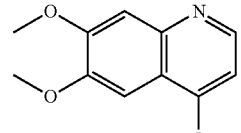 | white solid; ¹H-NMR (MeOD, 400 MHz): δ 8.39 (d, J = 5.2 Hz, 1H), 7.74 (br s, 2H), 7.63-7.70 (m, 2H), 7.36 (s, 1H), 7.16 (d, J = 8.8 Hz, 1H), 6.39 (d, J = 5.2 Hz, 1H), 4.84 (t, J = 7.2 Hz, 2H), 4.55-4.66 (m, 4H), 4.49 (d, J = 7.6 Hz, 2H), 4.02 (s, 6H), 3.50-3.63 (m, 1H), 2.19 (s, 3H); LCMS: 100%, MS (ESI): m/z 573.2 [M + H]+. |
| 100 | 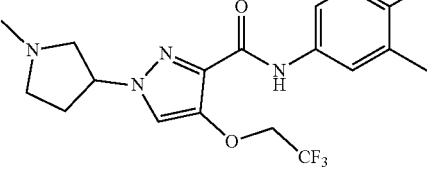 | yellow solid; ¹H-NMR (CDCl3, 400 MHz): δ 8.69 (s, 1H), 8.50 (d, J = 5.2 Hz, 1H), 7.77 (d, J = 8.8 Hz, 2H), 7.59 (d, J = 2.8 Hz, 2H), 7.43 (s, 1H), 7.20 (d, J = 8.4 Hz, 2H), 6.49 (d, J = 5.2 Hz, 1H), 4.86-4.91 (m, 1H), 4.56 (q, J = 8.0 Hz, 2H), 4.07 (s, 6H), 2.97-3.03 (m, 2H), 2.76-2.78 (m, 1H), 2.43-2.45 (m, 5H), 2.10-2.15 (m, 1H), 1.55-1.70 (m, 2H); LCMS: 97.9%, MS (ESI): m/z 572.3 [M + H]+. |

TABLE 8-continued

Summarizes compounds 1-179 in terms of their structures and corresponding characteristics.

| # cpd | Structure | Characterization Data |
|---|---|---|
| 101 | 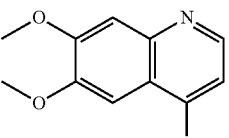 | white solid; ¹H-NMR (MeOD, 400 MHz): δ 8.42 (d, J = 5.6 Hz, 1H), 7.84 (s, 1H), 7.82 (s, 1H), 7.74 (s, 1H), 7.63 (s, 1H), 7.35 (s, 1H), 7.26 (s, 1H), 7.24 (s, 1H), 6.55 (d, J = 5.2 Hz, 1H), 4.84 (t, J = 7.2 Hz, 2H), 4.55-4.65 (m, 4H), 4.49 (d, J = 7.2 Hz, 2H), 4.01 (br s, 3H), 4.00 (br s, 3H), 3.50-3.63 (m, 1H); LCMS: 100%, MS (ESI): m/z 559.2 [M + H]+. |
| 102 | 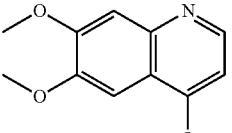 | white solid; ¹H-NMR (CDCl3, 400 MHz): δ 9.79 (s, 1H), 8.97 (d, J = 8.8 Hz, 1H), 8.60-8.63 (m, 1H), 8.23 (s, 1H), 7.58-7.61 (m 2H), 7.36-7.40 (m, 2H), 4.53 (q, J = 8.0 Hz, 2H), 4.21 (s, 3H), 4.12 (s, 3H), 3.98 (s, 3H); LCMS: 98.9%, MS (ESI): m/z 505.2 [M + H]+. |
| 103 | 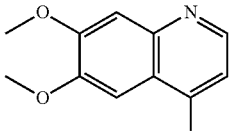 | white solid; ¹H-NMR (DMSO-d6, 400 MHz): δ 10.32 (s, 1H), 8.75-8.76 (m, 2H), 8.45 (dd, J = 2.0, 8.8 Hz, 1H), 7.90 (s, 1H), 7.60 (s, 1H), 7.55 (s, 1H), 7.43 (d, J = 9.2 Hz, 1H), 7.11 (d, J = 6.4 Hz, 1H), 4.68 (q, J = 9.2 Hz, 2H), 4.00 (s, 3H), 3.96 (s, 3H), 3.93 (d, J = 7.2 Hz, 2H), 2.11-2.20 (m, 1H), 0.87 (s, 3H), 0.85 (s, 3H); LCMS: 96.8%, MS (ESI): m/z 546.3 [M + H]+. |
| 104 | 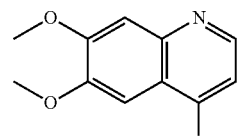 | white solid; ¹H-NMR (MeOD, 400 MHz): δ 8.62 (s, 1H), 8.49-8.53 (m, 1H), 8.36-8.38 (m, 1H), 7.69 (m, 1H), 7.49-7.51 (m, 1H), 7.35-7.38 (m, 1H), 7.29-7.30 (m, 1H), 6.88-6.89 (m, 2H), 4.59 (q, J = 8.8 Hz, 2H), 4.31-4.33 (m, 2H), 4.40 (d, J = 3.6 Hz, 3H), 3.95 (d, J = 4.0 Hz, 3H), 3.78-3.80 (m, 2H), 3.35 (s, 3H); LCMS: 99.7%, MS (ESI): m/z 548.2 [M + H]+. |

TABLE 8-continued

Summarizes compounds 1-179 in terms of their structures and corresponding characteristics.

| # cpd | Structure | Characterization Data |
|---|---|---|
| 105 | 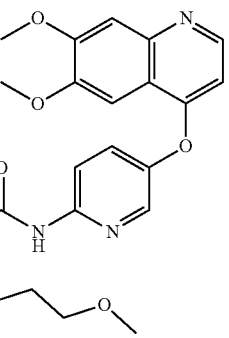 | yellow solid; ¹H-NMR (MeOD, 400 MHz): δ 8.75 (d, J = 6.8 Hz, 1H), 8.53 (d, J = 2.4 Hz, 1H), 8.43 (d, J = 9.2 Hz, 1H), 8.10 (dd, J = 2.4, 9.2 Hz, 1H), 7.87 (s, 1H), 7.71 (s, 1H), 7.53 (s, 1H), 7.12 (d, J = 6.8 Hz, 1H), 4.24-4.27 (m, 2H), 4.15-4.16 (m, 5H), 4.10 (s, 3H), 3.81-3.83 (m, 2H), 3.45 (s, 3H), 1.95 (d, J = 7.2 Hz, 2H), 0.96 (t, J = 7.6 Hz, 3H); LCMS: 99.2%, MS (ESI): m/z 508.2 [M + H]+. |
| 106 | 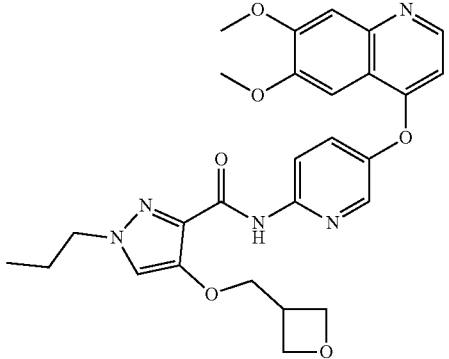 [SMILES: CCCn1cc(OCC2COC2)c(C(=O)Nc2ccc(Oc3ccnc4cc(OC)c(OC)cc34)cn2)n1] | yellow solid; ¹H-NMR (MeOD, 400 MHz): δ 8.46-8.48 (m, 2H), 8.33 (d, J = 2.8 Hz, 1H), 7.79 (dd, J = 2.8, 3.2 Hz, 1H), 7.73 (s, 1H), 7.66 (s, 1H), 7.39 (s, 1H), 6.61 (d, J = 5.2 Hz, 1H), 4.91-4.95 (m, 2H), 4.67 (t, J = 6.0 Hz, 2H), 4.36 (d, J = 6.8 Hz, 2H), 4.16 (t, J = 6.8 Hz, 2H), 4.03 (d, J = 3.2 Hz, 6H), 3.52-3.68 (s, 1H), 1.92-1.98 (m, 2H), 0.97 (t, J = 7.2 Hz, 3H); LCMS: 99.5%, MS (ESI): m/z 520.1 [M + H]+. |
| 107 | 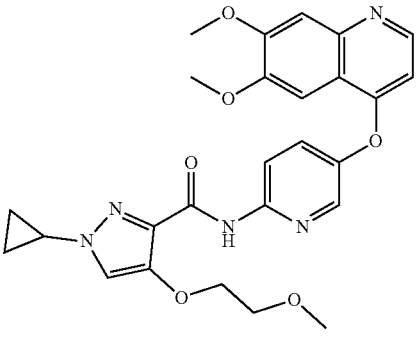 [SMILES: COCCOc1cn(C2CC2)nc1C(=O)Nc1ccc(Oc2ccnc3cc(OC)c(OC)cc23)cn1] | yellow solid; ¹H-NMR (MeOD, 400 MHz): δ 8.76 (d, J = 6.4 Hz, 1H), 8.53 (d, J = 1.8 Hz, 1H), 8.43 (d, J = 9.2 Hz, 1H), 8.10 (dd, J = 2.4, 9.2 Hz, 1H), 7.87 (s, 1H), 7.76 (s, 1H), 7.54 (s, 1H), 7.11 (d, J = 6.8 Hz, 1H), 4.24 (dd, J = 4.4, 5.2 Hz, 2H), 4.16 (s, 3H), 4.12 (s, 3H), 3.79-3.83 (m, 3H), 3.47 (s, 3H), 1.22-1.26 (m, 2H), 1.10-1.13 (m, 2H); LCMS: 97.7%, MS (ESI): m/z 506.1 [M + H]+. |
| 108 | 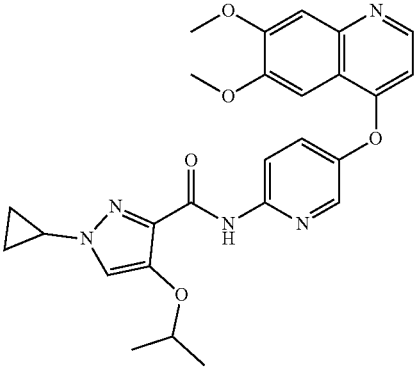 | yellow solid; ¹H-NMR (MeOD, 400 MHz): δ 8.74 (d, J = 6.8 Hz, 1H), 8.53 (d, J = 2.4 Hz, 1H), 8.42 (d, J = 9.2 Hz, 1H), 8.12 (dd, J = 9.2, 2.8 Hz, 1H), 7.85 (s, 1H), 7.73 (s, 1H), 7.53 (s, 1H), 7.11 (d, J = 6.8 Hz, 1H), 4.45 (quin, J = 6.0 Hz, 1H), 4.14 (s, 3H), 4.10 (s, 3H), 3.75-3.84 (m, 1H), 1.43 (s, 3H), 1.42 (s, 3H), 1.21-1.26 (m, 2H), 1.05-1.12 (m, 2H); LCMS: 98.1%, MS (ESI): m/z 490.2 [M + H]+. |

TABLE 8-continued

Summarizes compounds 1-179 in terms of their structures and corresponding characteristics.

| # cpd | Structure | Characterization Data |
|---|---|---|
| 109 | 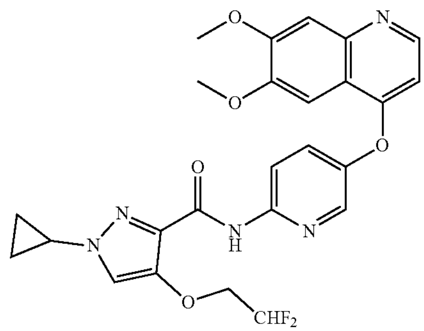 | yellow solid; $^1$H-NMR (CDCl3, 400 MHz): δ 8.79 (d, J = 6.8 Hz, 1H), 8.63 (s, 1H), 8.30-8.37 (m, 2H), 7.87 (s, 1H), 7.84 (s, 1H), 7.57 (s, 1H), 7.20 (d, J = 6.8 Hz, 1H), 6.11-6.40 (m, 1H), 4.30-4.37 (m, 2H), 4.16 (s, 3H), 4.12 (s, 3H), 3.80-3.86 (m, 1H), 3.32-3.34 (m, 1H), 1.26-1.29 (m, 2H), 1.11-1.15 (m, 2H); LCMS: 99.2%, MS (ESI): m/z 512.3 [M + H]+. |
| 110 | 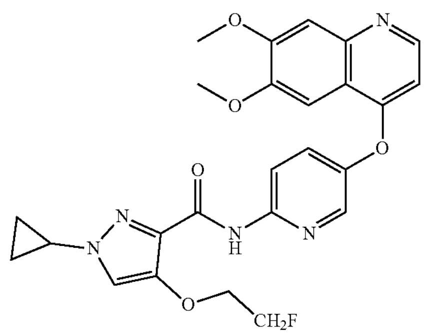 | white solid; $^1$H-NMR (MeOD, 400 MHz): δ 8.74 (d, J = 6.4 Hz, 1H), 8.51 (s, 2H), 8.03 ( d, J = 9.2 Hz, 1H), 7.87 (s, 1H), 7.78 (s, 1H), 7.52 (s, 1H), 7.08 (d, J = 6.8 Hz, 1H), 4.86-4.88 (m, 1H), 4.74-4.76 (m, 1H), 4.38-4.40 (m, 1H), 4.31-4.32 (m, 1H), 4.15 (s, 3 H), 4.12 (s, 3H), 3.78-3.81 (m, 1H), 1.22-1.27 (m, 2H), 1.08-1.13 (m, 2H); LCMS: 99.1%, MS (ESI): m/z 494.2 [M + H]+. |
| 111 | 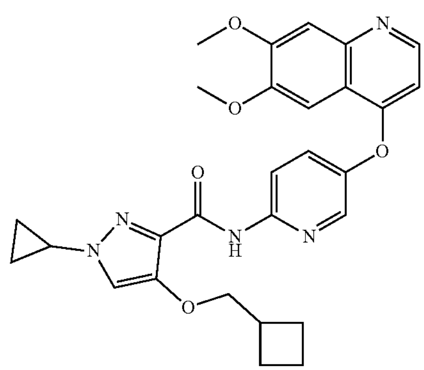 [SMILES: COc1cc2nccc(Oc3ccc(NC(=O)c4nn(C5CC5)cc4OCC4CCC4)nc3)c2cc1OC] | yellow solid; $^1$H-NMR (MeOD, 400 MHz): δ 8.74 (d, J = 6.4 Hz, 1H), 8.52 (br s, 1H), 8.41 (d, J = 7.2 Hz, 1H), 8.12 (d, J = 5.6 Hz, 1H), 7.84 (s, 1H), 7.71 (s, 1H), 7.53 (s, 1H), 7.11 (d, J = 6.4 Hz, 1H), 4.13 (s, 3H), 4.10 (s, 3H), 4.05 (d, J = 6.4 Hz, 2H), 3.73-3.80 (m, 1H), 2.80-2.93 (m, 1H), 2.11-2.24 (m, 2H), 2.00 (br s, 4H), 1.19-1.26 (m, 2H), 1.04-1.12 (m, 2H); LCMS: 99.1%, MS (ESI): m/z 516.2 [(M + H)]+. |
| 112 | 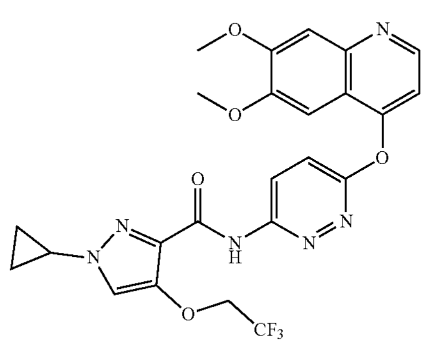 | white solid; $^1$H-NMR (MeOD, 400 MHz): δ 8.77 (d, J = 9.6 Hz, 1H), 8.54 (d, J = 5.6 Hz, 1H), 7.81 (s, 1H), 7.23(d, J = 9.6 Hz, 1H), 7.49 (s, 1H), 7.41 (s, 1H), 7.07 (d, J = 5.2 Hz, 1H), 4.62 (q, J = 8.4 Hz, 1H), 4.03 (s, 3H), 3.96 (s, 3H), 3.75-3.79 (m, 1H), 1.20-1.24 (m, 2H), 1.05-1.10 (m, 2H); LCMS: 98.9%, MS (ESI): m/z 531.2 [(M + H)]+. |

TABLE 8-continued

Summarizes compounds 1-179 in terms of their structures and corresponding characteristics.

| # cpd | Structure | Characterization Data |
|---|---|---|
| 113 | 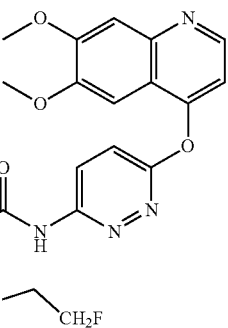 | yellow solid; ¹H-NMR (CDCl3, 400 MHz): δ 9.75 (s, 1H), 8.86 (d, J = 9.6 Hz, 1H), 8.67 (d, J = 5.2 Hz, 1H), 7.51 (s, 1H), 7.42 (d, J = 9.2 Hz, 2H), 7.34 (s, 1H), 6.97 (d, J = 5.2 Hz, 1H), 4.86-4.88 (m, 1H), 4.75-4.77 (m, 1H), 4.36-4.38 (m, 1H), 4.26-4.31 (m, 1H), 4.08 (s, 3H), 4.03 (s, 3H), 3.62-3.68 (m, 1H), 1.23-1.27 (m, 2H), 1.05-1.14 (m, 2H); LCMS: 98.9%, MS (ESI): m/z 495.2 [(M + H)]+. |
| 114 | 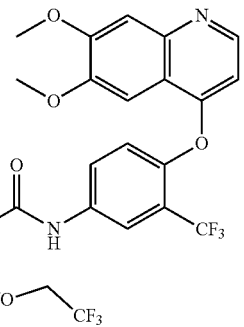 | yellow solid; ¹H-NMR (MeOD, 400 MHz): δ 8.74 (d, J = 6.8 Hz, 1H), 8.45 (d, J = 2.4 Hz, 1H), 8.23 (dd, J = 8.8, 2.4 Hz, 1H), 7.82 (s, 1H), 7.76 (s, 1H), 7.60 (d, J = 8.8 Hz, 1H), 7.52 (s, 1H), 7.03 (d, J = 6.8 Hz, 1H), 4.63 (q, J = 8.4 Hz, 2H), 4.16-4.19 (m, 5H), 4.11 (s, 3H), 1.92-2.01 (m, 2H), 0.97 (t, J = 7.6 Hz, 3H); LCMS: 98.7%, MS (ESI): m/z 599.2 [(M + H)]+. |
| 115 | 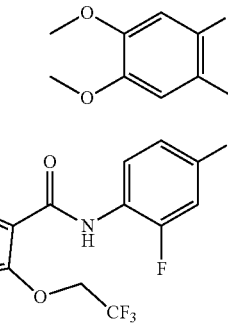 | white solid; ¹H-NMR (MeOD, 400 MHz): δ 8.69 (d, J = 6.8 Hz, 1H), 8.49 (t, J = 8.8 Hz, 1H), 7.83 (s, 1H), 7.74 (s, 1H), 7.48 (s, 1H), 7.41 (dd, J = 2.4,11.2 Hz, 1H), 7.27 (d, J = 9.2 Hz, 1H), 7.03 (d, J = 6.8 Hz, 1H), 4.65 (q, J = 8.4 Hz, 2H), 4.33 (t, J = 5.2 Hz, 2H), 4.13 (s, 3H), 4.09 (s, 3H), 3.92 (t, J = 5.2 Hz, 2H), 3.33-3.36 (m, 1H), 0.46-0.48 (m, 4H); LCMS: 95.6%, MS (ESI): m/z 591.2 [(M + H)]+. |
| 116 | 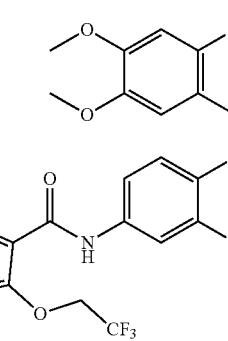 | off-white solid; ¹H-NMR (MeOD, 400 MHz): δ 8.71 (d, J = 6.8 Hz, 1H), 8.06 (dd, J = 2.4,12.8 Hz, 1H), 7.85 (s, 1H), 7.70 (s, 1H), 7.65 (d, J = 8.8 Hz, 1H), 7.46-7.53 (m, 2H), 7.01 (d, J = 6.8 Hz, 1H), 4.61 (q, J = 8.8 Hz, 2H), 4.33 (t, J = 4.8 Hz, 2H), 4.14 (s, 3H), 4.10 (s, 3H), 3.92 (t, J = 4.8 Hz, 2H), 3.34-3.37 (m, 1H), 0.46-0.48 (m, 4H); LCMS: 95.7%, MS (ESI); m/z 591.2 [(M + H)]+. |

TABLE 8-continued

Summarizes compounds 1-179 in terms of their structures and corresponding characteristics.

| # cpd | Structure | Characterization Data |
|---|---|---|
| 117 | 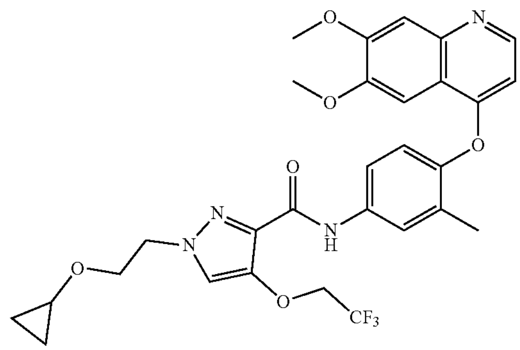 | light yellow solid; $^1$H-NMR (MeOD, 400 MHz): δ 8.65 (d, J = 6.8 Hz, 1H), 7.88 (s, 1H), 7.83 (d, J = 2.0 Hz, 1H), 7.76 (dd, J = 2.4,8.8 Hz, 1H), 7.70 (s, 1H), 7.48 (s, 1H), 7.27 (d, J = 8.4 Hz, 1H), 6.84 (d, J = 6.8 Hz, 1H), 4.61 (q, J = 8.4 Hz, 2H), 4.32 (t, J = 5.2 Hz, 2H), 4.13 (s, 3H), 4.11 (s, 3H), 3.92 (t, J = 5.2 Hz, 2H), 3.33-3.37 (m, 1H), 2.23 (s, 3H), 0.44-0.50 (m, 4H); LCMS: 96.7%, MS (ESI): m/z 587.2 [(M + H)]+. |
| 118 | 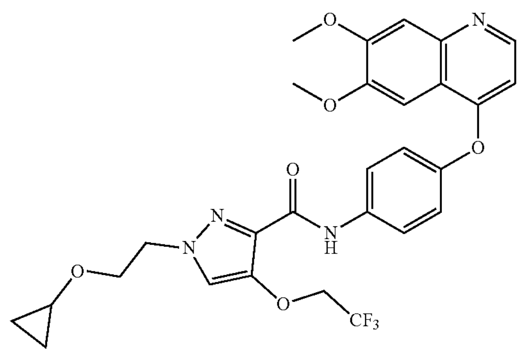 [SMILES: COc1cc2nccc(Oc3ccc(NC(=O)c4nn(CCOC5CC5)cc4OCC(F)(F)F)cc3)c2cc1OC] | yellow solid; $^1$H-NMR (MeOD, 400 MHz): δ 8.67 (d, J = 6.8 Hz, 1H), 7.94 (d, J = 8.8 Hz, 2H), 7.84 (s, 1H), 7.70 (s, 1H), 7.49 (s, 1H), 7.37 (d, J = 8.8 Hz, 2H), 6.95 (d, J = 6.8 Hz, 1H), 4.62 (q, J = 8.8 Hz, 2H), 4.33 (t, J = 5.2 Hz, 2H), 4.13 (s, 3H), 4.10 (s, 3H), 3.92 (t, J = 5.2 Hz, 2H), 3.31-3.35 (m, 1H), 0.46-0.49 (m, 4H); LCMS: 97.0%, MS (ESI): m/z 573.2 [(M + H)]+. |
| 119 | 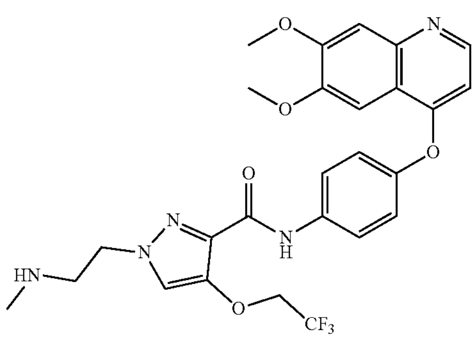 | HCl salt, yellow solid; 1H-NMR (MeOD, 400 MHz): δ 8.68 (d, J = 6.8 Hz, 1H), 7.97 (d, J = 8.8 Hz, 2H), 7.87 (s, 1H), 7.83 (s, 1H), 7.51 (s, 1H), 7.40 (d, J = 8.8 Hz, 2H), 6.95 (d, J = 6.8 Hz, 1H), 4.66 (q, J = 8.4 Hz, 2H), 4.60 (t, J = 4.8 Hz, 2H), 4.12 (s, 3H), 4.09 (s, 3H), 3.63 (t, J = 4.8 Hz, 2H), 2.83 (s, 3H); LCMS: 94.0%, MS (ESI): m/z 546.2 [(M + H)]+. |
| 120 | 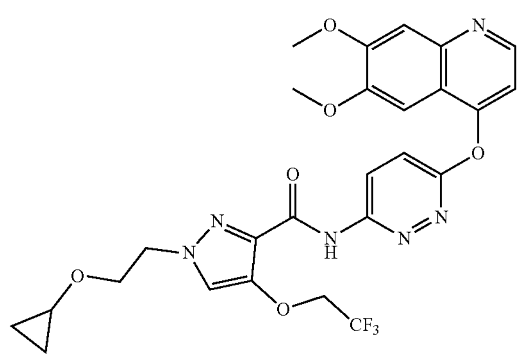 | off-white solid; $^1$H-NMR (MeOD, 400 MHz): δ 8.64 (d, J = 9.6 Hz, 1H), 8.45 (d, J = 5.6 Hz, 1H), 7.59 (t, J = 4.4 Hz, 2H), 7.36 (s, 1H), 7.28 (s, 1H), 6.94 (d, J = 5.6 Hz, 1H), 4.51 (q, J = 8.4 Hz, 2H), 4.20 (t, J = 5.2 Hz, 2H), 3.90 (s, 3H), 3.84 (s, 3H), 3.79 (t, J = 5.2 Hz, 2H), 3.21-3.24 (m, 1H), 0.33-0.35 (m, 4H); LCMS: 98.6%, MS (ESI): m/z 575.2 [(M + H)]+. |

TABLE 8-continued

Summarizes compounds 1-179 in terms of their structures and corresponding characteristics.

| # cpd | Structure | Characterization Data |
|---|---|---|
| 121 | 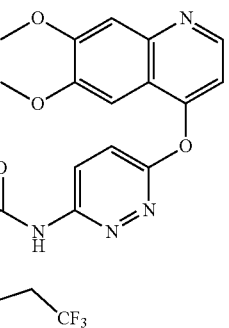 | yellow solid; $^1$H-NMR (MeOD, 400 MHz): δ 8.90 (d, J = 9.2 Hz, 1H), 8.79 (d, J = 6.8 Hz, 1H), 7.89 (d, J = 9.6 Hz, 1H), 7.82 (d, J = 8.4 Hz, 1H), 7.55 (d, J = 6.8 Hz, 1H), 7.49 (s, 1H), 4.21-4.77 (m, 1H), 4.65 (dd, J = 8.4 Hz, 2H), 4.14 (s, 3H), 4.09 (s, 3H), 2.09-2.21 (m, 2H), 2.08-2.09 (m, 2H), 1.93-1.94 (m,2H), 1.76-1.77 (m, 2H); LCMS: 93.2%, MS (ESI): m/z 559.2 [M + H]+. |
| 122 | 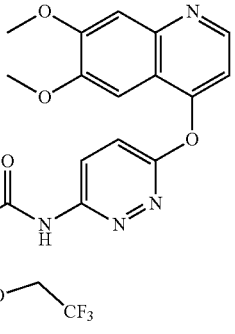 | HCl salt, yellow solid; $^1$H-NMR (MeOD, 400 MHz): δ 8.91 (d, J = 9.6 Hz, 1H), 8.82 (d, J = 6.8 Hz, 1H, 7.89-7.97 (m, 2H), 7.84 (s, 1H), 7.56 (d, J = 6.4 Hz, 1H), 7.52 (s, 1H), 5.31 (t, J = 6.0 Hz, 1H ), 4.69 (q, J = 8.4 Hz, 2H), 4.15 (s, 3H), 4.10 (s, 3H), 3.93 (br d, J = 13.2 Hz, 1H), 3.63-3.76 (m, 2H), 3.51-3.60 (m, 1H), 2.54-2.73 (m, 1H), 2.34-2.44 (m, 1H); LCMS: 97.5%, MS (ESI): m/z 560.2 [M + H]+. |
| 123 | 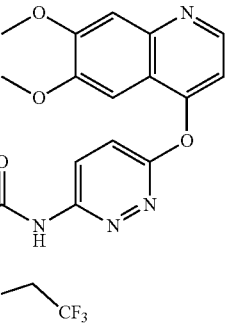 | white solid; $^1$H-NMR (MeOD, 400 MHz): δ 8.78 (d, J = 9.6 Hz, 1H), 8.60 (d, J = 5.2 Hz, 1H), 7.80 (s, 1H), 7.74 (d, J = 9.6 Hz, 1H), 7.50 (s, 1H), 7.43 (s, 1H), 7.08 (d, J = 5.2 Hz, 1H), 4.84-4.86 (m, 2H), 4.63 (q, J = 8.4 Hz, 2H), 4.59 (t, J = 6.4 Hz, 2H), 4.52 (d, J = 7.6 Hz, 2H), 4.05 (s, 3H), 3.98 (s, 3H), 3.53-3.63 (m, 1H); LCMS: 96.0%, MS (ESI): m/z 561.0 [M + H]+. |
| 124 | 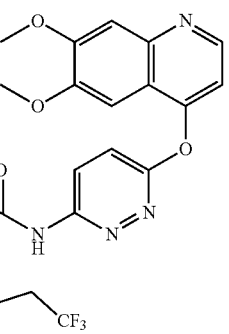 | yellow solid; $^1$H-NMR (MeOD, 400 MHz): δ 8.85 (d, J = 9.2 Hz, 1H), 8.82 (d, J = 6.8 Hz, 1H), 7.97 (d, J = 9.6 Hz, 1H), 7.83 (s, 1H), 7.78 (s, 1H), 7.60 (d, J = 6.8 Hz, 1H), 7.52 (s, 1H), 4.65 (q, J = 8.4 Hz, 2H), 4.14 (s, 3H), 4.09 (s, 3H), 4.01 (d, J = 7.2 Hz, 2H), 2.21-2.31 (m, 1H), 0.96 (s, 3H), 0.94 (s, 3H); LCMS: 98.6%, MS (ESI): m/z 547.2 [M + H]+. |

TABLE 8-continued

Summarizes compounds 1-179 in terms of their structures and corresponding characteristics.

| # cpd | Structure | Characterization Data |
|---|---|---|
| 125 | 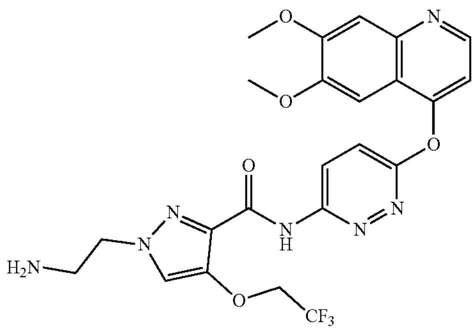 | HCl salt, white solid; $^1$H-NMR (MeOD, 400 MHz): δ 8.89 (d, J = 9.6 Hz, 1H), 8.85 (d, J = 6.4 Hz, 1H), 8.07 (d, J = 9.2 Hz, 1H), 7.89 (s, 1H), 7.83 (s, 1H), 7.65 (d, J = 6.8 Hz, 1H), 7.55 (s, 1H), 4.66 (q, J = 8.4 Hz, 2H), 4.55 (t, J = 5.2 Hz, 2H), 4.15 (s, 3H), 4.09 (s, 3H), 3.56 (d, J = 4.8 Hz, 2H); LCMS: 96.3%, MS (ESI): m/z 534.2 [M + H]+. |
| 126 | 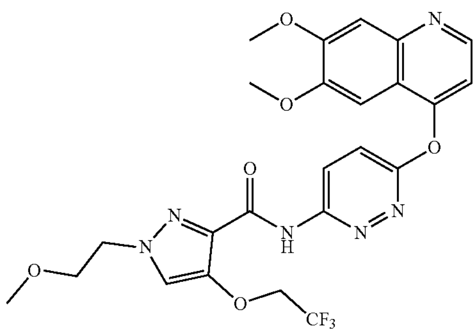 | yellow solid; $^1$H-NMR (MeOD, 400 MHz): δ 8.80-8.83 (m, 2H), 8.00 (d, J = 9.26 Hz, 1H), 7.81 (s, 1H), 7.78 (s, 1H), 7.61 (d, J = 6.8 Hz, 1H), 7.55 (s, 1H), 4.64 (q, J = 8.4 Hz, 2H), 4.37 (t, J = 4.8 Hz, 2H), 4.14 (s, 3H), 4.09 (s, 3H), 3.81 (t, J = 4.8 Hz, 2H), 3.36 (s, 3H); LCMS: 93.4%, MS (ESI): m/z 549.2 [M + H]+. |
| 127 | 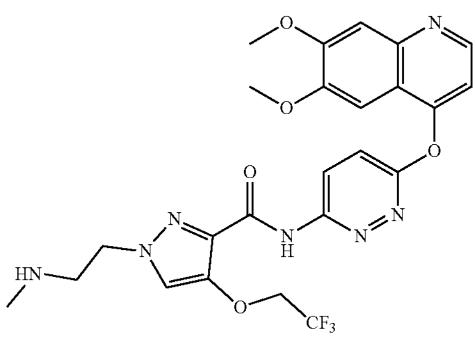 [SMILES: CNCCn1cc(OCC(F)(F)F)c(C(=O)Nc2ccc(Oc3ccnc4cc(OC)c(OC)cc34)nn2)n1] | HCl salt, off-white solid; $^1$H-NMR (MeOD, 400 MHz): δ 8.88 (d, J = 9.6 Hz, 1H), 8.82 (d, J = 6.4 Hz, 1H), 7.96 (d, J = 9.6 Hz, 1H), 7.91 (s, 1H), 7.82 (s, 1H), 7.57 (d, J = 6.8 Hz, 1H), 7.55 (s, 1H), 4.68 (q, J = 8.4 Hz, 2H), 4.61 (t, J = 4.8 Hz, 2H), 4.15 (s, 3H), 4.09 (s, 3H), 3.64 (t, J = 4.8 Hz, 2H), 2.83 (s, 3H); LCMS: 98.3%, MS (ESI): m/z 548.2 [(M + H)]+. |
| 128 | 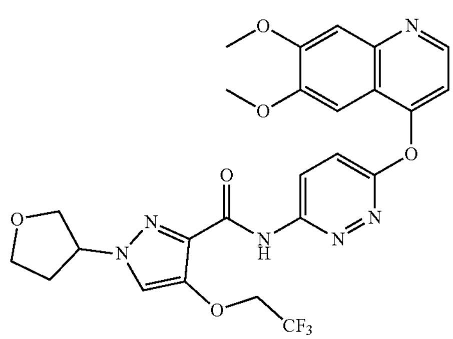 | off-white solid; $^1$H-NMR (MeOD, 400 MHz): δ 8.87 (d, J = 9.6 Hz, 1H), 8.81 (d, J = 6.4 Hz, 1H), 7.91 (d, J = 9.6 Hz, 1H), 7.84 (s, 1H), 7.83 (s, 1H), 7.56 (d, J = 6.4 Hz, 1H), 7.51 (s, 1H), 5.08-5.10 (m, 1H), 4.64 (q, J = 8.4 Hz, 2H), 4.12-4.22 (m, 5H), 4.09 (s, 3H), 4.01-4.05 (m, 1H), 3.91-3.93 (m, 1H), 2.53-2.56 (m, 1H), 2.37-2.42 (m, 1H); LCMS: 98.6%, MS (ESI): m/z 561.2 [M + H]+. |

TABLE 8-continued

Summarizes compounds 1-179 in terms of their structures and corresponding characteristics.

| # cpd | Structure | Characterization Data |
|---|---|---|
| 129 | 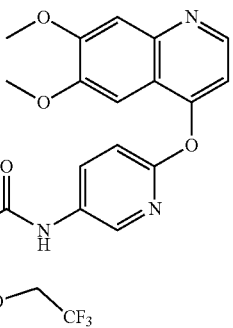 | white solid; $^1$H-NMR (MeOD, 400 MHz): δ 8.79 (d, J = 2.4 Hz, 1H), 8.73 (d, J = 6.8 Hz, 1H), 8.48 (dd, J = 2.8, 8.8 Hz, 1H), 7.81 (s, 1H), 7.73 (s, 1H), 7.47-7.49 (m, 2H), 7.33 (d, J = 6.8 Hz, 1H), 4.61 (q, J = 8.8 Hz, 2H), 4.27 (t, J = 5.2 Hz, 2H), 4.13 (s, 3H), 4.09 (s, 3H), 3.96 (t, J = 5.2 Hz, 2H); LCMS: 100%, MS (ESI): m/z 534.2 [M + H]+. |
| 130 | 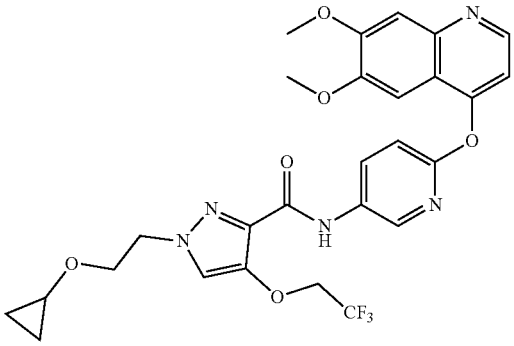 | off-white solid; $^1$H-NMR (MeOD, 400 MHz): δ 8.63 (d, J = 2.4 Hz, 1H), 8.52 (d, J = 5.2 Hz, 1H), 8.38 (dd, J = 2.8, 8.8 Hz, 1H), 7.67 (s, 1H), 7.52 (s, 1H), 7.38 (s, 1H), 7.30 (d, J = 8.8 Hz, 1H), 6.89 (d, J = 5.6 Hz, 1H), 4.59 (q, J = 8.4 Hz, 2H), 4.31 (t, J = 5.2 Hz, 2H), 4.02 (s, 3H), 3.97 (s, 3H), 3.90 (t, J = 5.2 Hz, 2H), 3.33-3.34 (m, 1H), 0.45-0.47 (m, 4H); LCMS: 98.6%, MS (ESI): m/z 574.2 [(M + H)]+. |
| 131 | 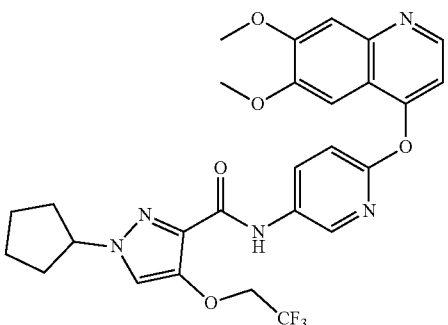 | white solid; $^1$H-NMR (MeOD, 400 MHz): δ 8.79 (d, J = 2.8 Hz, 1H), 8.73 (d, J = 6.8 Hz, 1H), 8.48 (dd, J = 2.8, 8.8 Hz, 1H), 7.82 (s, 1H), 7.77 (s, 1H), 7.46-7.49 (m, 2H), 7.33 (d, J = 7.2 Hz, 1H), 4.72-4.76 (m, 1H), 4.58-4.64 (m, 2H), 4.13 (s, 3H), 4.09 (s, 3H), 2.19-2.22 (m, 2H), 2.08-2.11 (m, 2H), 1.92-1.93 (m, 2H), 1.75-1.78 (m, 2H); LCMS: 100%, MS (ESI): m/z 558.2 [M + H]+. |
| 132 | 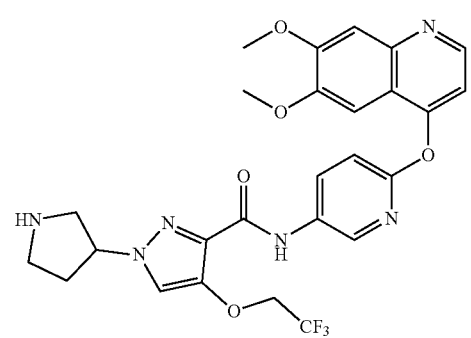 | HCl salt, yellow solid; $^1$H-NMR (MeOD, 400 MHz): δ 8.89 (d, J = 2.4 Hz, 1H), 8.72 (d, J = 6.8 Hz, 1H), 8.56 (dd, J = 2.4, 8.8 Hz, 1H), 7.89 (s, 1H), 7.74 (s, 1H), 7.45-7.48 (m, 2H), 7.33 (d, J = 6.8 Hz, 1H), 5.26-5.33 (m, 1H), 4.62-4.64 (m, 2H), 4.11 (s, 3H), 4.07 (s, 3H), 3.99 (d, J = 12.8 Hz, 1H), 3.71-3.76 (m, 2H), 3.53-3.59 (m, 1H), 2.59-2.62 (m, 1H), 2.39-2.41 (m, 1H); LCMS: 96.1%, MS (ESI): m/z 559.2 [M + H]+. |

TABLE 8-continued

Summarizes compounds 1-179 in terms of their structures and corresponding characteristics.

| # cpd | Structure | Characterization Data |
|---|---|---|
| 133 | 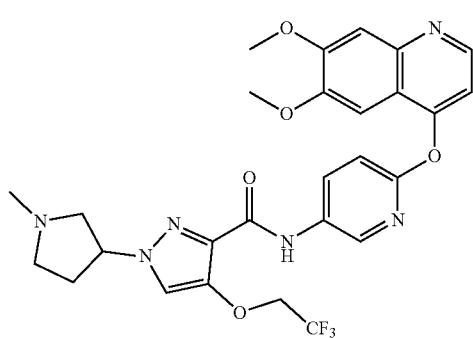 | yellow solid; ¹H-NMR (DMSO-d6, 400 MHz): δ 11.02 (s, 1H), 9.13 (d, J = 2.4 Hz, 1H), 8.87 (d, J = 6.4 Hz, 1H), 8.76 (dd, J = 2.8, 9.2 Hz, 1H), 8.03 (s, 1H), 7.74 (s, 1H), 7.69 (s, 1H), 7.53 (d, J = 8.8 Hz, 1H), 7.26 (d, J = 6.4 Hz, 1H), 5.29-5.32 (m, 1H), 4.70 (q, J = 9.2 Hz, 2H), 4.05 (s, 3H), 4.04 (s, 3H), 3.78-3.85 (m, 2H), 3.16-3.23 (m, 2H), 2.90-2.91 (m, 3H), 2.74-2.77 (m, 1H), 2.17-2.22 (m, 1H); LCMS: 95.4%, MS (ESI): m/z 573.3 [M + H]+. |
| 134 | 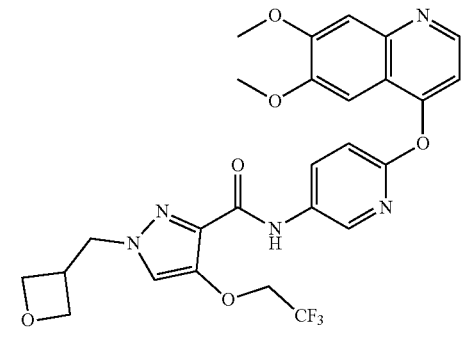 | white solid; ¹H-NMR (MeOD, 400 MHz): δ 8.61 (d, J = 2.8 Hz, 1H), 8.51 (d, J = 5.6 Hz, 1H), 8.36 (dd, J = 2.8, 8.8 Hz, 1H), 7.73 (s, 1H), 7.50 (s, 1H), 7.38 (s, 1H), 7.30 (d, J = 8.8 Hz, 1H), 6.88 (d, J = 5.2 Hz, 1H), 4.83 (t, J = 6.8 Hz, 2H), 4.55-4.62 (m, 4H), 4.48 (d, J = 7.6 Hz, 2H), 4.01 (s, 3H), 3.96 (s, 3H), 3.52-3.61 (m, 1H).; LCMS: 98.4%, MS (ESI): m/z 560.2 [M + H]+. |
| 135 | 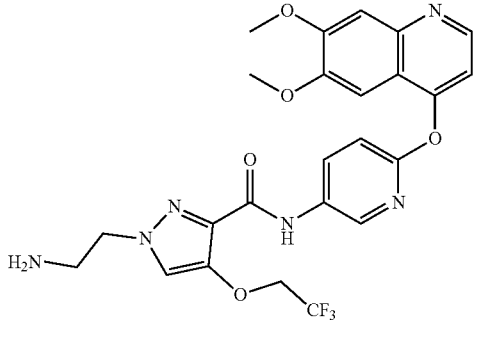 [SMILES: COc1cc2nccc(Oc3ccc(NC(=O)c4nn(CCN)cc4OCC(F)(F)F)cn3)c2cc1OC] | HCl salt, yellow solid; ¹H-NMR (MeOD, 400 MHz): δ 8.88 (d, J = 5.2 Hz, 1H), 8.80 (d, J = 2.4 Hz, 1H), 8.73 (d, J = 6.8 Hz, 1H), 8.50 (dd, J = 2.4, 8.8 Hz, 1H), 8.13 (t, J = 6.8 Hz, 1H), 7.83 (s, 1H), 7.81 (s, 1H), 7.50 (d, J = 8.8 Hz, 1H), 7.48 (s, 1H), 7.35 (d, J = 6.8 Hz, 1H), 4.64 (q, J = 8.8 Hz, 2H), 4.51 (t, J = 6.4 Hz, 2H), 4.13 (s, 3H), 4.08 (s, 3H), 3.54 (t, J = 5.6 Hz, 2H); LCMS: 93.6%, MS (ESI): m/z 533.2 [M + H]+. |
| 136 | 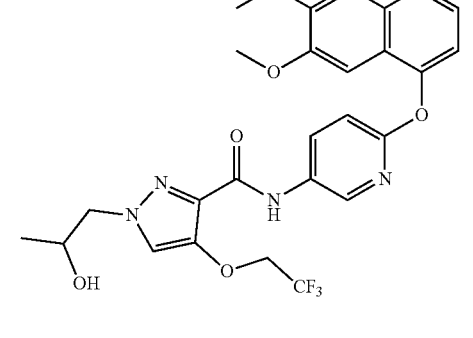 | yellow solid; ¹H-NMR (MeOD, 400 MHz): δ 8.79 (d, J = 2.4 Hz, 1H), 8.72 (d, J = 6.4 Hz, 1H), 8.48 (dd, J = 2.8, 8.8 Hz, 1H), 7.81 (s, 1H), 7.71 (s, 1H), 7.47-7.49 (m, 2H), 7.33 (d, J = 6.8 Hz, 1H), 4.60 (q, J = 8.8 Hz, 2H), 4.18-4.21 (m, 2H), 4.13 (s, 3H), 4.03-4.08 (m, 4H), 1.20 (d, J = 6.0 Hz, 3H); LCMS: 98.9%, MS (ESI): m/z 548.2 [M + H]+. |

TABLE 8-continued

Summarizes compounds 1-179 in terms of their structures and corresponding characteristics.

| # cpd | Structure | Characterization Data |
|---|---|---|
| 137 | 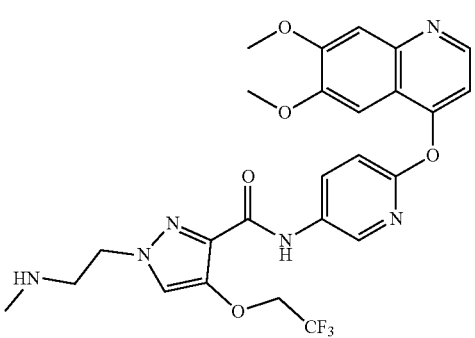 | HCl salt, off-white solid; $^1$H-NMR (MeOD, 400 MHz): δ 8.83 (d, J = 2.4 Hz, 1H), 8.73 (d, J = 6.8 Hz, 1H), 8.52 (dd, J = 8.8, 2.4 Hz, 1H), 7.85 (s, 1H), 7.78 (s, 1H), 7.48-7.51 (m, 2H), 7.35 (d, J = 6.4 Hz, 1H), 4.64 (q, J = 8.8 Hz, 2H), 4.59 (t, J = 5.6 Hz, 2H), 4.13 (S, 3H), 4.08 (s, 3H), 3.63 (t, J = 5.2 Hz, 2H), 2.83 (s, 3H); LCMS: 96.6%, MS (ESI): m/z 547.2 [(M + H)]+. |
| 138 | 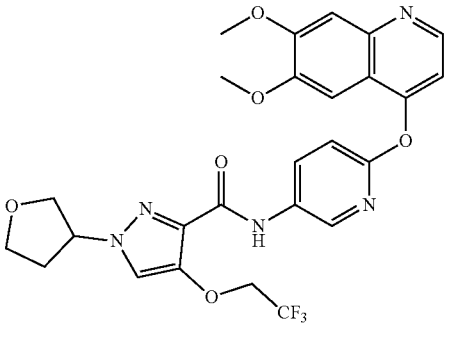 | yellow solid; $^1$H-NMR (MeOD, 400 MHz): δ 8.79 (d, J = 2.8 Hz, 1H), 8.73 (d, J = 6.8 Hz, 1H), 8.48 (dd, J = 8.4, 2.4 Hz, 1H), 7.78 (s, 1H), 7.81 (s, 1H), 7.47 (t, J = 4.8 Hz, 2H), 7.34 (d, J = 6.4 Hz, 1H), 5.06-5.09 (m, 1H), 4.60-4.62 (m, 2H), 4.17-4.19 (m, 2H), 4.13 (s, 3H), 4.09 (s, 3H), 4.02-4.04 (m, 1H), 3.91-3.93 (m, 1H), 2.50-2.57 (m, 1H), 2.37-2.40 (m, 1H); LCMS: 96.1%, MS (ESI): m/z 560.0 [M + H]+. |
| 139 | 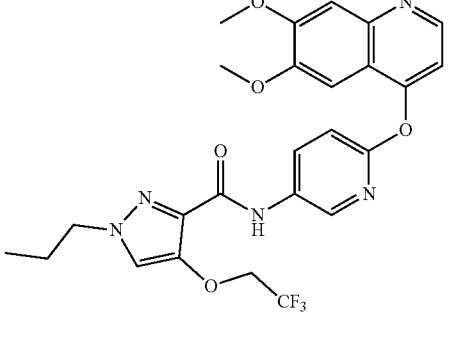 | white solid; $^1$H-NMR (MeOD, 400 MHz): δ 8.79 (d, J = 2.4 Hz, 1H), 8.73 (d, J = 6.8 Hz, 1H), 8.49 (dd, J = 8.4, 3.2 Hz, 1H), 7.81 (s, 1H), 7.74 (s, 1H), 7.47-7.49 (m, 2H), 7.33 (d, J = 7.2 Hz, 1H), 4.60 (q, J = 8.4 Hz, 2H), 4.14-4.16 (m, 2H), 4.13 (s, 3H), 4.09 (s, 3H), 1.93-1.95 (m, 2H), 0.95 (t, J = 7.2 Hz, 3H); LCMS: 99.5%, MS (ESI): m/z 532.2 [M + H]+. |
| 140 | 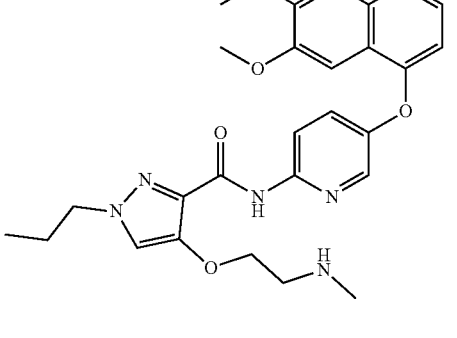 | HCl salt, yellow solid; $^1$H-NMR (MeOD, 400 MHz): δ 8.71 (s, 1H), 8.61 (s, 1H), 8.29 (s, 2H), 7.75 (d, J = 9.2 Hz, 2H), 7.49 (s, 1H), 7.14 (s, 1H), 4.27 (s, 2H), 4.12 (t, J = 6.8 Hz, 2H), 4.05 (s, 3H), 4.02 (s, 3H), 3.41 ( s, 2H), 2.78 (s, 3H), 1.85-1.90 (m, 2H), 0.87 (t, J = 7.2 Hz, 3H); LCMS: 99.8%, MS (ESI): m/z 507.3 [M + H]+. |

TABLE 8-continued

Summarizes compounds 1-179 in terms of their structures and corresponding characteristics.

| # cpd | Structure | Characterization Data |
|---|---|---|
| 141 | 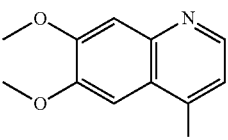 | HCl salt, yellow solid; ¹H-NMR (MeOD, 400 MHz): δ 8.71 (d, J = 6.4 Hz, 1H), 8.49 (d, J = 6.4 Hz, 1H), 8.48 (s, 1H), 7.98 (dd, J = 9.2, 2.8 Hz, 1H), 7.85 (s, 1H), 7.81 (s, 1H), 7.49 (s, 1H), 7.04 (d, J = 6.4 Hz, 1H), 4.29 (t, J = 4.8 Hz, 2H), 4.13 (s, 3H), 4.09 (s, 3H), 3.77-3.83 (m, 1H), 3.46 (t, J = 4.8 Hz, 2H), 2.84 (s, 3H), 1.22-1.26 (m, 2H), 1.08-1.13 (m, 2H); LCMS: 94.9%, MS (ESI): m/z 505.3 [M + H]+. |
| 142 | 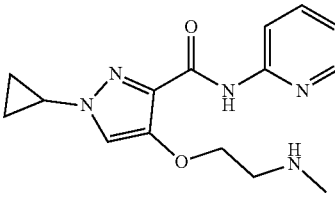 | yellow solid; ¹H-NMR (MeOD, 400 MHz): δ 8.72 (d, J = 6.4 Hz, 1H), 8.46-8.48 (m, 2H), 8.00 (dd, J = 3.2, 9.2 Hz, 1H), 7.86 (s, 1H), 7.70 (S, 1H), 7.48 (s, 1H), 7.06 (d, J = 6.8 Hz, 1H), 4.14 (s, 3H), 4.10 (s, 3H), 3.82-3.84 (m, 1H), 3.52 (t, J = 7.2 Hz, 2H), 2.60-2.66 (m, 2H), 1.25-1.27 (m, 2H), 1.10-1.12 (m, 2H); LCMS: 98.4%, MS (ESI): m/z 543.2 [M + H]+. |
| 143 | 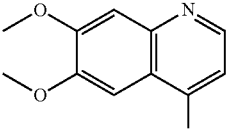 | white solid; ¹H-NMR (DMSO-d6, 400 MHz): δ 9.54 (s, 1H), 8.50 (d, J = 4.8 Hz, 1H), 8.38 (d, J = 2.4 Hz, 1H), 8.32 (d, J = 9.2 Hz, 1H), 7.95 (s, 1H), 7.82-7.89 (m, 1H), 7.54 (s, 1H), 7.42 (s, 1H), 6.55 (d, J = 5.2 Hz, 1H), 4.71-4.74 (m, 2H), 4.46 (t, J = 6.0 Hz, 2H), 4.28 (d, J = 6.4 Hz, 2H), 3.95 (d, J = 3.6 Hz, 6H), 3.78-3.87 (m, 1H), 3.39-3.55 (m, 1H), 1.13-1.14 (m, 2H), 1.02-1.04 (m, 2H); LCMS: 99.3%, MS (ESI): m/z 518.1 [M + H]+. |
| 144 | 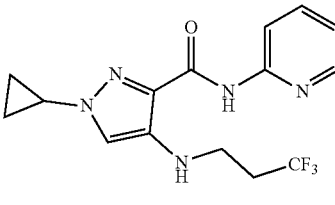 | HCl salt, yellow solid; ¹H-NMR (MeOD, 400 MHz): δ 8.76 (d, J = 6.8 Hz, 1H), 8.58 (s, 1H), 8.42 (d, J = 9.2 Hz, 1H), 8.18 (dd, J = 8.8, 2.0 Hz, 1H), 7.84 (d, J = 7.6 Hz, 2H), 7.55 (s, 1H), 7.14 (d, J = 6.8 Hz, 1H), 4.29-4.34 (m, 2H), 4.20-4.24 (m, 4H), 4.14 (s, 3H), 4.10 (s, 3H), 3.81-3.84 (m, 1H), 3.37-3.38 (m, 1H), 1.24-1.28 (m, 2H), 1.11-1.14 (m, 2H); LCMS: 97.0%, MS (ESI): m/z 517.2 [M + H]+. |

TABLE 8-continued

Summarizes compounds 1-179 in terms of their structures and corresponding characteristics.

| # cpd | Structure | Characterization Data |
|---|---|---|
| 145 | 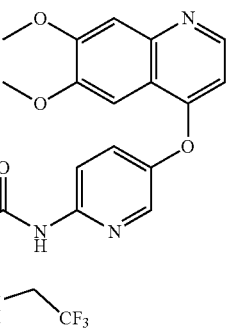 | yellow solid; ¹H-NMR (CDCl3, 400 MHz): δ 9.69-9.70 (m, 1H), 8.64-8.66 (m, 1H), 8.54-8.57 (m, 1H), 8.34 (s, 1H), 8.13 (s, 1H), 7.72-7.74 (m, 1H), 7.65 (s, 1H), 7.08 (s, 1H); 6.78 (br s, 1H), 4.19 (s, 3H), 4.15 (s, 3H), 3.60-3.68 (m, 3H), 1.24-1.28 (m, 2H); 1.06-1.08 (m, 2H); LCMS: 98.4%, MS (ESI): m/z 529.2 [M + H]+. |
| 146 | 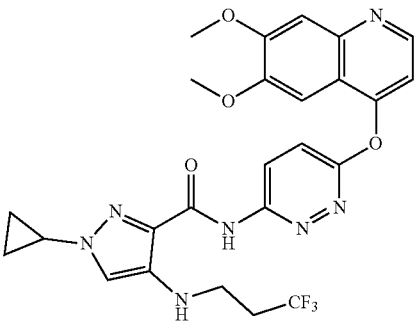 [SMILES: COc1cc2nccc(Oc3ccc(NC(=O)c4nn(C5CC5)cc4NCCC(F)(F)F)nn3)c2cc1OC] | yellow solid; ¹H-NMR (CDCl3, 400 MHz): δ 9.58 (d, J = 7.6 Hz, 1H), 8.79 (d, J = 6.8 Hz, 1H), 8.63 (d, J = 5.6 Hz, 1H), 7.61 (s, 1H), 7.49 (s, 1H), 7.43 (d, J = 9.6 Hz, 1H), 7.01-7.02 (m, 2H), 5.21 - 5.37 (m, 1H), 4.10 (s, 3H), 4.04 (s, 3H), 3.59-3.63 (m, 1H), 3.33 (t, J = 6.8 Hz, 2H), 2.43-2.50 (m, 2H), 1.20-1.24 (m, 2H), 1.04-1.09 (m, 2H); LCMS: 99.3%, MS (ESI): m/z 544.2 [M + H]+. |
| 147 | 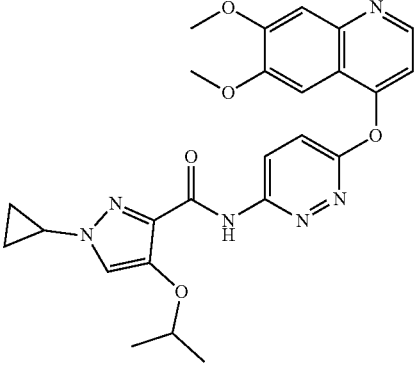 | white solid; ¹H-NMR (MeOD, 400 MHz): δ 8.79 (d, J = 9.6 Hz, 1H), 8.53-8.58 (m, 1H), 7.71-7.73 (m, 2H), 7.48 (s, 1H), 7.40 (s, 1H), 7.05 (d, J = 5.2 Hz, 1H), 4.46 (q, J = 6.0 Hz, 1H), 4.02 (s, 3H), 3.96 (s, 3H), 3.73-3.77 (m, 1H), 1.43 (s, 3H), 1.42 (s, 3H), 1.19-1.22 (m, 2H), 1.06-1.09 (m, 2H).; LCMS: 99.1%, MS (ESI): m/z 491.2 [M + H]+. |
| 148 | 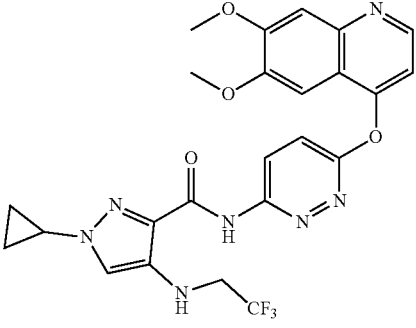 | yellow solid; ¹H-NMR (CDCl3, 400 MHz): δ 9.50 (s, 1H), 8.70 (d, J = 9.6 Hz, 1H), 8.57 (d, J = 5.6 Hz, 1H), 7.50 (s, 1H), 7.40 (s, 1H), 7.35 (d, J = 9.2 Hz, 1H), 7.00 (s, 1H), 6.93 (d, J = 5.2 Hz, 1H), 5.54 (br t, J = 6.8 Hz, 1H), 4.01 (s, 3H), 3.96 (s, 3H), 3.51-3.58 (m, 3H), 1.11-1.16 (m, 2H), 0.96-1.01 (m, 2H); LCMS: 97.6%, MS (ESI): m/z 530.2 [M + H]+. |

TABLE 8-continued

Summarizes compounds 1-179 in terms of their structures and corresponding characteristics.

| # cpd | Structure | Characterization Data |
|---|---|---|
| 149 | 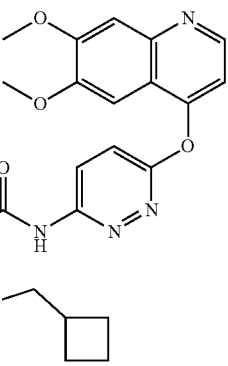 | yellow solid; $^1$H-NMR (MeOD, 400 MHz): δ 8.91 (d, J = 9.6 Hz, 1H), 8.79 (d, J = 6.8 Hz, 1H), 7.87 (d, J = 9.2 Hz, 1H), 7.83 (s, 1H), 7.73 (s, 1H), 7.54(d, J = 6.8 Hz, 1H), 7.50 (s, 1H), 4.14 (s, 3H), 4.07-4.09 (m, 5H), 3.74-3.79 (m, 1H), 2.88-2.91 (m, 1H), 2.16-2.21 (m, 2H), 1.99-2.02 (m, 4H), 1.20-1.24 (m, 2H), 1.07-1.10 (m, 2H); LCMS: 99.4%, MS (ESI): m/z 517.3 [(M + H)]+. |
| 150 | 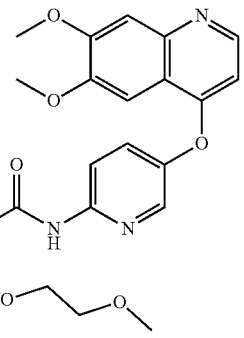 | white solid; $^1$H-NMR (CDCl3, 400 MHz): δ 9.50 (s, 1H), 8.55 (d, J = 9.2 Hz, 1H), 8.52 (d, J = 5.2 Hz, 1H), 8.26 (d, J = 2.8 Hz, 1H), 7.59 (dd, J = 3.2, 9.2 Hz, 1H), 7.57 (s, 1H), 7.44 (s, 1H), 7.34 (s, 1H), 6.47 (d, J = 5.2 Hz, 1H), 4.30 - 4.33 (m, 1H), 4.20-4.24 (m, 2 H), 4.18 (d, J = 2.8 Hz, 1H), 4.07 (d, J = 2.0 Hz, 6H), 3.97 - 4.05 (m, 1H), 3.83 (dd, J = 3.2, 4.8 Hz, 2H), 3.48 (s, 3H), 2.42 (br s, 1H), 1.28 (d, J = 6.4 Hz, 3H); LCMS: 97.6%, MS (ESI): m/z 524.2 [(M + H)]+. |
| 151 | 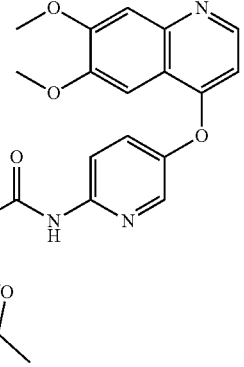 | white solid; $^1$H-NMR (CDCl3, 400 MHz): δ 9.59 (s, 1H), 8.56 (d, J = 8.8 Hz, 1H), 8.50 (d, J = 5.2 Hz, 1H), 8.25 (d, J = 2.8 Hz, 1H), 7.57-7.60 (m, 1H), 7.56 (s, 1H), 7.44 (s, 1H), 7.26 (s, 1H), 6.46 (d, J = 5.2 Hz, 1H), 4.31-4.36 (m, 2H), 4.20-4.23 (m, 1H), 4.07 (d, 6H), 3.04-4.06 (m, 1H), 2.66 (br, s, 1H), 1.47 (d, 6H), 1.28 (d, J = 6.0 Hz, 3H); LCMS: 99.6%, MS (ESI): m/z 508.2 [(M + H)]+. |
| 152 | 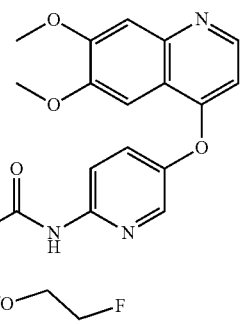 | white solid; $^1$H-NMR (DMSO-d6, 400 MHz) δ 9.64 (s, 1H), 8.85 (d, J = 6.8 Hz, 1H), 8.52 (d, J = 2.8 Hz, 1H), 8.42 (d, J = 9.2 Hz, 1H), 8.02 (dd, J = 9.2, 2.8 Hz, 1H), 7.80 (d, J = 6.4 Hz, 2H), 7.74 (s, 1H), 7.06 (d, J = 6.8 Hz, 1H), 4.83 (t, J =3.6 Hz 1H), 4.71 (t, J = 3.6 Hz, 1H), 4.28-4.33 (m, 2H), 4.26-4.28 (m, 2H), 4.05 (s, 6H), 4.02-4.03 (m, 1H), 1.08 (d, J = 5.2 Hz, 3H); LCMS: 99.1%, MS (ESI): m/z 512.2 [M + H]+. |

TABLE 8-continued

Summarizes compounds 1-179 in terms of their structures and corresponding characteristics.

| # cpd | Structure | Characterization Data |
| --- | --- | --- |
| 153 | 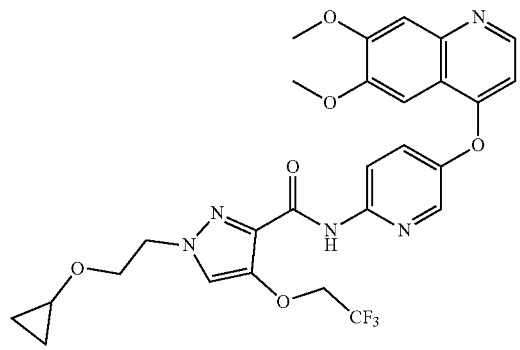 | off-white solid; ¹H-NMR (MeOD, 400 MHz): δ 8.74 (d, J = 6.8 Hz, 1H), 8.52 (s, 1H), 8.41 (d, J = 9.2 Hz, 1H), 8.10 (dd, J = 2.4, 8.8 Hz, 1H), 7.84 (s, 1H), 7.75 (s, 1H), 7.54 (s, 1H), 7.10 (d, J = 6.4 Hz, 1H), 4.64 (q, J = 8.8 Hz, 2H), 4.35 (t, J = 4.8 Hz, 2H), 4.13 (s, 3H), 4.10 (s, 3H), 3.93 (t, J = 5.2 Hz, 2H), 3.30-3.36 (m, 1H), 0.46-0.47 (m, 4H); LCMS: 97.9%, MS (ESI): m/z 574.2 [(M + H)]+. |
| 154 | 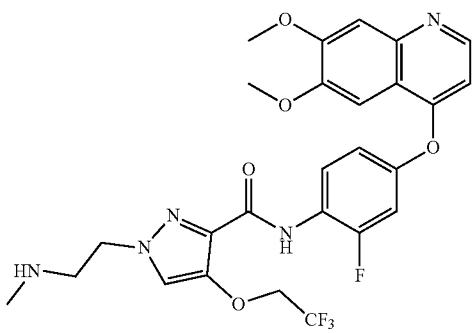 [SMILES: CNCCn1cc(OCC(F)(F)F)c(C(=O)Nc2ccc(Oc3ccnc4cc(OC)c(OC)cc34)cc2F)n1] | HCl salt, white solid; ¹H-NMR (MeOD, 400 MHz): δ 8.46 (d, J = 5.2 Hz, 1H), 8.34 (t, J = 8.8 Hz, 1H), 7.76 (s, 1H), 7.61 (s, 1H), 7.37 (s, 1H), 7.22 (dd, J = 11.2, 2.4 Hz, 1H), 7.13 (dd, J = 8.8, 1.6 Hz, 1H), 6.65 (d, J = 5.6 Hz, 1H), 4.65 (q, J = 8.4 Hz, 2H), 4.30 (t, J = 6.0 Hz, 2H), 4.02 (s, 1H), 4.00 (s, 1H), 3.07 (t, J = 6.0 Hz, 2H), 2.42 (s, 3H); LCMS: 100%, MS (ESI): m/z 564.2 [(M + H)]+. |
| 155 | 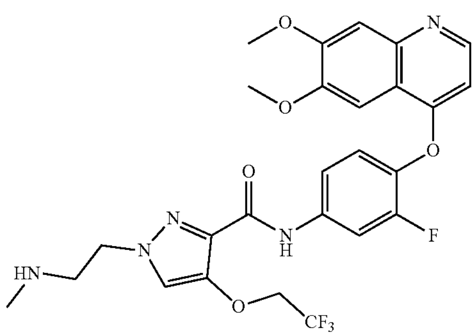 | HCl salt, yellow solid; ¹H-NMR (MeOD, 400 MHz): δ 8.72 (d, J = 6.8 Hz, 1H), 8.09 (dd, J = 12.8, 2.4 Hz, 1H), 7.85 (s, 1H), 7.84 (s, 1H), 7.68 (d, J = 8.8 Hz, 1H), 7.54 (t, J = 8.4 Hz, 1H), 7.50 (s, 1H), 7.02 (d, J = 6.0 Hz, 1H), 4.65 (q, J = 8.8 Hz, 2H), 4.57 (t, J = 5.2 Hz, 2H), 4.14 (s, 3H), 4.11 (s, 3H), 3.62 (t, J = 5.2 Hz, 2H), 2.82 (s, 3H); LCMS: 98.9%, MS (ESI): m/z 564.2 [(M + H)]+. |
| 156 | 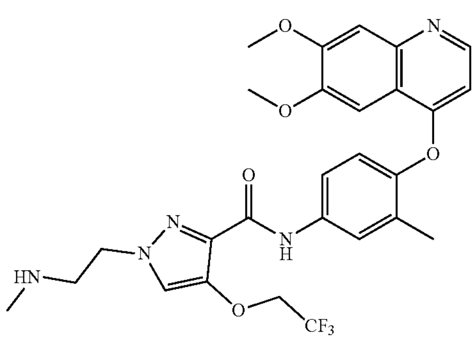 | HCl salt, off-white solid; ¹H-NMR (MeOD, 400 MHz): δ 8.66 (d, J = 6.8 Hz, 1H), 7.88 (s, 1H), 7.85 (s, 1H), 7.84 (s, 1H), 7.80 (d, J = 8.4Hz, 1H), 7.51 (s, 1H), 7.30 (d, J = 8.8 Hz, 1H), 6.84 (d, J = 6.8 Hz, 1H), 4.66 (q, J = 8.8 Hz, 2H), 4.57 (t, J = 4.8 Hz, 2H), 4.14 (s, 3H), 4.11 (s, 3H), 3.62 (t, J = 4.8 Hz, 2H), 2.82 (s, 3H), 2.24 (s, 3H); LCMS: 99.1%, MS (ESI): m/z 560.2 [(M + H)]+. |

TABLE 8-continued

Summarizes compounds 1-179 in terms of their structures and corresponding characteristics.

| # cpd | Structure | Characterization Data |
|---|---|---|
| 157 | 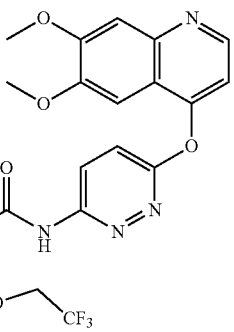 | off-white solid; $^1$H-NMR (MeOD, 400 MHz): δ 8.74 (d, J = 9.6 Hz, 1H), 8.56 (d, J = 5.6 Hz, 1H), 7.79 (s, 1H), 7.69 (d, J = 9.2 Hz, 1H), 7.47 (s, 1H), 7.39 (s, 1H), 7.04 (d, J = 5.6 Hz, 1H), 4.94-4.99 (m, 1H), 4.61 (q, J = 8.8 Hz, 2H), 4.01 (s, 3H), 3.95 (s, 3H), 3.06-3.09 (m, 2H), 2.81-2.85 (m, 1H), 2.45-2.52 (m, 5H), 2.27-2.28 (m, 1H); LCMS: 97.8%, MS (ESI): m/z 574.2 [M + H]+. |
| 158 | 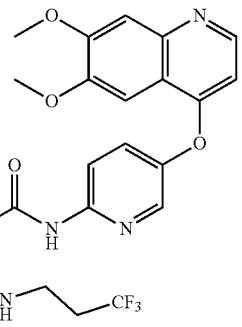 | yellow solid; $^1$H-NMR (MeOD, 400 MHz): δ 8.71 (d, J = 6.4 Hz, 1H), 8.50 (d, J = 9.2 Hz, 1H), 8.45 (d, J = 2.8 Hz, 1H), 7.94-7.97 (dd, J = 2.8, 9.2 Hz, 1H), 7.87 (s, 1H), 7.55 (s, 1H), 7.46 (s, 1H), 7.05 (d, J = 6.8 Hz, 1H), 4.17 (t, J = 7.2 Hz, 2H), 4.14 (s, 3H), 4.10 (s, 3H), 3.47 (t, J = 6.8 Hz, 2H), 2.58-2.61 (m, 2H), 1.93-1.98 (m, 2H), 0.97 (t, J = 7.2 Hz, 3H); LCMS: 98.0%, MS (ESI): m/z 545.2 [M + H]+. |
| 159 | 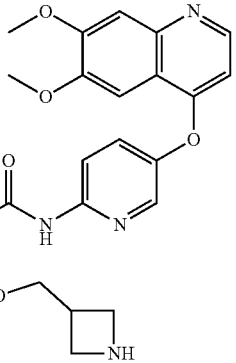 | HCl salt, yellow solid; $^1$H-NMR (D$_2$O, 400 MHz): δ 8.47 (d, J = 6.8 Hz, 1H), 8.22 (d, J = 2.8 Hz, 1H), 8.05 (d, J = 8.8 Hz, 1H), 7.72-7.81 (m, 1H), 7.54 (d, J = 7.6 Hz, 2H), 7.30 (s, 1H), 6.90 (d, J = 6.8 Hz, 1H), 4.20 (t, J = 9.6 Hz, 2H), 4.12-4.14 (m, 4H), 3.98-4.00 (m, 2H), 3.96 (s, 3H), 3.80 (s, 3H), 3.28-3.47 (m, 1H), 1.72-1.74 (m, 2H), 0.74 (t, J = 7.6 Hz, 3H); LCMS: 95.6%, MS (ESI): m/z 519.1 [M + H]+. |
| 160 | 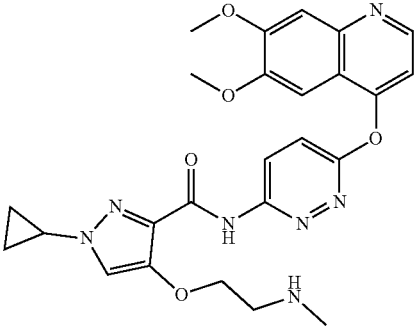 | HCl salt, yellow solid; $^1$H-NMR (MeOD, 400 MHz): δ 8.83-8.87 (m, 2H), 7.94 (d, J = 9.6 Hz, 1H), 7.85 (s, 1H), 7.84 (s, 1H), 7.59 (d, J = 6.8 Hz, 1H), 7.53 (s, 1H), 4.32 (t, J = 4.8 Hz, 2H), 4.17 (s, 3H), 4.11 (s, 3H), 3.81-3.86 (m, 1H), 3.49 (t, J = 4.8 Hz, 1H), 2.86 (s, 3H), 1.25-1.29 (m, 2H), 1.10-1.15 (m, 2H); LCMS: 96.4%, MS (ESI): m/z 506.2 [M + H]+. |

TABLE 8-continued

Summarizes compounds 1-179 in terms of their structures and corresponding characteristics.

| # cpd | Structure | Characterization Data |
|---|---|---|
| 161 | 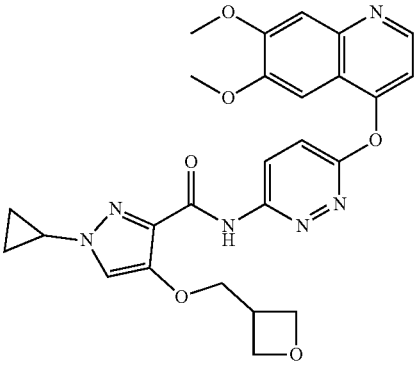 [SMILES: COc1cc2nccc(Oc3ccc(NC(=O)c4nn(C5CC5)cc4OCC4COC4)nn3)c2cc1OC] | white solid; ¹H-NMR (MeOD, 400 MHz): δ 8.66 (d, J = 9.6 Hz, 1H), 8.48 (d, J = 5.2 Hz, 1H), 7.66 (s, 1H), 7.61 (d, J = 9.6 Hz, 1H), 7.37 (s, 1H), 7.31 (s, 1H), 6.95 (d, J = 5.6 Hz, 1H), 4.51 (t, J = 6.0 Hz, 3H), 4.22 (d, J = 6.4 Hz, 2H), 3.92 (s, 3H), 3.85 (s, 3H), 3.56-3.66 (m, 1H), 3.35-3.53 (m, 1H), 1.17-1.30 (m, 1H), 1.01-1.12 (m, 2H), 0.96-0.99 (m, 2H); LCMS: 98.5%, MS (ESI): m/z 519.2 [M + H]+. |
| 162 | 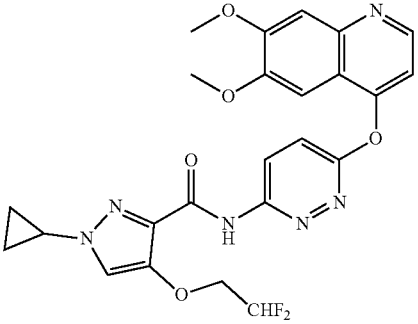 | yellow solid; ¹H-NMR (MeOD, 400 MHz): δ 8.77 (d, J = 9.6 Hz, 1H), 8.58 (d, J = 5.2 Hz, 1H), 7.78 (s, 1H), 7.72 (d, J = 9.6 Hz, 1H), 7.49 (s, 1H), 7.42 (s, 1H), 7.07 (d, J = 5.2 Hz, 1H), 6.10-6.42 (m, 1H), 4.29-4.34 (m, 2H), 4.04 (s, 3H), 3.97 (s, 3H), 3.77-3.97 (m, 1H), 1.36 (d, J = 6.4 Hz, 1H), 1.22-1.24 (m, 2H), 1.08-1.10 (m, 2H); LCMS: 99.1%, MS (ESI): m/z 513.2 [(M + H)]+. |
| 163 | 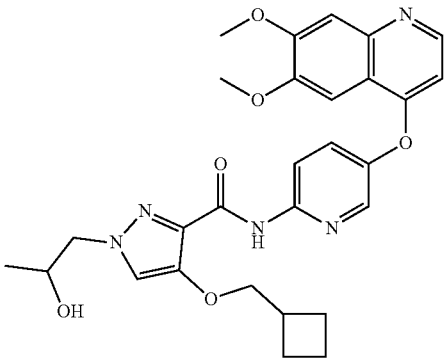 [SMILES: COc1cc2nccc(Oc3ccc(NC(=O)c4nn(CC(C)O)cc4OCC4CCC4)nc3)c2cc1OC] | white solid; ¹H-NMR (MeOD, 400 MHz): δ 8.70 (d, J = 6.8 Hz, 1H), 8.54 (d, J = 8.8 Hz, 1H), 8.45 (d, J = 2.4 Hz, 1H), 7.93 (dd, J = 2.8, 9.2 Hz, 1H), 7.87 (s, 1H), 7.64 (s, 1H), 7.47 (s, 1H), 7.04 (d, J = 6.8 Hz, 1H), 4.06-4.19 (m, 11H), 2.87-2.94 (m, 1H), 2.19-2.22 (m, 2H), 1.99-2.05 (m, 4H), 1.21 (d, J = 6.0 Hz, 3H); HPLC: 96.0%, MS (ESI): m/z 534.3 [(M + H)]+. |
| 164 | 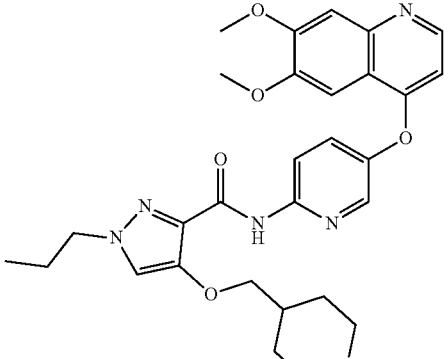 | yellow solid; ¹H-NMR (MeOD, 400 MHz): δ 8.72 (d, J = 6.8 Hz, 1H), 8.56 (d, J = 9.2 Hz, 1H), 8.46 (d, J = 2.8 Hz, 1H), 7.96 (d, J = 2.8 Hz, 1H), 7.89 (s, 1H), 7.71 (s, 1H), 7.49 (s, 1H), 7.06 (d, J = 6.8 Hz, 1H), 4.14-4.18 (m, 5H), 4.12 (s, 8H), 4.00-4.14 (m, 4H), 3.49-3.55 (m, 2H), 2.21-2.24 (m, 1H), 1.92-2.00 (m, 2H), 1.86-1.90 (m, 2H), 1.53-1.60 (m, 2H), 0.97 (t, J = 7.6 Hz, 3H); LCMS: 96.2%, MS (ESI): m/z 548.3 [(M + H)]+. |

TABLE 8-continued

Summarizes compounds 1-179 in terms of their structures and corresponding characteristics.

| # cpd | Structure | Characterization Data |
|---|---|---|
| 165 | 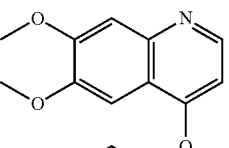 | white powder; ¹H-NMR (DMSO-d6, 400 MHz): δ 10.29 (1H, brs), 8.83 (1H, d, J = 6.4 Hz), 8.13 (1H, dd, J = 13.2, 2.0 Hz), 7.91 (1H, s), 7.85 (1H, d, J = 8.8 Hz), 7.76 (1H, s), 7.70 (1H, s), 7.54-7.61 (1H, m), 6.95 (1H, d, J = 6.0 Hz), 4.31-4.37 (2H, m), 4.12 (2H, t, J = 7.2 Hz), 4.05 (6H, s), 3.48-3.66 (2H, m), 2.90 (6H, d, J = 4.8 Hz), 1.80-1.92 (2H, m), 0.89 (3H, t, J = 7.2 Hz); LCMS: 95.7%, MS (ESI): m/z 538.2 [M + H]+. |
| 166 | 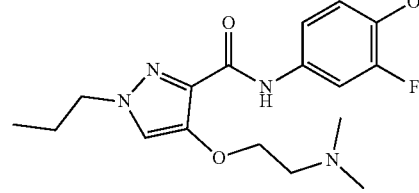 | white powder; ¹H-NMR (CDCl3, 400 MHz): δ 9.84 (1H, brs), 8.72 (1H, d, J = 8.4 Hz), 8.51-8.57 (1H, m), 8.31 (1H, s), 8.20 (1H, s), 7.63-7.72 (2H, m), 7.14 (1H, s), 6.72-6.79 (1H, m), 4.39 (2H, t, J = 7.2 Hz), 4.19 (3H, s), 4.13 (3H, s), 4.03 (2H, d, J = 6.4 Hz), 2.78-2.94 (3H, m), 2.14-2.23 (2H, m), 1.95-2.03 (4H, m); LCMS: 100%, MS (ESI): m/z 572.2 [M + H]+. |
| 167 | 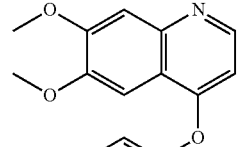 | white solid; ¹H-NMR (CDCl3, 400 MHz): δ 9.57 (1H, brs), 8.63 (1H, d, J = 5.2 Hz), 8.57 (1H, d, J = 9.2 Hz), 8.24 (1H, d, J = 2.8 Hz), 8.18 (1H, s), 7.51-7.59 (2H, m), 7.15 (1H, s), 6.46 (1H, d, J = 5.2 Hz), 4.06-4.11 (2H, m), 4.05 (3H, s), 4.01 (1H, d, J = 6.4 Hz), 2.85-2.95 (1H, m), 2.15-2.24 (2H, m), 1.88-2.02 (6H, m), 0.95 (3H, t, J = 7.2 Hz); LCMS: 100%, MS (ESI): 572.1 m/z [(M + H)]+. |
| 168 | 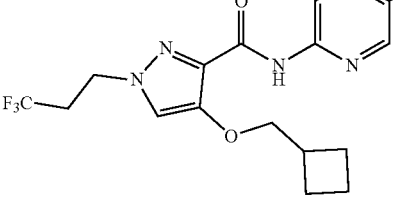 | HCl salt, yellow solid; ¹H-NMR (MeOD, 400 MHz): δ 8.71 (d, J = 6.4 Hz, 1H), 8.53 (d, J = 9.2 Hz, 1H), 8.48 (d, J = 2.4 Hz, 1H), 7.97 (dd, J = 2.4, 9.2 Hz, 1H), 7.90 (s, 1H), 7.86 (s, 1H), 7.50 (s, 1H), 7.04 (d, J = 6.8 Hz, 1H), 4.69 (q, J = 8.4 Hz, 2H), 4.61 (t, J = 5.2 Hz, 2H), 4.13 (s, 3H), 4.10 (s, 3H), 3.76 (t, J = 5.2 Hz, 2H), 2.87-2.89 (m, 2H), 0.96-0.99 (m, 4H); HPLC: 96.8%, MS (ESI): 573.2 m/z [(M + H)]+. |

TABLE 8-continued

Summarizes compounds 1-179 in terms of their structures and corresponding characteristics.

| # cpd | Structure | Characterization Data |
|---|---|---|
| 169 | 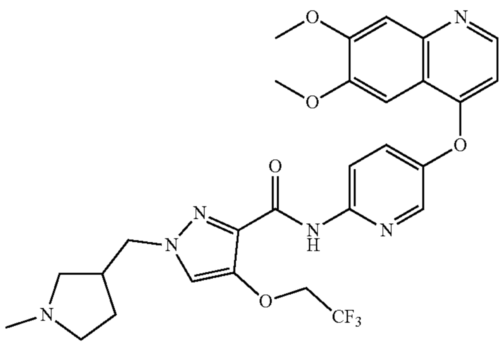 | white solid; ¹H-NMR (MeOD, 400 MHz): δ 8.43-8.46 (m, 2H), 8.32 (d, J = 2.8 Hz, 1H), 7.76-7.80 (m, 2H), 7.64 (s, 1H), 7.36 (s, 1H), 6.59 (d, J = 5.2 Hz, 1H), 4.64 (q, J = 8.4 Hz, 2H), 4.16 (d, J = 8.4 Hz, 2H), 4.01 (d, J = 3.2 Hz, 6H), 2.66-2.85 (m, 1H), 2.62-2.65 (m, 3H), 2.42-2.45 (m, 1H), 2.38 (s, 1H), 2.02-2.04 (m, 1H), 1.63-1.66 (m, 1H); HPLC: 98.3%, MS (ESI): 544.2 m/z [(M + H)]+. |
| 170 | 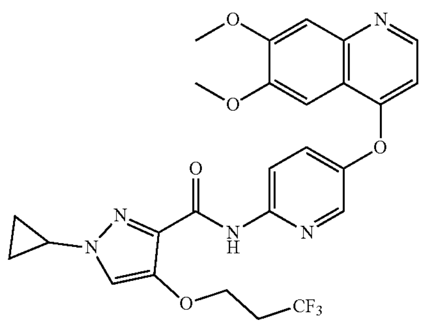 [SMILES: COc1cc2nccc(Oc3ccc(NC(=O)c4nn(C5CC5)cc4OCCC(F)(F)F)nc3)c2cc1OC] | yellow solid; ¹H-NMR (MeOD, 400 MHz): δ 8.72 (d, J = 6.8 Hz, 1H), 8.50 (br s, 1H), 8.45 (d, J = 9.2 Hz, 1H), 8.06 (dd, J = 9.2, 2.8 Hz, 1H), 7.85 (s, 1H), 7.78 (s, 1H), 7.50 (s, 1H), 7.08 (d, J = 6.8 Hz, 1H), 4.31 (t, J = 6.0 Hz, 2H), 4.13 (s, 3H), 4.09 (s, 3H), 3.76-3.80 (m, 1H), 2.77-2.83 (m, 2H), 1.21-1.25 (m, 2H), 1.08-1.11 (m, 2H); HPLC: 97.9%, MS (ESI): 544.2 m/z [(M + H)]+. |
| 171 | 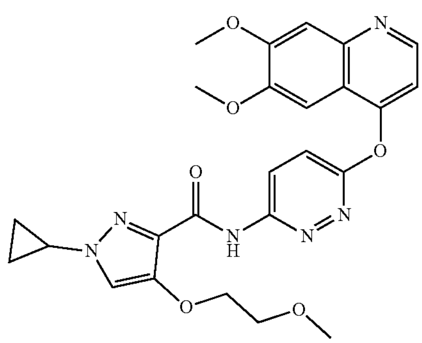 [SMILES: COCCOc1cn(C2CC2)nc1C(=O)Nc1ccc(Oc2ccnc3cc(OC)c(OC)cc23)nn1] | yellow solid; ¹H-NMR (MeOD, 400 MHz): δ 8.90 (d, J = 9.6 Hz, 1H), 8.79 (d, J = 6.8 Hz, 1H), 7.87 (d, J = 9.6 Hz, 1H), 7.84 (s, 1H), 7.76 (s, 1H), 7.52 (d, J = 6.8 Hz, 1H), 7.49 (s, 1H), 4.24-4.26 (m, 2H), 4.14 (s, 3H), 4.09 (s, 3H), 3.79-3.81 (m, 3H), 3.43 (s, 3H), 1.30 (d, J = 6.4 Hz, 1H), 1.19-1.21 (m, 2H), 1.04-1.10 (m, 2H); HPLC: 97.7%, MS (ESI): 507.2 m/z [(M + H)]+. |
| 172 | 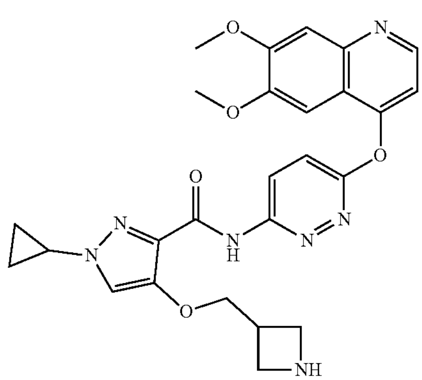 [SMILES: COc1cc2nccc(Oc3ccc(NC(=O)c4nn(C5CC5)cc4OCC4CNC4)nn3)c2cc1OC] | HCl salt, yellow solid; ¹H-NMR (MeOD, 400 MHz): δ 8.81-8.07 (m, 2H), 8.06 (d, J = 9.6 Hz, 1H), 7.82 (d, J = 7.2 Hz, 2H), 7.66 (d, J = 6.8 Hz, 1H), 7.57 (s, 1H), 4.24-4.30 (m, 2H), 4.19-4.23 (m, 4H), 4.15 (s, 3H), 4.09 (s, 3H), 3.80-3.85 (m, 1H), 3.37-3.38 (m, 1H), 1.24-1.27 (m, 2H), 1.07-1.12 (m, 2H); HPLC: 94.3%, MS (ESI): m/z 518.3 [M + H]+. |

TABLE 8-continued

Summarizes compounds 1-179 in terms of their structures and corresponding characteristics.

| # cpd | Structure | Characterization Data |
|---|---|---|
| 173 | 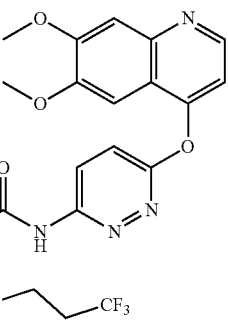 | yellow solid; $^1$H-NMR (MeOD, 400 MHz): δ 8.89 (d, J = 10 Hz, 1H), 8.79 (d, J = 6.8 Hz, 1H), 7.87 (d, J = 9.6 Hz, 1H) 7.82 (s, 1H), 7.79 (s, 1H), 7.53 (d, J = 6.8 Hz, 1H), 7.48 (s, 1H), 4.33 (t, J = 5.6 Hz, 2H), 4.14 (s, 3H), 4.09 (s, 3H), 3.76-3.78 (m, 1H), 2.78-2.83 (m, 2H), 1.21-1.25 (m, 2H), 1.07-1.09 (m, 1H); HPLC: 98.6%, MS (ESI): m/z 545.2 [M + H]+. |
| 174 | 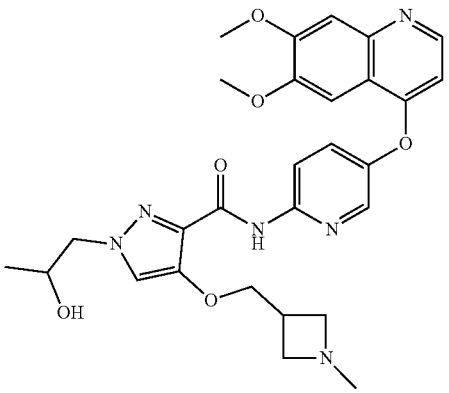 [SMILES: COc1cc2nccc(Oc3ccc(NC(=O)c4nn(CC(C)O)cc4OCC4CN(C)C4)nc3)c2cc1OC] | white solid; $^1$H-NMR (CDCl3, 400 MHz): δ 9.47 (s, 1H), 8.54 (d, J = 9.2 Hz), 8.51 (d, J = 5.2 Hz), 8.24 (d, J = 2.8 Hz, 1H), 7.58-7.62 (m, 2H), 7.45 (s, 1H), 7.30 (s, 1H), 6.46 (d, J = 5.2 Hz, 1H), 4.32 (s, 1H), 4.20-4.23 (m, 3H), 4.09 (d, 6H), 3.43 (t, J = 7.6 Hz, 2H), 3.18 (t, J = 6.0 Hz, 2H), 2.96-3.03 (m, 1H), 2.50-2.53 (m, 1H), 2.36 (s, 3H), 1.29 (d, J = 6.4 Hz, 3H); HPLC: 94.8%, MS (ESI): m/z 549.3 [M + H]+. |
| 175 | 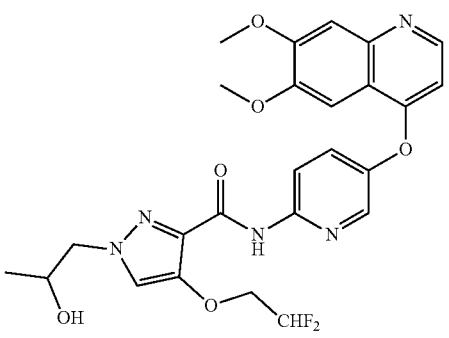 [SMILES: COc1cc2nccc(Oc3ccc(NC(=O)c4nn(CC(C)O)cc4OCC(F)F)nc3)c2cc1OC] | white solid; $^1$H-NMR (MeOD, 400 MHz) δ 8.44-8.47 (m, 2H), 8.33 (d, J = 2.4 Hz, 1H), 7.78 (dd, J =8.8, 2.8 Hz, 1H), 7.70 (s, 1H), 7.65 (s, 1H), 7.38 (s, 1H), 6.60 (d, J = 5.6 Hz, 1H), 6.12-6.42 (m, 1H), 4.30-4.38 (m, 2H), 4.15-4.22 (m, 2H), 4.05-4.09 (m, 1H), 4.02 (d, J = 3.6 Hz, 6H), 1.21 (d, J = 6.0 Hz, 3H); HPLC: 96.3%, MS (ESI): m/z 530.2 [M + H]+. |
| 176 | 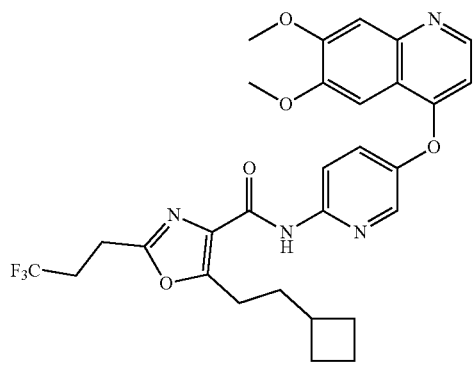 [SMILES: COc1cc2nccc(Oc3ccc(NC(=O)c4nc(CCC(F)(F)F)oc4CCC4CCC4)nc3)c2cc1OC] | white solid; $^1$H-NMR (MeOD, 400 MHz) δ 8.46 (1H, d, J = 5.2 Hz), 8.42 (1H, d, J = 9.2 Hz), 8.33 (1H, d, J = 2.8 Hz), 7.79 (1H, dd, J = 9.2, 2.8 Hz), 7.65 (1H, s), 7.38 (1H, s), 6.61 (1H, d, J = 5.2 Hz), 4.02 (6H, d, J = 4.0 Hz), 3.11 (2H, t, J = 7.6 Hz), 3.04 (2H, t, J = 7.6 Hz), 2.72-2.83 (2H, m), 2.32-2.39 (1H, m), 2.03-2.12 (3H, m), 1.78-1.89 (4H, m), 1.63-1.72 (2H, m); LCMS: 99.1%, MS (ESI): m/z 571.1 [M + H]+. |

TABLE 8-continued

Summarizes compounds 1-179 in terms of their structures and corresponding characteristics.

| # cpd | Structure | Characterization Data |
|---|---|---|
| 177 | 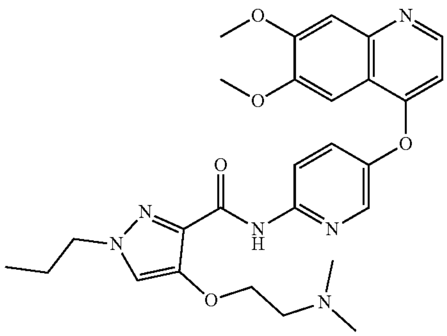 [SMILES: CCCn1cc(OCCN(C)C)c(C(=O)Nc2ccc(Oc3ccnc4cc(OC)c(OC)cc34)cn2)n1] | HCl salt, yellow powder; $^1$H-NMR (DMSO-d6, 400 MHz): δ 9.63 (1H, brs), 8.86 (1H, d, J = 6.8 Hz), 8.52 (1H, d, J = 2.8 Hz), 8.38 (1H, d, J = 8.8 Hz), 8.02 (1H, dd, J = 9.2, 2.8 Hz), 7.96 (1H, s), 7.79 (1H, s), 7.74 (1H, s), 7.02 (1H, d, J = 6.8 Hz), 4.38-4.43 (2H, m), 4.12 (2H, t, J = 6.8 Hz), 4.02-4.07 (7H, m), 3.48-3.51 (1H, m, overlap with water signal), 2.91 (6H, d, J = 4.8 Hz), 1.80-1.92 (2H, m), 0.89 (3H, t, J = 7.2 Hz); LCMS: 94.7%, MS (ESI): m/z 521.2 [M + H]+. |
| 178 | 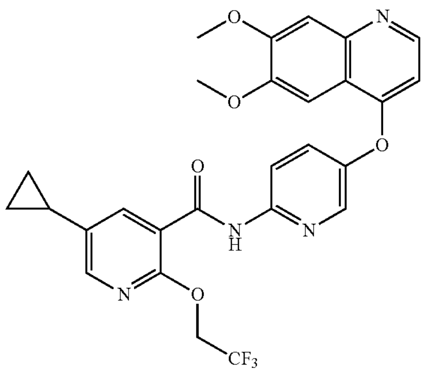 [SMILES: COc1cc2nccc(Oc3ccc(NC(=O)c4cc(C5CC5)cnc4OCC(F)(F)F)nc3)c2cc1OC] | white powder; $^1$H-NMR (400 MHz, CDCl3) δ 12.37 (1H, s), 8.51 (1H, d, J = 5.2 Hz), 8.44-8.48 (2H, m), 8.31 (1H, d, J = 2.8 Hz), 7.54-7.61 (2H, m), 7.44 (1H, s), 7.37 (1H, s), 6.46 (1H, d, J = 5.2 Hz), 4.74 (2H, q, J = 8.4 Hz), 4.06 (6H, d, J = 1.6 Hz), 1.74-1.88 (1H, m), 0.93-1.09 (2H, m), 0.57-0.75 (2H, m); LCMS: 99.7%, MS (ESI): m/z 541.1 [M + H]+. |
| 179 | 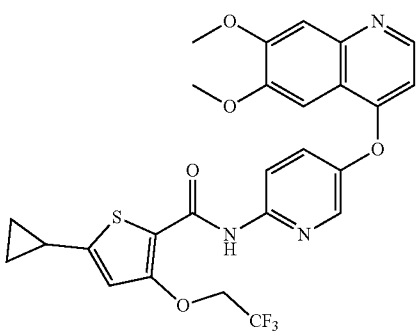 [SMILES: COc1cc2nccc(Oc3ccc(NC(=O)c4sc(C5CC5)cc4OCC(F)(F)F)nc3)c2cc1OC] | white powder; $^1$H-NMR (CDCl3, 400 MHz): δ 9.37 (1H, s), 8.51 (1H, d, J = 5.6 Hz), 8.41 (1H, d, J = 8.8 Hz), 8.25 (1H, d, J = 2.8 Hz), 7.52-7.58 (2H, m), 7.43 (1H, s), 6.59 (1H, s), 6.46 (1H, d, J = 5.2 Hz), 4.60 (2H, q, J = 8.0 Hz), 4.06 (3H, s), 4.06 (3H, s), 2.05-2.15 (1H, m), 1.09-1.19 (2H, m), 0.79-0.86 (2H, m); LCMS: 100%, MS (ESI): m/z 546.0 [M + H]+. |

The invention claimed is:

1. A compound having the general formula I:

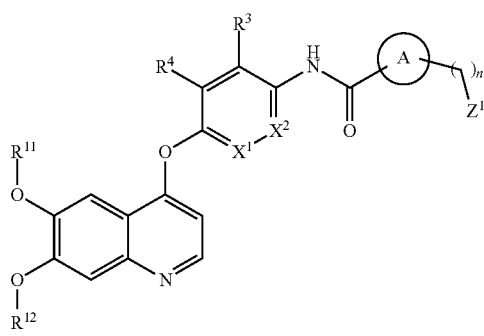

I wherein

X$^1$ is, independently at each occurrence, selected from CR$^3$ and N;

X$^2$ is, independently at each occurrence, selected from CR$^4$ and N;

n is, independently at each occurrence, selected from 0 and 1;

A is, at each occurrence, independently selected from any structure as depicted in the following group W;

Group W

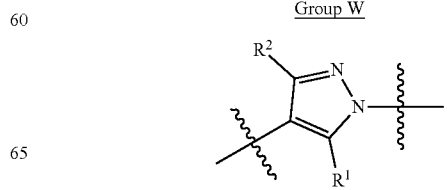

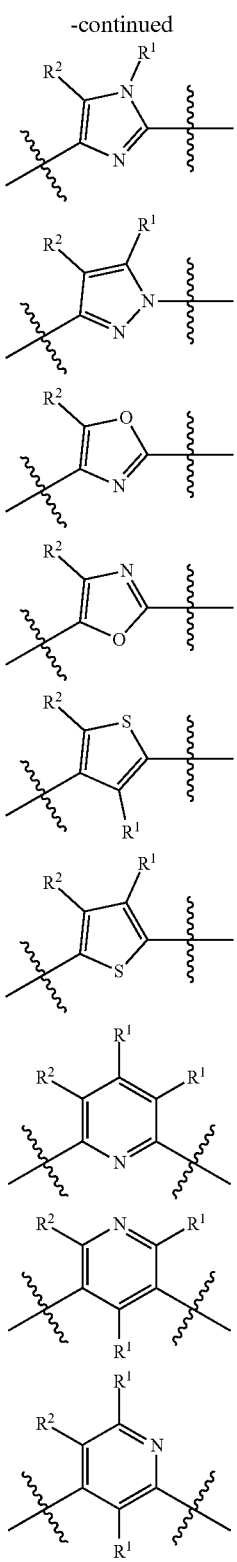

R[1] is, at each occurrence, independently selected from the group consisting of hydrogen; C1-C6 alkyl; C1-C6 alkyl substituted with one or two of OR[5] and NR[5]R[6]; C3-C10 cycloalkyl; C1-C4 haloalkyl; and —(C=O) R[5]; any of which is optionally substituted;

R[2] is —OR[8];

R[3] and R[4] are, at each occurrence, independently selected from the group consisting of hydrogen; halogen; C1-C3 alkyl; OR[5]; and C1-C4 haloalkyl; any of which is optionally substituted;

R[5] and R[6] are, at each occurrence, independently selected from the group consisting of hydrogen; C1-C6 alkyl; C3-C10 cycloalkyl; and C1-C4 haloalkyl; any of which is optionally substituted;

R[8] is, at each occurrence, independently selected from the group consisting of C1-C4 haloalkyl; and C1-C6 alkyl substituted with C1-C4 haloalkyl;

Z[1] is, at each occurrence, independently selected from the group consisting of hydrogen; C1-C6 alkyl; C1-C6 alkyl substituted with one or two of —OR[5] and NR[5]R[6]; C3-C10 cycloalkyl; and C3-C10 heterocycloalkyl;

R[11] and R[12] are, at each occurrence, independently selected from the group consisting of C1-C6 alkyl; C3-C10 cycloalkyl; C3-C10 heterocycloalkyl; and C1-C4 haloalkyl; any of which is optionally substituted;

and pharmaceutically acceptable salts thereof.

2. The compound according to claim 1, having the general formula II:

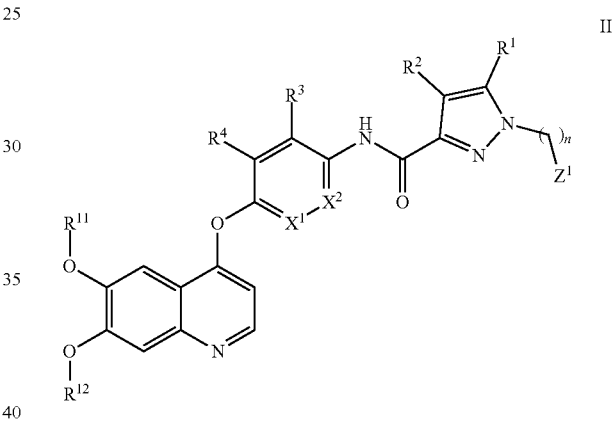

wherein
R[1], R[2], R[3], R[4], R[11], R[12], Z[1], X[1], X[2] and n are as defined in claim 1; and pharmaceutically acceptable salts thereof.

3. The compound according to claim 1, having the general formula III:

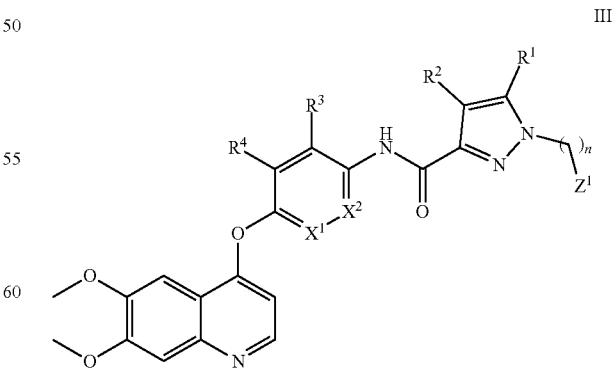

wherein
R[1], R[2], R[3], R[4], Z[1], X[1], X[2] and n are as defined in claim 1; and pharmaceutically acceptable salts thereof.

4. The compound according to claim 1, having the general formula IV:

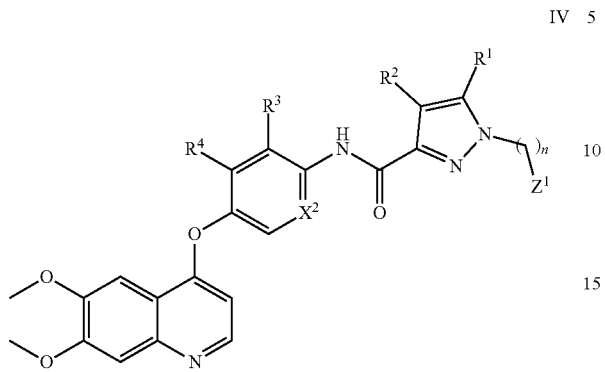

wherein
$R^1$, $R^2$, $R^3$, $R^4$, $Z^1$, $X^2$ and n are as defined in claim 1; and pharmaceutically acceptable salts thereof.

5. The compound according to claim 1, having the general formula V:

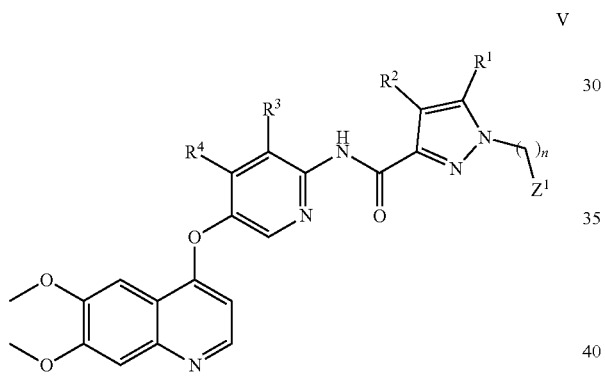

wherein
$R^1$, $R^2$, $R^3$, $R^4$, $Z^1$ and n are as defined in claim 1.

6. The compound according to claim 1, wherein n=0 or 1, and $Z^1$ is selected from methyl; ethyl; propyl; isopropyl; C3 cycloalkyl; C3-C10 heterocycloalkyl; and C1-C6 alkyl substituted with one or two of $OR^5$ and $NR^5R^6$; and pharmaceutically acceptable salts thereof.

7. The compound according to claim 1, wherein $R^2$ is $OR$, and $R^8$ is selected from C1-C4 haloalkyl; and C1-C6 alkyl substituted with one of trifluoromethyl, difluoromethyl, fluoromethyl, trifluoroethyl, difluoroethyl, fluoroethyl, trifluoropropyl, difluoropropyl, fluoropropyl, trifluoroisopropyl, difluoroisopropyl, and fluoroisopropyl; and pharmaceutically acceptable salts thereof.

8. The compound according to claim 1, wherein
n=0 or 1, and Z' is selected from methyl; ethyl; propyl; isopropyl; C3 cycloalkyl; C3-C10 heterocycloalkyl; C1-C6 alkyl substituted with one or two of $OR^5$ and $NR^5R^6$; wherein $R^5$ and $R^6$ are, at each occurrence, independently selected from the group consisting of hydrogen; C1-C6 alkyl; C3-C10 cycloalkyl; and C1-C4 haloalkyl; any of which is optionally substituted; and
$R^2$ is $OR^8$, and $R^8$ is selected from C1-C4 haloalkyl; and C1-C6 alkyl substituted with one of trifluoromethyl, difluoromethyl, fluoromethyl, trifluoroethyl, difluoroethyl, fluoroethyl, trifluoropropyl, difluoropropyl, fluoropropyl, trifluoroisopropyl, difluoroisopropyl, and fluoroisopropyl,
and pharmaceutically acceptable salts thereof.

9. The compound according to claim 1, wherein
$R^2$ is $OR^8$, and $R^8$ is selected from one of trifluoromethyl, difluoromethyl, fluoromethyl, trifluoroethyl, difluoroethyl, fluoroethyl, trifluoropropyl, difluoropropyl, fluoropropyl, trifluoroisopropyl, difluoroisopropyl, and fluoroisopropyl; or C1-C6 alkyl substituted with one of trifluoromethyl, difluoromethyl, fluoromethyl, trifluoroethyl, difluoroethyl, fluoroethyl, trifluoropropyl, difluoropropyl, fluoropropyl, trifluoroisopropyl, difluoroisopropyl, and fluoroisopropyl.

10. The compound according to claim 1, wherein
n=0 or 1; and $Z^1$ is selected from methyl; ethyl; propyl; isopropyl; C3 cycloalkyl; C4 cycloalkyl; and C5 cycloalkyl.

11. The compound according to claim 1, wherein
n=0 or 1; $Z^1$ is selected from methyl; ethyl; propyl; isopropyl; C3 cycloalkyl; C4 cycloalkyl; and C5 cycloalkyl; and
$R^2$ is $OR^8$; and $R^8$ is selected from one of trifluoromethyl, difluoromethyl, fluoromethyl, trifluoroethyl, difluoroethyl, fluoroethyl, trifluoropropyl, difluoropropyl, fluoropropyl, trifluoroisopropyl, difluoroisopropyl, and fluoroisopropyl; or C1-C6 alkyl substituted with one of trifluoromethyl, difluoromethyl, fluoromethyl, trifluoroethyl, difluoroethyl, fluoroethyl, trifluoropropyl, difluoropropyl, fluoropropyl, trifluoroisopropyl, difluoroisopropyl, and fluoroisopropyl.

12. The compound according to claim 1 having one of the structures as shown hereafter:

| # cpd | Structure |
|---|---|
| 1 | 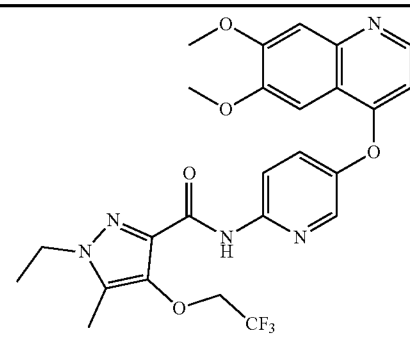 |
| 2 | 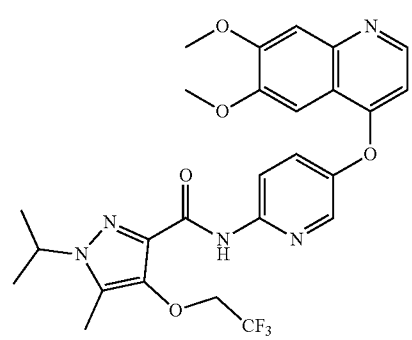 [SMILES: COc1cc2nccc(Oc3ccc(NC(=O)c4nn(C(C)C)c(C)c4OCC(F)(F)F)nc3)c2cc1OC] |

| # cpd | Structure |
|---|---|
| 3 | 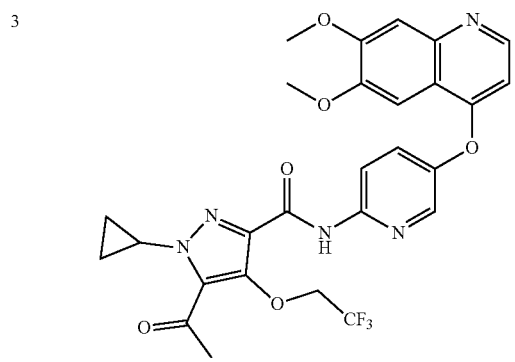 |
| 4 | 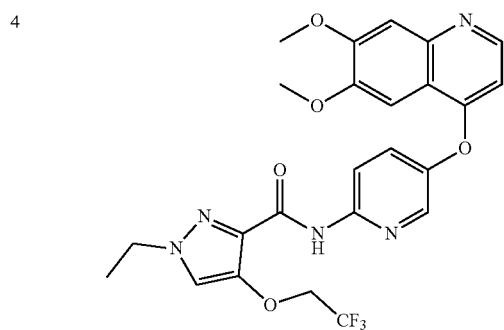 |
| 5 | 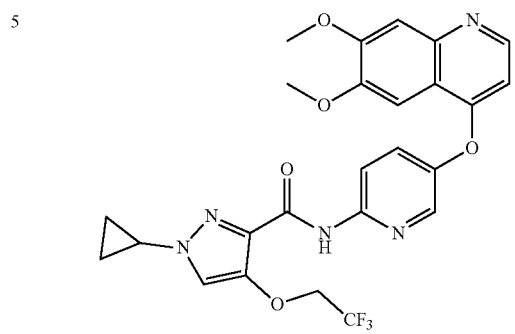 |
| 7 | 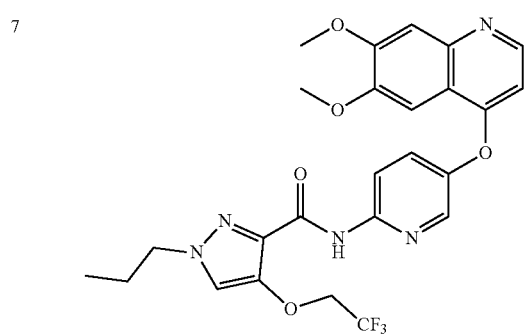 |
| # cpd | Structure |
|---|---|
| 9 | 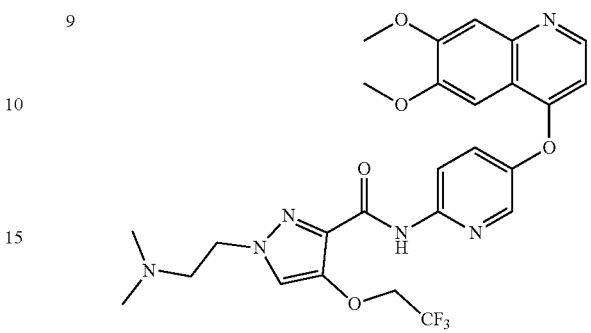 |
| 10 | 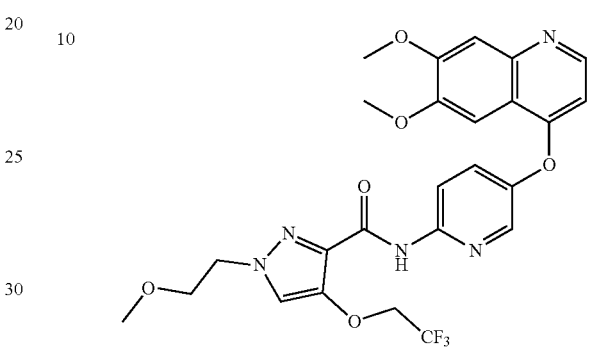 |
| 11 | 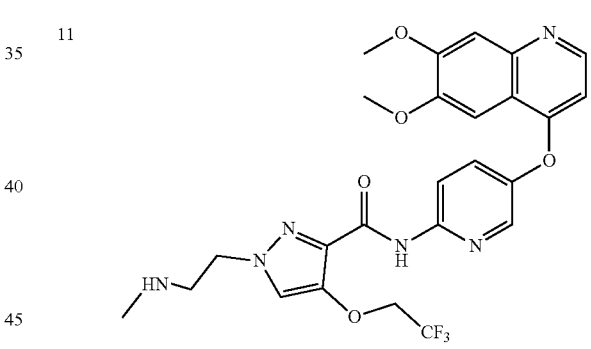 |
| 12 | 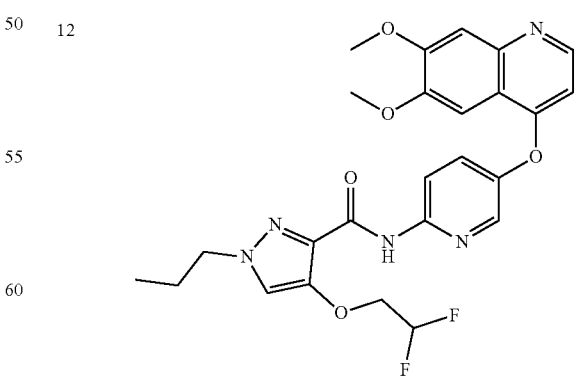 |

| # cpd | Structure |
|---|---|
| 13 | 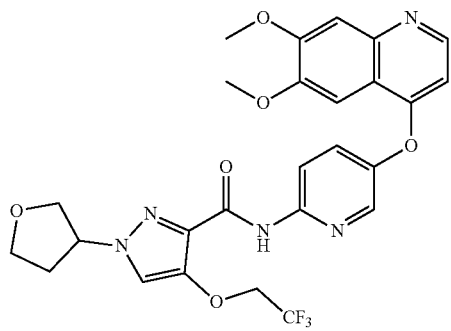 |
| 14 | 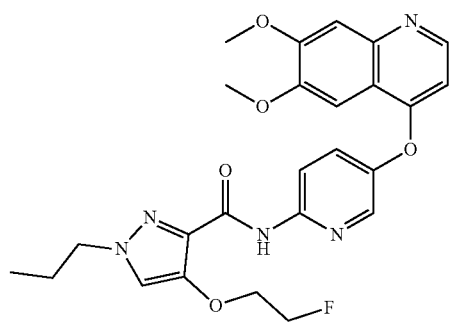 [SMILES: CCCn1cc(OCCF)c(C(=O)Nc2ccc(Oc3ccnc4cc(OC)c(OC)cc34)cn2)n1] |
| 16 | 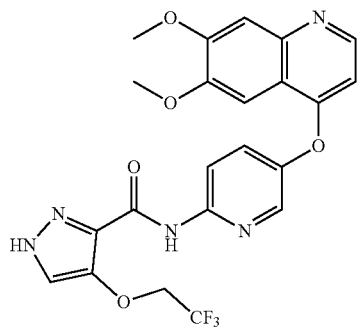 [SMILES: COc1cc2nccc(Oc3ccc(NC(=O)c4n[nH]cc4OCC(F)(F)F)nc3)c2cc1OC] |
| 17 | 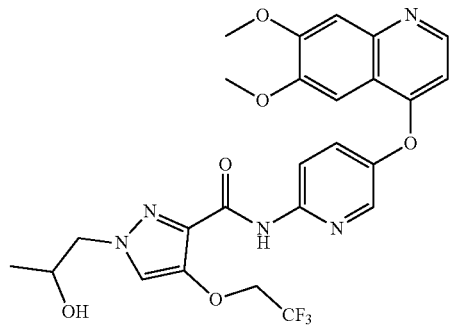 |
| # cpd | Structure |
|---|---|
| 18 | 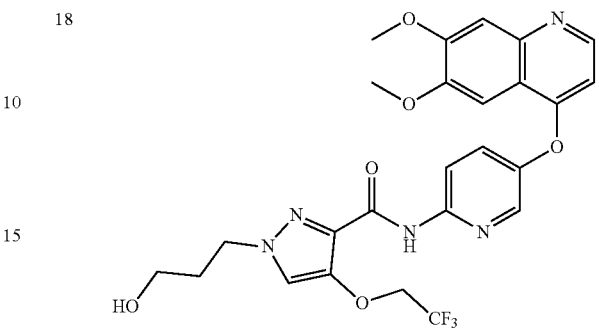 |
| 21 | 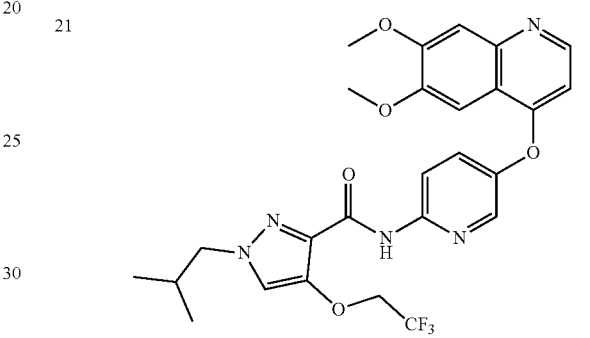 |
| 22 | 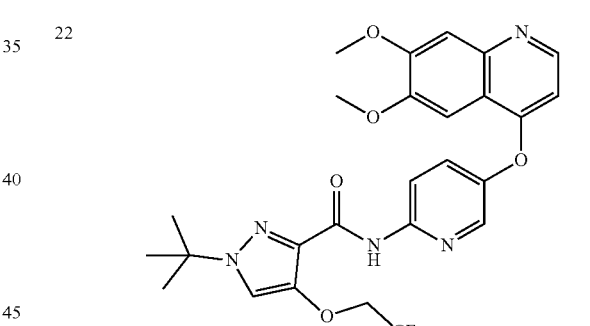 |
| 24 | 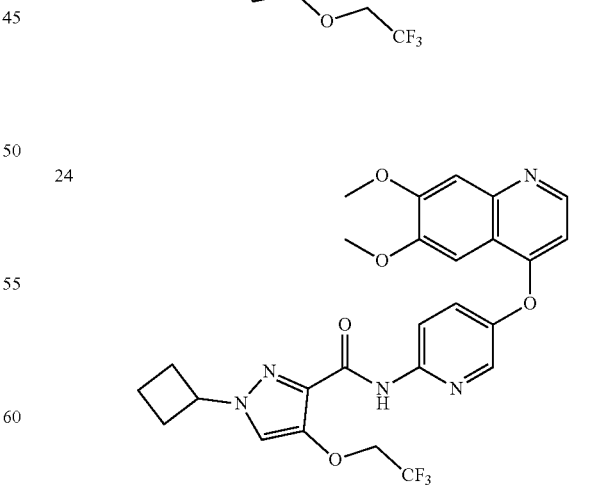 |

-continued

| # cpd | Structure |
|---|---|
| 25 | (6,7-dimethoxyquinolin-4-yloxy)-linked to 3-fluoro-4-substituted phenyl amide of 1-propyl-4-(2,2,2-trifluoroethoxy)-1H-pyrazole-3-carboxamide |
| 26 | (6,7-dimethoxyquinolin-4-yloxy)-linked to 3-methyl-4-substituted phenyl amide of 1-propyl-4-(2,2,2-trifluoroethoxy)-1H-pyrazole-3-carboxamide |
| 27 | (6,7-dimethoxyquinolin-4-yloxy)-linked to 2-methyl-4-substituted phenyl amide of 1-propyl-4-(2,2,2-trifluoroethoxy)-1H-pyrazole-3-carboxamide |
| 28 | (6,7-dimethoxyquinolin-4-yloxy)-linked to 2-fluoro-4-substituted phenyl amide of 1-propyl-4-(2,2,2-trifluoroethoxy)-1H-pyrazole-3-carboxamide |

| # cpd | Structure |
|---|---|
| 29 | (6,7-dimethoxyquinolin-4-yloxy)-pyridin-2-yl amide of 1-((R)-2-hydroxypropyl)-4-(2,2,2-trifluoroethoxy)-1H-pyrazole-3-carboxamide |
| 30 | (6,7-dimethoxyquinolin-4-yloxy)-pyridin-2-yl amide of 1-((S)-2-hydroxypropyl)-4-(2,2,2-trifluoroethoxy)-1H-pyrazole-3-carboxamide |
| 31 | (6,7-dimethoxyquinolin-4-yloxy)-pyridin-2-yl amide of 1-propyl-4-(2,2,2-trifluoroethoxy)-1H-pyrazole-3-carboxamide |
| 32 | (6,7-dimethoxyquinolin-4-yloxy)-pyridazin-3-yl amide of 1-propyl-4-(2,2,2-trifluoroethoxy)-1H-pyrazole-3-carboxamide |

| # cpd | Structure |
|---|---|
| 33 | 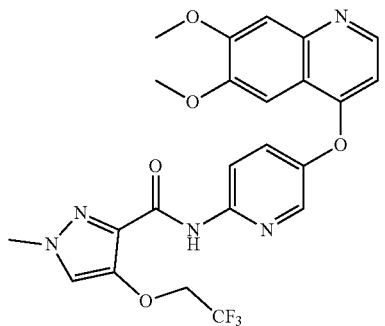 |
| 36 | 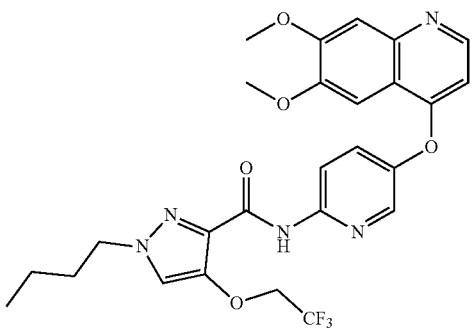 |
| 37 | 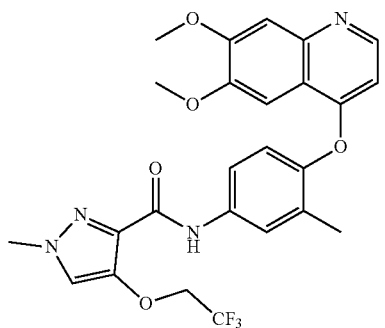 |
| 38 | 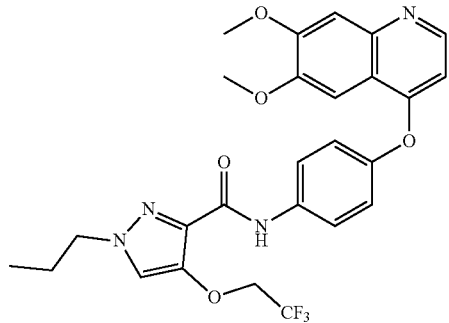 |
| # cpd | Structure |
|---|---|
| 40 | 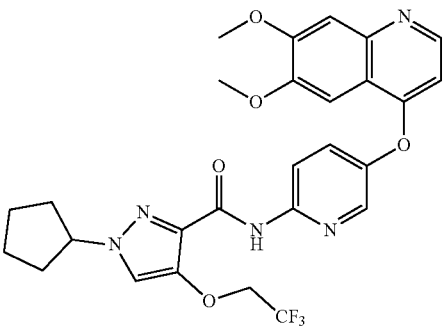 [SMILES: COc1cc2nccc(Oc3ccc(NC(=O)c4nn(C5CCCC5)cc4OCC(F)(F)F)nc3)c2cc1OC] |
| 41 | 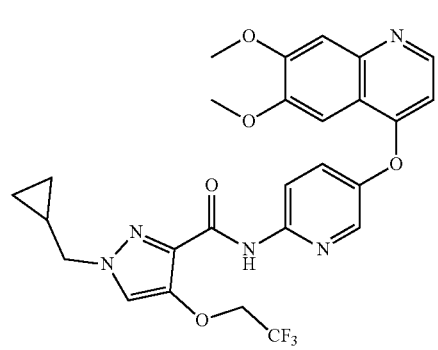 [SMILES: COc1cc2nccc(Oc3ccc(NC(=O)c4nn(CC5CC5)cc4OCC(F)(F)F)nc3)c2cc1OC] |
| 42 | 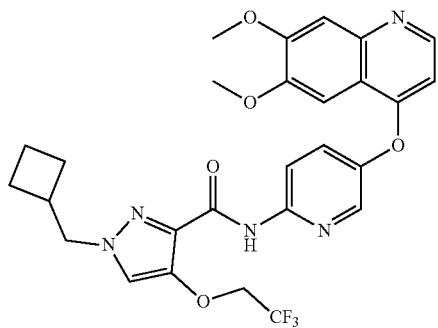 [SMILES: COc1cc2nccc(Oc3ccc(NC(=O)c4nn(CC5CCC5)cc4OCC(F)(F)F)nc3)c2cc1OC] |
| 43 | 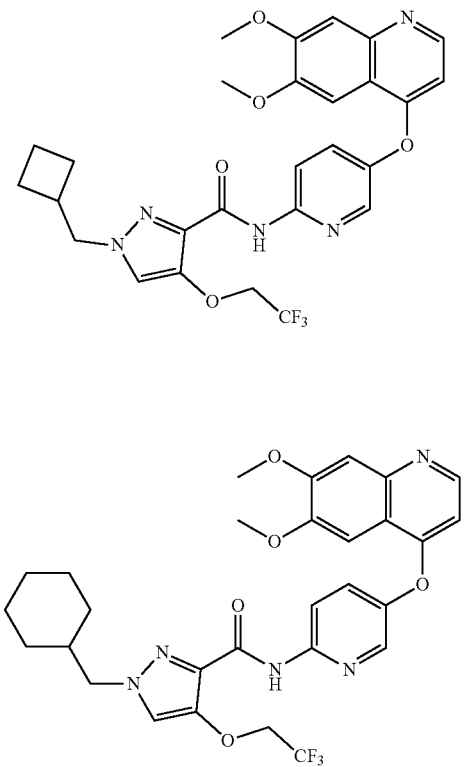 |

-continued
| # cpd | Structure |
|---|---|
| 44 | 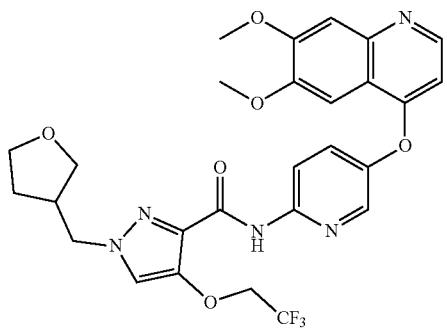 [SMILES: COc1cc2nccc(Oc3ccc(NC(=O)c4nn(CC5CCOC5)cc4OCC(F)(F)F)nc3)c2cc1OC] |
| 45 | 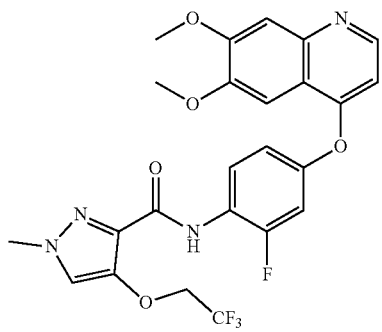 [SMILES: COc1cc2nccc(Oc3ccc(NC(=O)c4nn(C)cc4OCC(F)(F)F)c(F)c3)c2cc1OC] |
| 46 | 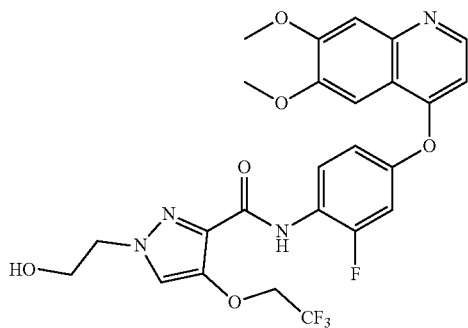 |
| 47 | 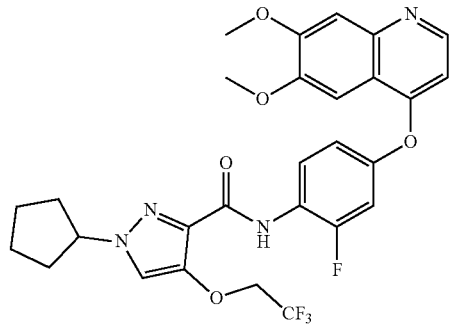 [SMILES: COc1cc2nccc(Oc3ccc(NC(=O)c4nn(C5CCCC5)cc4OCC(F)(F)F)c(F)c3)c2cc1OC] |
-continued
| # cpd | Structure |
|---|---|
| 48 | 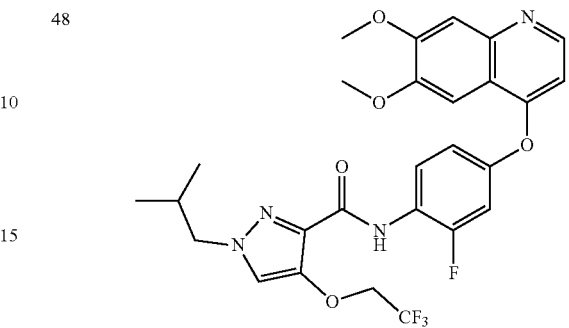 |
| 49 | 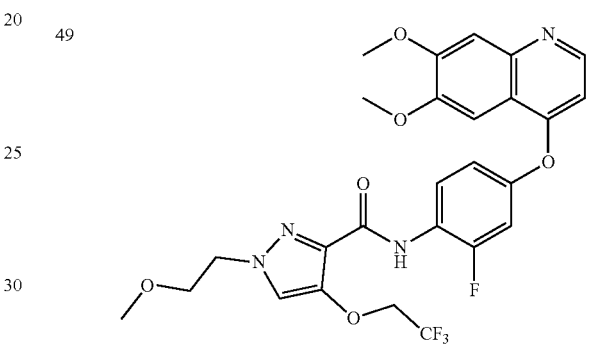 |
| 50 | 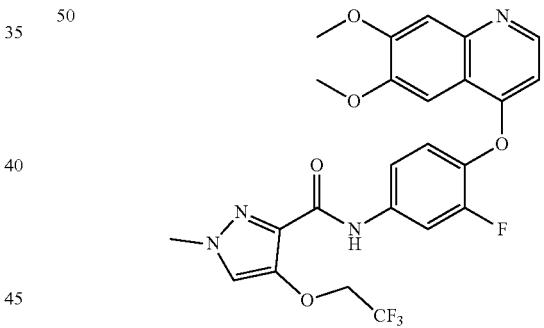 |
| 51 | 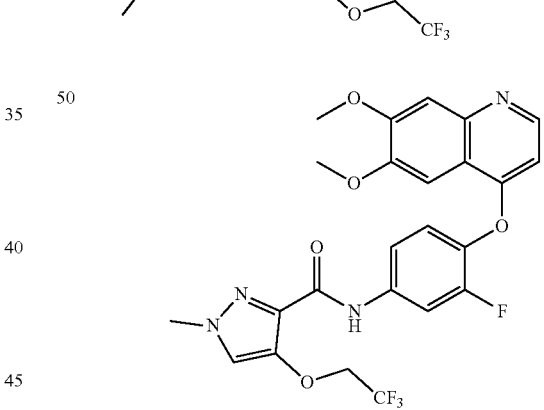 |

| # cpd | Structure |
|---|---|
| 52 | 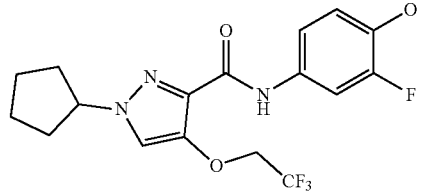 |
| 53 | 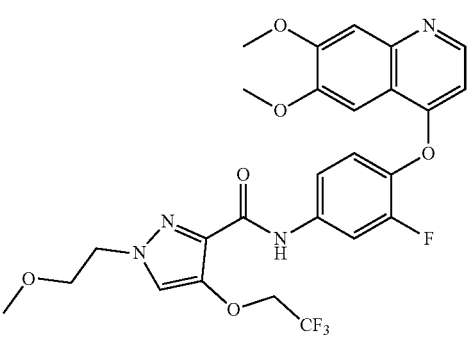 [SMILES: COCCn1cc(OCC(F)(F)F)c(C(=O)Nc2ccc(Oc3ccnc4cc(OC)c(OC)cc34)c(F)c2)n1] |
| 54 | |
| 55 | 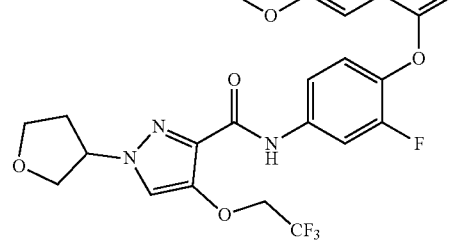 |
| # cpd | Structure |
|---|---|
| 56 | 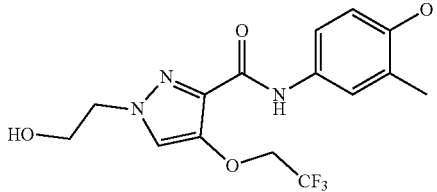 |
| 57 | 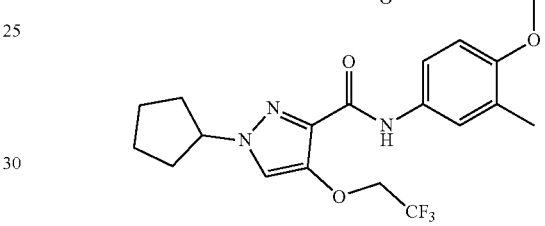 |
| 58 | 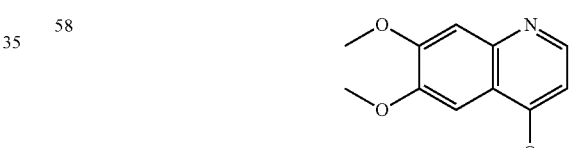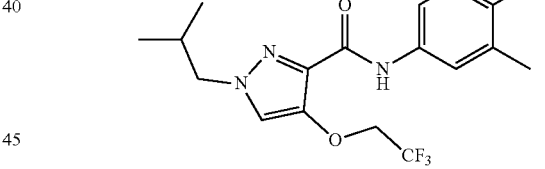 |
| 59 | 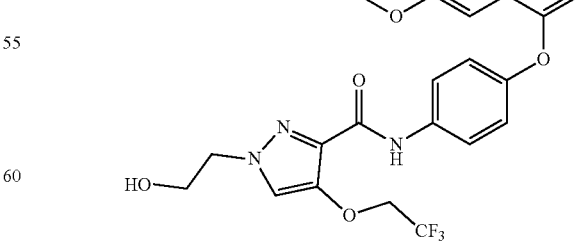 |

| # cpd | Structure |
|---|---|
| 60 | 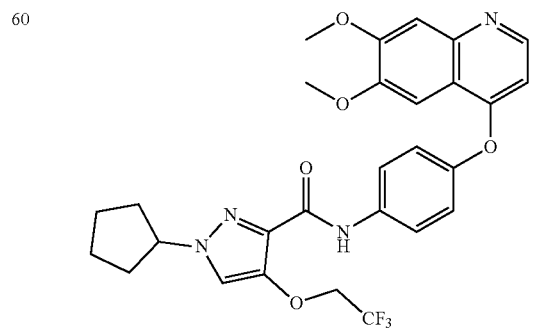 |
| 61 | 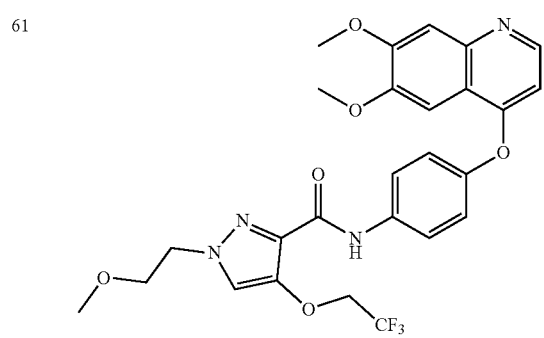 |
| 62 | 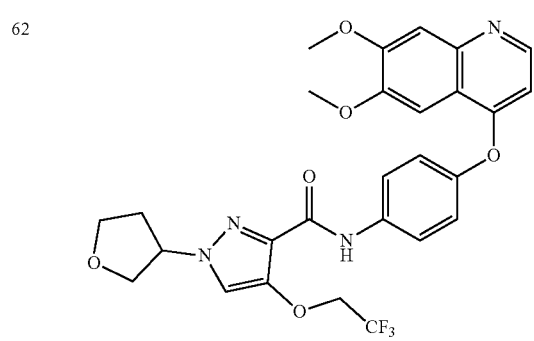 |
| 63 | 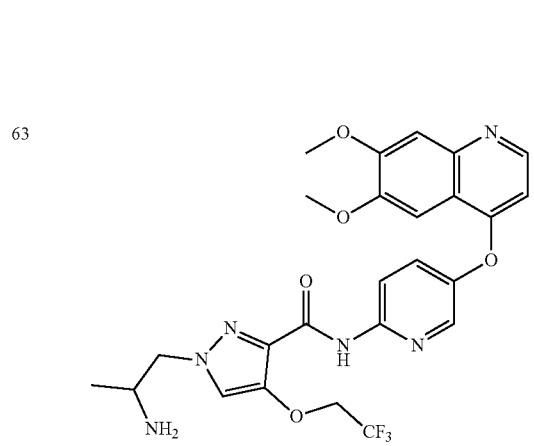 |
| # cpd | Structure |
|---|---|
| 65 | 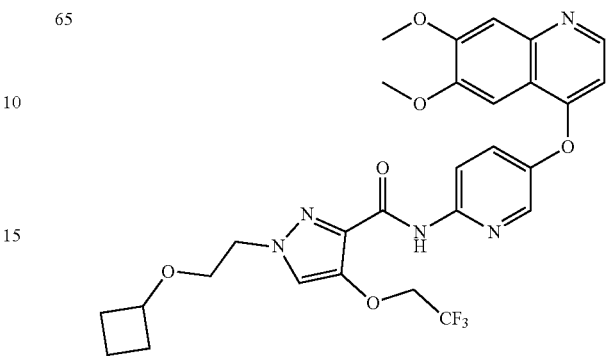 |
| 66 | 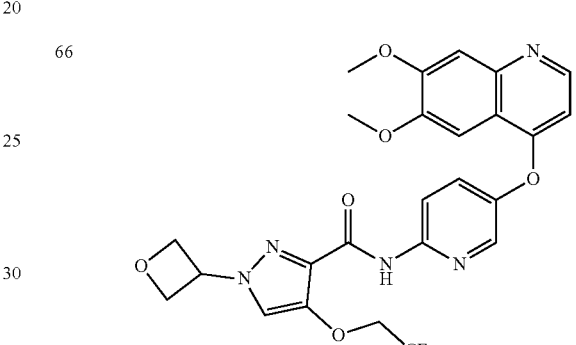 |
| 67 | 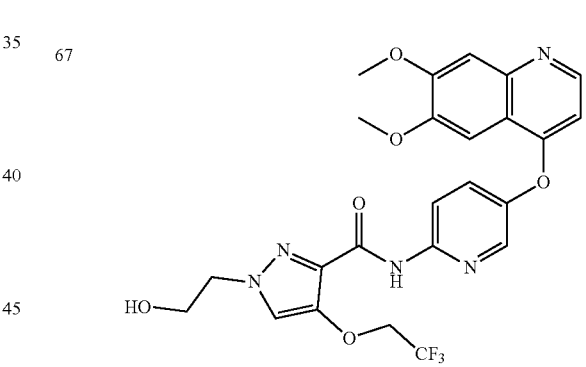 |
| 68 | 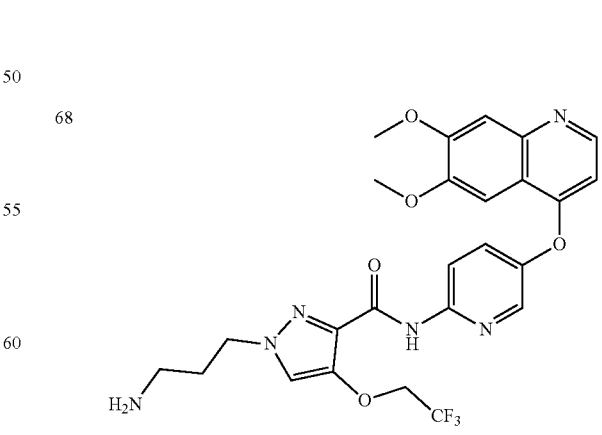 |

| # cpd | Structure |
|---|---|
| 69 | (structure) |
| 70 | (structure) |
| 71 | (structure) |
| 72 | (structure) |
| 73 | (structure) |
| 74 | (structure) |
| 75 | (structure) |
| 76 | (structure) |

| # cpd | Structure |
|---|---|
| 77 | 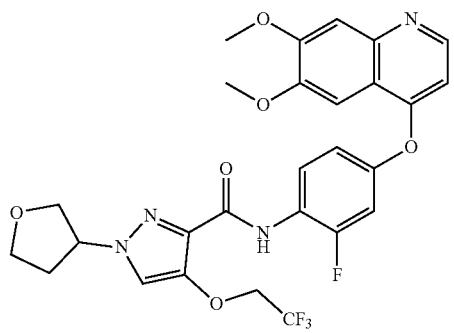 |
| 78 | 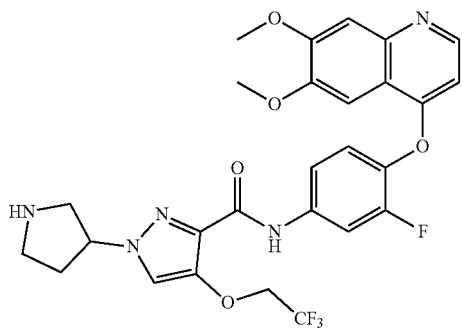 |
| 79 | 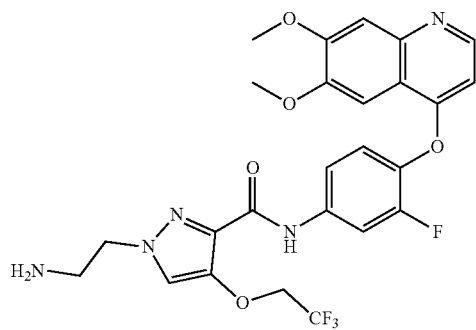 |
| 80 | 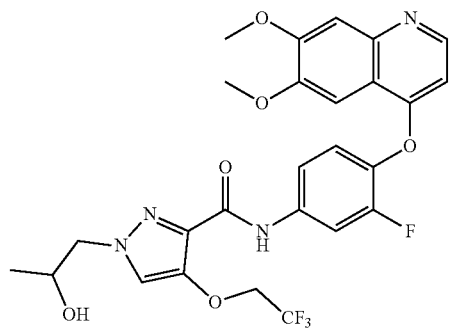 [SMILES: COc1cc2nccc(Oc3ccc(NC(=O)c4nn(CC(C)O)cc4OCC(F)(F)F)cc3C)c2cc1OC] |
| # cpd | Structure |
|---|---|
| 81 | 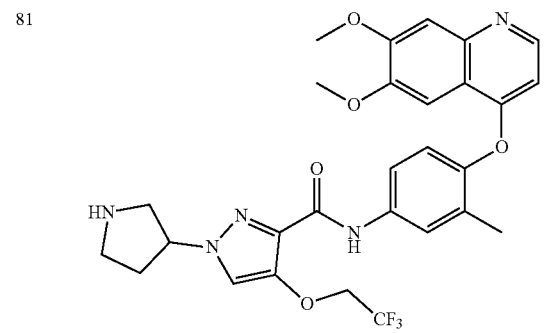 |
| 82 | 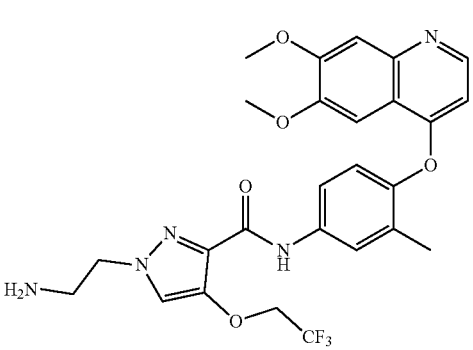 |
| 83 | 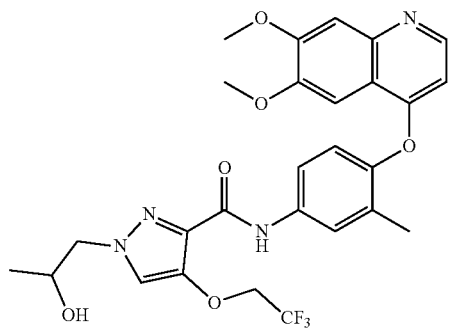 |
| 84 | 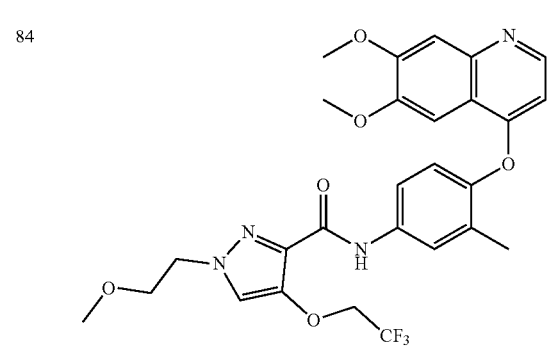 |

| # cpd | Structure |
|---|---|
| 85 | 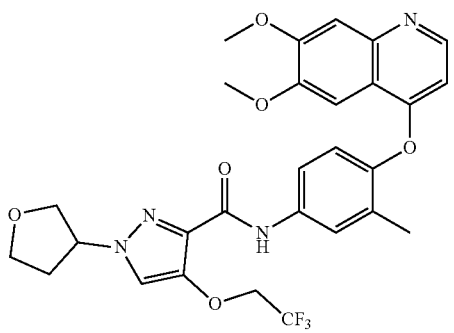 [SMILES: COc1cc2nccc(Oc3ccc(NC(=O)c4nn(C5CCOC5)cc4OCC(F)(F)F)cc3C)c2cc1OC] |
| 86 | 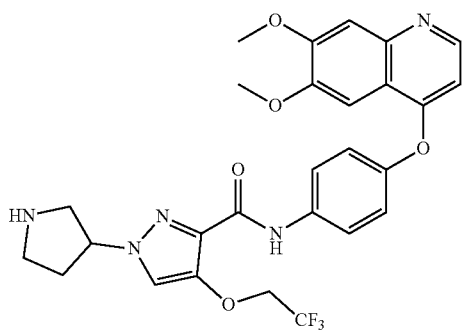 [SMILES: COc1cc2nccc(Oc3ccc(NC(=O)c4nn(C5CCNC5)cc4OCC(F)(F)F)cc3)c2cc1OC] |
| 87 | 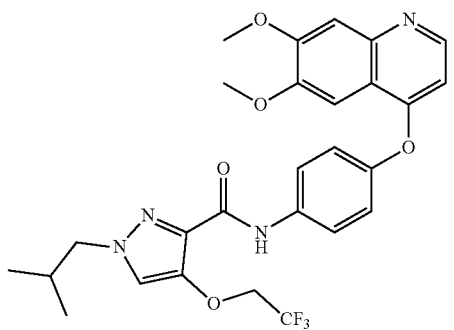 [SMILES: COc1cc2nccc(Oc3ccc(NC(=O)c4nn(CC(C)C)cc4OCC(F)(F)F)cc3)c2cc1OC] |
| 88 | 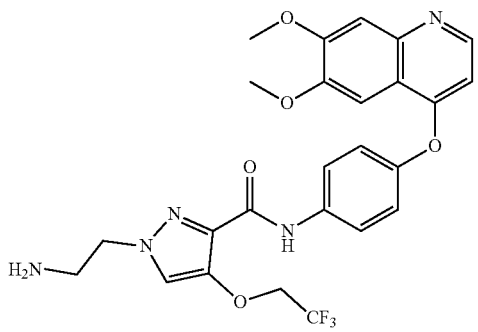 |
| # cpd | Structure |
|---|---|
| 89 | 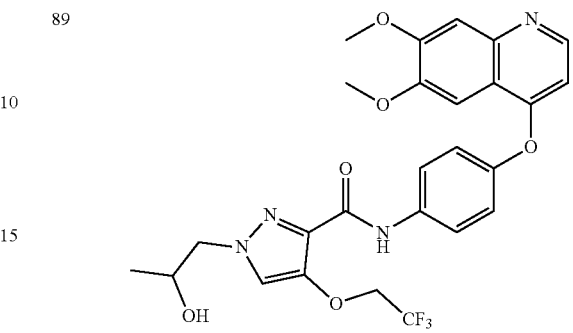 |
| 90 | 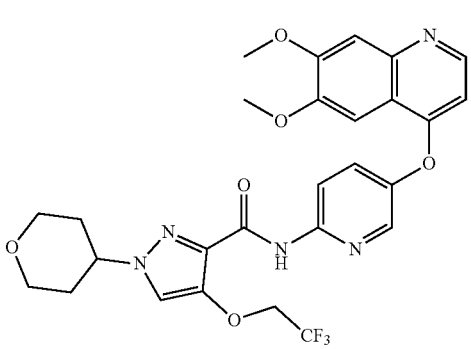 [SMILES: COc1cc2nccc(Oc3ccc(NC(=O)c4nn(C5CCOCC5)cc4OCC(F)(F)F)nc3)c2cc1OC] |
| 91 | 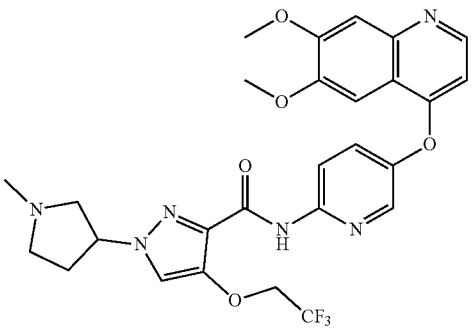 |
| 92 | 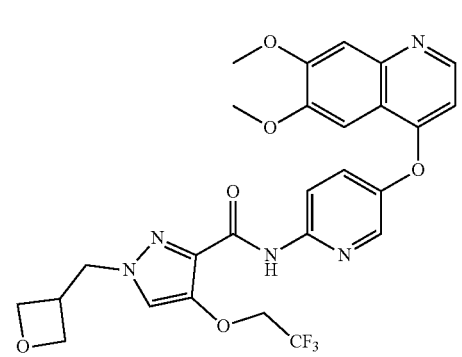 [SMILES: COc1cc2nccc(Oc3ccc(NC(=O)c4nn(CC5COC5)cc4OCC(F)(F)F)nc3)c2cc1OC] |

-continued
| # cpd | Structure |
|---|---|
| 93 | 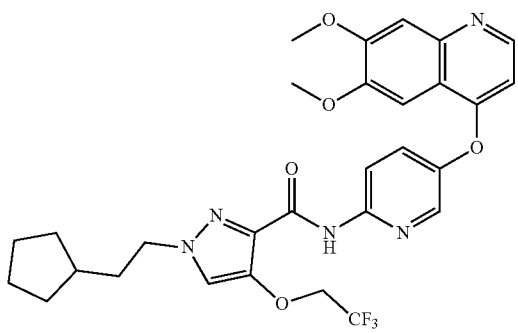 [SMILES: COc1cc2nccc(Oc3ccc(NC(=O)c4nn(CCC5CCCC5)cc4OCC(F)(F)F)nc3)c2cc1OC] |
| 94 | 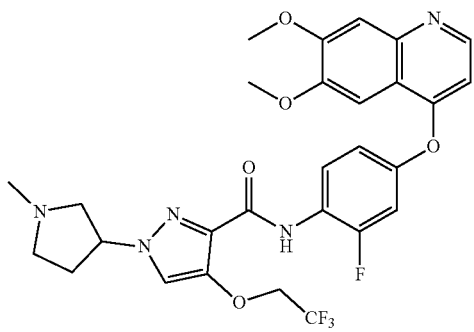 |
| 95 | 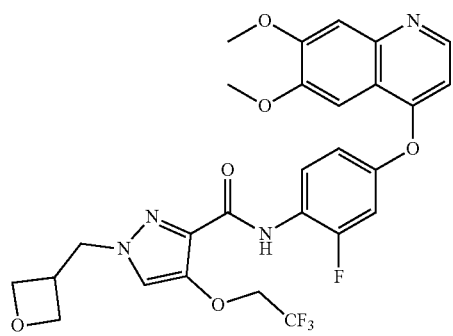 [SMILES: COc1cc2nccc(Oc3ccc(NC(=O)c4nn(CC5COC5)cc4OCC(F)(F)F)c(F)c3)c2cc1OC] |
| 96 | 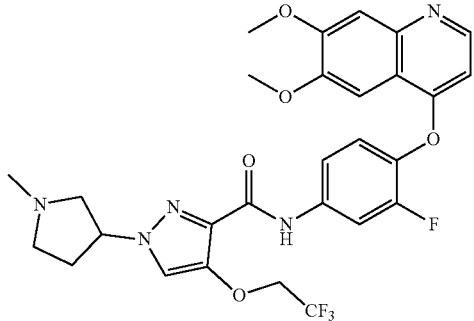 |
-continued
| # cpd | Structure |
|---|---|
| 97 | 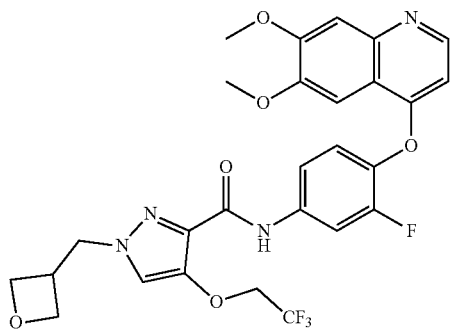 |
| 98 | 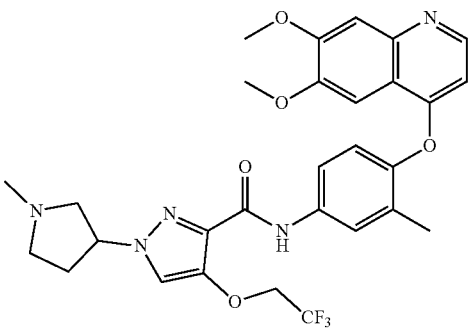 |
| 99 | 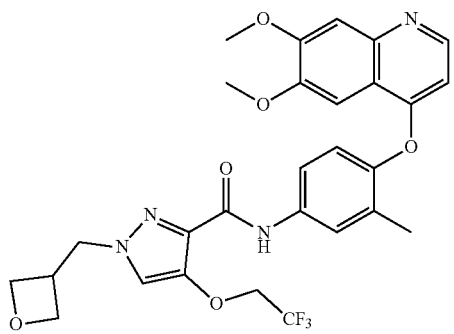 [SMILES: COc1cc2nccc(Oc3ccc(NC(=O)c4nn(CC5COC5)cc4OCC(F)(F)F)cc3C)c2cc1OC] |
| 100 | 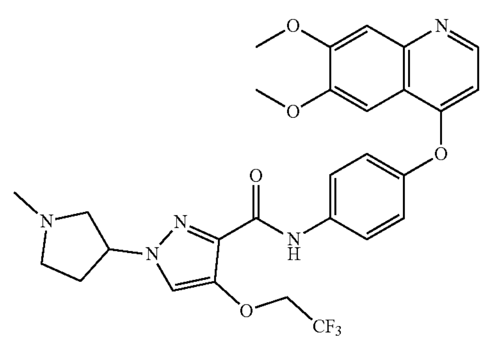 [SMILES: COc1cc2nccc(Oc3ccc(NC(=O)c4nn(C5CCN(C)C5)cc4OCC(F)(F)F)cc3)c2cc1OC] |

-continued
| # cpd | Structure |
|---|---|
| 101 | 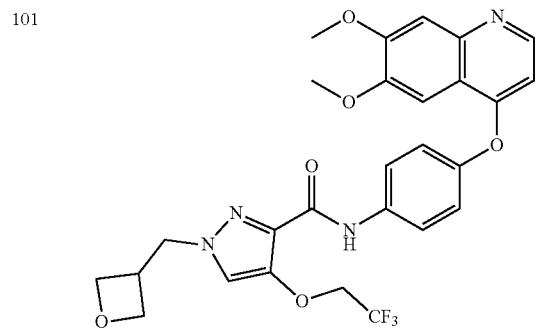 |
| 102 | 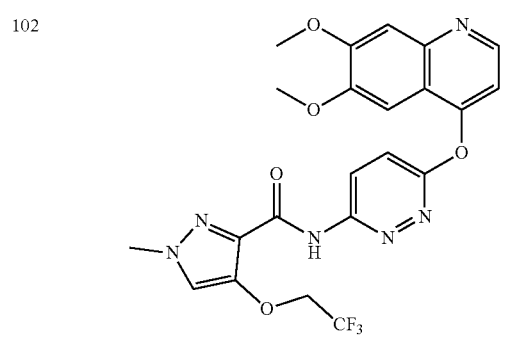 |
| 103 | 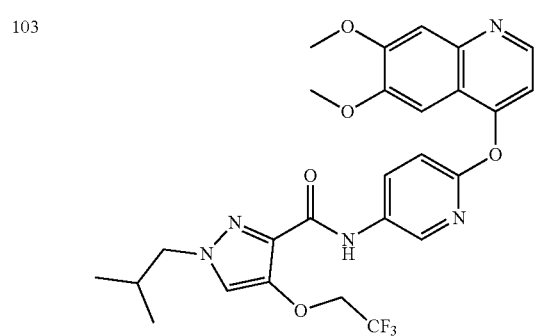 |
| 104 | 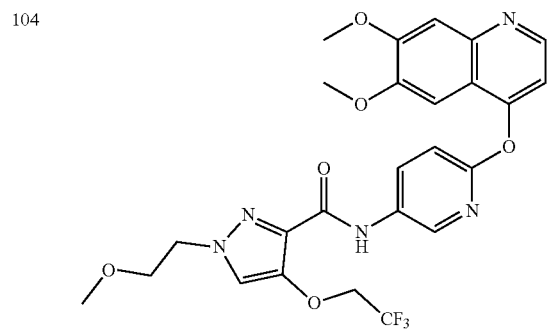 |
-continued
| # cpd | Structure |
|---|---|
| 109 | 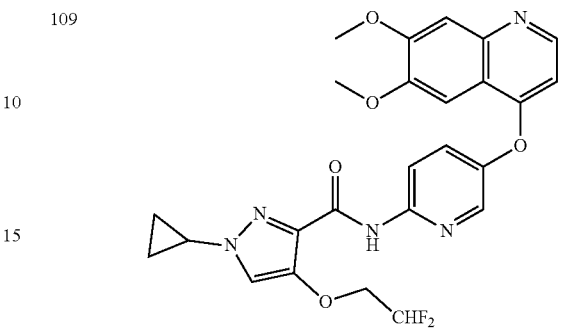 |
| 110 | 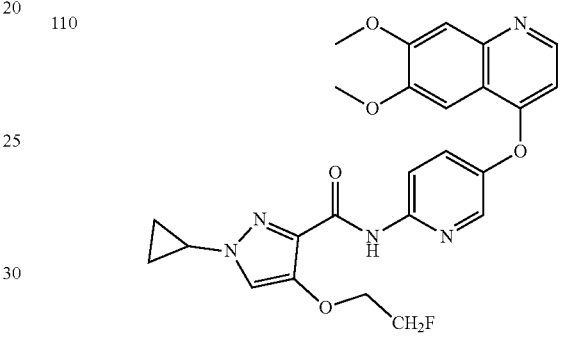 |
| 112 | 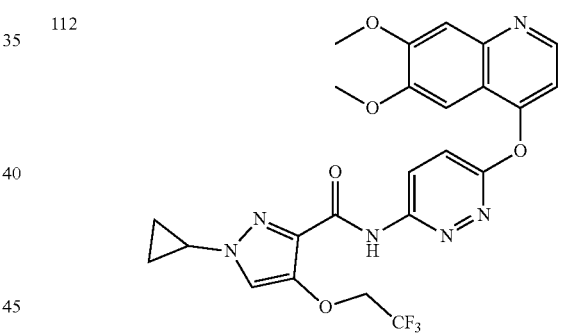 |
| 113 | 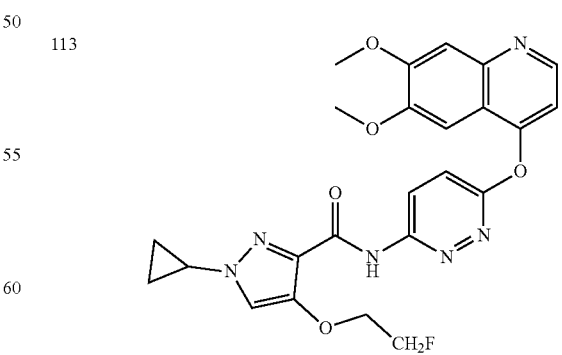 |

| # cpd | Structure |
|---|---|
| 114 | 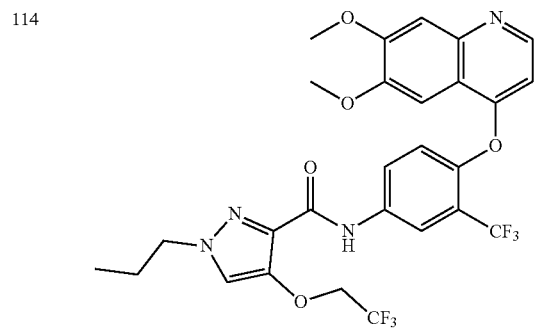 |
| 115 | 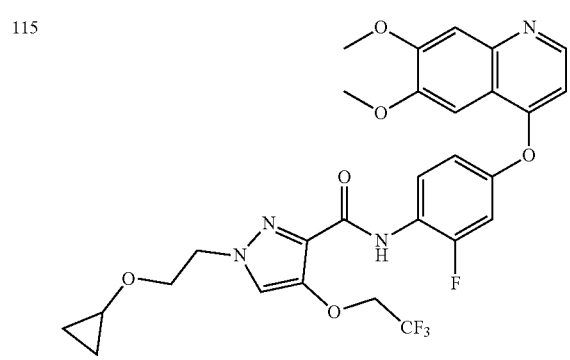 |
| 116 | 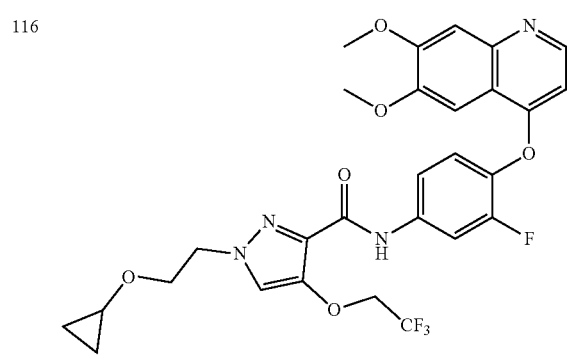 |
| 117 | 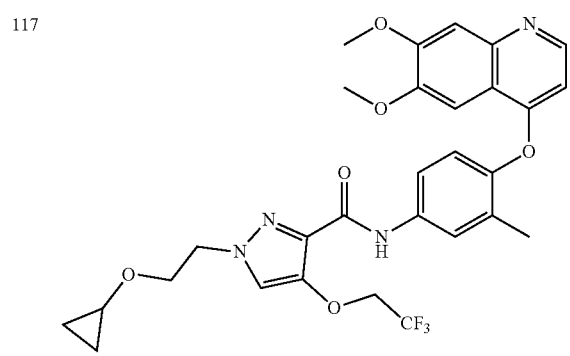 |
| # cpd | Structure |
|---|---|
| 118 | 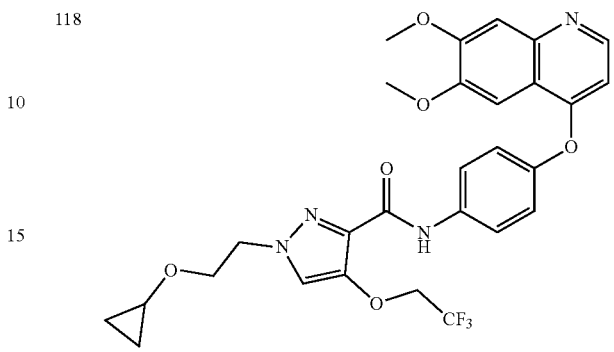 |
| 119 | 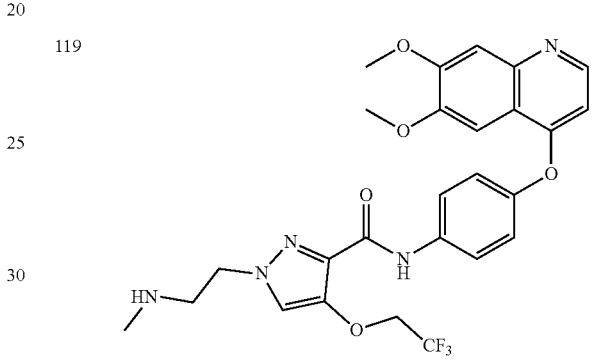 |
| 120 | 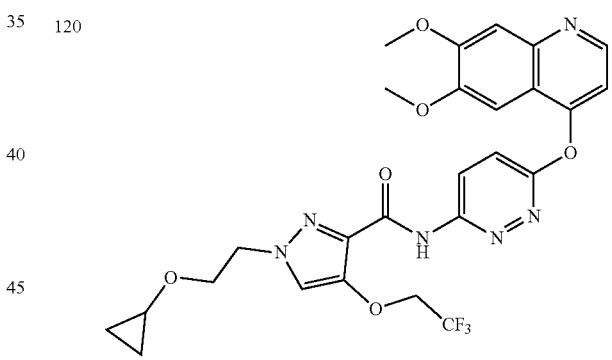 |
| 121 | 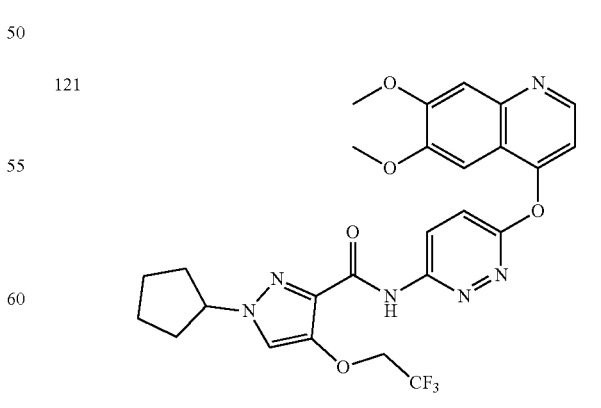 |

| # cpd | Structure |
|---|---|
| 122 | 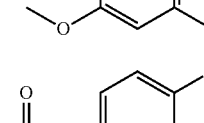 |
| 123 | 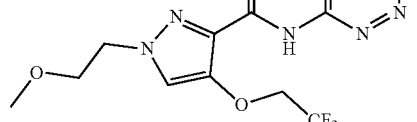 |
| 124 | 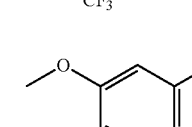 |
| 125 | 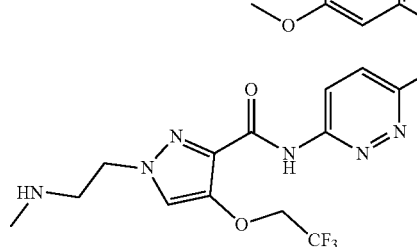 |
| # cpd | Structure |
|---|---|
| 126 | 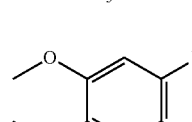 |
| 127 | 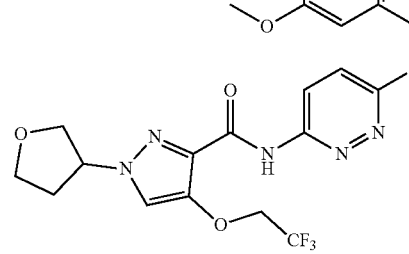 |
| 128 |  |
| 129 | 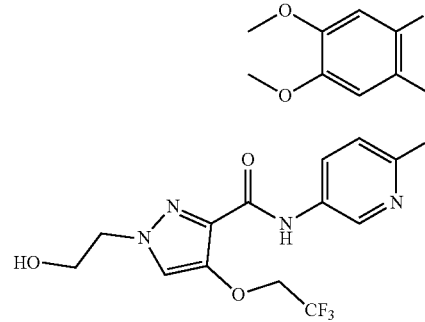 |

-continued

| # cpd | Structure |
|---|---|
| 130 | (structure) |
| 131 | (structure) |
| 132 | (structure) |
| 133 | (structure) |
| 134 | (structure) |
| 135 | (structure) |
| 136 | (structure) |
| 137 | (structure) |

-continued

| # cpd | Structure |
|---|---|
| 138 | (structure) |
| 139 | (structure) |
| 152 | (structure) |
| 153 | (structure) |

-continued

| # cpd | Structure |
|---|---|
| 154 | (structure) |
| 155 | (structure) |
| 156 | (structure) |
| 157 | (structure) |

-continued

| # cpd | Structure |
|---|---|
| 162 | (structure) |
| 168 | (structure) |
| 169 | (structure) |
| 170 | (structure) |

-continued

| # cpd | Structure |
|---|---|
| 173 | (structure) |
| 175 | (structure) |
| 178 | (structure) |
| 179 | (structure) |

13. A composition comprising at least one compound according to claim 1, together with at least one pharmaceutically acceptable carrier, excipient and/or diluent.

14. The composition according to claim 13, further comprising at least one other pharmaceutically active agent.

15. A method for the treatment of a disorder associated with, accompanied by, caused by or induced by a Axl/Mer and CSF1R receptor tyrosine kinase wherein said method comprises administering, to subject in need of such treatment, a compound of claim 1.

16. The method according to claim 15, wherein said disorder is selected from hyperproliferative disorders, inflammatory disorders and neurodegenerative disorders.

17. The method according to claim 16, wherein said hyperproliferative disorder is a cancer selected from adenocarcinoma, acoustic neuroma, acute lymphoblastic leukemia, acute myeloid leukemia, adrenocortical carcinoma, aids-related cancers, aids-related lymphoma, anal cancer, appendix cancer, astrocytomas, atypical teratoid/rhabdoid tumor, ampullary carcinoma, basal cell carcinoma, bile duct cancer, bladder cancer, bone cancer, osteosarcoma and malignant fibrous histiocytoma, brain stem glioma, brain tumor, central nervous system atypical teratoid/rhabdoid tumor, craniopharyngioma, ependymoblastoma, ependymoma, medulloblastoma, medulloepithelioma, pineal parenchymal tumors of intermediate differentiation, supratentorial primitive neuroectodermal tumors and pineoblastoma, brain and spinal cord tumors, breast cancer, urachal tumors, burkitt lymphoma, carcinoid tumor, choroidal melanoma, gastrointestinal cancer, central nervous system lymphoma, cervical cancer, corpus cancer, chordoma, chronic lymphocytic leukemia, chronic myelogenous leukemia, chronic myeloproliferative disorders, colon cancer, colorectal cancer, cutaneous t-cell lymphoma, desmoid tumor, mycosis fungoides, endometrial cancer, esophageal cancer, esthesioneuroblastoma, Ewing sarcoma family of tumors, extracranial germ cell tumor, extragonadal germ cell tumor, extrahepatic bile duct cancer, ear tumors, intraocular melanoma, retinoblastoma, gallbladder cancer, gastric cancer, gastrointestinal carcinoid tumor, gastrointestinal stromal tumor, gastrointestinal stromal cell tumor, gynecologic tumors, ovarian germ cell tumor, gestational trophoblastic tumor, glioma, gallbladder carcinomas, hairy cell leukemia, head and neck cancer, heart cancer, hepatocellular cancer, histiocytosis, hypopharyngeal cancer, hematologic neoplasias, islet cell tumors (endocrine pancreas), renal cell cancer, kidney cancer, langerhans cell histiocytosis, laryngeal cancer, leukemia, lip and oral cavity cancer, liver cancer, lung cancer, non-small cell lung cancer, small intestinal tumors, small cell lung cancer, hodgkin lymphoma, non-hodgkin lymphoma, primary central nervous system lymphoma, macroglobulinemia, malignant fibrous histiocytoma of bone and osteosarcoma, melanoma, merkel cell carcinoma, mesothelioma, metastatic squamous neck cancer with occult primary, spinaliosms, multiple endocrine neoplasia syndromes, myelodysplastic syndromes, myelodysplastic/myeloproliferative neoplasms, myeloid leukemia, multiple myeloma, myeloproliferative disorders, nasal cavity and paranasal sinus cancer, nasopharyngeal cancer, neuroblastoma, oral cavity cancer, oropharyngeal cancer, osteosarcoma and malignant fibrous histiocytoma of bone, ovarian cancer, ovarian epithelial cancer, ovarian low malignant potential tumor, oligodendroglioma, plasmacytomas, pancreatic cancer, papillomatosis, parathyroid cancer, penile cancer, pharyngeal cancer, pituitary tumor, plasma cell neoplasm/multiple myeloma, pleuropulmonary blastoma, prostate cancer, rectal cancer, renal cell cancer, transitional cell cancer, respiratory tract cancer, rhabdomyosarcoma, salivary gland cancer, sarcoma, skin testis cancer, ewing sarcoma, kaposi sarcoma, uterine sarcoma, non-melanoma skin cancer, melanoma skin cancer, skin carcinoma, small intestine cancer, soft tissue sarcoma, squamous cell carcinoma, squamous neck cancer, stomach cancer, soft tissue tumors, testicular cancer, throat cancer, thymoma and thymic carcinoma, thyroid cancer, transitional cell cancer of the renal pelvis and ureter, trophoblastic tumor, testicle cancer, gestational cancer, urologic tumors, ureter and renal pelvis cancer, urethral cancer, urothelial carcinoma, uterine cancer, vaginal cancer, vulvar cancer, waldenström macroglobulinemia and wilms tumor, tumors that cause effusions in potential spaces of the body, pleural effusions, pericardial effusions, peritoneal effusion aka ascites, giant cell tumor (GCT), GCT of bone, pigmented villonodular synovitis (PVNS), and tenosynovial giant cell tunor (TGCT), TGCT of tendon sheath (TGCT-TS).

18. The method according to claim 16, wherein said inflammatory disorder is selected from osteoarthritis, inflammatory bowel syndrome, tramsplant rejection, systemic lupus erythematosis, ulcerative colitis, crohn's disease, chronic obstructive pulmonary disease, emphysema, Kawasaki's Disease, hemophagocytic syndrome (macrophage activation syndrome), multicentric reticulohistiocytosis, atherosclerosis, primary progressive multiple sclerosis, tenpsy Type I diabetes, Type II diabetes, insulin resistance, hyperglycemia, obesity, lipolysis, hypcreosinophilia, osteoporosis, increased risk of fracture, Paget's disease, hypercalcemia, infectionmediated osteolysis (e.g. osteomyelitis), peri-prosthetic or wear-debris-mediated osteolysis, endometriosis, inflammatory pain, chronic pain, and bone pain.

19. The method according to claim 16, wherein said neurodegenerative disorder is selected from Binswanger type dementia, prosencephaly, microcephaly, cerebral palsy, congenital hydrocephalus, abdominal dropsy, progress supranuclear palsy, glaucoma, Wilson disease, Alzheimer's disease and other dementias, Parkinson's disease (PD) and PD-related disorders, multi infarct dementia, Frontotemporal dementia, pseudo-dementia, Prion disease, Motor neuron diseases, Huntington's disease, spinocerebellar ataxia, and spinal muscular atrophy.

20. The method according to claim 15, which further comprises the administration of radiation therapy, chemotherapy agents, targeted drugs and/or immune check point inhibitor drugs.

21. The compound according to claim 3, wherein,
$R^3$ and $R^4$ are, at each occurrence, independently selected from the group consisting of hydrogen; halogen; and C1-C3 alkyl, which is optionally substituted;
$R^8$ is, at each occurrence, independently selected from the group consisting of C1-C4 haloalkyl; and C1-C6 alkyl substituted with C1-C4 haloalkyl; and
$Z^1$ is, at each occurrence, independently selected from the group consisting of hydrogen; C1-C6 alkyl; C1-C6 alkyl substituted with one or two of $OR^5$ and $NR^5R^6$; C3-C10 cycloalkyl; and C3-C10 heterocycloalkyl;
and pharmaceutically acceptable salts thereof.

22. The compound according to claim 5, wherein,
$R^3$ and $R^4$ are hydrogen;
and pharmaceutically acceptable salts thereof.

23. A compound having one of the following structures:
| #cpd | Structure |
|---|---|
| 6 | 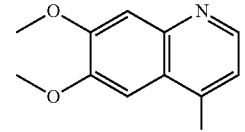 |
| 8 | 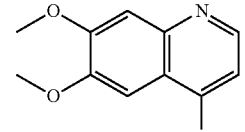 |
| 15 | 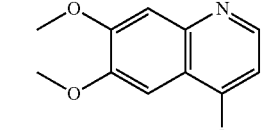 |
| 19 | 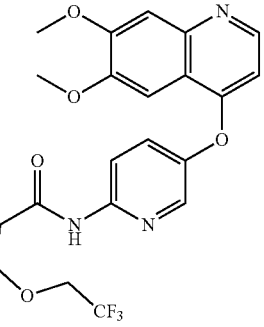 |
-continued
| #cpd | Structure |
|---|---|
| 20 | 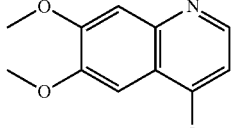 |
| 23 | 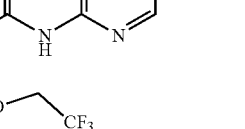 |
| 34 | 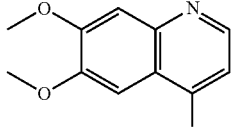 |
| 35 | 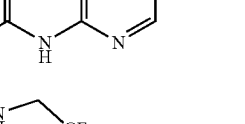 |

|  #cpd | Structure |
| --- | --- |
| 39 | (structure) |
| 64 | (structure) |
| 105 | (structure) |
| 106 | (structure) |

|  #cpd | Structure |
| --- | --- |
| 107 | (structure) |
| 108 | (structure) |
| 111 | (structure) |
| 140 | (structure) |

| #cpd | Structure |
|---|---|
| 141 | (structure) |
| 142 | (structure) |
| 143 | (structure) |
| 144 | (structure) |
| 145 | (structure) |
| 146 | (structure) |
| 147 | (structure) |
| 148 | (structure) |

| #cpd | Structure | | #cpd | Structure |
|---|---|---|---|---|
| 149 | 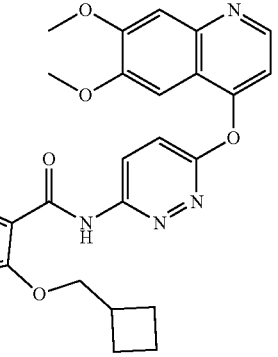 | | 159 | 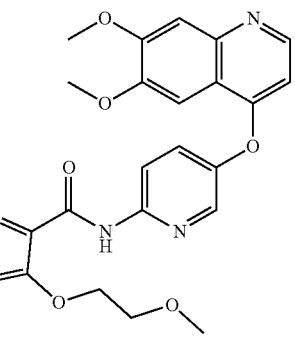 |
| 150 | 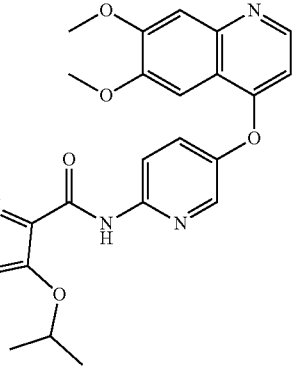 | | 160 | 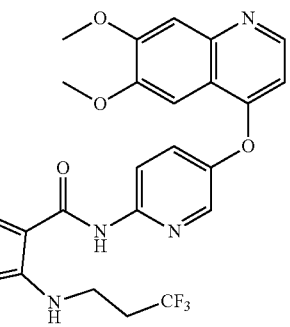 |
| 151 | 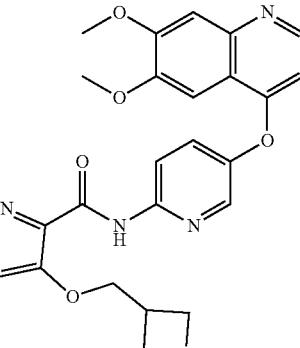 | | 161 | 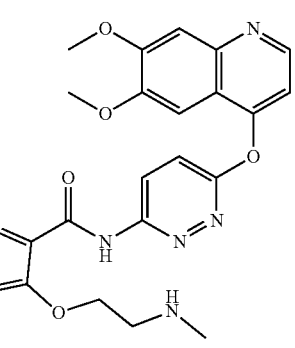 |
| 158 | 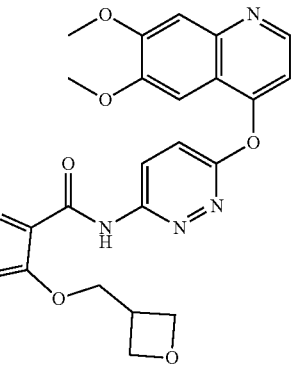 | | 163 | 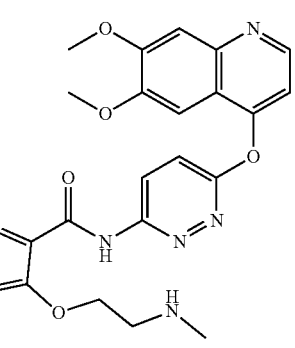 |

| #cpd | Structure |
|---|---|
| 164 | 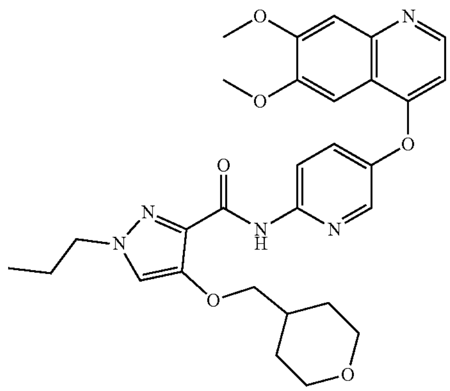 [SMILES: CCCn1cc(OCC2CCOCC2)c(C(=O)Nc2ccc(Oc3ccnc4cc(OC)c(OC)cc34)cn2)n1] |
| 165 | 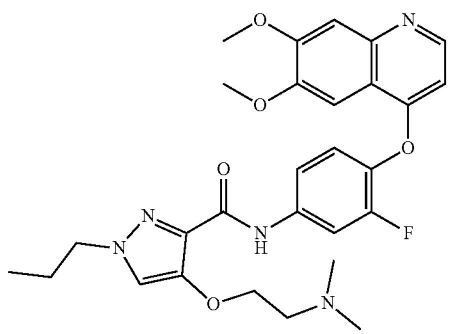 [SMILES: CCCn1cc(OCCN(C)C)c(C(=O)Nc2ccc(Oc3ccnc4cc(OC)c(OC)cc34)c(F)c2)n1] |
| 166 | 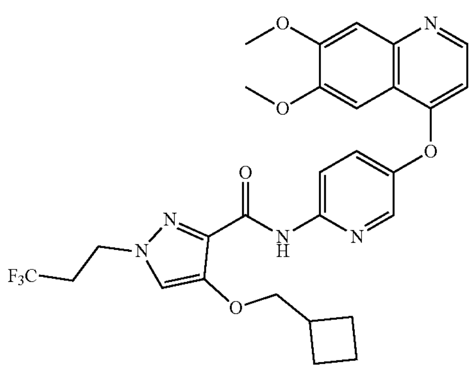 [SMILES: COc1cc2nccc(Oc3ccc(NC(=O)c4nn(CCC(F)(F)F)cc4OCC4CCC4)nc3)c2cc1OC] |
| 167 | 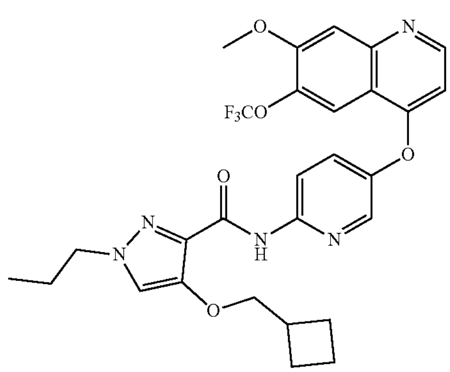 [SMILES: CCCn1cc(OCC2CCC2)c(C(=O)Nc2ccc(Oc3ccnc4cc(OC)c(OC(F)(F)F)cc34)cn2)n1] |
| 171 | |
| 172 | |
| 174 | |
| 176 | |

-continued
| #cpd | Structure |
|---|---|
| 177 | 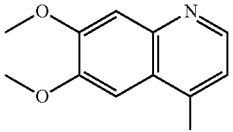 |

UNITED STATES PATENT AND TRADEMARK OFFICE
CERTIFICATE OF CORRECTION

PATENT NO. : 12,162,858 B2
APPLICATION NO. : 17/047961
DATED : December 10, 2024
INVENTOR(S) : Kiyean Nam et al.

Page 1 of 1

It is certified that error appears in the above-identified patent and that said Letters Patent is hereby corrected as shown below:

In the Specification

Column 134 (Table 8):
Lines 4-5, ":9.56 (1H, brs)," should read -- δ 9.56 (1H, brs), --
Line 11, "(DMSO-d6, 400 MHz):" should read -- (DMSO, 400 MHz): --

Signed and Sealed this
Eighteenth Day of November, 2025

John A. Squires
*Director of the United States Patent and Trademark Office*